US008912184B1

(12) United States Patent
Fleischer et al.

(10) Patent No.: US 8,912,184 B1
(45) Date of Patent: Dec. 16, 2014

(54) THERAPEUTIC AND DIAGNOSTIC METHODS

(75) Inventors: Tracey C. Fleischer, Sandy, UT (US); Daniel M. Cimbora, Salt Lake City, UT (US); Jeffrey S. Flick, Salt Lake City, UT (US); Andrew D. Gassman, Salt Lake City, UT (US); Vijay R. Baichwal, Salt Lake City, UT (US); Damon I. Papac, Mountain Brook, AL (US)

(73) Assignee: Alzheimer's Institute of America, Inc., Kansas City, KS (US)

( * ) Notice: Subject to any disclaimer, the term of this patent is extended or adjusted under 35 U.S.C. 154(b) by 111 days.

(21) Appl. No.: 13/235,221

(22) Filed: Sep. 16, 2011

Related U.S. Application Data

(63) Continuation-in-part of application No. PCT/US2011/026752, filed on Mar. 1, 2011.

(60) Provisional application No. 61/309,342, filed on Mar. 1, 2010, provisional application No. 61/360,364, filed on Jun. 30, 2010, provisional application No. 61/380,083, filed on Sep. 3, 2010, provisional application No. 61/384,302, filed on Sep. 19, 2010, provisional application No. 61/470,871, filed on Apr. 1, 2011.

(51) Int. Cl.
*A61K 31/535* (2006.01)

(52) U.S. Cl.
USPC ........ 514/236.5; 514/332; 514/335; 514/341; 514/356; 514/394; 514/343; 514/266.21; 514/253; 514/235.5; 514/357; 514/318

(58) Field of Classification Search
CPC .. C07C 275/28; C07C 275/32; C07C 275/34; C07C 275/40; C07C 275/30; C07D 471/04; C07D 209/14; C07D 213/42; C07D 213/65; C07D 213/75; C07D 213/46; C07D 213/12; C07D 213/06
USPC .............. 514/236.5, 332, 335, 341, 356, 394, 514/343, 266.21, 253, 235.5, 357, 318
See application file for complete search history.

(56) References Cited

U.S. PATENT DOCUMENTS

| 4,350,706 | A | 9/1982 | Brouwer et al. |
|---|---|---|---|
| 4,426,385 | A | 1/1984 | Cain |
| 5,314,902 | A | 5/1994 | Tjoeng et al. |
| 5,547,966 | A | 8/1996 | Atwal et al. |
| 5,574,042 | A | 11/1996 | Oku |
| 5,696,140 | A | 12/1997 | Bramm et al. |
| 6,174,905 | B1 | 1/2001 | Suzuki et al. |
| 6,255,323 | B1 | 7/2001 | Huang et al. |
| 6,403,632 | B1 | 6/2002 | Duan et al. |
| 6,525,077 | B2 | 2/2003 | Binderup et al. |
| 7,393,873 | B2 | 7/2008 | Anthony et al. |
| 7,547,804 | B2 | 6/2009 | Bajji et al. |
| 7,550,499 | B2 | 6/2009 | Tuerdi et al. |
| 7,652,022 | B2 | 1/2010 | Floersheimer et al. |
| 7,674,828 | B2 | 3/2010 | Chao et al. |
| 2004/0116476 | A1 | 6/2004 | Chern et al. |
| 2004/0259912 | A1 | 12/2004 | Matsumoto et al. |
| 2005/0159416 | A1 | 7/2005 | Morgan et al. |
| 2005/0215588 | A1 | 9/2005 | Binderup et al. |
| 2006/0128766 | A1 | 6/2006 | Erik |
| 2006/0166990 | A1 | 7/2006 | Ottosen et al. |
| 2007/0161677 | A1 | 7/2007 | Buchstaller |
| 2007/0197504 | A1 | 8/2007 | Morgan et al. |
| 2007/0244117 | A1 | 10/2007 | Fensholdt et al. |
| 2007/0249676 | A1 | 10/2007 | Binderup et al. |
| 2008/0020413 | A1 | 1/2008 | Tong et al. |
| 2008/0090842 | A1 | 4/2008 | Bjorkling |
| 2008/0171783 | A1 | 7/2008 | Cameron et al. |
| 2008/0261961 | A1 | 10/2008 | Flynn et al. |
| 2008/0261965 | A1 | 10/2008 | Flynn et al. |
| 2008/0269254 | A1 | 10/2008 | Flynn et al. |
| 2008/0269267 | A1 | 10/2008 | Flynn et al. |
| 2008/0280905 | A1 | 11/2008 | Chao et al. |
| 2008/0312275 | A1 | 12/2008 | Bjorkling et al. |
| 2009/0012091 | A1 | 1/2009 | Yu |
| 2009/0054389 | A1 | 2/2009 | Sonne |
| 2009/0162454 | A1 | 6/2009 | Roulston et al. |
| 2009/0163545 | A1 | 6/2009 | Goldfarb |
| 2009/0215823 | A1 | 8/2009 | Roulston et al. |
| 2009/0306077 | A1 | 12/2009 | Mogi et al. |
| 2009/0325923 | A1 | 12/2009 | Leo et al. |
| 2010/0056522 | A1 | 3/2010 | Yoneda et al. |
| 2010/0221215 | A1 | 9/2010 | Qiu et al. |
| 2012/0010172 | A1 | 1/2012 | Christensen et al. |

FOREIGN PATENT DOCUMENTS

| CN | 101875643 A | 11/2010 |
|---|---|---|
| EP | 0050321 B1 | 4/1982 |
| EP | 0073145 A1 | 3/1983 |
| EP | 0984936 B1 | 3/2000 |

(Continued)

OTHER PUBLICATIONS

STN CAS Compound Entry Date for Compound# 296.*

(Continued)

*Primary Examiner* — Jason Sims
*Assistant Examiner* — Ibrahim D Bori
(74) *Attorney, Agent, or Firm* — Stoel Rives LLC

(57) ABSTRACT

The invention relates to methods of treating diseases, particularly cancers, that respond favorably to the inhibition of Nicotinamide phosphoribosyltransferase (Nampt); it also relates to therapeutic methods that utilize Nampt inhibitors in combination with NAD biosynthesis precursors to intentionally kill cancer cells while limiting or minimizing toxicity to normal host cells; and it relates to methods of identifying cancers that will be most responsive to treatment with Nampt inhibitors, particularly when administered in combination with nicotinic acid.

17 Claims, 13 Drawing Sheets

(56) References Cited

FOREIGN PATENT DOCUMENTS

| | | | |
|---|---|---|---|
| EP | 1277738 A | 1/2003 |
| EP | 1210325 B1 | 10/2004 |
| FR | 2921657 A1 | 4/2009 |
| JP | 10-152462 | 6/1998 |
| JP | 11-302173 | 11/1999 |
| JP | 2000026294 A | 1/2000 |
| JP | 2000256194 | 9/2000 |
| JP | 2003128643 A | 5/2003 |
| RU | 2384063 C2 | 3/2010 |
| WO | WO94/06770 A1 | 3/1994 |
| WO | WO98/08847 A | 3/1998 |
| WO | WO98/21185 A1 | 5/1998 |
| WO | WO98/54142 A1 | 5/1998 |
| WO | WO98/54144 A1 | 12/1998 |
| WO | WO99/32437 A1 | 7/1999 |
| WO | WO99/53920 A1 | 10/1999 |
| WO | WO00/50399 A1 | 8/2000 |
| WO | WO00/61559 A1 | 10/2000 |
| WO | WO01/36403 A1 | 5/2001 |
| WO | WO02/055484 A1 | 7/2002 |
| WO | WO02/064572 A1 | 8/2002 |
| WO | WO02/094813 A1 | 11/2002 |
| WO | WO03/097604 A1 | 11/2003 |
| WO | WO2004/041788 A1 | 5/2004 |
| WO | WO2004/058234 A2 | 7/2004 |
| WO | WO2004/064730 A2 | 8/2004 |
| WO | WO2005/004810 A2 | 1/2005 |
| WO | WO2005/035508 A2 | 4/2005 |
| WO | WO2005/113511 A1 | 12/2005 |
| WO | WO2007/004749 A1 | 1/2007 |
| WO | WO2007/119055 A1 | 10/2007 |
| WO | WO2008/025857 A2 | 3/2008 |
| WO | WO2008/137102 A2 | 11/2008 |
| WO | WO2009/072004 A2 | 6/2009 |
| WO | WO2009/074749 A2 | 6/2009 |
| WO | WO2009/086835 A1 | 7/2009 |
| WO | WO2009/152735 A1 | 12/2009 |
| WO | WO2010/023307 A1 | 3/2010 |
| WO | WO2010/146236 A1 | 12/2010 |
| WO | WO2010/151799 A2 | 12/2010 |
| WO | WO2011/006988 A1 | 1/2011 |
| WO | WO2011/109441 | 9/2011 |

OTHER PUBLICATIONS

Bromidge, et al., "Model studies on a synthetically facile series of N-substituted phenyl -N'-pyridin-3-yl ureas leading to 1-(3-pyridylcarbamoyl) indolines that are potent and selective 5-HT$_{2C/2B}$ receptor antagonists," Science Direct, Bioorganic & Medicinal Chemistry, vol. 7, Issue 12, pp. 2767-2773, Dec. 1999.

Colombano, et al., "A Novel Potent Nicotinamide Phosphoribosyltransferase Inhibitor Synthesized via Click Chemistry," Journal of Medicinal Chemistry, vol. 53, No. 2, pp. 616-623, 2010 (published on the Web Dec. 4, 2009).

Dzimbeg G., et al., "The novel primaquine derivatives of N-alkyl, cycloalky or aryl urea: Synthesis, cytostatic and antiviral activity evaluations," European Journal of Medicinal Chemistry, Editions Scientifique Elsevier, Paris, France, vol. 43, No. 6, Jun. 1, 2008.

El-Maghraby, et al., "Quinoline sulfonamides and related compounds," Proceedings of the Indian National Science Academy, Part A: Physical Sciences, vol. 53, No. 6, pp. 729-735, 1987.

European Patent Office, Supplementary European Search Report and Search Opinion, mailed Aug. 7, 2013, for European Patent Application No. EP2011751234, filed Mar. 1, 2011.

Khan, et al., "Nicotinamide adenine dinucleaotide metabolism as an attractive target for drug discovery," Expert Opinion Ther. Targets, 11(5), pp. 695-705, 2007.

Petersen, et al., "Synthesis and Hypotensive Activity of N-Alkyl-N"-cyano-N'-pyridylguanidines," Journal of Medicinal Chemistry, vol. 21, No. 8, pp. 773-781, 1978.

Pubchem Compound, Compound Summary for CID 584132, http://pubchem.ncbi.nlm.nih.gov/summary/summary.cgi?cl, Date: Mar. 28, 2005, retrieved from the Internet May 5, 2011.

Zhang, et al., "A General Method for the Preparation of 4-and 6-Azaindoles," Journal of Organic Chemistry, vol. 67 (7), pp. 2345-2347, published on the Web Mar. 9, 2002.

USPTO, Office Action, mailed Oct. 23, 2013, for U.S. Appl. No. 13/601,879, filed Aug. 31, 2012.

WIPO, Notification of Transmittal of International Search Report and Written Opinion, mailed Sep. 12, 2012, for PCT Application No. PCT/US12/43376, filed Jun. 20, 2012.

WIPO, Notification of Transmittal of International Search Report and Written Opinion, mailed Jul. 26, 2011, for PCT Application No. PCT/US11/26752, filed Mar. 1, 2011.

Pavia, M.R., et al., N-Phenyl-N'-pyridinylureas as anticonvulsive agents, Journal of Medicinal Chemistry, 1990, 33:854-861.

Jiao, Yu, et al., Design, synthesis and bioactivity evaluation of novel Raf kinase inhibitors, Journal of China Pharmaceutical University, 2009, 40(2):104-109.

Final Office Action mailed Jul. 3, 2014, issued for U.S. Appl. No. 13/601,879.

* cited by examiner

THERAPEUTIC AND DIAGNOSTIC METHODS

CROSS-REFERENCE TO RELATED APPLICATIONS

This application is a continuation-in-part of International Patent Application No. PCT/US2011/026752, filed Mar. 1, 2011, which claims the benefit of U.S. provisional application Ser. No. 61/309,342, filed Mar. 1, 2010; U.S. provisional application Ser. No. 61/360,364, filed Jun. 30, 2010; and U.S. provisional application Ser. No. 61/380,083, filed Sep. 3, 2010; the contents of each of which are hereby incorporated by reference herein in their entirety. This application also claims the benefit under 35 U.S.C. §119(e) of U.S. provisional application Ser. No. 61/384,302, filed Sep. 19, 2010; and U.S. provisional application Ser. No. 61/470,871, filed Apr. 1, 2011; the contents of each of which are hereby incorporated by reference herein in their entirety.

FIELD OF THE INVENTION

The present invention relates generally to methods of treating diseases that respond favorably to the inhibition of Nicotinamide phosphoribosyltransferase (Nampt); particularly methods of treating cancer, as well as systemic or chronic inflammation, rheumatoid arthritis, diabetes, obesity, T-cell mediated autoimmune disease, ischemia, and other complications associated with these diseases and disorders. The present invention provides therapeutic methods that utilize compounds that inhibit Nampt to intentionally kill cells, while minimizing toxicity to normal host cells through the coadministration of nicotinic acid (NA). The present invention also provides methods to identify cancers that will be most responsive to treatment with Nampt inhibitors.

BACKGROUND OF THE INVENTION

Nicotinamide phosphoribosyltransferase (NAmPRTase or Nampt; also known as Visfatin) catalyzes the condensation of nicotinamide (Nam) with 5-phosphoribosyl-1-pyrophosphate to yield nicotinamide mononucleotide (NaMN). This is the first and rate-limiting step in one biosynthetic pathway that cells use to make nicotinamide adenine dinucleotide (NAD). See FIG. 1.

NAD has many important cellular functions. Classically, it plays a role as a key coenzyme in metabolic pathways, where it continually cycles between its oxidized form (NAD) and its reduced form (NADH). More recently, NAD has been shown to be involved in genome integrity maintenance, stress response, and $Ca^{2+}$ signaling, where it is consumed by enzymes including poly(ADP-ribose) polymerases (PARPs), sirtuins, and cADP-ribose synthases, respectively, and converted to Nam. (Reviewed in Belenky, P. et al., NAD metabolism in health and disease. *Trends Biochem. Sci.* 32, 12-19 (2007).) The Nam produced in such enzymatic reactions is reconverted to NAD by way of the cyclic "Nam salvage pathway," the first and rate-limiting step of which is catalyzed by Nampt.

As a critical coenzyme in redox reactions, NAD is required in glycolysis and the citric acid cycle; where it accepts the high energy electrons produced and, as NADH, passes these electrons on to the electron transport chain. The NADH-mediated supply of high energy electrons is the driving force behind oxidative phosphorylation, the process by which the majority of ATP is generated in aerobic cells. Consequently, having sufficient levels of NAD available is critical for the maintenance of proper ATP levels in a cell. Reduction in cellular NAD levels by Nampt inhibition can be expected to eventually lead to depletion of ATP, and ultimately to cell death.

Cancer cells have an increased demand for NAD due to elevated dependence on glycolysis, and due to increased activity of enzymes that consume NAD, such as sirtuins and poly(ADP-ribose) polymerases (PARPS). Cancer cells rely on the Nam salvage pathway to maintain NAD at levels sufficient for their demands.

Naprt1 is the rate limiting enzyme in the de novo pathway for NAD biosynthesis from nicotinic acid (NA). See FIG. 1. Naprt1 expression has been documented in a subset of normal tissues (Shibata, K. et al. Tissue distribution of the enzymes concerned with the biosynthesis of NAD in rats. *Agric. Biol. Chem.* 50, 3037-3041 (1986); Hara, N. et al. Elevation of cellular NAD levels by nicotinic acid and involvement of nicotinic acid phosphoribosyltransferase in human cells. *J. Biol. Chem.* 282, 24574-24582 (2007)), but can be deficient in some tumors. Co-administration of NA with a Nampt inhibitor can theoretically be used to exploit a difference in Naprt1 expression between normal cells and tumor cells by preventing NAD depletion in normal tissues, but not in Naprt 11-deficient tumors.

In view of the above, it is perhaps not surprising that inhibitors of Nampt are being developed as chemotherapeutic agents for the treatment of cancer. In fact, there are currently two Nampt inhibitors in clinical trials for the treatment of cancer (Holen, K. et al. The pharmacokinetics, toxicities, and biologic effects of FK866, a nicotinamide adenine dinucleotide biosynthesis inhibitor. *Invest. New Drugs.* 26, 45-51 (2008); Hovstadius, P. et al. A Phase I study of CHS 828 in patients with solid tumor malignancy. *Clin. Cancer Res.* 8, 2843-2850 (2002); Ravaud, A. et al., Phase I study and pharmacokinetic of CHS-828, a guanidino-containing compound, administered orally as a single dose every 3 weeks in solid tumours: an ECSG/EORTC study. *Eur. J. Cancer.* 41, 702-707 (2005); and von Heideman, A. et al. Safety and efficacy of NAD depleting cancer drugs: results of a phase I clinical trial of CHS 828 and overview of published data. *Cancer Chemother. Pharmacol.* (2009) September 30 [Epub ahead of print]).

Consequently, there is a clear need for methods that utilize these compounds that inhibit Nampt to kill cells, particularly cancer cells, while limiting unwanted toxicity to normal host cells. There is also a clear need for methods of identifying those cancers that would most likely respond to treatment with Nampt inhibitors, as well as a clear need for methods to exploit potential differences in Naprt expression between normal cells and tumor cells in treatment protocols based upon the inhibition of Nampt.

BRIEF SUMMARY OF THE INVENTION

The present invention provides therapeutic methods that utilize chemical compounds that selectively inhibit the activity of Nampt. These methods can be used particularly in the treatment of cancer, but also in the treatment of systemic or chronic inflammation, rheumatoid arthritis, diabetes, obesity, T-cell mediated autoimmune disease, ischemia, and other complications associated with these diseases and disorders.

It is believed that the therapeutic methods of the present invention can be used with any compounds that inhibit Nampt, such as, for example, those compounds disclosed in U.S. Utility Pat. Nos. 5,696,140, 5,563,160, 6,525,077, 7,253,193 and 6,255,323; and International Patent Application Publications WO 1998/54141, WO 1998/54143, WO 1998/54144, WO 1998/54145, WO 2000/61559, WO 2000/61561, WO 1994/006770, WO 2003/097602, WO 2009/086835, WO 2009/156421, WO 2010/023307, WO 2010/066709, WO 2009/074749, WO 2010/004198, WO 1997/

048696 and WO 2000/061561. However, it is believed that the compounds disclosed in International Patent Application No. PCT/US2011/026752, filed Mar. 1, 2011, and published as WO 2011/109441, specific examples of which are shown in Tables 1 and 2, herein, as well as compounds of Formulae I, II, III, or IV, as described below, are particularly well suited for use in the therapeutic methods of the present invention. Additional specific examples of Nampt-inhibiting compounds that can be used in these methods, some of which have been described in one or more of the above-identified patents or patent applications, or are duplicated from Tables 1 and 2, are provided in Table 3.

As noted above, compounds of Formula I

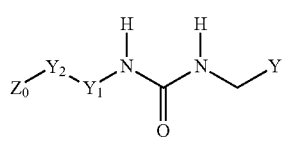

Formula I and pharmaceutically acceptable salts and solvates thereof; wherein Y, $Y_1$, $Y_2$, and $Z_0$ are as defined herein below, are particularly well suited for use in the therapeutic methods of the present invention.

Compounds of Formula II

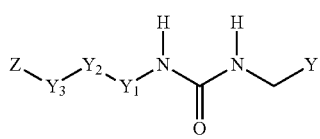

Formula II and pharmaceutically acceptable salts and solvates thereof; wherein Y, $Y_1$, $Y_2$, $Y_3$, and Z are as defined herein below, are also particularly well suited for use in the therapeutic methods of the present invention.

Compounds of Formula III

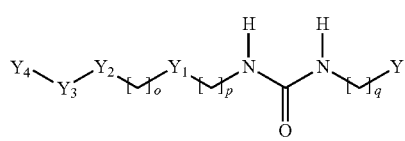

Formula III and pharmaceutically acceptable salts and solvates thereof; wherein Y, $Y_1$, $Y_2$, $Y_3$, and $Y_4$ are as defined herein below, as well, are particularly well suited for use in the therapeutic methods of the present invention.

Compounds of Formula IV

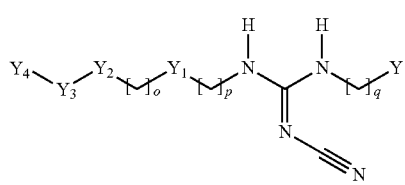

Formula IV and pharmaceutically acceptable salts and solvates thereof; wherein o, p, q, Y, $Y_1$, $Y_2$, $Y_3$, and $Y_4$ are as defined herein below, as well, are particularly well suited for use in the therapeutic methods of the present invention.

Additionally, the therapeutic methods of the present invention can also be used with the geometric isomers, enantiomers, diastereomers, or racemates of compounds of Formulae I through IVc, as defined herein, and can be used with pharmaceutically acceptable salts, prodrugs and solvates of all such compounds.

As noted above, the present invention provides therapeutic methods that utilize chemical compounds that selectively inhibit the activity of Nampt to kill cells and therefore can be used advantageously in the treatment of cancer, as well as in the treatment of systemic or chronic inflammation, rheumatoid arthritis, diabetes, obesity, T-cell mediated autoimmune disease, ischemia, and other complications associated with these diseases and disorders. Such methods, generally comprise administering to a patient in need of such treatment a therapeutically effective amount of a Nampt-inhibiting compound, but can also comprise administering to the same patient a protective amount of nicotinic acid (NA) that reduces, offsets, or limits the toxicity of the administered Nampt-inhibiting compound to normal host cells and tissues. These toxicity-limiting methods include treatment regimens that allow for the administration of amounts of Nampt-inhibiting compounds that would otherwise be greater than the maximum amount tolerated by the patient being treated (i.e., the maximum tolerated dose, or "MTD"). These toxicity-limiting methods effectively expand the therapeutic index for the Nampt-inhibiting compounds used in the methods. Wherein the therapeutic index is defined as the amount of a therapeutic agent that causes the therapeutic effect as compared to the amount that causes drug toxicity.

Importantly, in addition to the therapeutic methods disclosed, the present invention also provides diagnostic methods that can be used to identify abnormal cells, particularly cancer cells, and even cancerous tumors, that are likely to respond favorably to the therapeutic methods of the present invention. These diagnostic methods can be employed prior to the start of the therapeutic methods, in order to decide whether or not the therapeutic methods have significant likelihood of success. As such, these diagnostic methods have the potential to reduce treatments with Nampt-inhibiting compounds that will not lead to the desired results, or treatments in which the outcome is less than certain.

Finally, the present invention also provides methods for limiting the toxicity of Nampt inhibiting compounds to normal, non-cancerous, cells by the administration of nicotinic acid in addition to Nampt inhibiting therapeutic compounds, thereby expanding the therapeutic index of the Nampt inhibiting therapeutic compounds for the treatment of cancerous cells and tumors.

The foregoing and other advantages and features of the embodiments of the present invention, and the manner in which they are accomplished, will become more readily apparent upon consideration of the following detailed description of the invention taken in conjunction with the accompanying examples, which illustrate preferred and exemplary embodiments.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. In case of conflict, the present specification, including definitions, will control. In addition, the materials, methods, and examples are illustrative only, and are not intended to be limiting.

Other features and advantages of the invention will be apparent to one of skill in the art from the following detailed description, and from the claims below.

BRIEF DESCRIPTION OF THE DRAWINGS

FIG. 7(a) depicts Naprt1 expression levels, as determined by Western blot (expressed as a percentage of an HCT116 control), and the NA rescue phenotype observed for a panel of 145 different cancer cell lines, while FIG. 7(b) shows the Naprt1 expression levels determined from normal murine tissues (also expressed as a percentage of an HCT116 control).

DETAILED DESCRIPTION OF THE INVENTION

Definitions

Figure 1:
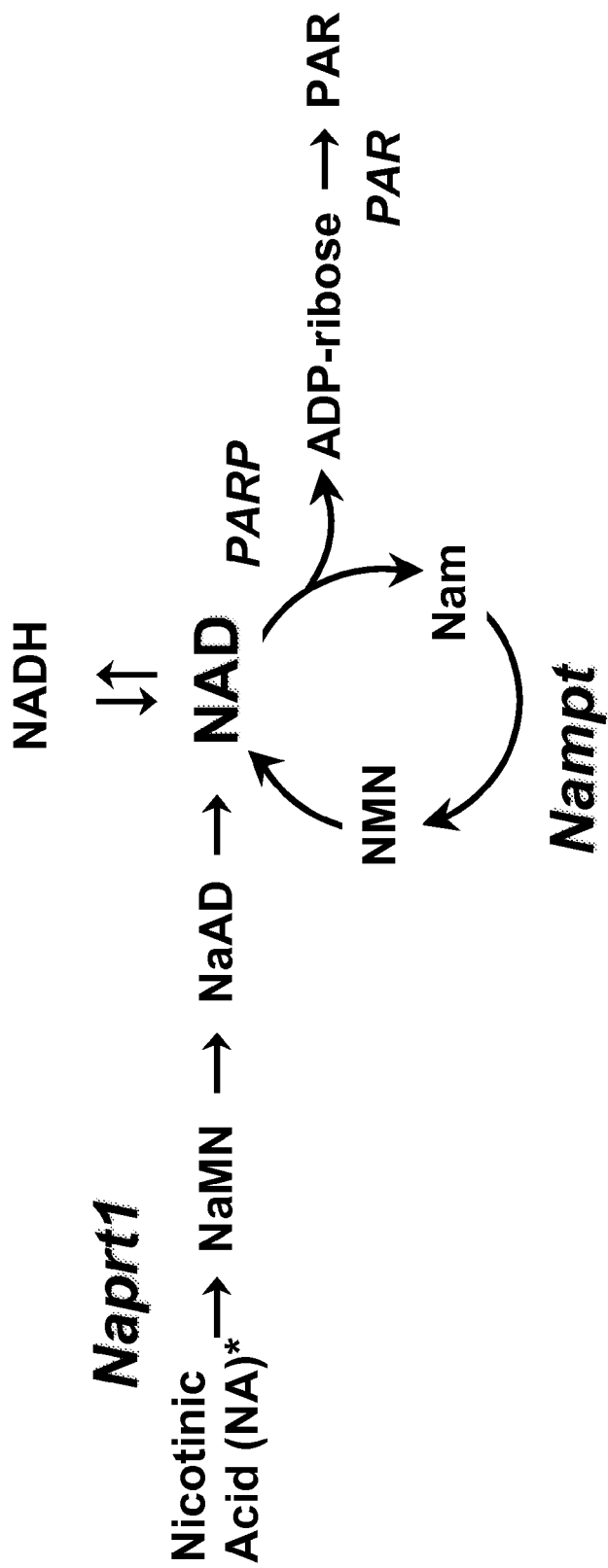
FIG. 1 depicts the biochemical pathways involved in the biosynthesis, regeneration, and utilization of NAD in human cells, and shows the roles of the enzymes Nampt, Naprt1, PARP and PAR in these pathways, including the de novo biosynthetic pathway beginning with nicotinic acid (NA) and involving Narpt1, and the "nicotinamide (Nam) salvage pathway," involving Nampt.

As used herein, the term "alkyl" as employed herein by itself or as part of another group refers to a saturated aliphatic hydrocarbon straight chain or branched chain group having, unless otherwise specified, 1 to 20 carbon atoms (whenever it appears herein, a numerical range such as "1 to 20" refers to each integer in the given range; e.g., "1 to 20 carbon atoms" means that the alkyl group can consist of 1, 2 or 3 carbon atoms, or more carbon atoms, up to a total of 20). An alkyl group can be in an unsubstituted form or substituted form with one or more substituents (generally one to three substitutents can be present except in the case of halogen substituents, e.g., perchloro). For example, a $C_{1-6}$ alkyl group refers to a straight or branched aliphatic group containing 1 to 6 carbon atoms (e.g., include methyl, ethyl, propyl, isopropyl, butyl, sec-butyl, tert-butyl, 3-pentyl, hexyl, etc.), which can be optionally substituted.

As used herein, "lower alkyl" refers to an alkyl group having from 1 to 6 carbon atoms.

The term "alkylene" as used herein means a saturated aliphatic hydrocarbon straight chain or branched chain group having from 1 to 20 carbon atoms having two connecting points (i.e., a "divalent" chain). For example, "ethylene" represents the group —$CH_2$—$CH_2$— and "methylene" represents the group —$CH_2$—. Alkylene chain groups can also be thought of as multiple methylene groups. For example, ethylene contains two methylene groups. Alkylene groups can also be in an unsubstituted form or substituted form with one or more substituents.

The term "alkenyl" as employed herein by itself or as part of another group means a straight or branched divalent chain radical of 2-10 carbon atoms (unless the chain length is otherwise specified), including at least one double bond between two of the carbon atoms in the chain. The alkenyl group can also be in an unsubstituted form or substituted form with one or more substituents (generally one to three substituents except in the case of halogen substituents, e.g., perchloro or perfluoroalkyls). For example, a $C_{2-6}$ alkenyl group refers to a straight or branched chain radical containing 2 to 6 carbon atoms and having at least one double bond between two of the carbon atoms in the chain (e.g., ethenyl, 1-propenyl, 2-propenyl, 2-methyl-1-propenyl, 1-butenyl and 2-butenyl, which can be optionally substituted).

The term "alkenylene" as used herein means an alkenyl group having two connecting points. For example, "ethenylene" represents the group —CH=CH—. Alkenylene groups can also be in an unsubstituted form or substituted form with one or more substituents.

The term "alkynyl" as used herein by itself or as part of another group means a straight or branched chain radical of 2-10 carbon atoms (unless the chain length is otherwise specified), wherein at least one triple bond occurs between two of the carbon atoms in the chain. The alkynyl group can be in an unsubstituted form or substituted form with one or more substituents (generally one to three substitutents except in the case of halogen substituents, e.g., perchloro or perfluoroalkyls). For example, a $C_{2-6}$ alkynyl group refers to a straight or branched chain radical containing 2 to 6 carbon atoms, which can be optionally substituted, and having at least one triple bond between two of the carbon atoms in the chain (e.g., ethynyl, 1-propynyl, 1-methyl-2-propynyl, 2-propynyl, 1-butynyl and 2-butynyl).

The term "alkynylene" as used herein means an alkynyl having two connecting points. For example, "ethynylene" represents the group —C≡C—. Alkynylene groups can also be in an unsubstituted form or substituted form with one or more substituents.

The term "carbocycle" as used herein by itself or as part of another group means cycloalkyl and non-aromatic partially saturated carbocyclic groups such as cycloalkenyl and cycloalkynyl. A carbocycle can be in an unsubstituted form or substituted form with one or more substituents so long as the resulting compound is sufficiently stable and suitable for use in the embodiments of the present invention.

The term "cycloalkyl" as used herein by itself or as part of another group refers to a fully saturated 3- to 8-membered cyclic hydrocarbon ring (i.e., a cyclic form of an alkyl) alone ("monocyclic cycloalkyl") or fused to another cycloalkyl, cycloalkynyl, cycloalkenyl, heterocycle, aryl or heteroaryl ring (i.e., sharing an adjacent pair of carbon atoms with other such rings) ("polycyclic cycloalkyl"). Thus, a cycloalkyl can exist as a monocyclic ring, bicyclic ring, or a spiral ring. When a cycloalkyl is referred to as a $C_x$ cycloalkyl, this means a cycloalkyl in which the fully saturated cyclic hydrocarbon ring (which may or may not be fused to another ring) has x number of carbon atoms. When a cycloalkyl is recited as a substituent on a chemical entity, it is intended that the cycloalkyl moiety is attached to the entity through a single carbon atom within the fully saturated cyclic hydrocarbon ring of the cycloalkyl. In contrast, a substituent on a cycloalkyl can be attached to any carbon atom of the cycloalkyl. A cycloalkyl group can be unsubstituted or substituted with one or more substitutents so long as the resulting compound is sufficiently stable and suitable for use in the embodiments of the present invention. Examples of cycloalkyl groups include, for example, cyclopropyl, cyclobutyl, cyclopentyl, cyclohexyl and cycloheptyl.

The term "cycloalkenyl" as used herein by itself or as part of another group refers to a non-aromatic partially saturated 3- to 8-membered cyclic hydrocarbon ring having a double bond therein (i.e., a cyclic form of an alkenyl) alone ("monocyclic cycloalkenyl") or fused to another cycloalkyl, cycloalkynyl, cycloalkenyl, heterocycle, aryl or heteroaryl ring (i.e., sharing an adjacent pair of carbon atoms with such other rings) ("polycyclic cycloalkenyl"). Thus, a cycloalkenyl can exist as a monocyclic ring, bicyclic ring, polycyclic or a spiral ring. When a cycloalkenyl is referred to as a $C_x$ cycloalkenyl, this means a cycloalkenyl in which the non-aromatic partially saturated cyclic hydrocarbon ring (which may or may not be fused to another ring) has x number of carbon atoms. When a cycloalkenyl is recited as a substituent on a chemical entity, it is intended that the cycloalkenyl moiety is attached to the entity through a carbon atom within the non-aromatic partially saturated ring (having a double bond therein) of the cycloalkenyl. In contrast, a substituent on a cycloalkenyl can be attached to any carbon atom of the cycloalkenyl. A cycloalkenyl group can be in an unsubstituted form or substituted form with one or more substitutents. Examples of cycloalkenyl groups include cyclopentenyl, cycloheptenyl and cyclooctenyl.

The term "heterocycle" (or "heterocyclyl" or "heterocyclic" or "heterocyclo") as used herein by itself or as part of another group means a saturated or partially saturated 3-7 membered non-aromatic cyclic ring formed with carbon atoms and from one to four heteroatoms independently selected from the group consisting of O, N, and S, wherein the nitrogen and sulfur heteroatoms can be optionally oxidized, and the nitrogen can be optionally quaternized ("monocyclic heterocycle"). The term "heterocycle" also encompasses a group having the non-aromatic heteroatom-containing cyclic ring above fused to another monocyclic cycloalkyl, cycloalkynyl, cycloalkenyl, heterocycle, aryl or heteroaryl ring (i.e., sharing an adjacent pair of atoms with such other rings) ("polycyclic heterocycle"). Thus, a heterocycle can exist as a monocyclic ring, bicyclic ring, polycyclic or a spiral ring. When a heterocycle is recited as a substituent on a chemical entity, it is intended that the heterocycle moiety is attached to the entity through an atom within the saturated or partially saturated ring of the heterocycle. In contrast, a substituent on a heterocycle can be attached to any suitable atom of the heterocycle. In a "saturated heterocycle" the non-aromatic heteroatom-containing cyclic ring described above is fully saturated, whereas a "partially saturated heterocyle" contains one or more double or triple bonds within the non-aromatic heteroatom-containing cyclic ring regardless of the other ring it is fused to. A heterocycle can be in an unsubstituted form or substituted form with one or more substituents so long as the resulting compound is sufficiently stable and suitable for use in the embodiments of the present invention.

Some examples of saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups.

As used herein, "aryl" by itself or as part of another group means an all-carbon aromatic ring with up to 7 carbon atoms in the ring ("monocylic aryl"). In addition to monocyclic aromatic rings, the term "aryl" also encompasses a group having the all-carbon aromatic ring above fused to another cycloalkyl, cycloalkynyl, cycloalkenyl, heterocycle, aryl or heteroaryl ring (i.e., sharing an adjacent pair of carbon atoms with such other rings) ("polycyclic aryl"). When an aryl is referred to as a $C_x$ aryl, this means an aryl in which the all-carbon aromatic ring (which may or may not be fused to another ring) has x number of carbon atoms. When an aryl is recited as a substituent on a chemical entity, it is intended that the aryl moiety is attached to the entity through an atom within the all-carbon aromatic ring of the aryl. In contrast, a substituent on an aryl can be attached to any atom of the aryl. Examples, without limitation, of aryl groups are phenyl, naphthalenyl and anthracenyl. An aryl can be in an unsubstituted form or substituted form with one or more substituents so long as the resulting compound is sufficiently stable and suitable for use in the embodiments of the present invention.

The term "heteroaryl" as employed herein refers to a stable aromatic ring having up to 7 ring atoms with 1, 2, 3 or 4 hetero ring atoms in the ring which are oxygen, nitrogen or sulfur or a combination thereof ("monocyclic heteroaryl"). In addition to monocyclic hetero-aromatic rings, the term "heteroaryl" also encompasses a group having the monocyclic hetero-aromatic ring above fused to another cycloalkyl, cycloalkynyl, cycloalkenyl, heterocycle, aryl or heteroaryl ring (i.e., sharing an adjacent pair of atoms with such other rings) ("polycyclic heteroaryl"). When a heteroaryl is recited as a substituent on a chemical entity, it is intended that the heteroaryl moiety is attached to the entity through an atom within the heteroaromatic ring of the heteroaryl. In contrast, a substituent on a heteroaryl can be attached to any suitable atom of the heteroaryl. A heteroaryl can be in an unsubstituted form or substituted form with one or more substituents so long as the resulting compound is sufficiently stable and suitable for use in the embodiments of the present invention.

Useful heteroaryl groups include thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, pyrazolo[1,5-a]pyrimidinyl, including without limitation pyrazolo[1,5-a]pyrimidin-3-yl, 1,2-benzoisoxazol-3-yl, benzimidazolyl, 2-oxindolyl and 2-oxobenzimidazolyl. Where the heteroaryl group contains a nitrogen atom in a ring, such nitrogen atom can be in the form of an N-oxide, e.g., a pyridyl N-oxide, pyrazinyl N-oxide and pyrimidinyl N-oxide.

As used herein, the term "halo" refers to chloro, fluoro, bromo, or iodo substitutents.

As used herein, the term "hydro" refers to a bound hydrogen atom (—H group).

As used herein, the term "hydroxyl" refers to an —OH group.

As used herein, the term "alkoxy" refers to an —O—($C_{1-12}$ alkyl). Lower alkoxy refers to —O-(lower alkyl) groups.

As used herein, the term "alkynyloxy" refers to an —O—($C_{2-12}$ alkynyl).

As used herein, the term "cycloalkyloxy" refers to an —O-cycloalkyl group.

As used herein, the term "heterocycloxy" refers to an —O-heterocycle group.

As used herein, the term "aryloxy" refers to an —O-aryl group. Examples of aryloxy groups include, but are not limited to, phenoxy and 4-methylphenoxy.

The term "heteroaryloxy" refers to an —O-heteroaryl group.

The terms "arylalkoxy" and "heteroarylalkoxy" are used herein to mean alkoxy group substituted with an aryl group and a heteroaryl group, respectively. Examples of arylalkoxy groups include, but are not limited to, benzyloxy and phenethyloxy.

As used herein, the term "mercapto" or "thiol" group refers to an —SH group.

The term "alkylthio" group refers to an —S-alkyl group.

The term "arylthio" group refers to an —S-aryl group.

The term "arylalkyl" is used herein to mean above-defined alkyl group substituted by an aryl group defined above. Examples of arylalkyl groups include benzyl, phenethyl and naphthylmethyl, etc. An arylalkyl group can be unsubstituted or substituted with one or more substituents so long as the resulting compound is sufficiently stable and suitable for use in the embodiments of the present invention.

The term "heteroarylalkyl" is used herein to mean an alkyl group, as defined above, substituted by any heteroaryl group. A heteroarylalkyl can be unsubstituted or substituted with one or more substituents, so long as the resulting compound is sufficiently stable and suitable for use in the embodiments of the present invention.

The term "heteroarylalkenyl" is used herein to mean any of the above-defined alkenyl groups substituted by any of the above-defined heteroaryl groups.

The term "arylalkynyl" is used herein to mean any of the above-defined alkynyl groups substituted by any of the above-defined aryl groups.

The term "heteroarylalkenyl" is used herein to mean any of the above-defined alkenyl groups substituted by any of the above-defined heteroaryl groups.

The term "arylalkoxy" is used herein to mean alkoxy group substituted by an aryl group as defined above.

"Heteroarylalkoxy" is used herein to mean any of the above-defined alkoxy groups substituted by any of the above-defined heteroaryl groups.

"Haloalkyl" means an alkyl group that is substituted with one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

As used herein, the term "carbonyl" group refers to a —C(=O)R" group, where R" is selected from the group consisting of hydro, alkyl, cycloalkyl, aryl, heteroaryl (bonded through a ring carbon) and heterocyclic (bonded through a ring carbon), as defined herein.

As used herein, the term "aldehyde" group refers to a carbonyl group where R" is hydro.

As used herein, the term "cycloketone" refer to a cycloalkyl group in which one of the carbon atoms which form the ring has an oxygen doubly-bonded to it; i.e. one of the ring carbon atoms is a —C(=O) group.

As used herein, the term "thiocarbonyl" group refers to a —C(=S)R" group, with R" as defined herein.

"Alkanoyl" refers to an —C(=O)-alkyl group.

The term "heterocyclonoyl" group refers to a heterocyclo group linked to the alkyl chain of an alkanoyl group.

The term "acetyl" group refers to a —C(=O)CH₃ group.

"Alkylthiocarbonyl" refers to an —C(=S)-alkyl group.

The term "cycloketone" refers to a carbocycle or heterocycle group in which one of the carbon atoms which form the ring has an oxygen doubly-bonded to it; i.e., one of the ring carbon atoms is a —C(=O) group.

The term "O-carboxy" group refers to a —OC(=O)R" group, where R" is as defined herein.

The term "C-carboxy" group refers to a —C(=O)OR" groups where R" is as defined herein.

As used herein, the term "carboxylic acid" refers to a C-carboxy group in which R" is hydro. In other words, the term "carboxylic acid" refers to —COOH.

As used herein, the term "ester" is a C-carboxy group, as defined herein, wherein R" is as defined above, except that it is not hydro (e.g., it is methyl, ethyl, or lower alkyl).

As used herein, the term "C-carboxy salt" refers to a —C(=O)O⁻M⁺ group wherein M⁺ is selected from the group consisting of lithium, sodium, magnesium, calcium, potassium, barium, iron, zinc and quaternary ammonium.

The term "carboxyalkyl" refers to —$C_{1-6}$ alkylene-C(=O)OR" (that is, a $C_{1-6}$ alkyl group connected to the main structure wherein the alkyl group is substituted with —C(=O)OR" with R" being defined herein). Examples of carboxyalkyl include, but are not limited to, —CH₂COOH, —(CH₂)₂COOH, —(CH₂)₃COOH, —(CH₂)₄COOH, and —(CH₂)₅COOH.

"Carboxyalkenyl" refers to -alkenylene-C(=O)OR" with R" being defined herein.

The term "carboxyalkyl salt" refers to a —(CH₂)ᵣC(=O)O⁻M⁺ wherein M⁺ is selected from the group consisting of lithium, sodium, potassium, calcium, magnesium, barium, iron, zinc and quaternary ammonium, and wherein r is 1-6.

The term "carboxyalkoxy" refers to —O—(CH₂)ᵣC(=O)OR" wherein r is 1-6, and R" is as defined herein.

"$C_x$ carboxyalkanoyl" means a carbonyl group (—(O=)C—) attached to an alkyl or cycloalkylalkyl group that is substituted with a carboxylic acid or carboxyalkyl group, wherein the total number of carbon atom is x (an integer of 2 or greater).

"$C_x$ carboxyalkenoyl" means a carbonyl group (—(O=)C—) attached to an alkenyl or alkyl or cycloalkylalkyl group that is substituted with a carboxylic acid or carboxyalkyl or carboxyalkenyl group, wherein at least one double bond (—CH=CH—) is present and wherein the total number of carbon atom is x (an integer of 2 or greater).

"Carboxyalkoxyalkanoyl" means refers to R"OC(=O)—$C_{1-6}$ alkylene-O—$C_{1-6}$ alkylene-C(=O)—, R" is as defined herein.

"Amino" refers to an —NR$^x$R$^y$ group, with R$^x$ and R$^y$ as defined herein.

"Alkylamino" means an amino group with a substituent being a $C_{1-6}$ alkyl.

"Aminoalkyl" means an alkyl group connected to the main structure of a molecule where the alkyl group has a substituent being amino.

"Quaternary ammonium" refers to a —⁺N(R$^x$)(R$^y$)(R$^z$) group wherein R$^x$, R$^y$, and R$^z$ are as defined herein.

The term "nitro" refers to a —NO₂ group.

The term "O-carbamyl" refers to a —OC(=O)N(R$^x$)(R$^y$) group with R$^x$ and R$^y$ as defined herein.

The term "N-carbamyl" refers to a R$^y$OC(=O)N(R$^x$)— group, with R$^x$ and R$^y$ as defined herein.

The term "O-thiocarbamyl" refers to a —OC(=S)N(R$^x$)(R$^y$) group with R$^x$ and R$^y$ as defined herein.

The term "N-thiocarbamyl" refers to a R$^x$C(=S)NR$^y$— group, with R$^x$ and R$^y$ as defined herein.

"C-amido" refers to a —C(=O)N(R$^x$)(R$^y$) group with R$^x$ and R$^y$ as defined herein.

"N-amido" refers to a R$^x$C(=O)N(R$^y$)— group with R$^x$ and R$^y$ as defined herein.

"Aminothiocarbonyl" refers to a —C(=S)N(R$^x$)(R$^y$) group with R$^x$ and R$^y$ as defined herein.

"Hydroxyaminocarbonyl" means a —C(=O)N(R$^x$)(OH) group with R$^x$ as defined herein.

"Alkoxyaminocarbonyl" means a —C(=O)N(R$^x$)(alkoxy) group with R$^x$ as defined herein.

The terms "cyano" and "cyanyl" refer to a —C≡N group.

The term "nitrile" group, as used herein, refers to a —C≡N substituent.

The term "cyanato" refers to a —CNO group.

The term "isocyanato" refers to a —NCO group.

The term "thiocyanato" refers to a —CNS group.

The term "isothiocyanato" refers to a —NCS group.

The term "oxo" refers to a —C(=O)— group.

The term "sulfinyl" refers to a —S(=O)R" group, where R" is as defined herein.

The term "sulfonyl" refers to a —S(=O)₂R" group, where R" is as defined herein.

The term "sulfonamide" refers to a —(R$^x$)N—S(=O)₂R" group, with R" and R$^x$ as defined herein.

"Aminosulfonyl" means (R$^x$)(R$^y$)N—S(=O)₂— with R$^x$ and R$^y$ as defined herein.

"Aminosulfonyloxy" means a (R$^x$)(R$^y$)N—S(=O)₂—O— group with R$^x$ and R$^y$ as defined herein.

"Sulfonamidecarbonyl" means R"—S(=O)₂—N(R$^x$)—C(=O)— with R" and R$^x$ as defined herein.

"Alkanoylaminosulfonyl" refers to an alkyl-C(=O)—N(R$^x$)—S(=O)₂— group with R$^x$ as defined herein.

The term "trihalomethylsulfonyl" refers to a X₃CS(=O)₂— group with X being halo.

The term "trihalomethylsulfonamide" refers to a X₃CS(=O)₂N(R$^x$)— group with X being halo and R$^x$ as defined herein.

R" is selected from the group consisting of hydro, alkyl, cycloalkyl, aryl, heteroaryl and heterocycle, each being optionally substituted.

R$^x$, R$^y$, and R$^z$ are independently selected from the group consisting of hydro and optionally substituted alkyl.

The term "methylenedioxy" refers to a —OCH₂O— group wherein the oxygen atoms are bonded to adjacent ring carbon atoms.

The term "ethylenedioxy" refers to a —OCH₂CH₂O— group wherein the oxygen atoms are bonded to adjacent ring carbon atoms.

As used herein, the phrase "optionally substituted" means substituted or unsubstituted.

Unless specifically stated otherwise or indicated by a bond symbol (dash, double dash, or triple dash), the connecting point to a recited group will be on the right-most stated group. Thus, for example, a hydroxyalkyl group is connected to the main structure through the alkyl and the hydroxyl is a substituent on the alkyl.

Therapeutic Compounds

The present invention provides methods that utilize chemical compounds that selectively inhibit the activity of Nampt. These therapeutic compounds can be used particularly in the treatment of cancer, but also in the treatment of systemic or chronic inflammation, rheumatoid arthritis, diabetes, obesity, T-cell mediated autoimmune disease, ischemia, as well as in the treatment of other complications associated with these diseases and disorders.

Several specific examples of Nampt-inhibiting compounds that can be used in the methods of the instant invention are depicted in Tables 1, 2 and 3, but other compounds that can be used in these methods are those according to Formulae I-IVc, as described below.

Specifically, the present invention provides therapeutic methods that utilize compounds of Formula I Formula I

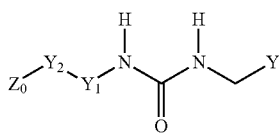

and pharmaceutically acceptable salts and solvates thereof;
wherein:

Y is phenyl, 2-pyridinyl, 3-pyridinyl, or 4-pyridinyl, wherein any ring carbon is optionally independently substituted with halo, $C_{1-5}$ alkyl, nitro, cyano, $C_{1-5}$ alkoxy, C-amido, N-amido, C-carboxy, O-carboxy, sulfonamide, amino, hydroxyl, mercapto, alkylthio, sulfonyl, or sulfinyl;

$Y_1$ is divalent carbocycle, divalent heterocycle, divalent phenyl or divalent heteroaryl, wherein any ring atom is optionally independently substituted with halo, $C_{1-5}$ alkyl, nitro, cyano, trihalomethyl, $C_{1-5}$ alkoxy, C-amido, N-amido, sulfonamide, amino, aminosulfonyl, hydroxyl, mercapto, alkylthio, sulfonyl, or sulfinyl, or $Y_1$ is $C_{2-8}$ alkylene or $C_{2-8}$ alkenylene, optionally interrupted one, two, or three times by —O—, —S—, —S(=O)—, —S(=O)$_2$—, —OC(=O)N(R)—, —N(R)C(=O)O—, —C(=O)N(R)—, —N(R)C(=O)—, —N(R)C(=O)N(R)—, —N(R)—, —C(=O)—, —OC(=O)—, —C(=O)O—, —OS(=O)$_2$N(R)—, —N(R)S(=O)$_2$O—, —SC(=O)—, —C(=O)S—, —OC(=S)N(R)—, —N(R)C(=S)O—, —C(=S)N(R)—, —N(R)C(=S)—, —N(R)C(=S)N(R)—, —C(=S)—, —OC(=S)—, —C(=S)O—, —S(=O)$_2$N(R)—, —N(R)S(=O)$_2$—, —S(=O)$_2$N(R)C(=O)—, or —C(=O)N(R)S(=O)$_2$—;

$Y_2$ is —OCH$_2$—, —SCH$_2$—, —N(R)CH$_2$—, —N(R)C(=O)—, —C(=O)N(R)—, —S(=O)$_2$CH$_2$—, —S(=O)CH$_2$—, —CH$_2$O—, —CH$_2$CH$_2$O—, —CH$_2$S—, —CH$_2$N(R)—, —CH$_2$S(=O)$_2$—, —CH$_2$S(=O)—, —C(=O)O—, —OC(=O)—, —SO$_2$N(R)—, —N(R)SO$_2$—, ethylene, propylene, n-butylene, —O—$C_{1-4}$ alkylene-N(R)C(=O)—, —O—$C_{1-4}$ alkylene-C(=O)N(R)—, —N(R)C(=O)—$C_{1-4}$ alkylene-O—, —C(=O)N(R)—$C_{1-4}$ alkylene-O—, —$C_{1-4}$ alkylene-S(=O)$_2$—, —$C_{1-4}$ alkylene-S(=O)—, —S(=O)$_2$—$C_{1-4}$ alkylene-, —S(=O)—$C_{1-4}$ alkylene-, —$C_{1-4}$ alkylene-SO$_2$N(R)—, —$C_{1-4}$ alkylene-N(R)SO$_2$—, —SO$_2$N(R)—$C_{1-4}$ alkylene-, —N(R)SO$_2$—$C_{1-4}$ alkylene-, —$C_{1-4}$ alkylene-O—$C_{1-4}$ alkylene-, —O—$C_{1-4}$ alkylene-O—, —S—$C_{1-4}$ alkylene-, —$C_{1-4}$ alkylene-S—, —$C_{1-4}$ alkylene-S—$C_{1-4}$ alkylene-, —N(R)—$C_{1-4}$ alkylene-, —$C_{1-4}$ alkylene-N(R)—, —$C_{1-4}$ alkylene-N(R)—$C_{1-4}$ alkylene-, —$C_{1-4}$ alkylene-C(=O)—O—$C_{1-4}$ alkylene-, —$C_{1-4}$ alkylene-O—C(=O)—$C_{1-4}$ alkylene-, —$C_{1-4}$ alkylene-C(=O)—N(R)—$C_{1-4}$ alkylene-, —$C_{1-4}$ alkylene-N(R)—C(=O)—$C_{1-4}$ alkylene-, —C(=O)—N(R)—$C_{1-4}$ alkylene-SO$_2$N(R)—, or —N(R)—C(=O)—$C_{1-4}$ alkylene-SO$_2$N(R)—;

$Z_0$ is carbocycle, cycloalkyl, cycloalkenyl, heterocycle, heterocyclonoyl, aryl, heteroaryl, carbocycloalkyl, heterocyclylalkyl, arylalkyl, arylalkenyl, heteroarylalkyl, heteroarylalkenyl, heteroarylalkynyl, or arylalkynyl, wherein any of the foregoing groups are optionally substituted at least once with alkyl, alkylene, alkenyl, alkenylene, alkynyl, alkynylene, carbocycle, cycloalkyl, cycloalkenyl, heterocycle, aryl, heteroaryl, halo, hydro, hydroxyl, alkoxy, alkynyloxy, cycloalkyloxy, heterocycloxy, aryloxy, heteroaryloxy, arylalkoxy, heteroarylalkoxy, mercapto, alkylthio, arylthio, arylalkyl, heteroarylalkyl, heteroarylalkenyl, arylalkynyl, haloalkyl, aldehyde, thiocarbonyl, heterocyclonoyl, O-carboxy, C-carboxy, carboxylic acid, ester, C-carboxy salt, carboxyalkyl, carboxyalkenylene, carboxyalkyl salt, carboxyalkoxy, carboxyalkoxyalkanoyl, amino, aminoalkyl, nitro, O-carbamyl, N-carbamyl, O-thiocarbamyl, N-thiocarbamyl, C-amido, N-amido, aminothiocarbonyl, hydroxyaminocarbonyl, alkoxyaminocarbonyl, cyano, nitrile, cyanato, isocyanato, thiocyanato, isothiocyanato, sulfinyl, sulfonyl, sulfonamide, aminosulfonyl, aminosulfonyloxy, sulfonamidecarbonyl, alkanoylaminosulfonyl, trihalomethylsulfonyl, or trihalomethylsulfonamide;

wherein any alkylene or alkenylene group is optionally independently substituted with $C_{1-4}$ alkyl, halo, $C_{1-4}$ haloalkyl, or $C_3$ or $C_4$ cycloalkyl;

wherein for the purposes of Y and $Y_1$, R is H, halo, $C_{1-4}$ alkyl, $C_{1-4}$ alkenyl, or $C_{1-4}$ alkynyl;

wherein for the purpose of $Y_2$, R is H, halo, $C_{1-5}$ alkyl, $C_{1-5}$ alkenyl, $C_{1-5}$ alkynyl, or forms a heterocycle with a carbon atom of $Z_0$; and with the proviso that the compound is NOT:

ethyl 3-(pyridin-3-yl)-4-({4-[(3-{[(pyridin-3-ylmethyl)carbamoyl]amino}benzyl)oxy]phenyl}sulfonyl)butanoate;

4-({4-[(3-{[(pyridin-3-ylmethyl)carbamoyl]amino}benzyl)oxy]phenyl}sulfonyl)-3-[4-(trifluoromethyl)phenyl]butanoic acid;

3-phenyl-4-({4-[(3-{[(pyridin-3-ylmethyl)carbamoyl]amino}benzyl)oxy]phenyl}sulfonyl)butanoic acid;

3-(4-chloro-3-fluorophenyl)-4-[(4-{[3-{[(pyridin-3-ylmethyl)carbamoyl]amino}-5-(trifluoromethyl)benzyl]oxy}phenyl)sulfonyl]butanoic acid;

3-phenyl-4-[(4-{[3-{[(pyridin-3-ylmethyl)carbamoyl]amino}-5-(trifluoromethyl)benzyl]oxy}phenyl)sulfonyl]butanoic acid;

3-(pyridin-3-yl)-4-({4-[(3-{[(pyridin-3-ylmethyl)carbamoyl]amino}benzyl)oxy]phenyl}sulfonyl)butanoic acid;

4-({4-[(4-fluoro-3-{[(pyridin-3-ylmethyl)carbamoyl]amino}benzyl)oxy]phenyl}sulfonyl)-3-(pyridin-3-yl)butanoic acid;

1,1'-butane-1,4-diylbis[3-(pyridin-3-ylmethyl)urea];

1-[(6-methoxypyridin-3-yl)methyl]-3-[3-(3-methylphenoxy)propyl]urea; or

1-[3-(2-fluorophenoxy)propyl]-3-[(6-methoxypyridin-3-yl)methyl]urea.

In some embodiments, the present invention provides therapeutic methods that utilize compounds of Formula Ia Formula Ia

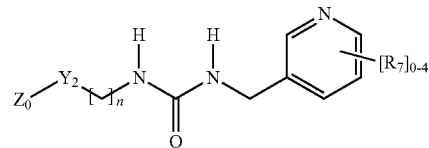

and pharmaceutically acceptable salts and solvates thereof;
wherein:

$Z_0$ and $Y_2$ are as defined for Formula I above;

n is 3, 4, 5, 6, or 7;

any methylene group is optionally independently substituted with $C_{1-4}$ alkyl, halo, $C_{1-4}$ haloalkyl, or $C_3$ or $C_4$ cycloalkyl;

$R_7$, if present one or more times, replaces a hydrogen atom on the pyridinyl ring and is independently selected from halo, $C_{1-5}$ alkyl, nitro, cyano, $C_{1-5}$ alkoxy, C-amido, N-amido, trihalomethyl, C-carboxy, O-carboxy, trihalomethyl, C-carboxy, O-carboxy, sulfonamide, amino, hydroxyl, mercapto, alkylthio, sulfonyl, and sulfinyl; and with the proviso that the compound is NOT: 1,1'-butane-1,4-diylbis[3-(pyridin-3-ylmethyl)urea].

In some embodiments, the present invention provides therapeutic methods that utilize compounds of Formula Ia1

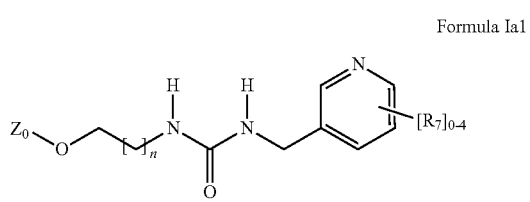

Formula Ia1 and pharmaceutically acceptable salts and solvates thereof; wherein:
$Z_0$ is as defined for Formula I above;
n is 3, 4, 5, 6, or 7;
any methylene group is optionally independently substituted with $C_{1-4}$ alkyl, halo, $C_{1-4}$ haloalkyl, or $C_3$ or $C_4$ cycloalkyl; and
$R_7$ is as defined for Formula Ia.

In some embodiments, the present invention provides therapeutic methods that utilize compounds of Formula Ia2

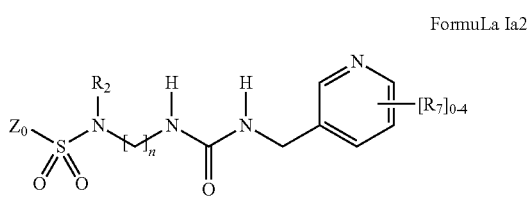

FormuLa Ia2 and pharmaceutically acceptable salts and solvates thereof; wherein:
$Z_0$ is as defined for Formula I above;
n is 3, 4, 5, 6, or 7;
any methylene group is optionally independently substituted with $C_{1-4}$ alkyl, halo, $C_{1-4}$ haloalkyl, or $C_3$ or $C_4$ cycloalkyl;
$R_2$ is H, $C_{1-55}$ alkyl, $C_{1-55}$ alkenyl, or $C_{1-5}$ alkynyl; and
$R_7$ is as defined for Formula Ia.

In some embodiments, the present invention provides therapeutic methods that utilize compounds of Formula Ib

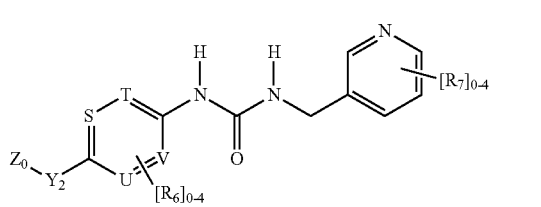

Formula Ib and pharmaceutically acceptable salts and solvates thereof; wherein:
$Z_0$ and $Y_2$ are as defined for Formula I above;
any methylene group is optionally independently substituted with $C_{1-4}$ alkyl, halo, $C_{1-4}$ haloalkyl, or $C_3$ or $C_4$ cycloalkyl;
$R_6$ and $R_7$ are each independently selected from halo, $C_{1-5}$ alkyl, nitro, cyano, $C_{1-5}$ alkoxy, C-amido, N-amido, trihalomethyl, C-carboxy, O-carboxy, sulfonamide, amino, hydroxyl, mercapto, alkylthio, sulfonyl, and sulfinyl; and S, T, U, and V are carbon or nitrogen, provided that when S, T, U, or V is nitrogen, then there is no substituent on the nitrogen.

In some embodiments, the present invention provides therapeutic methods that utilize compounds of Formula Ib1

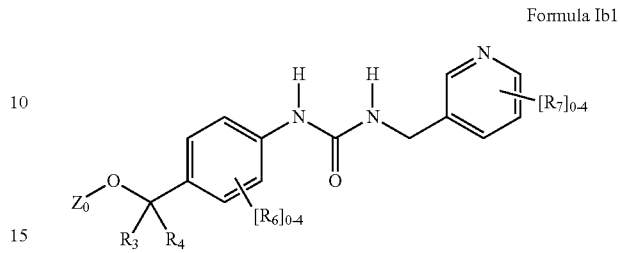

Formula Ib1 and pharmaceutically acceptable salts and solvates thereof; wherein:
$Z_0$ is as defined for Formula I above;
any methylene group is optionally independently substituted with $C_{1-4}$ alkyl, halo, $C_{1-4}$ haloalkyl, or $C_3$ or $C_4$ cycloalkyl;
$R_3$ and $R_4$ are each independently H or $C_{1-4}$ alkyl, or $R_3$ and $R_4$, taken together with the carbon to which they are attached, form a cyclopropyl or cyclobutyl ring; and
$R_6$ and $R_7$ are areas defined for Formula Ib above.

In some embodiments, the present invention provides therapeutic methods that utilize compounds of Formula Ib2

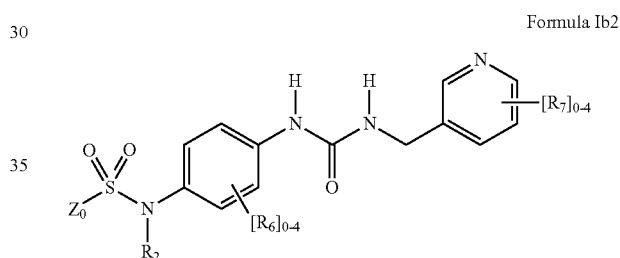

Formula Ib2 and pharmaceutically acceptable salts and solvates thereof; wherein:
$Z_0$ is as defined for Formula I above;
any methylene group is optionally independently substituted with $C_{1-4}$ alkyl, halo, $C_{1-4}$ haloalkyl, or $C_3$ or $C_4$ cycloalkyl;
$R_2$ is H, $C_{1-5}$ alkyl, $C_{1-5}$ alkenyl, or $C_{1-5}$ alkynyl; and
$R_6$ and $R_7$ are as defined for Formula Ib above.

In some embodiments, the present invention provides therapeutic methods that utilize compounds of Formula Ib3

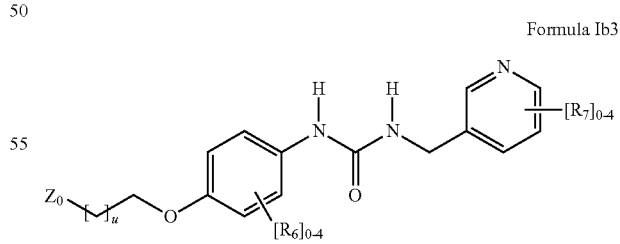

Formula Ib3 and pharmaceutically acceptable salts and solvates thereof; wherein:
$Z_0$ is as defined for Formula I above;
u is 0 or 1;
any methylene group is optionally independently substituted with $C_{1-4}$ alkyl, halo, $C_{1-4}$ haloalkyl, or $C_3$ or $C_4$ cycloalkyl; and
$R_6$ and $R_7$ are as defined for Formula Ib above.

In some embodiments, the present invention provides therapeutic methods that utilize compounds of Formula Ic

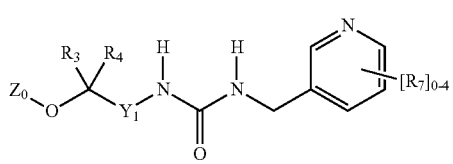

Formula Ic and pharmaceutically acceptable salts and solvates thereof; wherein:

$Z_0$ and $Y_1$ are as defined for Formula I above;

any methylene group is optionally independently substituted with $C_{1-4}$ alkyl, halo, $C_{1-4}$ haloalkyl, or $C_3$ or $C_4$ cycloalkyl;

$R_3$ and $R_4$ are each independently H or $C_{1-4}$ alkyl, or $R_3$ and $R_4$, taken together with the carbon to which they are attached, form a cyclopropyl or cyclobutyl ring;

$R_7$, if present one or more times, replaces a hydrogen atom on the pyridinyl ring and is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, hydroxyl, mercapto, alkylthio, sulfonyl, and sulfinyl; and with the proviso that the compound is NOT:

ethyl 3-(pyridin-3-yl)-4-({4-[(3-{[(pyridin-3-ylmethyl)carbamoyl]amino}benzyl)oxy]phenyl}sulfonyl)butanoate;

4-({4-[(3-{[(pyridin-3-ylmethyl)carbamoyl]amino}benzyl)oxy]phenyl}sulfonyl)-3-[4-(trifluoromethyl)phenyl]butanoic acid;

3-phenyl-4-({4-[(3-{[(pyridin-3-ylmethyl)carbamoyl]amino}benzyl)oxy]phenyl}sulfonyl)butanoic acid;

3-(4-chloro-3-fluorophenyl)-4-[(4-{[3-{[(pyridin-3-ylmethyl)carbamoyl]amino}-5-(trifluoromethyl)benzyl]oxy}phenyl)sulfonyl]butanoic acid;

3-phenyl-4-[(4-{[3-{[(pyridin-3-ylmethyl)carbamoyl]amino}-5-(trifluoromethyl)benzyl]oxy}phenyl)sulfonyl]butanoic acid;

3-(pyridin-3-yl)-4-({4-[(3-{[(pyridin-3-ylmethyl)carbamoyl]amino}benzyl)oxy]phenyl}sulfonyl)butanoic acid; or 4-({4-[(4-fluoro-3-{[(pyridin-3-ylmethyl)carbamoyl]amino}benzyl)oxy]phenyl}sulfonyl)-3-(pyridin-3-yl)butanoic acid.

In some embodiments, the present invention provides therapeutic methods that utilize compounds of Formula Id

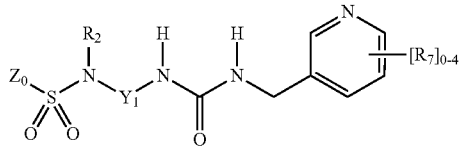

Formula Id and pharmaceutically acceptable salts and solvates thereof; wherein:

$Z_0$ and $Y_1$ are as defined for Formula I above;

any methylene group is optionally independently substituted with $C_{1-4}$ alkyl, halo, $C_{1-4}$ haloalkyl, or $C_3$ or $C_4$ cycloalkyl;

$R_2$ is H, $C_{1-5}$ alkyl, $C_{1-5}$ alkenyl, or $C_{1-5}$ alkynyl; and $R_7$, if present one or more times, replaces a hydrogen atom on the pyridinyl ring and is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, hydroxyl, mercapto, alkylthio, sulfonyl, and sulfinyl.

The present invention further provides therapeutic methods that utilize compounds of Formula II

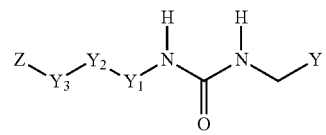

Formula II and pharmaceutically acceptable salts and solvates thereof; wherein:

Z is hydro, halo, $C_{1-5}$ alkyl, nitro, cyano, $C_{1-5}$ alkoxy, C-amido, N-amido, trihalomethyl, C-carboxy, O-carboxy, trihalomethyl, C-carboxy, O-carboxy, sulfonamide, amino, hydroxyl, mercapto, alkylthio, sulfonyl, or sulfinyl, wherein $C_{1-5}$ alkyl, $C_{1-5}$ alkoxy, C-amido, N-amido, amino, and alkylthio are each optionally substituted with heterocyclo, cycloalkyl, or amino;

or Z is $Z_0$, as defined for Formula I above;

Y and $Y_1$ R is as defined for Formula I above, wherein for the purpose of $Y_2$, R is H, $C_{1-5}$ alkyl, $C_{1-5}$ alkenyl, $C_{1-5}$ alkynyl, or forms a heterocycle with a carbon atom of $Y_3$;

$Y_3$ is aryl or heteroaryl, wherein any ring carbon is optionally independently substituted with halo, $C_{1-5}$ alkyl, nitro, cyano, trihalomethyl, $C_{1-5}$ alkoxy, C-amido, N-amido, sulfonamide, amino, aminosulfonyl, hydroxyl, mercapto, alkylthio, sulfonyl, or sulfinyl, wherein $C_{1-5}$ alkyl, $C_{1-5}$ alkoxy, C-amido, N-amido, amino, and alkylthio are each optionally substituted with heterocyclo, cycloalkyl, or amino;

any alkylene or alkenylene group is optionally independently substituted with $C_{1-4}$ alkyl, halo, $C_{1-4}$ haloalkyl, or $C_3$ or $C_4$ cycloalkyl; and with the proviso that the compound is NOT:

1-[(6-methoxypyridin-3-yl)methyl]-3-[3-(3-methylphenoxy)propyl]urea;

1-[3-(2-fluorophenoxy)propyl]-3-[(6-methoxypyridin-3-yl)methyl]urea;

ethyl 3-(pyridin-3-yl)-4-({4-[(3-{[(pyridin-3-ylmethyl)carbamoyl]amino}benzyl)oxy]phenyl}sulfonyl)butanoate;

4-({4-[(3-{[(pyridin-3-ylmethyl)carbamoyl]amino}benzyl)oxy]phenyl}sulfonyl)-3-[4-(trifluoromethyl)phenyl]butanoic acid;

3-phenyl-4-({4-[(3-{[(pyridin-3-ylmethyl)carbamoyl]amino}benzyl)oxy]phenyl}sulfonyl)butanoic acid;

3-(4-chloro-3-fluorophenyl)-4-[(4-{[3-{[(pyridin-3-ylmethyl)carbamoyl]amino}-5-(trifluoromethyl)benzyl]oxy}phenyl)sulfonyl]butanoic acid;

3-phenyl-4-[(4-{[3-{[(pyridin-3-ylmethyl)carbamoyl]amino}-5-(trifluoromethyl)benzyl]oxy}phenyl)sulfonyl]butanoic acid;

3-(pyridin-3-yl)-4-({4-[(3-{[(pyridin-3-ylmethyl)carbamoyl]amino}benzyl)oxy]phenyl}sulfonyl)butanoic acid; or 4-({4-[(4-fluoro-3-{[(pyridin-3-ylmethyl)carbamoyl]amino}benzyl)oxy]phenyl}sulfonyl)-3-(pyridin-3-yl)butanoic acid.

In some embodiments, the present invention provides therapeutic methods that utilize compounds of Formula IIa

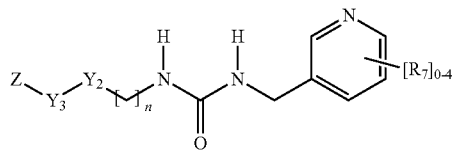

Formula IIa and pharmaceutically acceptable salts and solvates thereof; wherein
Z, $Y_2$, and $Y_3$ are as defined for Formula II above;
n is 3, 4, 5, 6, or 7;
any methylene group is optionally independently substituted with $C_{1-4}$ alkyl, halo, $C_{1-4}$ haloalkyl, or $C_3$ or $C_4$ cycloalkyl; and
$R_7$, if present one or more times, replaces a hydrogen atom on the pyridinyl ring and is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, hydroxyl, mercapto, alkylthio, sulfonyl, and sulfinyl.

In some embodiments, the present invention provides therapeutic methods that utilize compounds of Formula IIa1

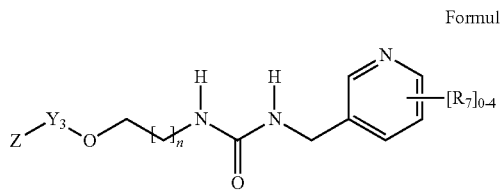

Formula IIa1 and pharmaceutically acceptable salts and solvates thereof; wherein:
Z and $Y_3$ are as defined for Formula II above;
n is 3, 4, 5, 6, or 7;
any methylene group is optionally independently substituted with $C_{1-4}$ alkyl, halo, $C_{1-4}$ haloalkyl, or $C_3$ or $C_4$ cycloalkyl; and
$R_7$ is as defined for Formula IIa above.

In some embodiments, the present invention provides therapeutic methods that utilize compounds of Formula IIa2

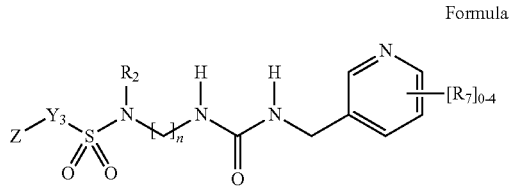

Formula IIa2 and pharmaceutically acceptable salts and solvates thereof; wherein:
Z and $Y_3$ are as defined for Formula II above;
n is 3, 4, 5, 6, or 7;
any methylene group is optionally independently substituted with $C_{1-4}$ alkyl, halo, $C_{1-4}$ haloalkyl, or $C_3$ or $C_4$ cycloalkyl;
$R_2$ is H, $C_{1-5}$ alkyl, $C_{1-5}$ alkenyl, or $C_{1-5}$ alkynyl; and
$R_7$ is as defined for Formula IIa above.

In some embodiments, the present invention provides therapeutic methods that utilize compounds of Formula IIa3

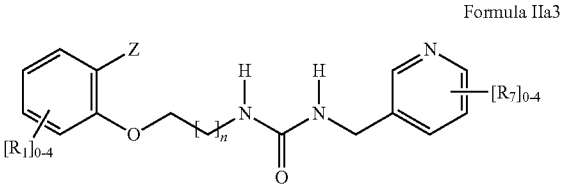

Formula IIa3 and pharmaceutically acceptable salts and solvates thereof; wherein:
Z is as defined for Formula II above;
n is 3, 4, 5, 6, or 7;
any methylene group is optionally independently substituted with $C_{1-4}$ alkyl, halo, $C_{1-4}$ haloalkyl, or $C_3$ or $C_4$ cycloalkyl;
$R_1$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino; and
$R_7$ is as defined for Formula IIa above.

In some embodiments, the present invention provides therapeutic methods that utilize compounds of Formula IIa4

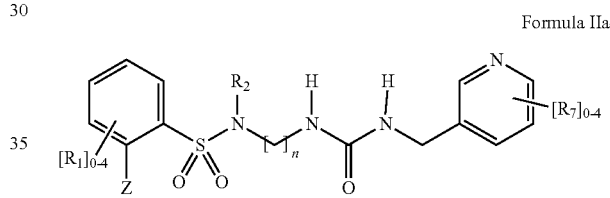

Formula IIa4 and pharmaceutically acceptable salts and solvates thereof; wherein:
Z is as defined for Formula II above;
n is 3, 4, 5, 6, or 7;
any methylene group is optionally independently substituted with $C_{1-4}$ alkyl, halo, $C_{1-4}$ haloalkyl, or $C_3$ or $C_4$ cycloalkyl;
$R_1$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;
$R_2$ is H, $C_{1-5}$ alkyl, $C_{1-5}$ alkenyl, or $C_{1-5}$ alkynyl; and
$R_7$ is as defined for Formula IIa above.

In some embodiments, the present invention provides therapeutic methods that utilize compounds of Formula IIb

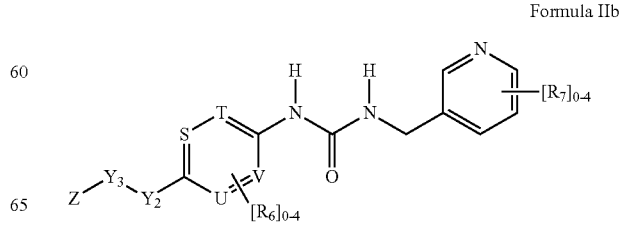

Formula IIb and pharmaceutically acceptable salts and solvates thereof;

wherein:

Z, $Y_2$, and $Y_3$ are as defined for Formula II above, any methylene group is optionally independently substituted with $C_{1-4}$ alkyl, halo, $C_{1-4}$ haloalkyl, or $C_3$ or $C_4$ cycloalkyl;

$R_6$ and $R_7$ are each independently selected from halo, $C_{1-5}$ alkyl, nitro, cyano, $C_{1-5}$ alkoxy, C-amido, N-amido, trihalomethyl, C-carboxy, O-carboxy, sulfonamide, amino, hydroxyl, mercapto, alkylthio, sulfonyl, and sulfinyl; and S, T, U, and V are carbon or nitrogen, provided that when S, T, U, or V is nitrogen, then there is no substituent on the nitrogen.

In some embodiments, the present invention provides therapeutic methods that utilize compounds of Formula IIb1

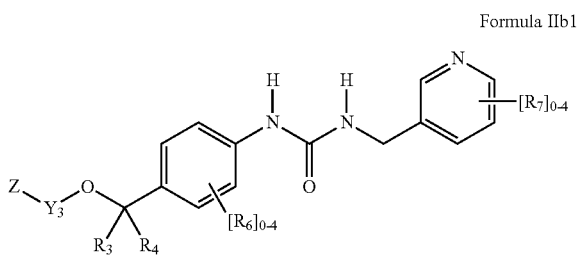

Formula IIb1 and pharmaceutically acceptable salts and solvates thereof; wherein:

Z and $Y_3$ are as defined for Formula II above, any methylene group is optionally independently substituted with $C_{1-4}$ alkyl, halo, $C_{1-4}$ haloalkyl, or $C_3$ or $C_4$ cycloalkyl;

$R_3$ and $R_4$ are each independently H or $C_{1-4}$ alkyl, or $R_3$ and $R_4$, taken together with the carbon to which they are attached, form a cyclopropyl or cyclobutyl ring; and $R_6$ and $R_7$ are as defined for Formula IIb above.

In some embodiments, the present invention provides therapeutic methods that utilize compounds Formula IIb2

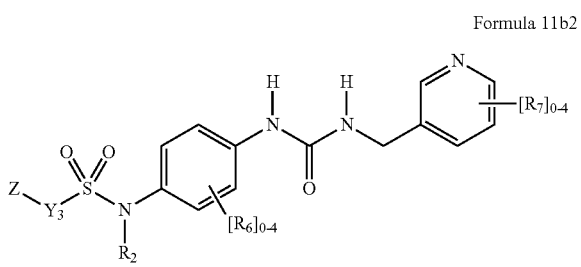

Formula 11b2 and pharmaceutically acceptable salts and solvates thereof; wherein:

Z and $Y_3$ are as defined for Formula II above;

any methylene group is optionally independently substituted with $C_{1-4}$ alkyl, halo, $C_{1-4}$ haloalkyl, or $C_3$ or $C_4$ cycloalkyl;

$R_2$ is H, $C_{1-5}$ alkyl, $C_{1-5}$ alkenyl, or $C_{1-5}$ alkynyl; and $R_6$ and $R_7$ are as defined for Formula IIb above.

In some embodiments, the present invention provides therapeutic methods that utilize compounds of Formula IIb3

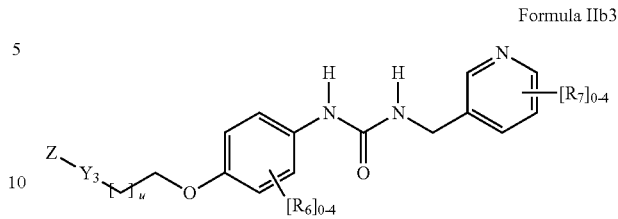

Formula IIb3 and pharmaceutically acceptable salts and solvates thereof; wherein:

Z and $Y_3$ are as defined for Formula II above, u is 0 or 1;

any methylene group is optionally independently substituted with $C_{1-4}$ alkyl, halo, $C_{1-4}$ haloalkyl, or $C_3$ or $C_4$ cycloalkyl; and $R_6$ and $R_7$ are as defined for Formula IIb above.

In some embodiments, the present invention provides therapeutic methods that utilize compounds of Formula IIb4

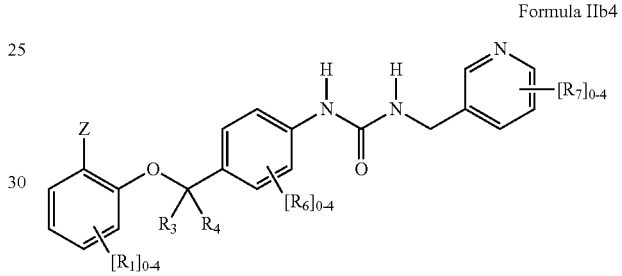

Formula IIb4 and pharmaceutically acceptable salts and solvates thereof; wherein:

Z is as defined for Formula II above;

any methylene group is optionally independently substituted with $C_{1-4}$ alkyl, halo, $C_{1-4}$ haloalkyl, or $C_3$ or $C_4$ cycloalkyl;

$R_1$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;

$R_3$ and $R_4$ are each independently H or $C_{1-4}$ alkyl, or $R_3$ and $R_4$, taken together with the carbon to which they are attached, form a cyclopropyl or cyclobutyl ring; and $R_6$ and $R_7$ are as defined for Formula IIb above.

In some embodiments, the present invention provides therapeutic methods that utilize compounds of Formula IIb5

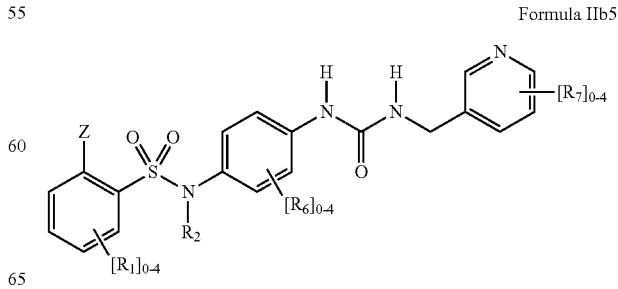

Formula IIb5 and pharmaceutically acceptable salts and solvates thereof;

wherein:

Z is as defined for Formula II above;

any methylene group is optionally independently substituted with $C_{1-4}$ alkyl, halo, $C_{1-4}$ haloalkyl, or $C_3$ or $C_4$ cycloalkyl;

$R_1$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;

$R_2$ is H, $C_{1-5}$ alkyl, $C_{1-5}$ alkenyl, or $C_{1-5}$ alkynyl; and $R_6$ and $R_7$ are as defined for Formula IIb above.

In some embodiments, the present invention provides therapeutic methods that utilize compounds of Formula IIb6

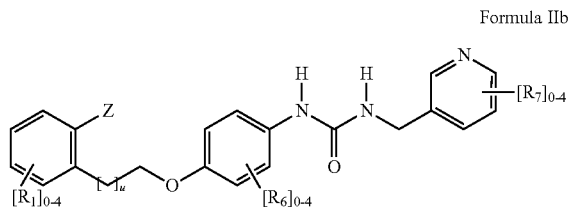

Formula IIb6 and pharmaceutically acceptable salts and solvates thereof; wherein:

Z is as defined for Formula II above;

u is 0 or 1;

any methylene group is optionally independently substituted with $C_{1-4}$ alkyl, halo, $C_{1-4}$ haloalkyl, or $C_3$ or $C_4$ cycloalkyl;

$R_1$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino; and $R_6$ and $R_7$ are as defined for Formula IIb above.

In some embodiments, the present invention provides therapeutic methods that utilize compounds of Formula IIb7

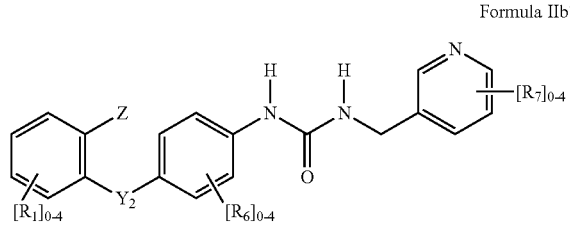

Formula IIb7 and pharmaceutically acceptable salts and solvates thereof; wherein:

Z and $Y_2$ are as defined for Formula II above;

any methylene group is optionally independently substituted with $C_{1-4}$ alkyl, halo, $C_{1-4}$ haloalkyl, or $C_3$ or $C_4$ cycloalkyl;

$R_1$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino; and $R_6$ and $R_7$ are as defined for Formula IIb above.

In some embodiments, the present invention provides therapeutic methods that utilize compounds of Formula IIc

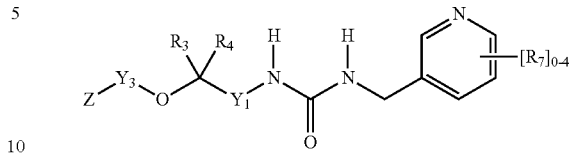

Formula IIc and pharmaceutically acceptable salts and solvates thereof; wherein:

Z, $Y_1$, and $Y_3$ are as defined for Formula II above;

any alkylene or alkenylene group is optionally independently substituted with $C_{1-4}$ alkyl, halo, $C_{1-4}$ haloalkyl, or $C_3$ or $C_4$ cycloalkyl;

$R_3$ and $R_4$ are each independently H or $C_{1-4}$ alkyl, or $R_3$ and $R_4$, taken together with the carbon to which they are attached, form a cyclopropyl or cyclobutyl ring; and $R_7$, if present one or more times, replaces a hydrogen atom on the pyridinyl ring and is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, hydroxyl, mercapto, alkylthio, sulfonyl, and sulfinyl.

In some embodiments, the present invention provides therapeutic methods that utilize compounds of Formula IIc1

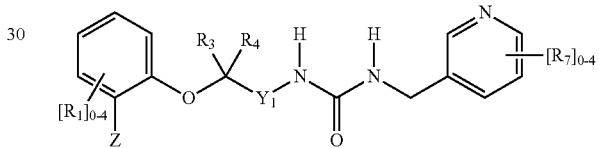

Formula IIc1 and pharmaceutically acceptable salts and solvates thereof; wherein:

Z and $Y_1$ are as defined in Formula II above;

any alkylene or alkenylene group is optionally independently substituted with $C_{1-4}$ alkyl, halo, $C_{1-4}$ haloalkyl, or $C_3$ or $C_4$ cycloalkyl;

$R_1$, if present one or more times, is independently selected from halo, $C_{1-5}$ alkyl, nitro, cyano, alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino; and $R_3$, $R_4$, and $R_7$ are as defined for Formula IIc.

In some embodiments, the present invention provides therapeutic methods that utilize compounds of Formula IId

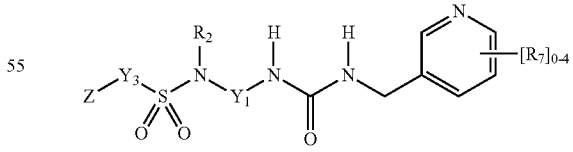

Formula IId and pharmaceutically acceptable salts and solvates thereof; wherein:

Z, $Y_1$, and $Y_3$ are as defined for Formula II above;

any alkylene or alkenylene group is optionally independently substituted with $C_{1-4}$ alkyl, halo, $C_{1-4}$ haloalkyl, or $C_3$ or $C_4$ cycloalkyl;

$R_2$ is H, $C_{1-5}$ alkyl, $C_{1-5}$ alkenyl, or $C_{1-5}$ alkynyl; and $R_7$, if present one or more times, replaces a hydrogen atom on the pyridinyl ring and is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, hydroxyl, mercapto, alkylthio, sulfonyl, and sulfinyl.

In some embodiments, the present invention provides therapeutic methods that utilize compounds of Formula IId1

Formula IId1

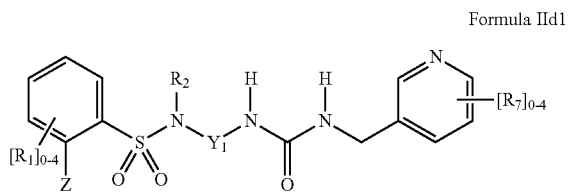

and pharmaceutically acceptable salts and solvates thereof; wherein:

Z and $Y_1$ are as defined for Formula II above;

any alkylene or alkenylene group is optionally independently substituted with $C_{1-4}$ alkyl, halo, $C_{1-4}$ haloalkyl, or $C_3$ or $C_4$ cycloalkyl;

$R_1$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino; and $R_2$ and $R_7$ are as defined for Formula IId.

The present invention further provides therapeutic methods that utilize compounds of Formula III Formula III

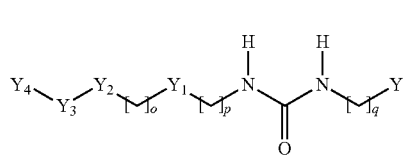

and pharmaceutically acceptable salts and solvates thereof; wherein:

Y, $Y_1$, $Y_2$, and $Y_3$ are as defined for Formula II;

$Y_4$ is optionally present, and when present is aryl, heteroaryl, carbocycle, or heterocycle, wherein any ring atom is optionally independently substituted with halo, $C_{1-5}$ alkyl, nitro, cyano, trihalomethyl, $C_{1-5}$ alkoxy, C-amido, N-amido, sulfonamide, amino, aminosulfonyl, hydroxyl, mercapto, alkylthio, sulfonyl, sulfinyl, wherein $C_{1-5}$ alkyl, $C_{1-5}$ alkoxy, C-amido, N-amido, amino, and alkylthio are each optionally substituted with heterocyclo, cycloalkyl, or amino;

o, p, and q are each independently 0, 1, or 2;

any alkylene or alkenylene group of the o, p, and q regions and of $Y_2$ is optionally substituted with unsubstituted $C_{1-4}$ alkyl, halo, unsubstituted $C_{1-4}$ haloalkyl, or unsubstituted $C_3$ or $C_4$ cycloalkyl;

with the proviso that when p is 0, $Y_1$ is divalent phenyl, $Y_2$ is —C(═O)N(H)— or —OC(H)$_2$C(═O)N(H)—, and $Y_3$ is phenyl or pyridinyl, then either $Y_4$ is present or any substituent on $Y_3$ is not —C(═O)NH$_2$; and with the proviso that the compound is NOT:

1-(6-methoxy-3-pyridyl)-3-[[4-(3-pyridylmethoxy)phenyl]methyl]urea;

1-[(6-methoxypyridin-3-yl)methyl]-3-[3-(3-methylphenoxy)propyl]urea;

1-[3-(2-fluorophenoxy)propyl]-3-[(6-methoxypyridin-3-yl)methyl]urea;

ethyl 3-(pyridin-3-yl)-4-({4-[(3-{[(pyridin-3-ylmethyl)carbamoyl]amino}benzyl)oxy]phenyl}sulfonyl)butanoate;

4-({4-[(3-{[(pyridin-3-ylmethyl)carbamoyl]amino}benzyl)oxy]phenyl}sulfonyl)-3-[4-(trifluoromethyl)phenyl]butanoic acid;

3-phenyl-4-({4-[(3-{[(pyridin-3-ylmethyl)carbamoyl]amino}benzyl)oxy]phenyl}sulfonyl)butanoic acid;

3-(4-chloro-3-fluorophenyl)-4-[(4-{[3-{[(pyridin-3-ylmethyl)carbamoyl]amino}-5-(trifluoromethyl)benzyl]oxy}phenyl)sulfonyl]butanoic acid;

3-phenyl-4-[(4-{[3-{[(pyridin-3-ylmethyl)carbamoyl]amino}-5-(trifluoromethyl)benzyl]oxy}phenyl)sulfonyl]butanoic acid;

3-(pyridin-3-yl)-4-({4-[(3-{[(pyridin-3-ylmethyl)carbamoyl]amino}benzyl)oxy]phenyl}sulfonyl)butanoic acid;

4-({4-[(4-fluoro-3-{[(pyridin-3-ylmethyl)carbamoyl]amino}benzyl)oxy]phenyl}sulfonyl)-3-(pyridin-3-yl)butanoic acid;

Benzoic acid, 2-hydroxy-4-[[(3-pyridinylamino)carbonyl]amino]-, phenyl ester;

Benzamide, N-(3-amino-4-pyridinyl)-4-[[[[(3-pyridinylmethyl)amino]carbonyl]amino]methyl]-;

Benzamide, N-(2-amino-3-pyridinyl)-4-[[[[(3-pyridinylmethyl)amino]carbonyl]amino]methyl]-;

Benzamide, N-(2-amino-5-fluorophenyl)-4-[[[[(3-pyridinylmethyl)amino]carbonyl]amino]methyl]-;

Benzamide, N-(2-hydroxyphenyl)-4-[[[[(3-pyridinylmethyl)amino]carbonyl]amino]methyl]-;

Benzamide, N-(2-amino-5-chlorophenyl)-4-[[[[(3-pyridinylmethyl)amino]carbonyl]amino]methyl]-;

Benzamide, 2-chloro-5-nitro-N-[4-[[(4-pyridinylamino)carbonyl]amino]phenyl]-;

Benzamide, N-[4-[[[3-(diethylamino)propyl]amino]carbonyl]phenyl]-4-[[(3-pyridinylamino)carbonyl]amino]-;

Benzamide, N-(2-aminophenyl)-4-[[[(3-pyridinylamino)carbonyl]amino]methyl]-;

Benzamide, N-(2-aminophenyl)-4-[2-[[[(3-pyridinylmethyl)amino]carbonyl]amino]ethyl]-;

Benzamide, N-(2-aminophenyl)-4-[[[[(3-pyridinylmethyl)amino]carbonyl]amino]methyl]-;

Benzoic acid, 2-hydroxy-4-[[(3-pyridinylamino)carbonyl]amino]-, phenyl ester;

1,3-Benzenedicarboxamide, N,N'-bis[3-(diethylamino)propyl]-5-[[4-[[(4-pyridinylamino)carbonyl]amino]benzoyl]amino]-;

Urea, N-[4-(phenylmethoxy)phenyl]-N'-[2-(3-pyridinyl)ethyl]-;

Urea, N-[4-(phenylmethoxy)phenyl]-N'-3-pyridinyl-;

Urea, N-(6-methyl-3-pyridinyl)-N'-[2-[2-(phenylmethoxy)phenyl]ethyl]-;

Urea, N-(6-methoxy-3-pyridinyl)-N'-[4-(phenylmethoxy)phenyl]-;

4,6-Pyrimidinedicarboxamide, N4-[[4-[[[(2,6-dichloro-4-pyridinyl)amino]carbonyl]amino]phenyl]methyl]-N-6-[(3-methoxyphenyl)methyl]-;

Benzenesulfonamide, 4-fluoro-N-[4-[[(3-pyridinylamino)carbonyl]amino]phenyl]-; or Hexanamide, 2-[2,4-bis(1,1-dimethylpropyl)phenoxy]-N-[2-chloro-4-[[[(2-chloro-3-pyridinyl)amino]carbonyl]amino]-5-hydroxyphenyl]-.

In some embodiments, the present invention provides therapeutic methods that utilize compounds of Formula IIIa

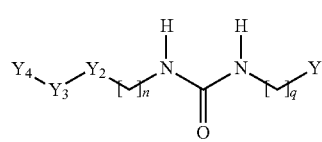

Formula IIIa and pharmaceutically acceptable salts and solvates thereof; wherein:

Y is 3-pyridinyl or 4-pyridinyl, optionally substituted as defined for Y for Formula I;

$Y_2$, $Y_3$, $Y_4$, and q are as defined for Formula III above;

n is 3, 4, 5, 6, or 7; and any methylene group of $Y_2$ and the n and q regions is optionally independently substituted with $C_{1-4}$ alkyl, halo, $C_{1-4}$ haloalkyl, or $C_3$ or $C_4$ cycloalkyl.

In some embodiments, the present invention provides therapeutic methods that utilize compounds of Formula IIIa1

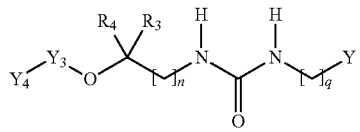

Formula IIIa1 and pharmaceutically acceptable salts and solvates thereof; wherein:

Y is 3-pyridinyl or 4-pyridinyl, optionally substituted as defined for Y for Formula I;

$Y_3$, $Y_4$, and q are as defined for Formula III above;

n is 3, 4, 5, 6, or 7;

any methylene group of the n and q regions is optionally independently substituted with $C_{1-4}$ alkyl, halo, $C_{1-4}$ haloalkyl, or $C_3$ or $C_4$ cycloalkyl; and $R_3$ and $R_4$ are each independently H, halo, or $C_{1-4}$ alkyl, or $R_3$ and $R_4$ taken together form a cyclopropyl or cyclobutyl ring.

In some embodiments, the present invention provides therapeutic methods that utilize compounds of Formula IIIa2

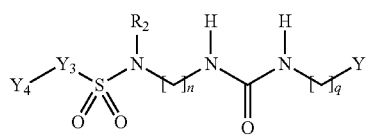

Formula IIIa2 and pharmaceutically acceptable salts and solvates thereof; wherein:

Y is 3-pyridinyl or 4-pyridinyl, optionally substituted as defined for Y for Formula I;

$Y_3$, $Y_4$, and q are as defined for Formula III above;

n is 3, 4, 5, 6, or 7;

any methylene group of the n and q regions is optionally independently substituted with $C_{1-4}$ alkyl, halo, $C_{1-4}$ haloalkyl, or $C_3$ or $C_4$ cycloalkyl; and $R_2$ is H, halo, $C_{1-5}$ alkyl, $C_{1-5}$ alkenyl, or $C_{1-5}$ alkynyl.

In some embodiments, the present invention provides therapeutic methods that utilize compounds of Formula IIIa3

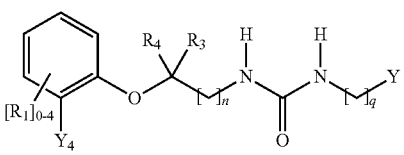

Formula IIIa3 and pharmaceutically acceptable salts and solvates thereof; wherein:

Y is 3-pyridinyl or 4-pyridinyl, optionally substituted as defined for Y for Formula I;

$Y_4$ and q are as defined for Formula III above;

n is 3, 4, 5, 6, or 7;

any methylene group of the n and q regions is optionally independently substituted with $C_{1-4}$ alkyl, halo, $C_{1-4}$ haloalkyl, or $C_3$ or $C_4$ cycloalkyl;

$R_1$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino; and $R_3$ and $R_4$ are each independently H, halo, or $C_{1-4}$ alkyl, or $R_3$ and $R_4$, taken together with the carbon to which they are attached, form a cyclopropyl or cyclobutyl ring.

In some embodiments, the present invention provides therapeutic methods that utilize compounds of Formula IIa4

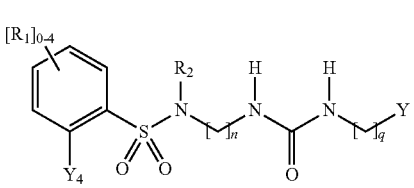

Formula IIIa4 and pharmaceutically acceptable salts and solvates thereof; wherein:

Y is 3-pyridinyl or 4-pyridinyl, optionally substituted as defined for Y for Formula I;

$Y_4$ and q are as defined for Formula III above;

n is 3, 4, 5, 6, or 7;

any methylene group of the n and q regions is optionally independently substituted with $C_{1-4}$ alkyl, halo, $C_{1-4}$ haloalkyl, or $C_3$ or $C_4$ cycloalkyl;

$R_1$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino; and $R_2$ is H, halo, $C_{1-5}$ alkyl, $C_{1-5}$ alkenyl, or $C_{1-5}$ alkynyl.

In some embodiments, the present invention provides therapeutic methods that utilize compounds of Formula IIIa5

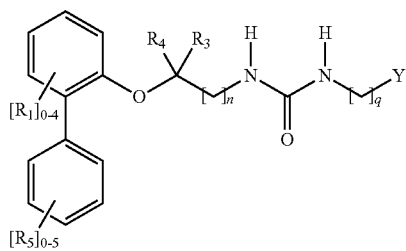

Formula IIIa5 and pharmaceutically acceptable salts and solvates thereof; wherein:

Y is 3-pyridinyl or 4-pyridinyl, optionally substituted as defined for Y for Formula I;

q is as defined for Formula III above;

n is 3, 4, 5, 6, or 7;

any methylene group of the n and q regions is optionally independently substituted with $C_{1-4}$ alkyl, halo, $C_{1-4}$ haloalkyl, or $C_3$ or $C_4$ cycloalkyl;

$R_1$ and $R_5$, if one or both are present one or more times, are each independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino; and $R_3$ and $R_4$ are each independently H, halo, or $C_{1-4}$ alkyl, or $R_3$ and $R_4$, taken together with the carbon to which they are attached, form a cyclopropyl or cyclobutyl ring.

In some embodiments, the present invention provides therapeutic methods that utilize compounds of Formula IIIa6

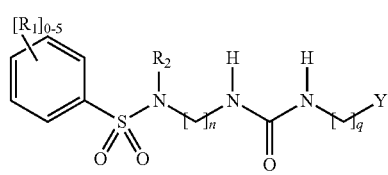

Formula IIIa6 and pharmaceutically acceptable salts and solvates thereof; wherein:

Y is 3-pyridinyl or 4-pyridinyl, optionally substituted as defined for Y for Formula I;

q is as defined for Formula III above;

n is 3, 4, 5, 6, or 7;

any methylene group of the n and q regions is optionally independently substituted with $C_{1-4}$ alkyl, halo, $C_{1-4}$ haloalkyl, or $C_3$ or $C_4$ cycloalkyl;

$R_1$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino; and $R_2$ is H, halo, $C_{1-5}$ alkyl, $C_{1-5}$ alkenyl, or $C_{1-5}$ alkynyl.

In some embodiments, the present invention provides therapeutic methods that utilize compounds of Formula IIIb

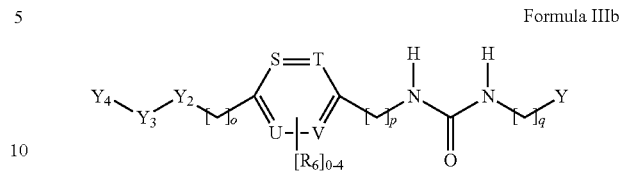

Formula IIIb and pharmaceutically acceptable salts and solvates thereof; wherein:

Y is 3-pyridinyl or 4-pyridinyl, optionally substituted as defined for Y for Formula I;

o, p, q, $Y_2$, $Y_3$, and $Y_4$ are as defined for Formula III above;

any methylene group of the o, p, and q regions and $Y_2$ is optionally independently substituted with $C_{1-4}$ alkyl, halo, $C_{1-4}$ haloalkyl, or $C_3$ or $C_4$ cycloalkyl;

$R_6$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, hydroxyl, mercapto, alkylthio, sulfonyl, and sulfinyl;

wherein S, T, U, and V are carbon or nitrogen, provided that when S, T, U, or V is nitrogen, then there is no substituent on the nitrogen;

with the proviso that when p is 0, $Y_2$ is —C(=O)N(H)— or —OC(H)$_2$C(=O)N(H)—, and $Y_3$ is phenyl or pyridinyl, then either $Y_4$ is present or any substituent on $Y_3$ is not —C(=O)NH$_2$; and with the proviso that the compound is NOT 1-(6-methoxy-3-pyridyl)-3-[[4-(3-pyridylmethoxy)phenyl] methyl]urea, ethyl 3-(pyridin-3-yl)-4-({4-[(3-{[(pyridin-3-ylmethyl)carbamoyl]amino}benzyl)oxy]phenyl}sulfonyl)butanoate;

4-({4-[(3-{[(pyridin-3-ylmethyl)carbamoyl]amino}benzyl) oxy]phenyl}sulfonyl)-3-[4-(trifluoromethyl)phenyl]butanoic acid;

3-phenyl-4-({4-[(3-{[(pyridin-3-ylmethyl)carbamoyl] amino}benzyl)oxy]phenyl}sulfonyl)butanoic acid;

3-(4-chloro-3-fluorophenyl)-4-[(4-{[3-{[(pyridin-3-ylmethyl)carbamoyl]amino}-5-(trifluoromethyl)benzyl] oxy}phenyl)sulfonyl]butanoic acid;

3-phenyl-4-[(4-{[3-{[(pyridin-3-ylmethyl)carbamoyl] amino}-5-(trifluoromethyl)benzyl]oxy}phenyl)sulfonyl] butanoic acid;

3-(pyridin-3-yl)-4-({4-[(3-{[(pyridin-3-ylmethyl)carbamoyl]amino}benzyl)oxy]phenyl}sulfonyl)butanoic acid;

4-({4-[(4-fluoro-3-{[(pyridin-3-ylmethyl)carbamoyl] amino}benzyl)oxy]phenyl}sulfonyl)-3-(pyridin-3-yl)butanoic acid;

Benzoic acid, 2-hydroxy-4-[[(3-pyridinylamino)carbonyl] amino]-, phenyl ester,

Benzamide, N-(3-amino-4-pyridinyl)-4-[[[[(3-pyridinylmethyl)amino]carbonyl]amino]methyl]-, Benzamide, N-(2-amino-3-pyridinyl)-4-[[[[(3-pyridinylmethyl)amino]carbonyl]amino]methyl]-, Benzamide, N-(2-amino-5-fluorophenyl)-4-[[[[(3-pyridinylmethyl)amino]carbonyl]amino]methyl]-, Benzamide, N-(2-hydroxyphenyl)-4-[[[[(3-pyridinylmethyl)amino]carbonyl]amino]methyl]-, Benzamide, N-(2-amino-5-chlorophenyl)-4-[[[[(3-pyridinylmethyl)amino]carbonyl]amino]methyl]-, Benzamide, 2-chloro-5-nitro-N-[4-[[(4-pyridinylamino)carbonyl]amino]phenyl]-, Benzamide, N-[4-[[[3-(diethylamino)propyl]amino]carbonyl]phenyl]-4-[[(3-pyridinylamino)carbonyl]amino]-,
Benzamide, N-(2-aminophenyl)-4-[[[(3-pyridinylamino)carbonyl]amino]methyl]-,
Benzamide, N-(2-aminophenyl)-4-[2-[[[(3-pyridinylmethyl)amino]carbonyl]amino]ethyl]-,
Benzamide, N-(2-aminophenyl)-4-[[[[(3-pyridinylmethyl)amino]carbonyl]amino]methyl]-,
Benzoic acid, 2-hydroxy-4-[[(3-pyridinylamino)carbonyl]amino]-, phenyl ester, 1,3-Benzenedicarboxamide, N,N'-bis[3-(diethylamino)propyl]-5-[[4-[[(4-pyridinylamino)carbonyl]amino]benzoyl]amino]-,
Urea, N-[4-(phenylmethoxy)phenyl]-N'-[2-(3-pyridinyl)ethyl]-,
Urea, N-[4-(phenylmethoxy)phenyl]-N'-3-pyridinyl-,
Urea, N-(6-methyl-3-pyridinyl)-N'-[2-[2-(phenylmethoxy)phenyl]ethyl]-,
Urea, N-(6-methoxy-3-pyridinyl)-N'-[4-(phenylmethoxy)phenyl]-,
4,6-Pyrimidinedicarboxamide, N4-[[4-[[[(2,6-dichloro-4-pyridinyl)amino]carbonyl]amino]phenyl]methyl]-N6-[(3-methoxyphenyl)methyl]-,
Benzenesulfonamide, 4-fluoro-N-[4-[[(3-pyridinylamino)carbonyl]amino]phenyl]-, or
Hexanamide, 2-[2,4-bis(1,1-dimethylpropyl)phenoxy]-N-[2-chloro-4-[[[(2-chloro-3-pyridinyl)amino]carbonyl]amino]-5-hydroxyphenyl]-.

In some embodiments, the present invention provides therapeutic methods that utilize compounds of Formula IIIb1

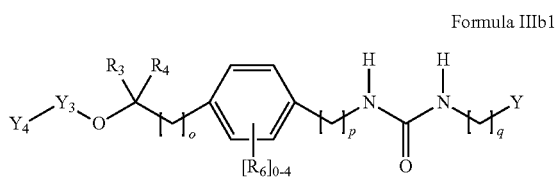

Formula IIIb1 and pharmaceutically acceptable salts and solvates thereof; wherein:

Y is 3-pyridinyl or 4-pyridinyl, optionally substituted as defined for Y for Formula I;

o, p, q, $Y_3$, and $Y_4$ are as defined for Formula III above;

any methylene group of the o, p, and q regions is optionally independently substituted with $C_{1-4}$ alkyl, halo, $C_{1-4}$ haloalkyl, or $C_3$ or $C_4$ cycloalkyl;

$R_3$ and $R_4$ are each independently H, halo, or $C_{1-4}$ alkyl, or $R_3$ and $R_4$, taken together with the carbon to which they are attached, form a cyclopropyl or cyclobutyl ring; and $R_6$ is as defined for Formula IIIb above.

In some embodiments, the present invention provides therapeutic methods that utilize compounds of Formula IIIb2

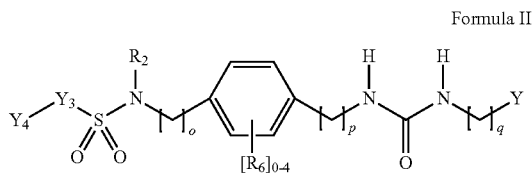

Formula IIIb2 and pharmaceutically acceptable salts and solvates thereof; wherein:

Y is 3-pyridinyl or 4-pyridinyl, optionally substituted as defined for Y for Formula I;

o, p, q, $Y_3$, and $Y_4$ are as defined for Formula III above;

any methylene group of the o, p, and q regions is optionally independently substituted with $C_{1-4}$ alkyl, halo, $C_{1-4}$ haloalkyl, or $C_3$ or $C_4$ cycloalkyl;

$R_6$ is as defined for Formula IIIb above; and $R_2$ is H, halo, $C_{1-5}$ alkyl, $C_{1-5}$ alkenyl, or $C_{1-5}$ alkynyl.

In some embodiments, the present invention provides therapeutic methods that utilize compounds of Formula IIIb3

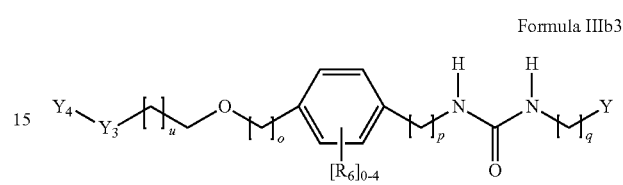

Formula IIIb3 and pharmaceutically acceptable salts and solvates thereof; wherein:

Y is 3-pyridinyl or 4-pyridinyl, optionally substituted as defined for Y for Formula I;

o, p, q, $Y_3$, and $Y_4$ are as defined for Formula III above;

u is 0 or 1;

any methylene group of the o, p, q, and u regions is optionally independently substituted with $C_{1-4}$ alkyl, halo, $C_{1-4}$ haloalkyl, or $C_3$ or $C_4$ cycloalkyl; and $R_6$ is as defined for Formula IIIb above.

In some embodiments, the present invention provides therapeutic methods that utilize compounds of Formula IIIb4

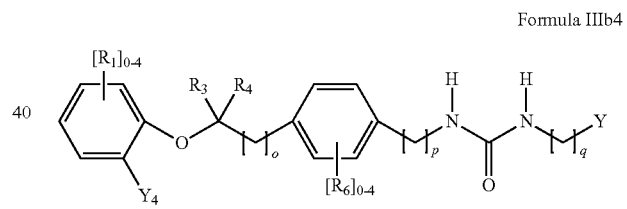

Formula IIIb4 and pharmaceutically acceptable salts and solvates thereof; wherein:

Y is 3-pyridinyl or 4-pyridinyl, optionally substituted as defined for Y for Formula I;

o, p, q, and $Y_4$ are as defined for Formula III above;

$R_1$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;

$R_3$ and $R_4$ are each independently H, halo, or $C_{1-4}$ alkyl, or $R_3$ and $R_4$, taken together with the carbon to which they are attached, form a cyclopropyl or cyclobutyl ring;

$R_6$ is as defined for Formula IIIb above; and any methylene group of the o, p, and q regions is optionally independently substituted with $C_{1-4}$ alkyl, halo, $C_{1-4}$ haloalkyl, or $C_3$ or $C_4$ cycloalkyl.

In some embodiments, the present invention provides therapeutic methods that utilize compounds of Formula IIIb5

Formula IIIb5

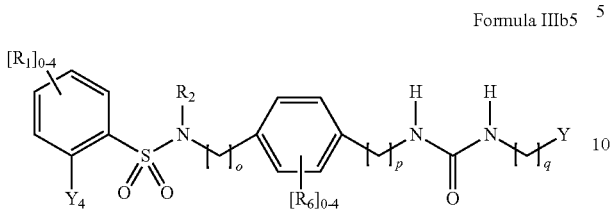

and pharmaceutically acceptable salts and solvates thereof; wherein:

Y is 3-pyridinyl or 4-pyridinyl, optionally substituted as defined for Y for Formula I;

o, p, q, and $Y_4$ are as defined for Formula III above;

$R_1$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;

$R_2$ is H, halo, $C_{1-5}$ alkyl, $C_{1-5}$ alkenyl, or $C_{1-5}$ alkynyl;

$R_6$ is as defined for Formula IIIb above; and any methylene group of the o, p, and q regions is optionally independently substituted with $C_{1-4}$ alkyl, halo, $C_{1-4}$ haloalkyl, or $C_3$ or $C_4$ cycloalkyl.

In some embodiments, the present invention provides therapeutic methods that utilize compounds of Formula IIIb6

Formula IIIb6

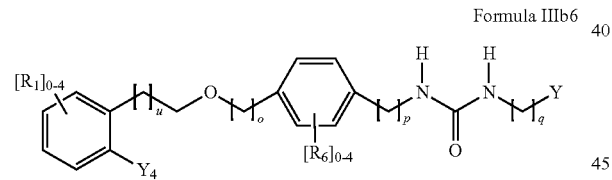

and pharmaceutically acceptable salts and solvates thereof; wherein:

Y is 3-pyridinyl or 4-pyridinyl, optionally substituted as defined for Y for Formula I;

o, p, q, and $Y_4$ are as defined for Formula III above;

u is 0 or 1;

$R_1$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;

$R_6$ is as defined for Formula IIIb above; and any methylene group of the o, p, q, and u regions is optionally independently substituted with $C_{1-4}$ alkyl, halo, $C_{1-4}$ haloalkyl, or $C_3$ or $C_4$ cycloalkyl.

In some embodiments, the present invention provides therapeutic methods that utilize compounds of Formula IIIb7

Formula IIIb7

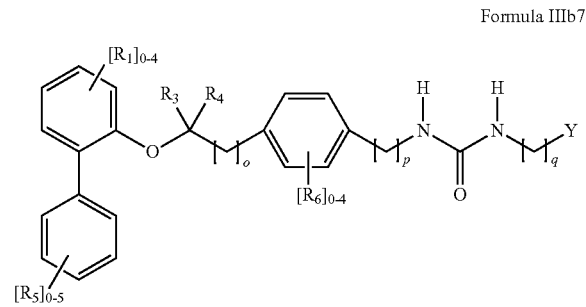

and pharmaceutically acceptable salts and solvates thereof; wherein:

Y is 3-pyridinyl or 4-pyridinyl, optionally substituted as defined for Y for Formula I;

o, p, and q are as defined for Formula III above;

$R_1$ and $R_5$, if one or both are present one or more times, are each independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;

$R_3$ and $R_4$ are each independently H, halo, or $C_{1-4}$ alkyl, or $R_3$ and $R_4$, taken together with the carbon to which they are attached, form a cyclopropyl or cyclobutyl ring;

$R_6$ is as defined for Formula IIIb above; and any methylene group of the o, p, and q regions is optionally independently substituted with $C_{1-4}$ alkyl, halo, $C_{1-4}$ haloalkyl, or $C_3$ or $C_4$ cycloalkyl.

In some embodiments, the present invention provides therapeutic methods that utilize compounds of Formula IIIb8

Formula IIIb8

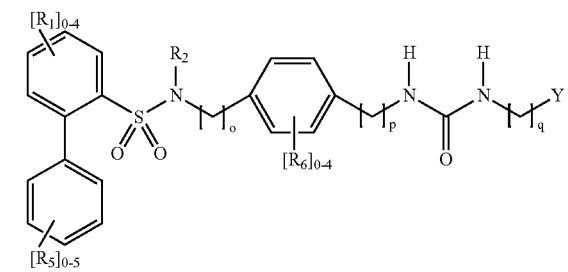

and pharmaceutically acceptable salts and solvates thereof; wherein:

Y is 3-pyridinyl or 4-pyridinyl, optionally substituted as defined for Y for Formula I;

o, p, and q are as defined for Formula III above;

$R_1$ and $R_5$, if one or both are present one or more times, are each independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;

$R_2$ is H, halo, $C_{1-5}$ alkyl, $C_{1-5}$ alkenyl, or $C_{1-5}$ alkynyl;

$R_6$ is as defined for Formula IIIb above; and any methylene group of the o, p, and q regions is optionally independently substituted with $C_{1-4}$ alkyl, halo, $C_{1-4}$ haloalkyl, or $C_3$ or $C_4$ cycloalkyl.

In some embodiments, the present invention provides therapeutic methods that utilize compounds of Formula IIIb9

Formula IIIb9

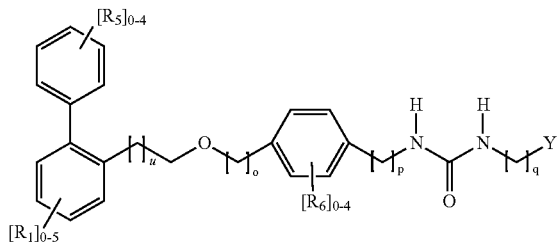

and pharmaceutically acceptable salts and solvates thereof; wherein:

Y is 3-pyridinyl or 4-pyridinyl, optionally substituted as defined for Y for Formula I;

o, p, and q are as defined for Formula III;

u is 0 or 1;

$R_1$ and $R_5$, if one or both are present one or more times, are each independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;

$R_6$ is as defined if Formula IIIb above; and any methylene group of the o, p, q, and u regions is optionally independently substituted with $C_{1-4}$ alkyl, halo, $C_{1-4}$ haloalkyl, or $C_3$ or $C_4$ cycloalkyl.

In some embodiments, the present invention provides therapeutic methods that utilize compounds of Formula IIIb10

Formula IIIb10

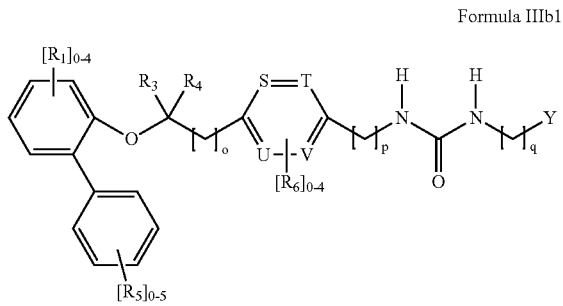

and pharmaceutically acceptable salts and solvates thereof; wherein:

Y is 3-pyridinyl or 4-pyridinyl, optionally substituted as defined for Y for Formula I;

o, p, and q are as defined for Formula III above;

$R_1$ and $R_5$, if one or both are present one or more times, are each independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;

$R_3$ and $R_4$ are each independently H, halo, or $C_{1-4}$ alkyl, or $R_3$ and $R_4$, taken together with the carbon to which they are attached, form a cyclopropyl or cyclobutyl ring;

$R_6$ is as defined for Formula IIIb above;

any methylene group of the o, p, and q regions is optionally independently substituted with $C_{1-4}$ alkyl, halo, $C_{1-4}$ haloalkyl, or $C_3$ or $C_4$ cycloalkyl; and S, T, U, and V are carbon or nitrogen, provided that at least one of S, T, U, and V is nitrogen and that when S, T, U, or V is nitrogen, then there is no substituent on the nitrogen.

In some embodiments, the present invention provides therapeutic methods that utilize compounds of Formula IIIb11

Formula IIIb11

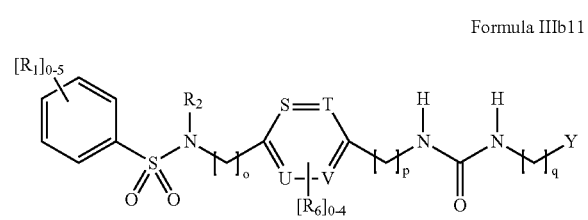

and pharmaceutically acceptable salts and solvates thereof; wherein:

Y is 3-pyridinyl or 4-pyridinyl, optionally substituted as defined for Y for Formula I;

o, p, and q are as defined for Formula III above;

$R_1$, if one or both are present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;

$R_2$ is H, halo, $C_{1-5}$ alkyl, $C_{1-5}$ alkenyl, or $C_{1-5}$ alkynyl;

$R_6$ is as defined for Formula IIIb above;

any methylene group of the o, p, and q regions is optionally independently substituted with $C_{1-4}$ alkyl, halo, $C_{1-4}$ haloalkyl, or $C_3$ or $C_4$ cycloalkyl; and S, T, U, and V are carbon or nitrogen, provided that at least one of S, T, U, and V is nitrogen and that when S, T, U, or V is nitrogen, then there is no substituent on the nitrogen.

In some embodiments, the present invention provides therapeutic methods that utilize compounds of Formula IIIc Formula IIIc

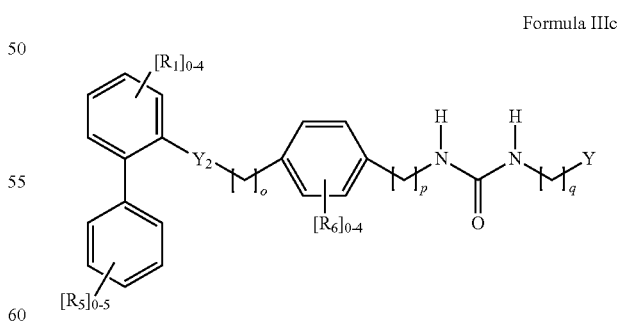

and pharmaceutically acceptable salts and solvates thereof; wherein:

Y is 3-pyridinyl or 4-pyridinyl, optionally substituted as defined for Y for Formula I;

$Y_2$, o, p, and q are as defined for Formula III;

$R_1$ and $R_5$, if one or both are present one or more times, are each independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;

$R_6$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, hydroxyl, mercapto, alkylthio, sulfonyl, and sulfinyl; and any methylene group of the o, p, and q regions, or $Y_2$, is optionally independently substituted with $C_{1-4}$ alkyl, halo, $C_{1-4}$ haloalkyl, or $C_3$ or $C_4$ cycloalkyl.

In some embodiments, the present invention provides therapeutic methods that utilize compounds of Formula IV

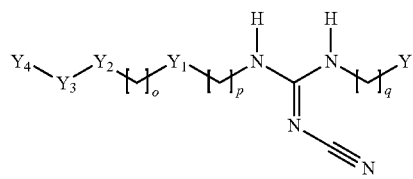

Formula IV and pharmaceutically acceptable salts and solvates thereof; wherein:

o, p, q, Y, $Y_1$, $Y_2$, $Y_3$, and $Y_4$ are as defined for Formula III above;

with the proviso that when $Y_1$ is divalent phenyl, q is 0, and p is 1, then $Y_4$ is present;

with the proviso that when $Y_1$ is $C_{2-8}$ alkylene and q is 0, then $Y_4$ is present; and with the proviso that the compound is NOT:

2-cyano-1-[[4-[(4-phenylphenyl)sulfonylamino]phenyl]methyl]-3-(4-pyridyl)guanidine.

In some embodiments, the present invention provides therapeutic methods that utilize compounds of Formula IVa

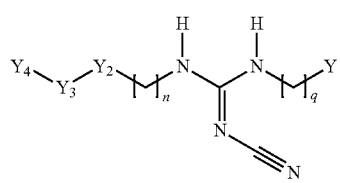

Formula IVa and pharmaceutically acceptable salts and solvates thereof; wherein:

Y is 3-pyridinyl or 4-pyridinyl, optionally substituted as defined for Y for Formula I;

$Y_2$, $Y_3$, $Y_4$, and q are as defined for Formula IV above;

n is 3, 4, 5, 6, or 7; and any methylene group of $Y_2$ and the n and q regions is optionally independently substituted with $C_{1-4}$ alkyl, halo, $C_{1-4}$ haloalkyl, or $C_3$ or $C_4$ cycloalkyl.

In some embodiments, the present invention provides therapeutic methods that utilize compounds of Formula IVa1

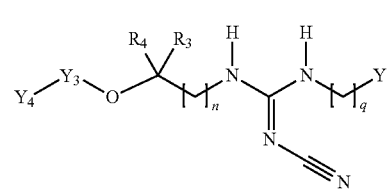

Formula IVa1 and pharmaceutically acceptable salts and solvates thereof; wherein:

Y is as defined for Formula IVa above;

$Y_3$, $Y_4$, and q are as defined for Formula IV above;

n is 3, 4, 5, 6, or 7;

any methylene group of the n and q regions is optionally independently substituted with $C_{1-4}$ alkyl, halo, $C_{1-4}$ haloalkyl, or $C_3$ or $C_4$ cycloalkyl; and $R_3$ and $R_4$ are each independently H, halo, or $C_{1-4}$ alkyl, or $R_3$ and $R_4$ taken together form a cyclopropyl or cyclobutyl ring.

In some embodiments, the present invention provides therapeutic methods that utilize compounds of Formula IVa2

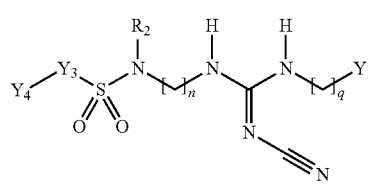

Formula IVa2 and pharmaceutically acceptable salts and solvates thereof; wherein:

Y is as defined for Formula IVa above;

$Y_3$, $Y_4$, and q are as defined for Formula IV above;

n is 3, 4, 5, 6, or 7;

any methylene group of the n and q regions is optionally independently substituted with $C_{1-4}$ alkyl, halo, $C_{1-4}$ haloalkyl, or $C_3$ or $C_4$ cycloalkyl; and $R_2$ is H, halo, $C_{1-5}$ alkyl, $C_{1-5}$ alkenyl, or $C_{1-5}$ alkynyl.

In some embodiments, the present invention provides therapeutic methods that utilize compounds of Formula IVa3

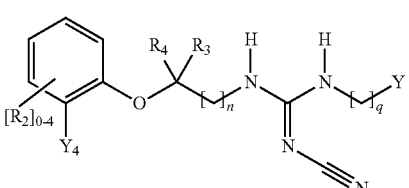

Formula IVa3 and pharmaceutically acceptable salts and solvates thereof; wherein:

Y is as defined for Formula IVa above;

$Y_4$ and q are as defined for Formula IV above;

n is 3, 4, 5, 6, or 7;

any methylene group of the n and q regions is optionally independently substituted with $C_{1-4}$ alkyl, halo, $C_{1-4}$ haloalkyl, or $C_3$ or $C_4$ cycloalkyl;

R₁, if present one or more times, is independently selected from halo, C₁₋₅ alkyl, nitro, cyano, C₁₋₅ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein C₁₋₅ alkyl, C₁₋₅ alkoxy, C-amido, N-amido, amino, aminoalkyl, and alkylthio are each optionally substituted with heterocyclo, cycloalkyl, or amino; and R₃ and R₄ are each independently H, halo, or C₁₋₄ alkyl, or R₃ and R₄, taken together with the carbon to which they are attached, form a cyclopropyl or cyclobutyl ring.

In some embodiments, the present invention provides therapeutic methods that utilize compounds of Formula IVa4

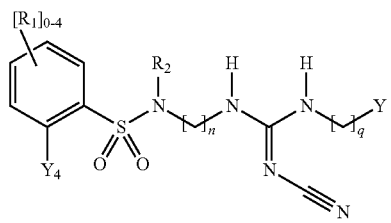

Formula IVa4 and pharmaceutically acceptable salts and solvates thereof; wherein:
Y is as defined for Formula IVa above;
Y₄ and q are as defined for Formula IV above;
n is 3, 4, 5, 6, or 7;
any methylene group of the n and q regions is optionally independently substituted with C₁₋₄ alkyl, halo, C₁₋₄ haloalkyl, or C₃ or C₄ cycloalkyl;
R₁, if present one or more times, is independently selected from halo, C₁₋₅ alkyl, nitro, cyano, C₁₋₅ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein C₁₋₅ alkyl, C₁₋₅ alkoxy, C-amido, N-amido, amino, aminoalkyl, and alkylthio are each optionally substituted with heterocyclo, cycloalkyl, or amino; and
R₂ is H, halo, C₁₋₅ alkyl, C₁₋₅ alkenyl, or C₁₋₅ alkynyl.

In some embodiments, the present invention provides therapeutic methods that utilize compounds of Formula IVa5

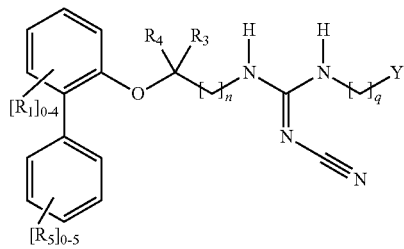

Formula IVa5 and pharmaceutically acceptable salts and solvates thereof; wherein:
Y is as defined for Formula IVa above;
q is as defined for Formula IV above;
n is 3, 4, 5, 6, or 7;
any methylene group of the n and q regions is optionally independently substituted with C₁₋₄ alkyl, halo, C₁₋₄ haloalkyl, or C₃ or C₄ cycloalkyl;
R₁ and R₅, if one or both are present one or more times, are each independently selected from halo, C₁₋₅ alkyl, nitro, cyano, C₁₋₅ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein C₁₋₅ alkyl, C₁₋₅ alkoxy, C-amido, N-amido, amino, aminoalkyl, and alkylthio are each optionally substituted with heterocyclo, cycloalkyl, or amino; and R₃ and R₄ are each independently H, halo, or C₁₋₄ alkyl, or R₃ and R₄, taken together with the carbon to which they are attached, form a cyclopropyl or cyclobutyl ring.

In some embodiments, the present invention provides therapeutic methods that utilize compounds of Formula IVa6

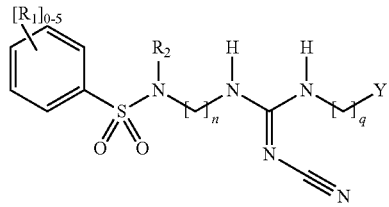

Formula IVa6 and pharmaceutically acceptable salts and solvates thereof; wherein:
Y is as defined for Formula IVa above;
q is as defined for Formula IV above;
n is 3, 4, 5, 6, or 7;
any methylene group of the n and q regions is optionally independently substituted with C₁₋₄ alkyl, halo, C₁₋₄ haloalkyl, or C₃ or C₄ cycloalkyl;
R₁, if present one or more times, is independently selected from halo, C₁₋₅ alkyl, nitro, cyano, C₁₋₅ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein C₁₋₅ alkyl, C₁₋₅ alkoxy, C-amido, N-amido, amino, aminoalkyl, and alkylthio are each optionally substituted with heterocyclo, cycloalkyl, or amino; and
R₂ is H, halo, C₁₋₅ alkyl, C₁₋₅ alkenyl, or C₁₋₅ alkynyl.

In some embodiments, the present invention provides therapeutic methods that utilize compounds of Formula IVb

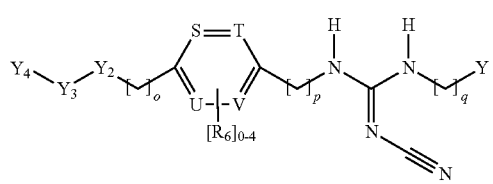

Formula IVb and pharmaceutically acceptable salts and solvates thereof; wherein:
Y is 3-pyridinyl or 4-pyridinyl, optionally substituted as defined for Y for Formula I;
o, p, q, Y₂, Y₃, and Y₄ are as defined for Formula IV above;
any methylene group of the o, p, and q regions and Y₂ is optionally independently substituted with C₁₋₄ alkyl, halo, C₁₋₄ haloalkyl, or C₃ or C₄ cycloalkyl;
R₆, if present one or more times, is independently selected from halo, C₁₋₅ alkyl, nitro, cyano, C₁₋₅ alkoxy, C-amido, N-amido, trihalomethyl, C-carboxy, O-carboxy, sulfonamide, amino, hydroxyl, mercapto, alkylthio, sulfonyl, and sulfinyl;
wherein S, T, U, and V are carbon or nitrogen, provided that when S, T, U, or V is nitrogen, then there is no substituent on the nitrogen;
with the proviso that when q is O, S, T, U, and V are carbon, and p is 1, then Y₄ is present; and
with the proviso that the compound is NOT 2-cyano-1-[[4-[(4-phenylphenyl)sulfonylamino]phenyl]methyl]-3-(4-pyridyl)guanidine.

In some embodiments, the present invention provides therapeutic methods that utilize compounds of Formula IVb1

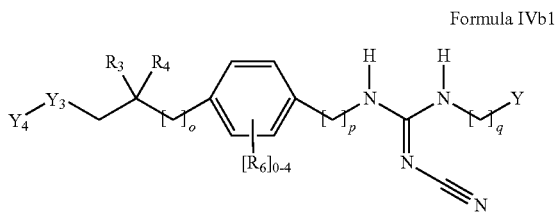

Formula IVb1 and pharmaceutically acceptable salts and solvates thereof; wherein:

Y and $R_6$ are as defined for Formula IVb above;

o, p, q, $Y_3$, and $Y_4$ are as defined for Formula IV above;

any methylene group of the o, p, and q regions is optionally independently substituted with $C_{1-4}$ alkyl, halo, $C_{1-4}$ haloalkyl, or $C_3$ or $C_4$ cycloalkyl; and $R_3$ and $R_4$ are each independently H, halo, or $C_{1-4}$ alkyl, or $R_3$ and $R_4$, taken together with the carbon to which they are attached, form a cyclopropyl or cyclobutyl ring.

In some embodiments, the present invention provides therapeutic methods that utilize compounds of Formula IVb2

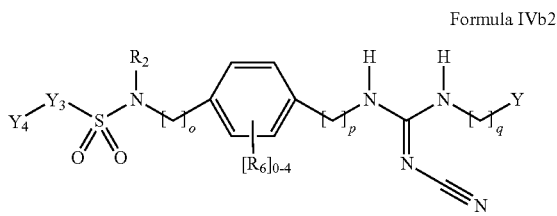

Formula IVb2 and pharmaceutically acceptable salts and solvates thereof; wherein:

Y and $R_6$ are as defined for Formula IVb above;

o, p, q, $Y_3$, and $Y_4$ are as defined for Formula IV above;

any methylene group of the o, p, and q regions is optionally independently substituted with $C_{1-4}$ alkyl, halo, $C_{1-4}$ haloalkyl, or $C_3$ or $C_4$ cycloalkyl;

$R_2$ is H, halo, $C_{1-5}$ alkyl, $C_{1-5}$ alkenyl, or $C_{1-5}$ alkynyl; and with the proviso that the compound is NOT 2-cyano-1-[[4-[(4-phenylphenyl)sulfonylamino]phenyl]methyl]-3-(4-pyridyl)guanidine.

In some embodiments, the present invention provides therapeutic methods that utilize compounds of Formula IVb3

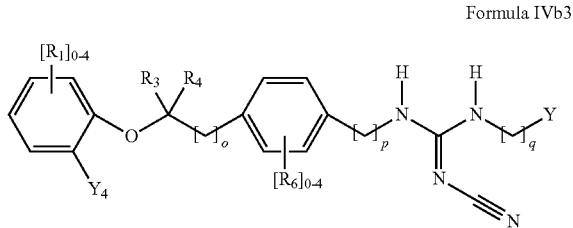

Formula IVb3 and pharmaceutically acceptable salts and solvates thereof; wherein:

Y and $R_6$ are as defined for Formula IVb above;

o, p, q, and $Y_4$ are as defined for Formula IV above;

$R_1$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;

$R_3$ and $R_4$ are each independently H, halo, or $C_{1-4}$ alkyl, or $R_3$ and $R_4$, taken together with the carbon to which they are attached, form a cyclopropyl or cyclobutyl ring; and any methylene group of the o, p, and q regions is optionally independently substituted with $C_{1-4}$ alkyl, halo, $C_{1-4}$ haloalkyl, or $C_3$ or $C_4$ cycloalkyl.

In some embodiments, the present invention provides therapeutic methods that utilize compounds of Formula IVb4

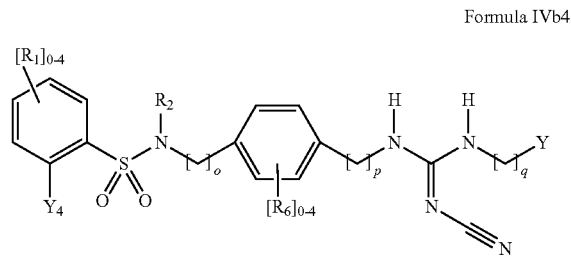

Formula IVb4 and pharmaceutically acceptable salts and solvates thereof; wherein:

Y and $R_6$ are as defined for Formula IVb above;

o, p, q, and $Y_4$ are as defined for Formula IV above;

$R_1$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;

$R_2$ is H, halo, $C_{1-5}$ alkyl, $C_{1-5}$ alkenyl, or $C_{1-5}$ alkynyl;

any methylene group of the o, p, and q regions is optionally independently substituted with $C_{1-4}$ alkyl, halo, $C_{1-4}$ haloalkyl, or $C_3$ or $C_4$ cycloalkyl.

In some embodiments, the present invention provides therapeutic methods that utilize compounds of Formula IVb5

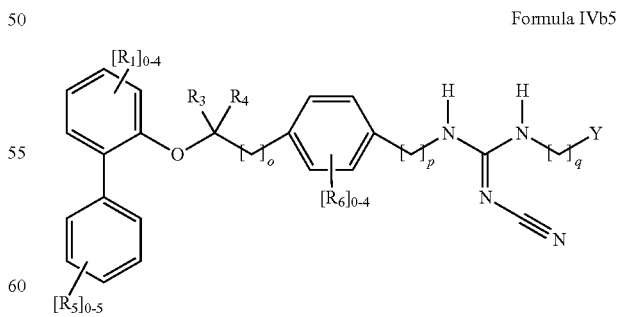

Formula IVb5 and pharmaceutically acceptable salts and solvates thereof; wherein:

Y and $R_6$ are as defined for Formula IVb above;

o, p, and q are as defined for Formula IV above;

$R_1$ and $R_5$, if one or both are present one or more times, are each independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;

$R_3$ and $R_4$ are each independently H, halo, or $C_{1-4}$ alkyl, or $R_3$ and $R_4$, taken together with the carbon to which they are attached, form a cyclopropyl or cyclobutyl ring; and any methylene group of the o, p, and q regions is optionally independently substituted with $C_{1-4}$ alkyl, halo, $C_{1-4}$ haloalkyl, or $C_3$ or $C_4$ cycloalkyl.

In some embodiments, the present invention provides therapeutic methods that utilize compounds of Formula IVb6

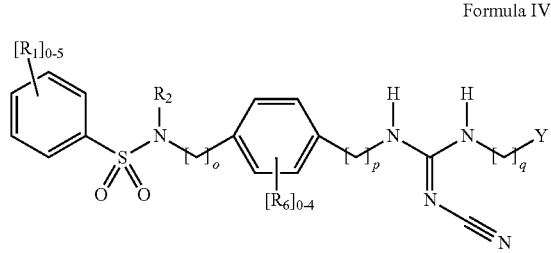

Formula IVb6 and pharmaceutically acceptable salts and solvates thereof; wherein:

Y and $R_6$ are as defined for Formula IVb above;

o, p, and q are as defined for Formula IV above;

$R_1$ and $R_5$, if one or both are present one or more times, are each independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;

$R_2$ is H, halo, $C_{1-5}$ alkyl, $C_{1-5}$ alkenyl, or $C_{1-5}$ alkynyl; and any methylene group of the o, p, and q regions is optionally independently substituted with $C_{1-4}$ alkyl, halo, $C_{1-4}$ haloalkyl, or $C_3$ or $C_4$ cycloalkyl.

In some embodiments, the present invention provides therapeutic methods that utilize compounds of Formula IVb7

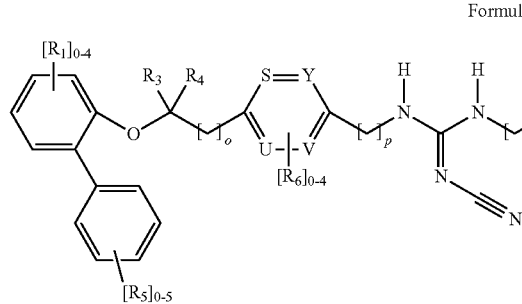

Formula IVb7 and pharmaceutically acceptable salts and solvates thereof; wherein:

Y and $R_6$ are as defined for Formula IVa above;

o, p, and q are as defined for Formula IV above;

$R_1$ and $R_5$, if one or both are present one or more times, are each independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;

$R_3$ and $R_4$ are each independently H, halo, or $C_{1-4}$ alkyl, or $R_3$ and $R_4$, taken together with the carbon to which they are attached, form a cyclopropyl or cyclobutyl ring;

any methylene group of the o, p, and q regions is optionally independently substituted with $C_{1-4}$ alkyl, halo, $C_{1-4}$ haloalkyl, or $C_3$ or $C_4$ cycloalkyl; and S, T, U, and V are carbon or nitrogen, provided that at least one of S, T, U, and V is nitrogen and that when S, T, U, or V is nitrogen, then there is no substituent on the nitrogen.

In some embodiments, the present invention provides therapeutic methods that utilize compounds of Formula IVb8

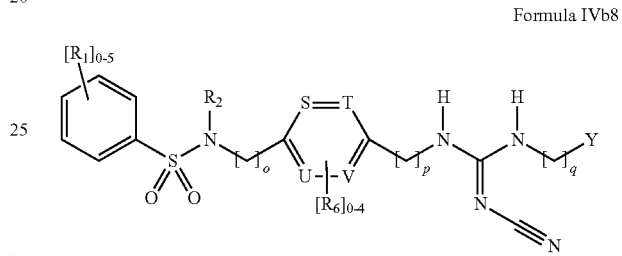

Formula IVb8 and pharmaceutically acceptable salts and solvates thereof; wherein:

Y and $R_6$ are as defined for Formula IVb above;

o, p, and q are as defined for Formula IV above;

$R_1$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;

$R_2$ is H, halo, $C_{1-5}$ alkyl, $C_{1-5}$ alkenyl, or $C_{1-5}$ alkynyl;

any methylene group of the o, p, and q regions is optionally independently substituted with $C_{1-4}$ alkyl, halo, $C_{1-4}$ haloalkyl, or $C_3$ or $C_4$ cycloalkyl; and S, T, U, and V are carbon or nitrogen, provided that at least one of S, T, U, and V is nitrogen and that when S, T, U, or V is nitrogen, then there is no substituent on the nitrogen.

In some embodiments, the present invention provides therapeutic methods that utilize compounds of Formula IVc

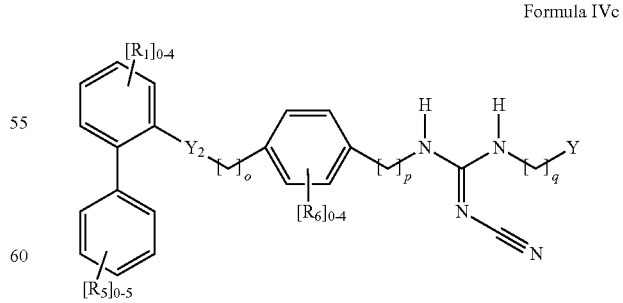

Formula IVc and pharmaceutically acceptable salts and solvates thereof; wherein:

Y is 3-pyridinyl or 4-pyridinyl, optionally substituted as defined for Y for Formula I;

$Y_2$, o, p, and q are as defined for Formula IV;

$R_1$ and $R_5$, if one or both are present one or more times, are each independently selected from halo, $C_{1-5}$ alkyl, nitro, cyano, $C_{1-5}$ alkoxy, C-amido, N-amido, trihalomethyl, C-carboxy, O-carboxy, sulfonamide, amino, aminoalkyl, hydroxyl, mercapto, alkylthio, sulfonyl, and sulfinyl, wherein $C_{1-5}$ alkyl, $C_{1-5}$ alkoxy, C-amido, N-amido, amino, aminoalkyl, and alkylthio are each optionally substituted with heterocyclo, cycloalkyl, or amino;

$R_6$, if present one or more times, is independently selected from halo, $C_{1-5}$ alkyl, nitro, cyano, $C_{1-5}$ alkoxy, C-amido, N-amido, trihalomethyl, C-carboxy, O-carboxy, sulfonamide, amino, hydroxyl, mercapto, alkylthio, sulfonyl, and sulfinyl; and any methylene group of the o, p, and q regions, or $Y_2$, is optionally independently substituted with $C_{1-4}$ alkyl, halo, $C_{1-4}$ haloalkyl, or $C_3$ or $C_4$ cycloalkyl; and with the proviso that when $Y_2$ is —C(=O)N(H)—, then $Y_4$ is present.

In some embodiments of the compounds of each of Formulae I, Ia, Ia1, Ia2, Ib, Ib1, Ib2, Ib3, Ic, and Id, $Z_0$ is carbocycle, cycloalkyl, cycloalkenyl, heterocycle, heterocyclonoyl, aryl, heteroaryl, carbocycloalkyl, heterocyclylalkyl, arylalkyl, arylalkenyl, heteroarylalkyl, heteroarylalkenyl, heteroarylalkynyl, or arylalkynyl, wherein each of the foregoing groups is substituted at least once with alkyl, alkylene, alkenyl, alkenylene, alkynyl, carbocycle, cycloalkyl, cycloalkenyl, heterocycle, aryl, heteroaryl, halo, hydro, hydroxyl, alkoxy, alkynyloxy, cycloalkyloxy, heterocycloxy, aryloxy, heteroaryloxy, arylalkoxy, heteroarylalkoxy, mercapto, alkylthio, arylthio, arylalkyl, heteroarylalkyl, heteroarylalkenyl, arylalkynyl, haloalkyl, aldehyde, thiocarbonyl, heterocyclonoyl, O-carboxy, C-carboxy, carboxylic acid, ester, C-carboxy salt, carboxyalkyl, carboxyalkenylene, carboxyalkyl salt, carboxyalkoxy, carboxyalkoxyalkanoyl, amino, aminoalkyl, nitro, O-carbamyl, N-carbamyl, O-thiocarbamyl, N-thiocarbamyl, C-amido, N-amido, aminothiocarbonyl, hydroxyaminocarbonyl, alkoxyaminocarbonyl, cyano, nitrile, cyanato, isocyanato, thiocyanato, isothiocyanato, sulfinyl, sulfonyl, sulfonamide, aminosulfonyl, aminosulfonyloxy, sulfonamidecarbonyl, alkanoylaminosulfonyl, trihalomethylsulfonyl, or trihalomethylsulfonamide.

In some embodiments of the compounds of each of Formulae I, Ia, Ia1, Ia2, Ib, Ib1, Ib2, Ib3, Ic, and Id, $Z_0$ is selected from optionally substituted aryl, optionally substituted heteroaryl, optionally substituted carbocycle, and optionally substituted heterocycle.

In some embodiments of the compounds of each of Formulae I, Ia, Ia1, Ia2, Ib, Ib1, Ib2, Ib3, Ic, and Id, $Z_0$ is aryl optionally independently substituted one or more times with optionally substituted alkyl, N-amido, optionally substituted carbocycle, optionally substituted carbocycloamino, optionally substituted heterocycle, optionally substituted heterocycloalkyl, optionally substituted heterocycloamino, optionally substituted heterocyclonoyl, optionally substituted aryl, optionally substituted heteroaryl, halo, hydro, hydroxyl, optionally substituted hydroxyalkyl, optionally substituted haloalkoxy, optionally substituted alkoxy, optionally substituted aminoalkoxy, optionally substituted heterocycloalkoxy, optionally substituted haloalkyl, optionally substituted amino, optionally substituted aminoalkyl, nitro, optionally substituted C-amido, optionally substituted N-amido, cyano, or optionally substituted sulfonamide.

In some embodiments of the compounds of each of Formulae I, Ia, Ia1, Ia2, Ib, Ib1, Ib2, Ib3, Ic, and Id, $Z_0$ is a first aryl substituted with a second aryl, wherein each of the first aryl and the second aryl are optionally independently substituted one or more times with alkyl, N-amido, optionally substituted carbocycle, carbocycloamino, optionally substituted heterocycle, heterocycloalkyl, heterocycloamino, heterocyclonoyl, halo, hydro, hydroxyl, hydroxyalkyl, haloalkoxy, alkoxy, aminoalkoxy, heterocycloalkoxy, haloalkyl, optionally substituted amino, aminoalkyl, nitro, optionally substituted C-amido, optionally substituted N-amido, cyano, or sulfonamide. In some of such embodiments, the first aryl is phenyl. In some of such embodiments, the second aryl is phenyl. In some of such embodiments, the first aryl and the second aryl are both phenyl.

In some embodiments of the compounds of each of Formulae I, Ia, Ia1, Ia2, Ib, Ib1, Ib2, Ib3, Ic, and Id, $Z_0$ is optionally substituted phenyl, optionally substituted 2-pyridinyl, optionally substituted 3-pyridinyl, optionally substituted 4-pyridinyl, optionally substituted pyrimidine, optionally substituted pyrazine, optionally substituted pyrazole, optionally substituted thiophene, optionally substituted ortho-biphenyl, optionally substituted 1-naphthalenyl, optionally substituted 2-naphthalenyl, optionally substituted quinazoline, optionally substituted benzothiadiazine, optionally substituted indole, and optionally substituted pyridopyrimidine.

In some embodiments of the compounds of each of Formulae II, IIa, IIa1, IIa2, IIa3, IIa4, IIb, IIb1, IIb2, IIb3, IIb4, IIb5, IIb6, IIb7, IIc, IIc1, IId, and IId1, Z is hydro, alkyl, N-amido, optionally substituted carbocycle, carbocycloamino, optionally substituted heterocycle, heterocycloalkyl, heterocycloamino, heterocyclonoyl, optionally substituted aryl, optionally substituted heteroaryl, halo, hydro, hydroxyl, hydroxyalkyl, haloalkoxy, alkoxy, aminoalkoxy, heterocycloalkoxy, haloalkyl, optionally substituted amino, aminoalkyl, nitro, optionally substituted C-amido, optionally substituted N-amido, cyano, or sulfonamide.

In some embodiments of the compounds of each of Formulae II, IIa, IIa1, IIa2, IIa3, IIa4, IIb, IIb1, IIb2, IIb3, IIb4, IIb5, IIb6, IIb7, IIc, IIc1, IId, and IId1, Z is hydro, optionally substituted phenyl, optionally substituted pyridinyl, optionally substituted pyrimidine, optionally substituted pyrazole, optionally substituted piperidine, optionally substituted morpholine, optionally substituted piperazine, optionally substituted thiophene, optionally substituted imidazole, optionally substituted oxadiazole, optionally substituted oxazole, optionally substituted isoxazole, optionally substituted cyclohexyl, optionally substituted cyclohexylamino, optionally substituted piperidinylamino, or optionally substituted pyrrolidine.

In some embodiments of the compounds of each of Formulae IIa3, IIa4, IIb4, IIb5, IIb6, IIb7, IIc1, IId1, IIIa3, IIIa4, IIIa5, IIIa6, IIIb4, IIIb5, IIIb6, IIIb7, IIIb8, IIIb9, IIIb10, IIIb11, and IIIc, $R_1$ is not present, or is present one, two, three, or four times. In some embodiments of the compounds of each of Formulae IIIa6, IIIb8, and IIIb11, $R_1$ is present five times.

In some embodiments of the compounds of each of Formulae IIa3, IIa4, IIb4, IIb5, IIb6, IIb7, IIc1, IId1, IIIa3, IIIa4, IIIa5, IIIa6, IIIb4, IIIb5, IIIb6, IIIb7, IIIb8, IIIb9, IIIb10, IIIb11, IIIc, IVa3, IVa4, IVa5, IVb3, IVb4, IVb5, IVb7, and IVc, $R_1$ is an electron-withdrawing group, such as by way of non-limiting example, halo, trihalomethyl, nitro, cyano, C-carboxy, O-carboxy, C-amido, and N-amido.

In some embodiments of the compounds of each of Formulae IIIa4, IIIb5, IVa4, and IVb4, $Y_4$ is not present, $R_1$ is present two or three times, and each instance of $R_1$ is an electron-withdrawing group.

In some embodiments of the compounds of each of Formulae IIa3, IIa4, IIb4, IIb5, IIb6, IIb7, IIc1, IId1, IIIa3, IIIa4, IIIa5, IIIa6, IIIb4, IIIb5, IIIb6, IIIb7, IIIb8, IIIb9, IIIb10, IIIb11, IIIc, IVa3, IVa4, IVa5, IVb3, IVb4, IVb5, IVb7, and IVc, $R_1$ is selected from $C_{1-5}$ alkyl, $C_{1-5}$ alkoxy, C-amido, N-amido, amino, aminoalkyl, or alkylthio, each further substituted with heterocyclo, cycloalkyl, or amino.

In some embodiments of the compounds of each of Formulae IIIa5, IIIb7, IIIb10, and IIIc, $R_5$ is not present or is present, one, two, three, four, or five times. In some embodiments of the compounds of each of Formulae IIIa5, IIIb7, IIIb8, IIIb9, IIIb10, IIIc, IVa5, IVb5, IVb7, and IVc, $R_5$ is selected from $C_{1-5}$ alkyl, $C_{1-5}$ alkoxy, C-amido, N-amido, amino, aminoalkyl, or alkylthio, each further substituted with heterocyclo, cycloalkyl, or amino.

In some embodiments of the compounds of each of Formulae IIa3, IIa4, IIb4, IIb5, IIb6, IIb7, IIc1, IId1, IIIa3, IIIa4, IIIa5, IIIa6, IIIb4, IIIb5, IIIb6, IIIb7, IIIb8, IIIb9, IIIb1, IIIb1, IIIc, IVa3, IVa4, IVa5, IVb3, IVb4, IVb5, IVb7, and IVc, $R_1$ is selected from the following:

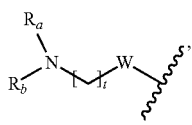

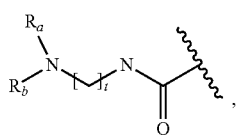

or

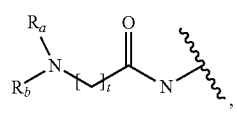

wherein t is 0, 1, 2, 3, or 4, W is N(H), O, C(H)$_2$, or S, and $R_a$ and $R_b$ are each independently hydro, $C_{3-6}$ cycloalkyl, or $C_{1-6}$ alkyl, or $R_a$ and $R_b$, together with the linking nitrogen between them, form azetidine, pyrrolidine, or piperidine.

In some embodiments of the compounds of each of Formulae IIIa5, IIIb7, IIIb8, IIIb9, IIIb10, IIIc, IVa5, IVb5, IVb7, and IVc, $R_5$ is selected from the following:

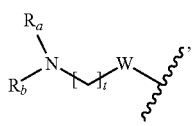

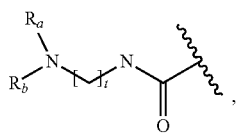

or

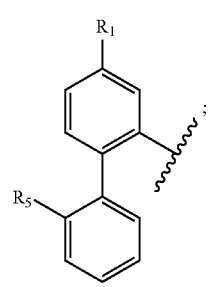

wherein t is 0, 1, 2, 3, or 4, W is N(H), O, C(H)$_2$, or S, and $R_a$ and $R_b$ are each independently hydro, $C_{3-6}$ cycloalkyl, or $C_{1-6}$ alkyl, or $R_a$ and $R_b$, together with the linking nitrogen between them, form azetidine, pyrrolidine, or piperidine.

In some embodiments of the compounds of each of Formulae IIIa5, IIIb7, IIIb8, IIIb9, IIIb10, IIIc, IVa5, IVb5, IVb7, and IVc, $R_1$ and/or $R_5$ is present and is located on the biphenyl ring as shown below:

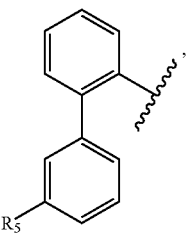

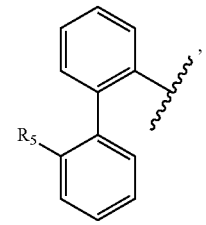

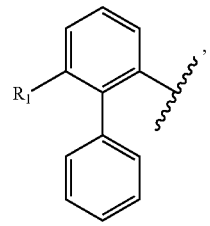

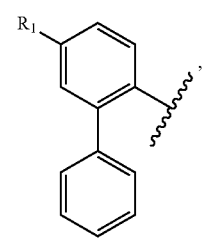

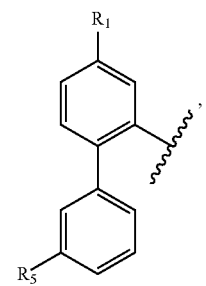

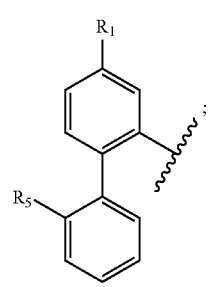

wherein $R_1$ and $R_5$ are each selected from the following:

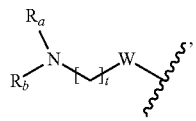

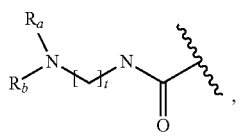

or

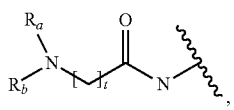

wherein t is 0, 1, 2, 3, or 4, W is N(H), O, C(H)$_2$, or S, and $R_a$ and $R_b$ are each independently hydro, $C_{3-6}$ cycloalkyl, or $C_{1-6}$ alkyl, or $R_a$ and $R_b$, together with the linking nitrogen between them, form azetidine, pyrrolidine, or piperidine; with the proviso that when $R_1$ and $R_5$ are both present on the biphenyl ring, then $R_1$ is $C_{1-4}$ haloalkyl (such as, for example, trifluoromethyl) or halo (such as, for example, chloro).

In some embodiments of the compounds of each of Formulae Ia2, Ib2, Id, IIa2, IIa4, IIb2, IIb5, IId, IId1, IIIa2, IIIa4, IIIa6, IIIb2, IIIb5, IIIb5IIIb8, IIIb11, IVa2, IVa4, IVa6, IVb2, IVb4, IVb6, and IVb8, $R_2$ is hydrogen or cyclopropyl. In some of such embodiments, $R_2$ is hydrogen.

In some embodiments of the compounds of each of Formulae I, II, III, and IV, R for the purposes of Y is hydrogen.

In some embodiments of the compounds of each of Formulae I, II, III, and IV, R for the purposes of $Y_1$ is hydrogen.

In some embodiments of the compounds of each of Formulae I, II, III, and IV, R for the purposes of $Y_2$ is hydrogen.

In some embodiments of the compounds of each of Formulae Ib1, Ic, IIb1, IIb4, IIc, IIc1, IIIa1, IIIa3, IIIa5, IIIb1, IIIb4, IIIb7, IIIb8, IIIb9, IIIb10, IIIc, IVa1, IVa3, IVa5, IVb1, IVb3, IVb5, and IVb7, $R_3$ and $R_4$ are both hydrogen or both fluoro. In some of such embodiments, $R_3$ and $R_4$ are both hydrogen.

In some embodiments of the compounds of each of Formulae Ib, Ib1, Ib2, Ib3, IIb, IIb1, IIb2, IIb3, IIb4, IIb5, IIb6, IIb7, IIIb, IIIb1, IIIb2, IIIb3, IIIb4, IIIb5, IIIb6, IIIb7, IIIb8, IIIb9, IIIb10, IIIb11, IIIc, IVb, IVb1, IVb2, IVb3, IVb4, IVb5, IVb6, IVb7, IVb8, and IVc, $R_6$ is not present, or is present one, two, three, or four times. In some of such embodiments $R_6$, is not present or is fluoro, methyl, or trifluormethyl. In some of such embodiments $R_6$ is not present.

In some embodiments of the compounds of each of Formulae Ia, Ia1, Ia2, IIa, IIa1, IIa2, IIa3, IIa4, IIIa, IIa1, IIIa2, IIIa3, IIIa4, IIIa5, IIIa6, IVa, IVa1, IVa2, Iva3, IVa4, IVa5, and IVa6, n is 4, 5, or 6. In some embodiments of the compounds of each of Formulae Ia, Ia1, Ia2, IIa, IIa1, IIa2, IIa3, IIa4, IIIa, IIa1, IIIa2, IIIa3, IIIa4, IIIa5, IIIa6, IVa, IVa1, IVa2, Iva3, IVa4, IVa5, and IVa6, n is 4. In some embodiments of the compounds of each of Formulae Ia, Ia1, Ia2, IIa, IIa1, IIa2, IIa3, IIa4, IIIa, IIa1, IIIa2, IIIa3, IIIa4, IIIa5, IIIa6, IVa, IVa1, IVa2, Iva3, IVa4, IVa5, and IVa6, n is 5. In some embodiments of the compounds of each of Formulae Ia, Ia1, Ia2, IIa, IIa1, IIa2, IIa3, IIa4, IIIa, IIa1, IIIa2, IIIa3, IIIa4, IIIa5, IIIa6, IVa, IVa1, IVa2, Iva3, IVa4, IVa5, and IVa6, n is 6. In some embodiments of the compounds of each of Formulae Ia, Ia1, Ia2, IIa, IIa1, IIa2, IIa3, IIa4, IIIa, IIa1, IIIa2, IIIa3, IIIa4, IIIa5, IIIa6, IVa, IVa1, IVa2, Iva3, IVa4, IVa5, and IVa6, any methylene groups of the n region are optionally substituted with fluoro or methyl. In some embodiments of the compounds of each of Formulae Ia, Ia1, Ia2, IIa, IIa1, IIa2, IIa3, IIa4, IIIa, IIa1, IIIa2, IIIa3, IIIa4, IIIa5, IIIa6, IVa, IVa1, IVa2, Iva3, IVa4, IVa5, and IVa6, any methylene groups of the n region are all fully saturated.

In some embodiments of the compounds of each of Formulae III, IIIb, IIIb1, IIIb2, IIIb3, IIIb4, IIIb5, IIIb6, IIIb7, IIIb8, IIIb9, IIIb10, IIIb11, IIIc, IVb, IVb1, IVb2, IVb3, IVb4, IVb5, IVb6, IVb7, IVb8, and IVc, o is 0. In some embodiments of the compounds of each of Formulae IIIIII, IIIb, IIIb1, IIIb2, IIIb3, IIIb4, IIIb5, IIIb6, IIIb7, IIIb8, IIIb9, IIIb10, IIIb11, IIIc, IVb, IVb1, IVb2, IVb3, IVb4, IVb5, IVb6, IVb7, IVb8, and IVc, o is 1. In some embodiments of the compounds of each of Formulae III, IIIb, IIIb1, IIIb2, IIIb3, IIIb4, IIIb5, IIIb6, IIIb7, IIIb8, IIIb9, IIIb10, IIIb11, IIIc, IVb, IVb1, IVb2, IVb3, IVb4, IVb5, IVb6, IVb7, IVb8, and IVc, o is 2. In some embodiments of the compounds of each of Formulae III, IIIb, IIIb1, IIIb2, IIIb3, IIIb4, IIIb5, IIIb6, IIIb7, IIIb8, IIIb9, IIIb1, IIIb11, IIIc, IVb, IVb1, IVb2, IVb3, IVb4, IVb5, IVb6, IVb7, IVb8, and IVc, any methylene groups of the o region are optionally substituted with fluoro or methyl. In some embodiments of the compounds of each of Formulae III, IIIb, IIIb1, IIIb2, IIIb3, IIIb4, IIIb5, IIIb6, IIIb7, IIIb8, IIIb9, IIIb10, IIIb11, IIIc, IVb, IVb1, IVb2, IVb3, IVb4, IVb5, IVb6, IVb7, IVb8, and IVc, any methylene groups of the o region are all fully saturated.

In some embodiments of the compounds of each of Formulae III, IIIb, IIIb1, IIIb2, IIIb3, IIIb4, IIIb5, IIIb6, IIIb7, IIIb8, IIIb9, IIIb10, IIIb11, IIIc, IVb, IVb1, IVb2, IVb3, IVb4, IVb5, IVb6, IVb7, IVb8, and IVc, p is 0. In some embodiments of the compounds of each of Formulae III, IIIb, IIIb1, IIIb2, IIIb3, IIIb4, IIIb5, IIIb6, IIIb7, IIIb8, IIIb9, IIIb10, IIIb11, IIIc, IVb, IVb1, IVb2, IVb3, IVb4, IVb5, IVb6, IVb7, IVb8, and IVc, p is 1. In some embodiments of the compounds of each of Formulae III, IIIb, IIIb1, IIIb2, IIIb3, IIIb4, IIIb5, IIIb6, IIIb7, IIIb8, IIIb9, IIIb10, IIIb11, IIIc, IVb, IVb1, IVb2, IVb3, IVb4, IVb5, IVb6, IVb7, IVb8, and IVc, p is 2. In some embodiments of the compounds of each of Formulae III, IIIb, IIIb1, IIIb2, IIIb3, IIIb4, IIIb5, IIIb6, IIIb7, IIIb8, IIIb9, IIIb10, IIIb11, IIIc, IVb, IVb1, IVb2, IVb3, IVb4, IVb5, IVb6, IVb7, IVb8, and IVc, any methylene groups of the p region are optionally substituted with fluoro or methyl. In some embodiments of the compounds of each of Formulae III, IIIb, IIIb1, IIIb2, IIIb3, IIIb4, IIIb5, IIIb6, IIIb7, IIIb8, IIIb9, IIIb10, IIIb11, IIIc, IVb, IVb1, IVb2, IVb3, IVb4, IVb5, IVb6, IVb7, IVb8, and IVc, any methylene groups of the p region are all fully saturated.

In some embodiments of the compounds of each of Formulae III, IIIa, IIIa1, IIa2, IIIa3, IIIa4, IIIa5, IIIa6, IIIb, IIIb1, IIIb2, IIIb3, IIIb4, IIIb5, IIIb6, IIIb7, IIIb8, IIIb9, IIIb10, IIIb11, IIIc, IV, IVa, IVa1, IVa2, Iva3, IVa4, IVa5, IVa6, IVb, IVb1, IVb2, IVb3, IVb4, IVb5, IVb6, IVb7, IVb8, and IVc, q is 0. In some embodiments of the compounds of each of Formulae III, IIIa, IIIa1, IIIa2, IIIa3, IIIa4, IIIa5, IIIa6, IIIb, IIIb1, IIIb2, IIIb3, IIIb4, IIIb5, IIIb6, IIIb7, IIIb8, IIIb9, IIIb10, IIIb11, IIIc, IV, IVa, IVa1, IVa2, Iva3, IVa4, IVa5, IVa6, IVb, IVb1, IVb2, IVb3, IVb4, IVb5, IVb6, IVb7, IVb8, and IVc, q is 1. In some embodiments of the compounds of each of Formulae III, IIIa, IIIa1, IIIa2, IIIa3, IIIa4, IIIa5, IIIa6, IIIb, IIIb1, IIIb2, IIIb3, IIIb4, IIIb5, IIIb6, IIIb7, IIIb8, IIIb9, IIIb1, IIIb11, IIIc, IV, IVa, IVa1, IVa2, Iva3, IVa4, IVa5, IVa6, IVb, IVb1, IVb2, IVb3, IVb4, IVb5, IVb6, IVb7, IVb8, and IVc, q is 2. In some embodiments of the compounds of each of Formulae III, IIIa, IIIa1, IIIa2, IIIa3, IIIa4, IIIa5, IIIa6, IIIb, IIIb1, IIIb2, IIIb3, IIIb4, IIIb5, IIIb6, IIIb7, IIIb8, IIIb9, IIIb1, IIIb11, IIIc, IV, IVa, IVa1, IVa2, Iva3, IVa4, IVa5, IVa6, IVb, IVb1, IVb2, IVb3, IVb4, IVb5, IVb6, IVb7, IVb8, and IVc, any methylene groups of the q region are optionally substituted with fluoro or methyl. In some embodiments of the compounds of each of Formulae III, IIIa, IIIa1, IIIa2, IIIa3, IIIa4, IIIa5, IIIa6, IIIb, IIIb1, IIIb2, IIIb3, IIIb4, IIIb5, IIIb6, IIIb7, IIIb8, IIIb9, IIIb10, IIIb11, IIIc, IV, IVa, IVa1, IVa2, Iva3, IVa4, IVa5, IVa6, IVb, IVb1, IVb2, IVb3, IVb4, IVb5, IVb6, IVb7, IVb8, and IVc, any methylene groups of the q region are all fully saturated.

In some embodiments of the compounds of each of Formulae Ib3, IIb3, IIb6, IIIb3, IIIb6, and IIIb9, u is 0. In some embodiments of the compounds of each of Formulae Ib3, IIb3, IIb6, IIIb3, IIIb6, and IIIb9, u is 1. In some embodiments of the compounds of each of Formulae Ib3, IIb3, IIb6, IIIb3, IIIb6, and IIIb9, when u is 1, then the methylene group of the u region is substituted with fluoro or methyl. In some embodiments of the compounds of each of Formulae Ib3, IIb3, IIb6, IIIb3, IIIb6, and IIIb9, when u is 1, then the methylene group of the u region is fully saturated.

In some embodiments of the compounds of each of Formulae I, Ia, Ia1, Ia2, Ib, Ib1, Ib2, Ib3, Ic, Id, II, IIa, IIa1, IIa2, IIa3, IIa4, IIb, IIb1, IIb2, IIb3, IIb4, IIb5, IIb6, IIb7, IIc, IIc1, IId, and IId1, any methylene groups are all fully saturated.

In some embodiments of the compounds of each of Formulae I, II, III, and IV, Y is phenyl. In some embodiments of the compounds of each of Formulae I, II, III, and IV, Y is 2-pyridinyl. In some of either of such embodiments, Y is not substituted or is substituted one, two, three, or four times as defined for Y for Formula I and II. Furthermore, in some of such embodiments, any substituent of Y is halo (such as, for example, fluoro), methyl, nitro, cyano, trihalomethyl, methoxy, amino, hydroxyl, or mercapto.

In some embodiments of the compounds of each of Formulae I, II, III, IIIa, IIIa1, IIIa2, IIIa3, IIIa4, IIIa5, IIIa6, IIIb, IIIb1, IIIb2, IIIb3, IIIb4, IIIb5, IIIb6, IIIb7, IIIb8, IIIb9, IIIb10, IIIb11, IIIc, IV, IVa, IVa1, IVa2, Iva3, IVa4, IVa5, IVa6, IVb, IVb1, IVb2, IVb3, IVb4, IVb5, IVb6, IVb7, IVb8, and IVc, Y is 3-pyridinyl. In some embodiments of the compounds of each of Formulae I, II, III, IIIa, IIIa1, IIIa2, IIIa3, IIIa4, IIIa5, IIIa6, IIIb, IIIb1, IIIb2, IIIb3, IIIb4, IIIb5, IIIb6, IIIb7, IIIb8, IIIb9, IIIb10, IIIb11, IIIc, IV, IVa, IVa1, IVa2, Iva3, IVa4, IVa5, IVa6, IVb, IVb1, IVb2, IVb3, IVb4, IVb5, IVb6, IVb7, IVb8, and IVc, Y is 4-pyridinyl. In some embodiments of the compounds of each of Formulae I, II, III, IIIa, IIIa1, IIIa2, IIIa3, IIIa4, IIIa5, IIIa6, IIIb, IIIb1, IIIb2, IIIb3, IIIb4, IIIb5, IIIb6, IIIb7, IIIb8, IIIb9, IIIb10, IIIb11, IIIc, IV, IVa, IVa1, IVa2, Iva3, IVa4, IVa5, IVa6, IVb, IVb1, IVb2, IVb3, IVb4, IVb5, IVb6, IVb7, IVb8, and IVc, Y is not substituted or is substituted one, two, three, or four times as defined for Y for Formula I. In some embodiments of the compounds of each of Formulae I, II, III, IIIa, IIIa1, IIIa2, IIIa3, IIIa4, IIIa5, IIIa6, IIb, IIIb1, IIIb2, IIIb3, IIIb4, IIIb5, IIIb6, IIIb7, IIIb8, IIIb9, IIIb10, IIIb11, IIIc, IV, IVa, IVa1, IVa2, Iva3, IVa4, IVa5, IVa6, IVb, IVb1, IVb2, IVb3, IVb4, IVb5, IVb6, IVb7, IVb8, and IVc, any substituent of Y is halo (such as, for example, fluoro), methyl, nitro, cyano, trihalomethyl, methoxy, amino, hydroxyl, or mercapto. In some embodiments of the compounds of each of Formulae I, II, III, IIIa, IIIa1, IIIa2, IIIa3, IIIa4, IIIa5, IIIa6, IIIb, IIIb1, IIIb2, IIIb3, IIIb4, IIIb5, IIIb6, IIIb7, IIIb8, IIIb9, IIIb10, IIIb11, IIIc, IV, IVa, IVa1, IVa2, Iva3, IVa4, IVa5, IVa6, IVb, IVb1, IVb2, IVb3, IVb4, IVb5, IVb6, IVb7, IVb8, and IVc, Y is unsubstituted 3-pyridinyl or is 3-pyridinyl substituted at the 4 position with $NH_2$.

In some embodiments of the compounds of each of Formulae II, IIa, IIa2, IIb, IIb2, and IId, Z and/or any substituents on $Y_3$ are selected so that $Y_3$ is an electron-deficient aryl or heteroaryl ring.

In some embodiments of the compounds of each of Formulae IIa4, IIb5, and IId1, Z and/or $R_1$ are selected so that the phenyl ring is electron deficient.

In some embodiments of the compounds of each of Formulae III, IIIa, IIIa2, IIIb, IIIb2, IV, IVa, IVa2, IVb, and IVb2, $Y_4$ is not present and any substituents on $Y_3$ are selected so that $Y_3$ is electron-deficient.

In some embodiments of the compounds of each of Formulae I, Ic, Id, II, IIc, IIc1, IId, IId1, III, and IV, $Y_1$ is divalent carbocycle, divalent heterocycle, divalent phenyl or divalent heteroaryl, wherein any ring carbon atom is optionally independently substituted with halo, $C_{1-5}$ alkyl, nitro, cyano, trihalomethyl, $C_{1-5}$ alkoxy, C-amido, N-amido, sulfonamide, amino, aminosulfonyl, hydroxyl, mercapto, alkylthio, sulfonyl, or sulfinyl.

In some embodiments of the compounds of each of Formulae I, Ic, Id, II, IIc, IIc1, IId, IId1, III, and IV, $Y_1$ is divalent cyclohexyl, divalent piperidinyl, divalent phenyl, divalent pyridinyl, divalent pyrimidinyl, divalent thiophenyl, and divalent triazolyl, wherein any ring carbon is optionally further independently substituted with halo, $C_{1-5}$ alkyl, nitro, cyano, trihalomethyl, $C_{1-5}$ alkoxy, C-amido, N-amido, sulfonamide, amino, aminosulfonyl, hydroxyl, mercapto, alkylthio, sulfonyl, or sulfinyl.

In some embodiments of the compounds of each of Formulae I, Ia, Ib, II, IIa, IIb, IIb7, III, IIIa, IIIb, IIIc, IV, IVa, IVb, and IVc, $Y_2$ is —$OCH_2$—, —$SCH_2$—, —$N(R)CH_2$—, —$CH_2O$—, —$CH_2S$—, —$CH_2N(R)$—, —$SO_2N(R)$—, —$N(R)SO_2$—, —$C_{1-4}$ alkylene-$SO_2N(R)$—, —$C_{1-4}$ alkylene-$N(R)SO_2$—, —$SO_2N(R)$—$C_{1-4}$ alkylene-, —$N(R)SO_2$—$C_{1-4}$ alkylene-, —$C_{1-4}$ alkylene-O—$C_{1-4}$ alkylene-, —O—$C_{1-4}$ alkylene-, —$C_{1-4}$ alkylene-O—, —S—$C_{1-4}$ alkylene-, —$C_{1-4}$ alkylene-S—, —$C_{1-4}$ alkylene-S—$C_{1-4}$ alkylene-, —$N(R)$—$C_{1-4}$ alkylene-, —$C_{1-4}$ alkylene-$N(R)$—, or —$C_{1-4}$ alkylene-$N(R)$—$C_{1-4}$ alkylene-, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is —$S(=O)_2CH_2$—, —$S(=O)CH_2$—, —$CH_2O$—, —$CH_2S$—, —$CH_2N(R)$—, —$CH_2S(=O)_2$—, —$CH_2S(=O)$—, —$C(=O)O$—, —$OC(=O)$—, —$SO_2N(R)$—, —$N(R)SO_2$—, —O—$C_{1-4}$ alkylene-$N(R)C(=O)$—, —$C_{1-4}$ alkylene-$S(=O)_2$—, —$C_{1-4}$ alkylene-$S(=O)$—, —$S(=O)_2$—$C_{1-4}$ alkylene-, —$S(=O)$—$C_{1-4}$ alkylene-, —$C_{1-4}$ alkylene-$SO_2N(R)$—, —$C_{1-4}$ alkylene-$N(R)SO_2$—, —$SO_2N(R)$—$C_{1-4}$ alkylene-, —$N(R)SO_2$—$C_{1-4}$ alkylene-, —$C_{1-4}$ alkylene-O—$C_{1-4}$ alkylene-, —O—$C_{1-4}$ alkylene-, —$C_{1-4}$ alkylene-O—, —$C_{1-4}$ alkylene-S—, —$C_{1-4}$ alkylene-S—$C_{1-4}$ alkylene-, —$C_{1-4}$ alkylene-$N(R)$—, —$C_{1-4}$ alkylene-$N(R)$—$C_{1-4}$ alkylene-, —$C_{1-4}$ alkylene-$C(=O)$—O—$C_{1-4}$ alkylene-, —$C_{1-4}$ alkylene-O—$C(=O)$—$C_{1-4}$ alkylene-, —$C_{1-4}$ alkylene-$C(=O)$—$N(R)$—$C_{1-4}$ alkylene-, or —$C_{1-4}$ alkylene-$N(R)$—$C(=O)$—$C_{1-4}$ alkylene-, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is —$SCH_2$—.

In some embodiments of the compounds of each of Formulae I, Ia, Ib, II, IIa, IIb, IIb7, III, IIIa, IIIb, IIIc, IV, IVa, IVb, and IVc, $Y_2$ is —N(R)CH$_2$—, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is —N(R)C(=O)—, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is —C(=O)N(R)—, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is —S(=O)$_2$CH$_2$—.

In some embodiments of the compounds of each of Formulae I, Ia, Ib, II, IIa, IIb, IIb7, III, IIIa, IIIb, IIIc, IV, IVa, IVb, and IVc, $Y_2$ is —S(=O)CH$_2$—.

In some embodiments of the compounds of each of Formulae I, Ia, Ib, II, IIa, IIb, IIb7, III, IIIa, IIIb, IIIc, IV, IVa, IVb, and IVc, $Y_2$ is —CH$_2$S—.

In some embodiments of the compounds of each of Formulae I, Ia, Ib, II, IIa, IIb, IIb7, III, IIIa, IIIb, IIIc, IV, IVa, IVb, and IVc, $Y_2$ is —CH$_2$N(R)—, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is —CH$_2$S(=O)$_2$—.

In some embodiments of the compounds of each of Formulae I, Ia, Ib, II, IIa, IIb, IIb7, III, IIIa, IIIb, IIIc, IV, IVa, IVb, and IVc, $Y_2$ is —CH$_2$S(=O)—.

In some embodiments of the compounds of each of Formulae I, Ia, Ib, II, IIa, IIb, IIb7, III, IIIa, IIIb, IIIc, IV, IVa, IVb, and IVc, $Y_2$ is —C(=O)O—.

In some embodiments of the compounds of each of Formulae I, Ia, Ib, II, IIa, IIb, IIb7, III, IIIa, IIIb, IIIc, IV, IVa, IVb, and IVc, $Y_2$ is —OC(=O)—.

In some embodiments of the compounds of each of Formulae I, Ia, Ib, II, IIa, IIb, IIb7, III, IIIa, IIIb, IIIc, IV, IVa, IVb, and IVc, $Y_2$ is —N(R)SO$_2$—, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is ethylene.

In some embodiments of the compounds of each of Formulae I, Ia, Ib, II, IIa, IIb, IIb7, III, IIIa, IIIb, IIIc, IV, IVa, IVb, and IVc, $Y_2$ is propylene.

In some embodiments of the compounds of each of Formulae I, Ia, Ib, II, IIa, IIb, IIb7, III, IIIa, IIIb, IIIc, IV, IVa, IVb, and IVc, $Y_2$ is n-butylene.

In some embodiments of the compounds of each of Formulae I, Ia, Ib, II, IIa, IIb, IIb7, III, IIIa, IIIb, IIIc, IV, IVa, IVb, and IVc, $Y_2$ is —O—$C_{1-4}$ alkylene-N(R)C(=O)—, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is —O—$C_{1-4}$ alkylene-C(=O)N(R)—, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is —N(R)C(=O)—$C_{1-4}$ alkylene-O—, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is —C(=O)N(R)—$C_{1-4}$ alkylene-O—, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is —$C_{1-4}$ alkylene-S(=O)$_2$—.

In some embodiments of the compounds of each of Formulae I, Ia, Ib, II, IIa, IIb, IIb7, III, IIIa, IIIb, IIIc, IV, IVa, IVb, and IVc, $Y_2$ is —$C_{1-4}$ alkylene-S(=O)—.

In some embodiments of the compounds of each of Formulae I, Ia, Ib, II, IIa, IIb, IIb7, III, IIIa, IIIb, IIIc, IV, IVa, IVb, and IVc, $Y_2$ is —S(=O)$_2$—$C_{1-4}$ alkylene-.

In some embodiments of the compounds of each of Formulae I, Ia, Ib, II, IIa, IIb, IIb7, III, IIIa, IIIb, IIIc, IV, IVa, IVb, and IVc, $Y_2$ is —S(=O)—$C_{1-4}$ alkylene-.

In some embodiments of the compounds of each of Formulae I, Ia, Ib, II, IIa, IIb, IIb7, III, IIIa, IIIb, IIIc, IV, IVa, IVb, and IVc, $Y_2$ is —$C_{1-4}$ alkylene-SO$_2$N(R)—, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is —$C_{1-4}$ alkylene-N(R)SO$_2$—, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is —SO$_2$N(R)—$C_{1-4}$ alkylene-, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is —N(R)SO$_2$—$C_{1-4}$ alkylene-, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is —$C_{1-4}$ alkylene-O—$C_{1-4}$ alkylene-.

In some embodiments of the compounds of each of Formulae I, Ia, Ib, II, IIa, IIb, IIb7, III, IIIa, IIIb, IIIc, IV, IVa, IVb, and IVc, $Y_2$ is —O—$C_{1-4}$ alkylene-.

In some embodiments of the compounds of each of Formulae I, Ia, Ib, II, IIa, IIb, IIb7, III, IIIa, IIIb, IIIc, IV, IVa, IVb, and IVc, $Y_2$ is —$C_{1-4}$ alkylene-O—.

In some embodiments of the compounds of each of Formulae I, Ia, Ib, II, IIa, IIb, IIb7, III, IIIa, IIIb, IIIc, IV, IVa, IVb, and IVc, $Y_2$ is —S—$C_{1-4}$ alkylene-.

In some embodiments of the compounds of each of Formulae I, Ia, Ib, II, IIa, IIb, IIb7, III, IIIa, IIIb, IIIc, IV, IVa, IVb, and IVc, $Y_2$ is —$C_{1-4}$ alkylene-S—.

In some embodiments of the compounds of each of Formulae I, Ia, Ib, II, IIa, IIb, IIb7, III, IIIa, IIIb, IIIc, IV, IVa, IVb, and IVc, $Y_2$ is —$C_{1-4}$ alkylene-S—$C_{1-4}$ alkylene-.

In some embodiments of the compounds of each of Formulae I, Ia, Ib, II, IIa, IIb, IIb7, III, IIIa, IIIb, IIIc, IV, IVa, IVb, and IVc, $Y_2$ is —N(R)—$C_{1-4}$ alkylene-, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is —$C_{1-4}$ alkylene-N(R)—, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is —$C_{1-4}$ alkylene-N(R)—$C_{1-4}$ alkylene-, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is —$C_{1-4}$ alkylene-C(=O)—O—$C_{1-4}$ alkylene-.

In some embodiments of the compounds of each of Formulae I, Ia, Ib, II, IIa, IIb, IIb7, III, IIIa, IIIb, IIIc, IV, IVa, IVb, and IVc, $Y_2$ is —$C_{1-4}$ alkylene-O—C(=O)—$C_{1-4}$ alkylene-.

In some embodiments of the compounds of each of Formulae I, Ia, Ib, II, IIa, IIb, IIb7, III, IIIa, IIIb, IIIc, IV, IVa, IVb, and IVc, $Y_2$ is —$C_{1-4}$ alkylene-C(=O)—N(R)—$C_{1-4}$ alkylene-, wherein R is H, halo, $C_{1-5}$ alkyl, $C_{1-5}$ alkenyl, or $C_{1-5}$ alkynyl.

In some embodiments of the compounds of each of Formulae I, Ia, Ib, II, IIa, IIb, IIb7, III, IIIa, IIIb, IIIc, IV, IVa, IVb, and IVc, $Y_2$ is —$C_{1-4}$ alkylene-N(R)—C(=O)—$C_{1-4}$ alkylene-, wherein R is H, halo, $C_{1-5}$ alkyl, $C_{1-5}$ alkenyl, or $C_{1-5}$ alkynyl.

In some embodiments of the compounds of each of Formulae II, IIa, IIa1, IIa2, IIb, IIb1, IIb2, IIb3, IIc, IId, III, IIIa, IIIa1, IIIa2, IIIb, IIIb1, IIIb2, IIIb3, IV, IVa, IVa1, IVa2, IVb, IVb1, and IVb2, $Y_3$ is phenyl, pyridinyl, pyrimidinyl, divalent phenyl, divalent pyridinyl, or divalent pyrimidinyl, wherein any ring carbon is optionally independently substituted, and in the case of divalent rings, optionally further independently substituted, with halo, $C_{1-5}$ alkyl, nitro, cyano, trihalomethyl, $C_{1-5}$ alkoxy, C-amido, N-amido, sulfonamide, amino, aminosulfonyl, hydroxyl, mercapto, alkylthio, sulfonyl, or sulfinyl, wherein $C_{1-5}$ alkyl, $C_{1-5}$ alkoxy, C-amido, N-amido, amino, and alkylthio are each optionally substituted with heterocyclo, cycloalkyl, or amino.

In some embodiments of the compounds of each of Formulae III, IIIa, IIIa1, IIa2, IIa3, IIIa4, IIIb, IIIb1, IIIb2, IIIb3, IIIb4, IIIb5, IIIb6, IV, IVa, IVa1, IVa2, Iva3, IVa4, IVb, IVb1, IVb2, IVb3, and IVb4, $Y_4$ is optionally present, and when present is aryl, heteroaryl, carbocycle, or heterocycle, wherein any ring carbon atom is optionally independently substituted with halo, $C_{1-5}$ alkyl, nitro, cyano, trihalomethyl, $C_{1-5}$ alkoxy, C-amido, N-amido, sulfonamide, amino, aminosulfonyl, hydroxyl, mercapto, alkylthio, sulfonyl, sulfinyl, wherein $C_{1-5}$ alkyl, $C_{1-5}$ alkoxy, C-amido, N-amido, amino, and alkylthio are each optionally substituted with heterocyclo, cycloalkyl, or amino.

In some embodiments of the compounds of each of Formulae III, IIIa, IIIa1, IIa2, IIa3, IIIa4, IIIb, IIIb1, IIIb2, IIIb3, IIIb4, IIIb5, IIIb6, IV, IVa, IVa1, IVa2, Iva3, IVa4, IVb, IVb1, IVb2, IVb3, and IVb4, $Y_4$ is present.

In some embodiments of the compounds of each of Formulae III, IIIa, IIIa1, IIa2, IIa3, IIIa4, IIIb, IIIb1, IIIb2, IIIb3, IIIb4, IIIb5, IIIb6, IV, IVa, IVa1, IVa2, Iva3, IVa4, IVb, IVb1, IVb2, IVb3, and IVb4, $Y_4$ is a group selected from phenyl, morpholino, piperazinyl, oxidiazolyl, oxazolyl, pyrrolidinyl, thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl (such as, for example, 2H-pyrrolyl), pyrroline, imidazolyl, imidazolidinyl, pyrazolyl, pyridyl (pyridinyl) (such as, for example, 2-pyridyl, 3-pyridyl, and 4-pyridyl), pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, thiazolyl, phenothiazinyl, isoxazolyl, furazanyl, phenoxazinyl, 1,4-dihydroquinoxaline-2,3-dione, 7-amino-isocoumarin, pyrido[1,2-a]pyrimidin-4-one, pyrazolo[1,5-a]pyrimidinyl (such as, for example, pyrazolo[1,5-a]pyrimidin-3-yl), 1,2-benzoisoxazol-3-yl, benzimidazolyl, 2-oxindolyl, 2-oxobenzimidazolyl, triazine, dioxoanyl, dithianyl, thiomorpholinyl, trithianyl, cyclobutyl, cyclohexyl, cycloheptyl, cyclooctyl, and cyclohexenyl, wherein each of the groups is optionally substituted as defined for $Y_4$ in Formula III.

In some embodiments of the compounds of each of Formulae III, IIIa, IIIa1, IIIa2, IIIa3, IIIa4, IIIb, IIIb1, IIIb2, IIIb3, IIIb4, IIIb5, IIIb6, IV, IVa, IVa1, IVa2, Iva3, IVa4, IVb, IVb1, IVb2, IVb3, and IVb4, $Y_4$ is a group selected from phenyl, 2-pyridinyl, 3-pyridinyl, 4-pyridinyl, pyrimidinyl, morpholino, piperazinyl, oxidiazolyl, oxazolyl, pyrrolidinyl, imidazolyl, and piperidinyl, wherein each of the groups is optionally substituted as defined for $Y_4$ in Formula III.

In some embodiments of the compounds of each of Formulae III, IIIa, IIIa1, IIIa2, IIIa3, IIIa4, IIIb, IIIb1, IIIb2, IIIb3, IIIb4, IIIb5, IIIb6, IV, IVa, IVa1, IVa2, Iva3, IVa4, IVb, IVb1, IVb2, IVb3, and IVb4, $Y_4$ is a group selected from:

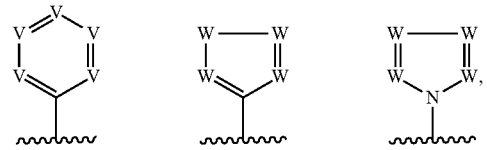

wherein V is N or C(H) and W is N, O, C(H), or S, wherein any ring atom is optionally independently substituted with halo, $C_{1-5}$ alkyl, nitro, cyano, trihalomethyl, $C_{1-5}$ alkoxy, C-amido, N-amido, sulfonamide, amino, aminosulfonyl, hydroxyl, mercapto, alkylthio, sulfonyl, sulfinyl, wherein $C_{1-5}$ alkyl, $C_{1-5}$ alkoxy, C-amido, N-amido, amino, and alkylthio are each optionally substituted with heterocyclo, cycloalkyl, or amino.

In some embodiments of the compounds of each of Formulae Ib, IIb, IIIb, IIIb10, IIIb11, IIIc, IVb, IVb7, IVb8, and IVc, at least two of S, T, U, and V are nitrogen. In some embodiments of the compounds of each of Formulae Ib, IIb, IIIb, IIIb10, IIIb11, IIIc, IVb, IVb7, IVb8, and IVc, only S is nitrogen. In some embodiments of the compounds of each of Formulae Ib, IIb, IIIb, IIIb10, IIIb11, IIIc, IVb, IVb7, IVb8, and IVc, only T is nitrogen. In some embodiments of the compounds of each of Formulae Ib, IIb, IIIb, IIIb10, IIIb11, IIIc, IVb, IVb7, IVb8, and IVc, only U is nitrogen. In some embodiments of the compounds of each of Formulae Ib, IIb, IIIb, IIIb10, IIIb11, IIIc, IVb, IVb7, IVb8, and IVc, only V is nitrogen. In some embodiments of the compounds of each of Formulae Ib, IIb, IIIb, IIIb1, IIIb11, IIIc, IVb, IVb7, IVb8, and IVc, T and V are nitrogen. In some embodiments of the compounds of each of Formulae Ib, IIb, IIIb, IIIb10, IIIb11, IIIc, IVb, IVb7, IVb8, and IVc, S and U are nitrogen.

In some embodiments of the compounds of each of Formulae III, IIIb, IIIb1, IIIb2, IIIb3, IIIb4, IIIb5, IIIb6, IIIb7, IIIb8, IIIb9, IIIb10, IIIb11, IIIc, IV, IVb, IVb1, IVb2, IVb3, IVb4, IVb5, IVb6, IVb7, IVb8, and IVc, Y is unsubstituted 3-pyridinyl and q is 1.

In some embodiments of the compounds of each of Formulae III, IIIb, IIIb1, IIIb2, IIIb3, IIIb4, IIIb5, IIIb6, IIIb7, IIIb8, IIIb9, IIIb10, IIIb11, IIIc, IV, IVb, IVb1, IVb2, IVb3, IVb4, IVb5, IVb6, IVb7, IVb8, and IVc, Y is unsubstituted 3-pyridinyl, q is 1, and p is 0.

In some embodiments of the compounds of each of Formulae III, IIIb, IIIb1, IIIb2, IIIb3, IIIb4, IIIb5, IIIb6, IIIb7, IIIb8, IIIb9, IIIb10, IIIb11, IIIc, IV, IVb, IVb1, IVb2, IVb3, IVb4, IVb5, IVb6, IVb7, IVb8, and IVc, Y is unsubstituted 3-pyridinyl, q is 1, p is 0, and o is 0.

In some embodiments of the compounds of each of Formulae III, IIIb, IIIb1, IIIb2, IIIb3, IIIb4, IIIb5, IIIb6, IIIb7, IIIb8, IIIb9, IIIb10, IIIb11, IIIc, IV, IVb, IVb1, IVb2, IVb3, IVb4, IVb5, IVb6, IVb7, IVb8, and IVc, Y is unsubstituted 3-pyridinyl, q is 1, p is 0, and o is 0.

In some embodiments of the compounds of each of Formulae III, IIIb, IIIb1, IIIb2, IIIb3, IIIb4, IIIb5, IIIb6, IIIb7, IIIb8, IIIb9, IIIb10, IIIb11, IIIc, IV, IVb, IVb1, IVb2, IVb3, IVb4, IVb5, IVb6, IVb7, IVb8, and IVc, Y is unsubstituted 3-pyridinyl, q is 1, p is 0, o is 0, and $R_6$ is not present.

In some embodiments of the compounds of each of Formulae III, IIIa, IIIa1, IIIa2, IIIa3, IIIa4, IIIa5, IIIa6, IV, IVa, IVa1, IVa2, Iva3, IVa4, IVa5, and IVa6, Y is unsubstituted 3-pyridinyl and q is 1.

In some embodiments of the compounds of each of Formulae III, IIIa, IIIa1, IIIa2, IIIa3, IIIa4, IIIa5, IIIa6, IV, IVa, IVa1, IVa2, Iva3, IVa4, IVa5, and IVa6, Y is unsubstituted 3-pyridinyl, q is 1, and n is 4, 5, or 6.

In some embodiments of the compounds of each of Formulae III, IIIa, IIIa1, IIIa2, IIIa3, IIIa4, IIIa5, IIIa6, IV, IVa, IVa1, IVa2, Iva3, IVa4, IVa5, and IVa6, Y is unsubstituted 3-pyridinyl, q is 1, n is 4, 5, or 6, and the methylene groups of n and q are all fully saturated.

In some embodiments of the compounds of each of Formulae Ib, Ib1, Ib2, Ib3, IIb, IIb1, IIb2, IIb3, IIb4, IIb5, IIb6, and IIb7, $R_6$ and $R_7$ are not present.

In some embodiments of the compounds of each of Formulae Ib, Ib1, Ib2, Ib3, IIb, IIb1, IIb2, IIb3, IIb4, IIb5, IIb6, and IIb7, $R_6$ and $R_7$ are not present and any methylene groups are fully saturated.

In some embodiments of the compounds of each of Formulae Ia, Ia1, Ia2, IIa, IIa1, IIa2, IIa3, and IIa4, n is 4, 5, or 6, and $R_7$ is not present.

In some embodiments of the compounds of each of Formulae Ia, Ia1, Ia2, IIa, IIa1, IIa2, IIa3, and IIa4, n is 4, 5, or 6, $R_7$ is not present, and any methylene groups are fully saturated.

For the therapeutic methods of the present invention, salts of the compounds used in the methods of the present invention are those particular salts wherein the counterion is pharmaceutically acceptable. However, salts of acids and bases which are non-pharmaceutically acceptable can also find use, for example, in the preparation or purification of a pharmaceutically acceptable compound. All salts, whether pharmaceutically acceptable or not, are within the ambit of the present invention.

The pharmaceutically acceptable addition salts as mentioned herein are meant to comprise the therapeutically active non-toxic acid addition salt forms which the compounds of Formula I are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxy-acetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds used in the methods of the present invention containing acidic protons can be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanedi-ol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds used in the methods of the present invention are able to form. Examples of such forms are e.g. hydrates, alcoholates and the like.

The term "quaternary amine" as used herein defines the quaternary ammonium salts which the compounds used in the methods of the present invention are able to form by reaction between a basic nitrogen of one of the compounds used in the methods of the present invention and an appropriate quaternizing agent, such as, for example, an optionally substituted alkylhalide, arylhalide or arylalkylhalide, e.g. methyliodide or benzyliodide. Other reactants with good leaving groups can also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Pharmaceutically acceptable salts of the compounds used in the methods of the present invention include all salts are exemplified by alkaline salts with an inorganic acid and/or a salt with an organic acid that are known in the art. In addition, pharmaceutically acceptable salts include acid salts of inorganic bases, as well as acid salts of organic bases. Their hydrates, solvates, and the like are also encompassed in the present invention. In addition, N-oxide compounds are also encompassed in the present invention.

It will be appreciated that some of the compounds used in the methods of the present invention and their N-oxides, addition salts, quaternary amines and stereochemically isomeric forms can contain one or more centers of chirality and exist as stereochemically isomeric forms.

The term "stereochemically isomeric forms" as used hereinbefore defines all the possible stereoisomeric forms which the compounds used in the methods of the present invention, and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of the compounds used in the methods of the present invention and their N-oxides, salts, solvates or quaternary amines substantially free, i.e. associated with less than 10%, preferably less than 5%, in particular less than 2% and most preferably less than 1% of the other isomers. In particular, stereogenic centers can have the R- or S-configuration; substituents on bivalent cyclic (partially) saturated radicals can have either the cis- or trans-configuration. Compounds encompassing double bonds can have an E or Z-stereochemistry at said double bond. Stereochemically isomeric forms of the compounds used in the methods of the present invention are fully intended to be embraced within the scope of the methods of the present invention.

The N-oxide forms of the compounds used in the methods of the present invention are meant to comprise the compounds used in the methods of the present invention wherein one or several nitrogen atoms are oxidized to the so-called N-oxide.

Some of the compounds described for use in the methods of the present invention can also exist in their tautomeric form.

Such forms although not explicitly indicated in the above formula are intended to be included within the scope of the present invention.

Whenever used herein, the phrase "compounds used in the methods of the present invention" is meant to also include the N-oxide forms, the salts, the quaternary amines, the prodrug forms, and the stereochemically isomeric forms of such compounds. Further, it should be understood that the methods of the present invention include the use of all such forms, and especially those forms that possesses Nampt inhibitory activity, or other advantageous properties. Of special interest are those compounds that are stereochemically pure.

In preferred embodiments, compounds used in the methods of the present invention are those having an $IC_{50}$ of less than about 100 nM, less than about 10 nM, or less than about 1 nM as determined in the cytotoxicity assays as described in the Examples below.

For all compounds used in the methods of the present invention, reference to any bound hydrogen atom can also encompass a deuterium atom bound at the same position. Substitution of hydrogen atoms with deuterium atoms is conventional in the art. See, e.g., U.S. Pat. Nos. 5,149,820 & 7,317,039, which are incorporated by reference herein their entirety. Such deuteration sometimes results in a compound that is functionally indistinct from its hydrogenated counterpart, but occasionally results in a compound having beneficial changes in the properties relative to the non-deuterated form. For example, in certain instances, replacement of specific bound hydrogen atoms with deuterium atoms slows the catabolism of the deuterated compound, relative to the non-deuterated compound, such that the deuterated compound exhibits a longer half-life in the bodies of individuals administered such compounds. This particularly so when the catabolism of the hydrogenated compound is mediated by cytochrome P450 systems. See Kushner et al., *Can. J. Physiol. Pharmacol.* (1999) 77:79-88, which is incorporated by reference herein its entirety.

Pharmaceutical Compositions and Formulations

In another aspect, the present invention further provides a medicament or a pharmaceutical composition for use in the methods of the present invention having a therapeutically or prophylactically effective amount of at least one of the compounds used in the methods of the present invention.

Typically, one of the compounds used in the methods of the present invention can be effective at an amount of from about 0.01 µg/kg to about 100 mg/kg per day based on total body weight. The active ingredient can be administered at once, or can be divided into a number of smaller doses to be administered at predetermined intervals of time. The suitable dosage unit for each administration can be, e.g., from about 1 µg to about 2000 mg, preferably from about 5 µg to about 1000 mg. The pharmacology and toxicology of many of such other anticancer compounds are known in the art. See e.g., *Physicians Desk Reference*, Medical Economics, Montvale, N.J.; and *The Merck Index*, Merck & Co., Rahway, N.J. The therapeutically effective amounts and suitable unit dosage ranges of such compounds used in art can be applicable to the compounds used in the methods of the present invention.

It should be understood that the dosage ranges set forth above are exemplary only and are not intended to limit the scope of this invention. The therapeutically effective amount for individual compounds used in the methods of the present invention can vary with factors including but not limited to the activity of the compound used, the stability of the compound used in the patient's body, the severity of the conditions to be alleviated, the total weight of the patient treated, the route of administration, the ease of absorption, distribution, and excretion of the compound by the body, the age and sensitivity of the patient to be treated, and the like, as will be apparent to a skilled artisan. The amount of administration can be adjusted as the various factors change over time.

In the pharmaceutical compositions, the compounds used in the methods of the present invention can be in any pharmaceutically acceptable salt form, as described above.

For oral delivery, the compounds used in the methods of the present invention can be incorporated into a formulation that includes pharmaceutically acceptable excipients or carriers such as binders, lubricants, disintegrating agents, and sweetening or flavoring agents, all known in the art. The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of a solution, suspension, syrup, chewing gum, wafer, elixir, and the like. If desired, conventional agents for modifying flavors, tastes, colors, and shapes of the special forms can also be included.

The compounds used in the methods of the present invention can also be administered parenterally in the form of a solution or suspension, or in a lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. The parenteral formulations can be stored in any conventional containers such as vials and ampoules.

Routes of topical administration include, but are not limited to, dermal, nasal, bucal, mucosal, rectal, or vaginal applications. For topical administration, the compounds used in the methods of the present invention can be formulated into lotions, creams, ointments, gels, powders, pastes, sprays, suspensions, drops and aerosols. Thus, one or more thickening agents, humectants, and stabilizing agents can be included in the formulations. A special form of topical administration is delivery by a transdermal patch. Methods for preparing transdermal patches that can be used with the compounds used in the methods of the present invention are disclosed, e.g., in Brown, et al., *Annual Review of Medicine*, 39:221-229 (1988), which is incorporated herein by reference.

Subcutaneous implantation for sustained release of the compounds used in the methods of the present invention can also be a suitable route of administration. This entails surgical procedures for implanting one or more of the compounds used in the methods of the present invention in any suitable formulation into a subcutaneous space, e.g., beneath the anterior abdominal wall. See, e.g., Wilson et al., *J. Clin. Psych.* 45:242-247 (1984). Hydrogels can be used as a carrier for the sustained release of the compounds used in the methods of the present invention. Hydrogels are generally known in the art. They are typically made by crosslinking high molecular weight biocompatible polymers into a network, which swells in water to form a gel-like material. Preferably, hydrogels are biodegradable or biosorbable. See, e.g., Phillips et al., *J. Pharmaceut. Sci.*, 73:1718-1720 (1984).

The compounds used in the methods of the present invention can also be conjugated, to a water soluble, non-immunogenic, non-peptidic, high molecular weight polymer to form a polymer conjugate. For example, one or more of the compounds used in the methods of the present invention is covalently linked to polyethylene glycol to form a conjugate. Typically, such a conjugate exhibits improved solubility, stability, and reduced toxicity and immunogenicity. Thus, when administered to a patient, compounds used in the methods of the present invention in the conjugate can have a longer half-life in the body, and exhibit better efficacy. See generally, Burnham, *Am. J. Hosp. Pharm.*, 15:210-218 (1994). PEGylated proteins are currently being used in protein replacement therapies and for other therapeutic uses. For example, PEGylated interferon (PEG-INTRON A®) is clinically used for treating Hepatitis B. PEGylated adenosine deaminase (AD-AGEN®) is being used to treat severe combined immunodeficiency disease (SCIDS). PEGylated L-asparaginase (ON-CAPSPAR®) is being used to treat acute lymphoblastic leukemia (ALL).

It is preferred that the covalent linkage between the polymer and one or more of the compounds used in the methods of the present invention and/or the polymer itself is hydrolytically degradable under physiological conditions. Such conjugates can readily release the compounds used in the methods of the present invention inside the body. Controlled release of the compounds used in the methods of the present invention can also be achieved by incorporating one or more of the compounds used in the methods of the present invention into microcapsules, nanocapsules, or hydrogels that are generally known in the art.

Liposomes can also be used as carriers for the compounds used in the methods of the present invention of the present invention. Liposomes are micelles made of various lipids such as cholesterol, phospholipids, fatty acids, and derivatives thereof. Various modified lipids can also be used. Liposomes can reduce toxicity of the compounds used in the methods of the present invention, and can increase their stability. Methods for preparing liposomal suspensions containing active ingredients therein are generally known in the art, and, thus, can be used with the compounds used in the methods of the present invention. See, e.g., U.S. Pat. No. 4,522, 811; Prescott, Ed., *Methods in Cell Biology*, Volume XIV, Academic Press, New York, N.Y. (1976).

The compounds used in the methods of the present invention can also be administered in combination with another active agent that synergistically treats or prevents the same symptoms or is effective for another disease or symptom in the patient being treated, so long as the other active agent does not interfere with, or adversely affect, the effects of the compounds used in the methods of the present invention. Such other active agents include but are not limited to anti-inflammation agents, antiviral agents, antibiotics, antifungal agents, antithrombotic agents, cardiovascular drugs, cholesterol lowering agents, anti-cancer drugs, hypertension drugs, immune adjuvants, and the like.

Therapeutic Methods

The present invention provides therapeutic methods for treating diseases and disorders that will respond to therapy with a Nampt inhibitor. Consequently, the present invention provides therapeutic methods for treating cancer, systemic or chronic inflammation, rheumatoid arthritis, diabetes, obesity, T-cell mediated autoimmune disease, ischemia, and other complications associated with these diseases and disorders. These therapeutic methods involve treating a patient (either a human or another animal) in need of such treatment, with a therapeutically effective amount of one or more of the Nampt-inhibiting compounds used in the methods of the present invention, or a pharmaceutical composition comprising a therapeutically effective amount of one or more of the Nampt-inhibiting compounds used in the methods of the present invention.

The present invention also comprises treating isolated cells with a therapeutically effective amount of one or more of the Nampt-inhibiting compounds used in the methods of the present invention, or a pharmaceutical composition comprising a therapeutically effective amount of one or more of the Nampt-inhibiting compounds used in the methods of the present invention.

As used herein, the phrase "treating . . . with . . . a compound" means either administering one or more of the compounds used in the methods of the present invention, or a pharmaceutical compositions comprising one or more of the compounds used in the methods of the present invention, directly to isolated cells or to an animal, or administering to cells or an animal another agent to cause the presence or formation of one or more of the compounds used in the methods of the present invention inside the cells or the animal. Preferably, the methods of the present invention comprise administering to cells in vitro or to a warm-blood animal, particularly mammal, and more particularly a human, a pharmaceutical composition comprising an effective amount of one or more of the compounds a of the present invention or another agent to cause the presence or formation of one or more of the compounds used in the methods of the present invention inside the cells or the animal.

As would be appreciated by the skilled artisan, one or more of the compounds used in the methods of the present invention can be administered in one dose at one time, or can be divided into a number of smaller doses to be administered at predetermined intervals of time. The suitable dosage unit for each administration can be determined based on the effective daily amount and the pharmacokinetics of the compounds.

Treating Cancer:

As noted previously, Nampt catalyzes the first and rate-limiting step in the generation of NAD from Nam, and NAD is critical for the generation of cellular ATP by glycolysis, the citric acid cycle, and oxidative phosphorylation. By these mechanisms and others, reduction in cellular NAD levels by Nampt inhibition causes depletion of cellular ATP and, ultimately, cell death. Tumor cells are thought to be more sensitive to NAD and ATP loss than normal cells due to their higher energy needs and an increased reliance on glycolysis. Known as the "Warburg effect" (Warburg, O. On respiratory impairment in cancer cells. *Science* 124, 269-270 (1956)), a wide spectrum of cancer cells exhibit increased glycolysis relative to oxidative phosphorylation, despite the availability of oxygen. The shift from oxidative phosphorylation to a reliance on glycolysis is thought to result from mitochondrial damage and/or a hypoxic tumor microenvironment (reviewed in Hsu, P. P and Sabatini, D. M. Cancer cell metabolism: Warburg and beyond. *Cell* 134, 703-707 (2008)). With regards to depleting energy levels in tumor cells, Nampt inhibitors would be analogous to inhibitors of other glycolytic enzymes, several of which are in cancer preclinical or clinical trials (reviewed in Pelicano H. et al. Glycolysis inhibition for anticancer treatment. *Oncogene* 25, 4633-4646 (2006).

In addition to increased energy needs, tumor cells are more susceptible to NAD loss due to a higher turnover of NAD in response to DNA damage and genomic instability. According to this model, poly(ADP-ribose) polymerases (PARPs) consume NAD as they generate poly(ADP-ribose) to repair DNA in response to alkylating agents, ionizing radiation, and oxidative stress (reviewed in Galli M. et al. The nicotinamide phosphoribosyltransferase: a molecular link between metabolism, inflammation, and cancer. *Cancer Res.* 70, 8-11 (2010)). Indeed, an inability to replenish this NAD loss, either by reducing Nampt expression or inhibiting Nampt activity, sensitizes cells to PARP activation (Rongvaux, et al. Nicotinamide phosphoribosyl transferase/pre-B cell colony-enhancing factor/visfatin is required for lymphocyte development and cellular resistance to genotoxic stress. *J. Immunol.* 181, 4685-4695 (2008)).

The increased metabolic demands of cancer cells (Luo et al., *Cell.* 136(5):823-37 (2009). Erratum in: *Cell.,* 2009 Aug. 21; 138(4):807.)) suggests that they should require NAD in sufficient levels to maintain cellular pools of ATP. This requirement, and the critical role played by Nampt in NAD synthesis further suggests that cancers cells have a critical need for adequate Nampt activity. Consistent with this hypothesis are reports of Nampt over-expression in colon cancers (Hufton et al., *FEBS Lett.* 463(1-2):77-82 (1999), Van Beijnum et al., *Int. J. Cancer.* 101(2):118-27 (2002)) and GBM cancers (Reddy et al., *Cancer Biol. Ther.* 7(5):663-8 (2008), and suggestions of the amplification of the gene encoding Nampt in multiple other cancers. In addition to the role played by NAD as a cofactor in redox reactions, NAD also serves as a substrate for mono and poly-ADP ribosyltransferases (PARPs), class III histone deacetylases (sirtuins) and ADP-ribose cyclases. PARPs appear to be major consumers of cellular NAD (Paine et al., *Biochem. J.* 202(2):551-3 (1982)), and evidence exists for increased polyADP-ribosylation activity in oral cancer (Das, B. R., *Cancer Lett.* 73(1): 29-34 (1993)), hepatocellular carcinoma (Shiobara et al., *J. Gastroenterol. Hepatol.* 16(3):338-44 (2001), Nomura et al., *J Gastroenterol. Hepatol.* 15(5):529-35 (2000), rectal cancer (Yalcintepe et al., *Braz. J. Med. Biol. Res.* 38(3):361-5 (2005); Epub 2005, Mar. 8.), and leukemia and ovarian cancers (Singh N, *Cancer Lett.* 58(1-2):131-5 (1991). Increased ADP-ribosylation in cancer can reflect PARPs' role in DNA repair (Durkacz et al., *Nature.* 283(5747):593-6 (1980); deMurcia et al., *Proc. Natl. Acad. Sci. U.S.A.* 94(14):7303-7 (1997), Simbulan-Rosenthal et al., Proc. Natl. Acad. Sci. U.S.A. 96(23):13191-6 (1999) and the need to maintain genome integrity in the face of genomic instability and the resulting accumulation of point mutations, deletions, chromosomal rearrangement and aneuploidy (Hartwell and Kastan, *Science.* 266(5192):1821-8 (1994)). PARP-1 itself is reported to be over-expressed in breast cancer, where its expression inversely correlates with genomic instability (Biechi et al., *Clin. Cancer Res.* 2(7):1163-7 (1996)).

Furthermore, the Nampt transcript is known to be upregulated in colon cancers (van Beijnum J R, et al. Target validation for genomics using peptide-specific phage antibodies: a study of five gene products overexpressed in colorectal cancer. *Int. J. Cancer.* 101, 118-127 (2002); and Hufton S E, et al. A profile of differentially expressed genes in primary colorectal cancer using suppression subtractive hybridization. *FEBS Lett.* 463, 77-82 (1999)) and glioblastoma cancers (Reddy P S, et al. PBEF1/NAmPRTase/Visfatin: a potential malignant astrocytoma/glioblastoma serum marker with prognostic value. *Cancer Biol. Ther.* 7, 663-668 (2008)), and it remains possible that the Nampt gene is amplified in other cancers.

However, without wishing to be bound by theory, cancers that express low levels of the Nampt enzyme may be more sensitive to treatment with a Nampt inhibitor, than a cancer that expresses high levels of the Nampt enzyme. Applicants have determined that Nampt expression inversely correlates with tumoricidal and NAD depletion potency and directly correlates with basal NAD levels in the xenograft cell lines. See, for example, the section "Inverse Correlation Between In Vitro Exemplary Compound A Potency and Expression of Nampt." Accordingly, in one aspect, the present invention provides methods of treating cancer, comprising first identifying a cancer exhibiting a low level of Nampt expression. The methods further comprise administering to a patient having a cancer exhibiting low levels of Nampt expression, a therapeutically effective dose of a compound of Formulae I-IVc or a compound of Tables 1 or 2, or a pharmaceutically-acceptable salt thereof.

In view of the above, it is believed that inhibition of Nampt activity would be effective in treating of a wide range of cancers. Support for this assertion is found in the Examples section below.

As used herein, the term "cancer" has its conventional meaning in the art. Cancer includes any condition of the animal or human body characterized by abnormal cellular proliferation. The cancers to be treated comprise a group of diseases characterized by the uncontrolled growth and spread of abnormal cells. Compounds of the present invention have been shown to be effective in a variety of standard cancer models, and are thus thought to have utility in treating a broad range of cancers. However, preferred methods of the invention involve treating cancers that have been found to respond favorably to treatment with Nampt inhibitors. Further, "treating cancer" should be understood as encompassing treating a patient who is at any one of the several stages of cancer, including diagnosed but as yet asymptomatic cancer.

A patient having cancer can be identified by conventional diagnostic techniques known in the art, and the identified patient can be treated with one or more of the compounds used in the methods of the present invention, preferably in a pharmaceutical composition having a pharmaceutically acceptable carrier.

Specific cancers that can be treated by the methods of the invention are those cancers that respond favorably to treatment with a Nampt inhibitor. Such cancers include, but are not limited to, Hodgkin's disease, non-Hodgkin's lymphoma, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

a. Methods of Identifying Cancers Most Likely to be Susceptible to Treatment with Nampt Inhibitors Importantly, NAD can be generated by several Nampt-independent pathways as well, including: (1) de novo synthesis from L-tryptophan via the kynurenine pathway; (2) from nicotinic acid (NA) via the Preiss-Handler pathway; and (3) from nicotinamide riboside via nicotinamide riboside kinase (reviewed in Khan, J. A. et al., Nicotinamide adenine dinucleotide metabolism as an attractive target for drug discovery. *Expert Opin. Ther. Targets.* 11(5):695-705 (2007)). However, these different routes of NAD synthesis are generally tissue specific: The de novo pathway is present in liver, brain, and immune cells, the Priess-Handler pathway is primarily active in the liver, kidney, and heart, and Nrk2, of the nicotinamide riboside kinase pathway, is expressed in brain, heart, and skeletal muscle (Bogan, K. L. and Brenner, C. Nicotinic acid, nicotinamide, and nicotinamide riboside: a molecular evaluation of NAD precursor vitamins in human nutrition. *Annu. Rev. Nutr.* 28:115-30 (2008) and Tempel, W. et al., Nicotinamide riboside kinase structures reveal new pathways to NAD. *PLoS Biol.* 5(10):e263 (2007)).

Of these alternative pathways of NAD, synthesis, the Preiss-Handler pathway is perhaps the most important for cancer cells. The first and rate-limiting step of this pathway, the conversion of nicotinic acid (NA) to nicotinic acid mononucleotide (NAMN), is catalyzed by the enzyme Naprt1. (See FIG. 1.)

While not wishing to be bound by theory it follows, therefore, that one way to stratify patients and to potentially expand the therapeutic window of the compounds used in the methods of the present invention would be to identify those cancers with reduced or absent levels of Naprt1 expression. Such cancers would theoretically be less able to replace cellular NAD through this alternative pathway, while being treated with Nampt inhibitors. Hence, they should be more sensitive to treatment by the compounds used in the methods of the present invention.

Accordingly, another aspect of the present invention includes methods of treating cancer, comprising first identifying a cancer exhibiting a low level of Naprt expression. These methods further comprise administering to a patient having a cancer exhibiting low levels of Naprt1 expression, a therapeutically effective dose of a compound of Formulae I-IVc or a compound of Tables 1 or 2, or a pharmaceutically-acceptable salt thereof.

In some embodiments, identifying a cancer exhibiting a low level of Naprt1 expression comprises determining the level of expression of Naprt1 protein. In some of such embodiments, determining the level of expression of Naprt1 protein is by way of a Western Blot and/or an Enzyme-Linked Immunosorbant Assay (ELISA).

In some embodiments, identifying a cancer exhibiting a low level of Naprt1 expression comprises determining the level of expression of the mRNA transcript encoding the Naprt1 protein. In some of such embodiments, determining the level of expression of the mRNA transcript encoding the Naprt1 protein is by way of a Northern Blot and/or by quantitative RT-PCR (qRT-PCT).

In some embodiments, identifying a cancer exhibiting a low level of Naprt1 expression further comprises determining whether such cancer expresses low levels of the Nampt enzyme.

Figure 7:
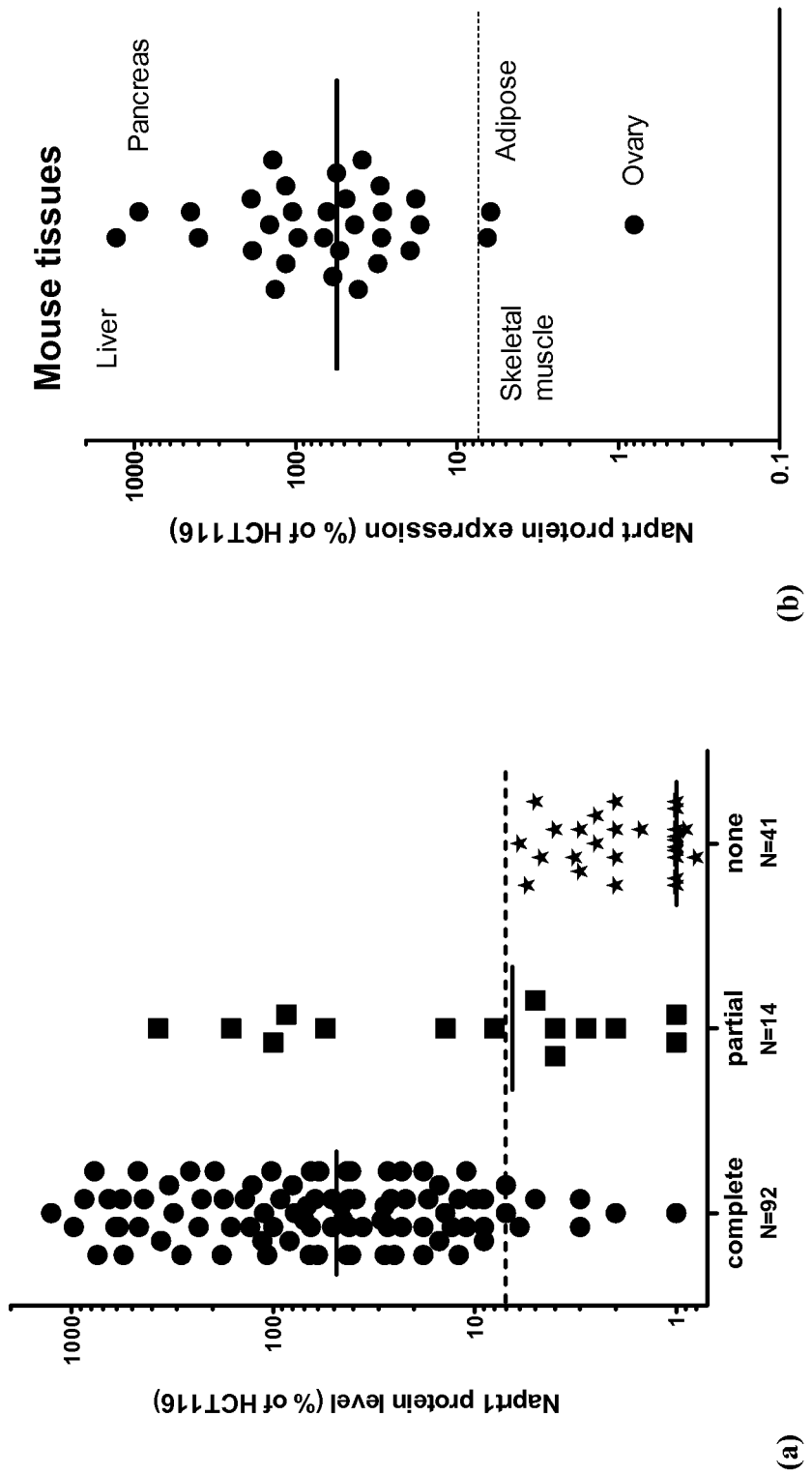

Additionally, while those cancers with reduced or absent levels of Naprt1 expression should be more susceptible to treatment with the Nampt inhibitors of the present invention, co-administration of NA to patients having such cancers could prevent toxicity in other tissues associated with Nampt inhibition. To support this concept, experiments were conducted to show that mice given NA survive doses of a Nampt inhibitor above the maximum tolerated dose (see also Beauparlant P., et al. Preclinical development of the nicotinamide phosphoribosyl transferase inhibitor prodrug GMX1777. *Anticancer Drugs.* 20(5):346-54 (2009) and Watson, et al. The small molecule GMX1778 is a potent inhibitor of NAD biosynthesis: strategy for enhanced therapy in nicotinic acid phosphoribosyltransferase 1-deficient tumors. *Mol. Cell. Biol.* 29(21):5872-88 (2009)). This phenomenon is referred to in the art as "NA rescue." Cells and/or cancers that are capable of NA rescue are also referred to herein as "exhibiting a NA Rescue Phenotype." Based on these results, cell lines were screened for NA rescue and Naprt1 expression was measured by immunoblotting. Of 142 cell lines tested so far, it was found that 87 cell lines were completely rescued from Nampt inhibitor-induced cytotoxicity by NA, 14 were partially rescued from Nampt inhibitor-induced cytotoxicity by NA, and 41 cell lines not rescued from Nampt inhibitor-induced cytotoxicity by NA. Analysis of the Naprt1 expression levels of all of the 142 cell lines was conducted by immunoblotting lysates with an anti-Naprt1 antibody. The results of these studies are shown in FIG. 7(*a*), and indicate that the level of expression of Naprt1 is correlated with the ability of the cell lines to be rescued from Nampt inhibitor-induced cytotoxicity by NA.

Accordingly, in the aspect of the present invention that includes methods of treating cancer, comprising identifying a cancer exhibiting a low level of Naprt expression. In some embodiments, such methods further comprise determining whether such cancer also exhibits a NA Rescue Phenotype. In some embodiments, when such cancer does not exhibit a NA Rescue Phenotype, then the patient is also administered nicotinic acid.

In view of the above, another aspect of the present invention comprises methods of identifying cancers that are likely susceptible to treatment with one or more of the compounds used in the methods of the present invention, and treating patients having such susceptible cancers. In this aspect of the invention, the method of identifying cancers that are likely susceptible to treatment with one or more of the compounds used in the methods of the present invention comprises (a) obtaining a biopsy sample of a cancer; and (b) determining the expression level of key enzymes in the main pathways for NAD biosynthesis (e.g. Nampt and Naprt1). Specifically, with regard to Naprt1, if the expression level of this enzyme is reduced, relative to the level seen in normal, non-cancerous tissues, the cancer is identified as likely susceptible to treatment with one or more of the compounds used in the methods of the present invention, since the cancer would be unlikely to synthesize NAD via the Preiss-Handler pathway.

In different subaspects, the methods of determining the expression level of the Naprt1 gene involve either determining levels of expression of the Naprt1-encoding transcript (i.e., Naprt1-encoding mRNA), or determining levels of expression of the Naprt1 protein itself. For these embodiments, any acceptable means of determining expression levels of either the Naprt1-encoding transcript, or the Naprt1 protein itself, can be utilized, and such acceptable means are well within the skill level of the artisan versed in determining expression levels of eukaryotic genes. Such acceptable means can include, for example, quantitative PCR (qPCR) to measure levels of Naprt1-encoding transcript, or ELISAs to measure levels of expressed Naprt1 protein. The specific methods involved in determining the expression of particular eukaryotic genes are well known in the art.

b. Methods of Limiting Toxicity of the Compounds of the Present Invention by Administering NA In view of the NA rescue phenomenon described above, yet another aspect of the present invention comprises methods of identifying cancers that are likely susceptible to treatment with one or more of the compounds used in the methods of the present invention by virtue of the cancer having low or undetectable levels of Naprt1 expression, and treating patients having such cancers with one or more of the compounds used in the methods of the present invention in combination with nicotinic acid (NA). In this aspect, the method of identifying cancers that are likely susceptible to treatment with one or more of the compounds used in the methods of the present invention are as described above, while the method of treating patients having such susceptible cancers can involve pretreating the patient with NA (i.e., administering NA prior to administering one or more of the compounds used in the methods of the present invention), co-administering NA with one or more of the compounds used in the methods of the present invention, or first treating the patient with a one or more of the compounds used in the methods of the present invention (i.e., administering one or more of the compounds used in the methods of the present invention), followed by thereafter administering NA. Additionally, the NA may be administered as part of the same dosage form comprising the therapeutically effective amount of one or more of the compounds used in the methods of the present invention.

In some embodiments, a protective amount of nicotinic acid is administered at a time ranging from about one hour before to about eight hours after administration of the therapeutically effective amount of a compound of Formulae I-IVc or a compound of Tables 1 or 2, or a pharmaceutically-acceptable salt thereof.

In a related aspect, the present invention includes method of treating cancers exhibiting low levels of Naprt1 expression, comprising administering to a patient having such a cancer a therapeutically effective dose of a compound of Formulae I-IVc or a compound of Tables 1 or 2, or a pharmaceutically-acceptable salt thereof, and administering to said patient a protective amount of nicotinic acid at a time ranging from about one hour before to about eight hours after administration of the therapeutically effective amount of such compound.

Experiments were conducted to show that mice given NA survive doses of a Nampt inhibitor above the maximum tolerated dose (see also Beauparlant P., et al. Preclinical development of the nicotinamide phosphoribosyl transferase inhibitor prodrug GMX1777. *Anticancer Drugs.* 20(5):346-54 (2009) and Watson, et al. The small molecule GMX1778 is a potent inhibitor of NAD$^+$ biosynthesis: strategy for enhanced therapy in nicotinic acid phosphoribosyltransferase 1-deficient tumors. *Mol. Cell. Biol.* 29(21):5872-88 (2009)). This phenomenon is referred to in the art as "NA rescue."

Cell lines were treated with exemplary compounds of the present invention and screened for NA rescue and Naprt1 expression by immunoblotting and quantitative RT-PCR (qRT-PCR). Lack of NA rescue was greatest in brain cancers, lung cancers, lymphoma, myeloma, and osteosarcoma. Further, glioblastoma and sarcoma cell lines that are reported to be resistant to NA rescue have been found to have reduced Naprt1 expression (Watson, et al. *Mol. Cell. Biol.* 29(21): 5872-88 (2009)).

In these methods of the present invention, the amount of NA that is administered is about 50 mg/kg, about 100 mg/kg, about 200 mg/kg, about 400 mg/kg, 800 mg/kg, 1,600 mg/kg or about 3,200 mg/kg. Further, the frequency of the NA administration can be tailored as required to minimize unwanted toxicity to normal tissues. In some embodiments, the frequency of the NA administration is matched to the frequency of the administration of the Nampt inhibitor used in the therapeutic method. That is to say, NA can be administered with the same frequency as the Nampt inhibitor, but the NA may be administered before, at the same time as, or after the Nampt inhibitor is administered. In other embodiments, the frequency of the NA administration is independent of the frequency of the administration of the Nampt inhibitor used in the therapeutic method. Additional studies will be required to discover the most appropriate dosing amounts and schedules for NA, in combination with cytotoxic Nampt-inhibitor.

Treating Systemic or Chronic Inflammation

Nampt expression in visceral adipose tissue has been found to correlate with the expression of proinflammatory genes, CD68 and TNFα (Chang et al.; *Metabolism.* 59(1):93-9 (2010). Several studies have noted an increase in reactive oxygen species and activation of NF-kappaB in response to Nampt expression (Oita et al.; *Pflugers Arch.* (2009); Romacho et al.; *Diabetologia.* 52(11):2455-63 (2009). Nampt serum levels were found to have been increased in patients with inflammatory bowel diseases and correlated with disease activity (Moschen et al.; *Mutat. Res.* (2009). One study has even suggested a specific mechanism for Nampt in inflammation: High levels of Nampt increase cellular NAD levels leading to a post-transcriptional upregulation of TNF via the NAD-dependent deacetylase, SirT6 (Van Gool et al. *Nat. Med.* 15(2):206-10 (2009)). Further, inhibition of Nampt reduced levels of inflammatory cytokines IL-6 and TNF-α (Busso et al. *PLoS One.* 21; 3(5):e2267 (2008)). In another study, Nampt inhibition was found to prevent TNF-α and IFN-γ production in T-lymphocytes (Bruzzone et al.; *PLoS One.;* 4(11):e7897 (2009)).

In view of the above, it is believed that inhibition of Nampt activity would be effective in treating systemic or chronic inflammation resulting from a wide range of causes. Consequently, the present invention provides methods of treating systemic or chronic inflammation by administering therapeutically effective amounts of one or more of the compounds used in the methods of the present invention.

Treating Rheumatoid Arthritis

Nampt levels increased in a mouse model of arthritis and treatment of these mice with a Nampt inhibitor reduced the arthritis symptoms (Busso et al. *PLoS One.* 21; 3(5):e2267 (2008)). Also, because Nampt inhibition can decrease the activity of polyADP ribose polymerases (PARPs) through the dependence of PARPs on NAD as a substrate, Nampt inhibitors, either alone or in combination with PARP inhibitors can be efficacious in any ailment treatable by PARP inhibitors. In this regard, PARP inhibitors have shown efficacy in models of arthritis (Kroger et al. Inflammation. 1996 April; 20(2):203-15 (1996)).

In view of the above, it is believed that inhibition of Nampt activity would be effective in treating RA. Consequently, the present invention provides methods of treating RA by administering therapeutically effective amounts of one or more of the compounds used in the methods of the present invention, either alone, or in combination with a PARP inhibitor.

Treating Obesity and Diabetes

Nampt, also known as visfatin, was described as an adipokine found in visceral fat that acted as an insulin mimetic (Fukuhara et al. *Science* 307:426-30 (2007). This paper was eventually retracted and other groups have failed to confirm that Nampt binds the insulin receptor. Nevertheless, many subsequent papers continue to report correlations between Nampt expression and obesity and/or diabetes. In one, increased expression of Nampt and levels of circulating Nampt were seen in obese patients (Catalan et al.; *Nutr. Metab. Cardiovasc. Dis.* (2010), although a different study found that the correlation was specific only to obese patients with type 2 diabetes (Laudes, et al.; *Horm. Metab. Res.* (2010). Yet another study reported a correlation between BMI and body fat mass and Nampt plasma levels, but an inverse correlation with cerebrospinal fluid levels of Nampt (Hallschmid et al.; *Diabetes.* 58(3):637-40 (2009)). Following bariatric surgery, patients with pronounced weight loss showed decreased levels of Nampt mRNA in liver (Moschen et al.; *J. Hepatol.* 51(4):765-77 (2009)). Finally, a rare single nucleotide polymorphism was identified in Nampt that correlated with severe obesity (Blakemore, et al.; *Obesity* 17(8): 1549-53 (2009)). In contrast to these reports, Nampt levels were not altered in rat models of obesity (Mercader et al.;

Horm. Metab. Res. 40(7):467-72 (2008)). Further, circulating levels of Nampt correlated with HDL-cholesterol and inversely with triglycerides (Wang et al.; *Pflugers Arch.* 454 (6):971-6 2007)), arguing against Nampt involvement in obesity. Finally Nampt has been show to be a positive regulator of insulin secretion by beta-cells (Revollo et al. *Cell Metab.* 6(5):363-75 (2007)). This effect seems to require the enzymatic activity of Nampt and can be mimicked in cell culture models by exogenous addition of NaMN.

Because Nampt inhibition can decrease the activity of polyADP ribose polymerases (PARPs) through the dependence of PARPs on NAD as a substrate, Nampt inhibitor, either alone or in combination with PARP inhibitors can be efficacious in any ailment treatable by PARP inhibitors. In this regard, PARP inhibitors have shown efficacy in models of type I diabetes (Drel et al. *Endocrinology.* 2009 December; 150(12):5273-83. Epub 2009 Oct. 23.

In view of the above, and despite the contrasting results mentioned, it is believed that inhibition of Nampt activity would be effective in treating obesity and diabetes, and other complications associated with these, and other, metabolic diseases and disorders. Consequently, the present invention provides methods of treating obesity and diabetes, and other complications associated with these, and other, metabolic diseases and disorders, by administering therapeutically effective amounts of one or more of the compounds used in the methods of the present invention.

Treating T-Cell Mediated Autoimmune Disease

Nampt expression has been shown to be upregulated in activated T-cells (Rongavaux et al.; *J. Immunol.* 181(7):4685-95 2008)) and Phase I clinical trials report lymphopenia in patients treated with Nampt inhibitors (reviewed in von Heideman et al.; *Cancer Chemother. Pharmacol.* (2009)). Additionally, in a mouse model of a T-cell autoimmune disease, experimental autoimmune encephalomyelitis (EAE), Nampt inhibition reduced the clinical disease score and demyelination in the spinal cord (Bruzzone et al.; *PLoS One.* 4(11):e7897 (2009)).

In view of the above, it is believed that inhibition of Nampt activity would be effective in treating T-cell mediated autoimmune disease, and other complications associated with diseases and disorders. Consequently, the present invention provides methods of treating T-cell mediated autoimmune disease, and other complications associated with these diseases and disorders, by administering therapeutically effective amounts of one or more of the compounds used in the methods of the present invention.

Treating Ischemia

Because Nampt inhibition can decrease the activity of polyADP ribose polymerases (PARPs) through the dependence of PARPs on NAD as a substrate, Nampt inhibitor, either alone or in combination with PARP inhibitors can be efficacious in any ailment treatable by PARP inhibitors. The PARP inhibitor FR247304 has been shown to attenuate neuronal damage in vitro and in vivo models of cerebral ischemia (Iwashita, et al. *J. Pharmacol Exp. Ther.* 310(2):425-36 (2004). Epub 2004 Apr. 9). Similarly there are suggestions that PARP inhibitors could be efficacious in clinical management of chronic hypoperfusion-induced neurodegenerative diseases including ocular ischemic syndrome (Mester et al. *Neurotox. Res.* 16(1):68-76 (2009) Epub 2009 Apr. 9) or ischemia reperfusion (Crawford et al. *Surgery.* 2010 Feb. 2. [Epub ahead of print]).

In view of the above, it is believed that inhibition of Nampt activity would be effective in treating ischemia, and other complications associated with this condition. Consequently, the present invention provides methods of treating ischemia, and other complications associated with this condition, by administering therapeutically effective amounts of one or more of the compounds used in the methods of the present invention, either alone, or in combination with a PARP inhibitor.

Methods of Making the Compounds of the Present Invention

Methods of making the compounds used in the methods of the present invention have been provided previously. For example, methods of making those compounds depicted in Tables 1 and 2, below are described in International Patent Application No. PCT/US2011/026752, filed Mar. 1, 2011, and published as WO 2011/109441. Such previously described methods are incorporated by reference herein in their entirety.

Examplary Compounds

Table 1, below, depicts several exemplary Nampt-inhibiting compound of Formulae I-III that can be used in the therapeutic methods of the present invention. All of the compounds depicted have been found in the 72-hour HCT116 cytotoxity assay described below to have an $IC_{50}$ of less than 100 nM.

TABLE 1

| Example Number | Structure | $^1$H NMR Data (400 MHz, DMSO-d6) |
|---|---|---|
| 1 | 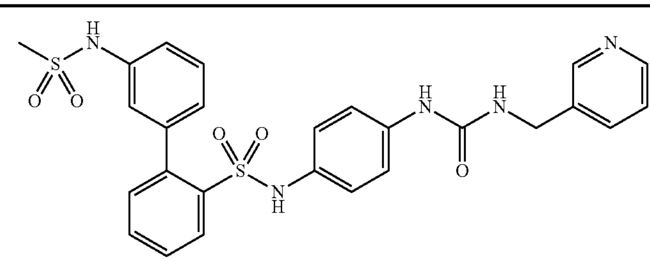 | 3'-[(methylsulfonyl)amino]-N-(4-{[(pyridin-3-ylmethyl)carbamoyl]amino}phenyl)biphenyl-2-sulfonamide |

TABLE 1-continued

| Example Number | Structure | ¹H NMR Data (400 MHz, DMSO-d6) |
|---|---|---|
| 2 | 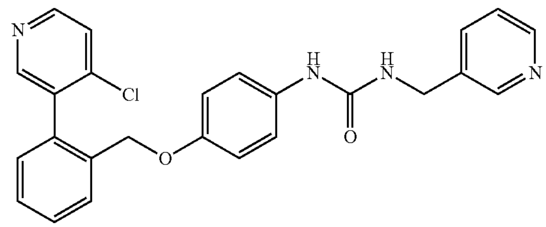 [SMILES: O=C(NCc1cccnc1)Nc1ccc(OCc2ccccc2-c2cnccc2Cl)cc1] | 1-(4-{[2-(4-Chloropyridin-3-yl)benzyl]oxy}phenyl)-3-(pyridin-3-ylmethyl)urea |
| 3 | 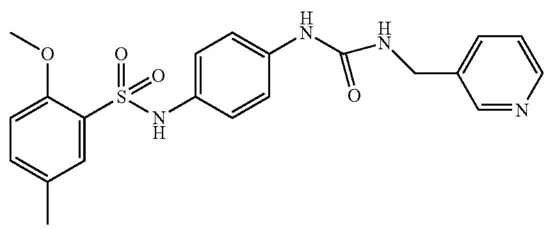 [SMILES: COc1ccc(C)cc1S(=O)(=O)Nc1ccc(NC(=O)NCc2cccnc2)cc1] | 2-Methoxy-5-methyl-N-(4-{[(pyridin-3-ylmethyl)carbamoyl]amino}phenyl)benzenesulfonamide |
| 4 | 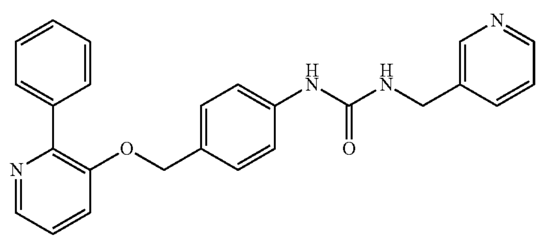 [SMILES: O=C(NCc1cccnc1)Nc1ccc(COc2cccnc2-c2ccccc2)cc1] | 1-(4-{[(2-Phenylpyridin-3-yl)oxy]methyl}phenyl)-3-(pyridin-3-ylmethyl)urea |
| 5 | 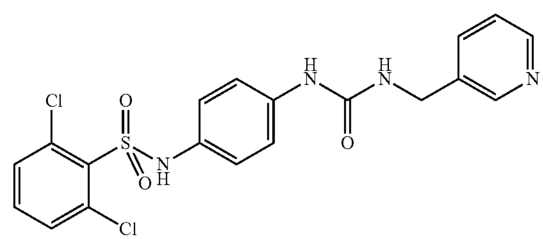 [SMILES: O=C(NCc1cccnc1)Nc1ccc(NS(=O)(=O)c2c(Cl)cccc2Cl)cc1] | 2,6-dichloro-N-(4-{[(pyridin-3-ylmethyl)carbamoyl]amino}phenyl)benzenesulfonamide |
| 6 | 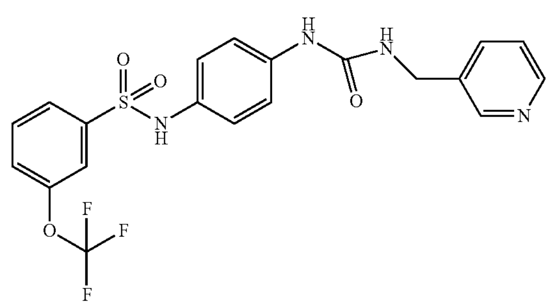 [SMILES: O=C(NCc1cccnc1)Nc1ccc(NS(=O)(=O)c2cccc(OC(F)(F)F)c2)cc1] | N-(4-{[(Pyridin-3-ylmethyl)carbamoyl]amino}phenyl)-3-(trifluoromethoxy)benzenesulfonamide |
| 7 | 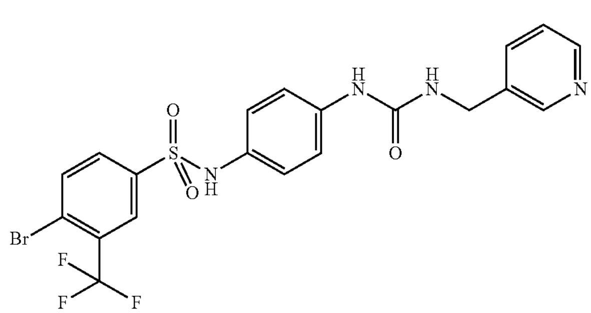 [SMILES: O=C(NCc1cccnc1)Nc1ccc(NS(=O)(=O)c2ccc(Br)c(C(F)(F)F)c2)cc1] | 4-bromo-N-(4-{[(pyridin-3-ylmethyl)carbamoyl]amino}phenyl)-3-(trifluoromethyl)benzenesulfonamide |

TABLE 1-continued

| Example Number | Structure | ¹H NMR Data (400 MHz, DMSO-d6) |
|---|---|---|
| 8 | 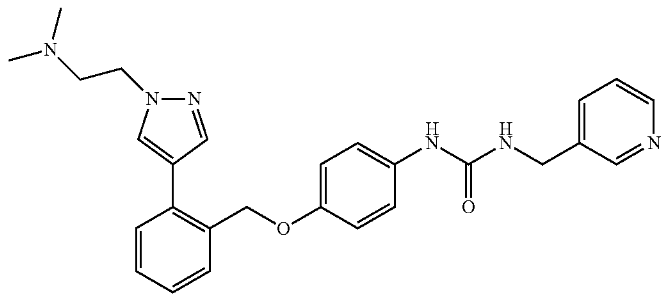 [SMILES: CN(C)CCn1cc(-c2ccccc2COc2ccc(NC(=O)NCc3cccnc3)cc2)cn1] | 1-{4-[(2-{1-[2-(Dimethylamino)ethyl]-1H-pyrazol-4-yl}benzyl)oxy]phenyl}-3-(pyridin-3-ylmethyl)urea |
| 9 | 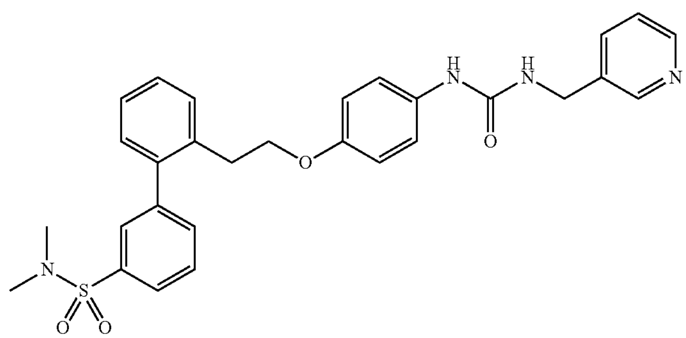 [SMILES: CN(C)S(=O)(=O)c1cccc(-c2ccccc2CCOc2ccc(NC(=O)NCc3cccnc3)cc2)c1] | N,N-Dimethyl-2'-[2-(4-{[(pyridin-3-ylmethyl)carbamoyl]amino}phenoxy)ethyl]biphenyl-3-sulfonamide |
| 10 | 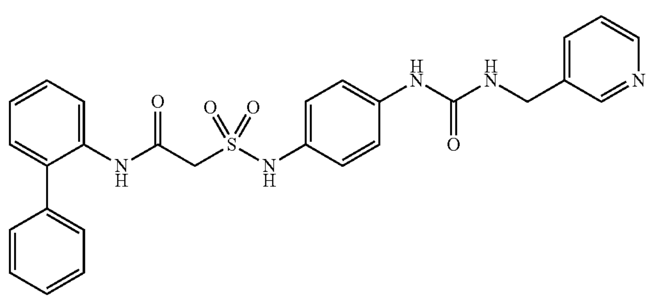 [SMILES: O=C(CS(=O)(=O)Nc1ccc(NC(=O)NCc2cccnc2)cc1)Nc1ccccc1-c1ccccc1] | N-(Biphenyl-2-yl)-2-[(4-{[(pyridin-3-ylmethyl)carbamoyl]amino}phenyl)sulfamoyl]acetamide |
| 11 | 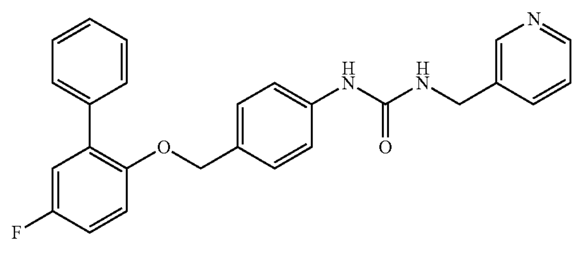 [SMILES: O=C(NCc1cccnc1)Nc1ccc(COc2ccc(F)cc2-c2ccccc2)cc1] | 1-(4-{[(5-Fluorobiphenyl-2-yl)oxy]methyl}phenyl)-3-(pyridin-3-ylmethyl)urea |
| 12 | 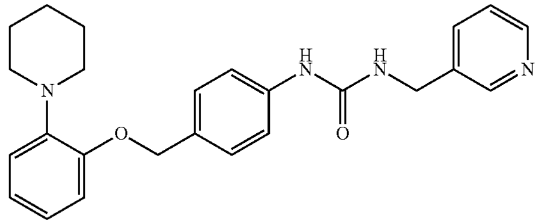 [SMILES: O=C(NCc1cccnc1)Nc1ccc(COc2ccccc2N2CCCCC2)cc1] | 1-(4-{[2-(Piperidin-1-yl)phenoxy]methyl}phenyl)-3-(pyridin-3-ylmethyl)urea |

TABLE 1-continued

| Example Number | Structure | ¹H NMR Data (400 MHz, DMSO-d6) |
|---|---|---|
| 13 | 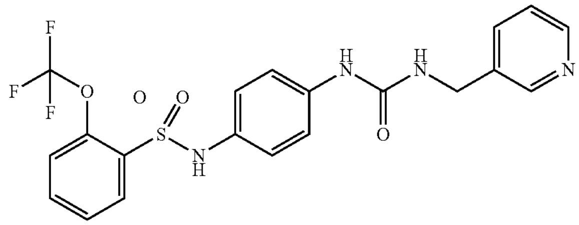 | |
| 14 | 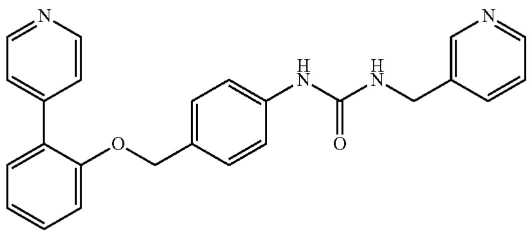 [SMILES: O=C(NCc1cccnc1)Nc1ccc(COc2ccccc2-c2ccncc2)cc1] | 1-(Pyridin-3-ylmethyl)-3-(4-{[2-(pyridin-4-yl)phenoxy]methyl}phenyl)urea |
| 15 | 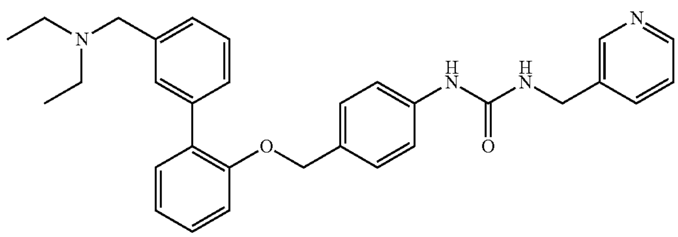 [SMILES: CCN(CC)Cc1cccc(-c2ccccc2OCc2ccc(NC(=O)NCc3cccnc3)cc2)c1] | 1-{4-[({3'-[(Diethylamino)methyl]biphenyl-2-yl}oxy)methyl]phenyl}-3-(pyridin-3-ylmethyl)urea |
| 16 | 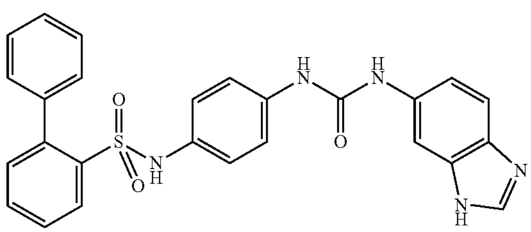 [SMILES: O=C(Nc1ccc(NS(=O)(=O)c2ccccc2-c2ccccc2)cc1)Nc1ccc2nc[nH]c2c1] | N-{4-[(1H-benzimidazol-6-ylcarbamoyl)amino]phenyl}biphenyl-2-sulfonamide |
| 17 | 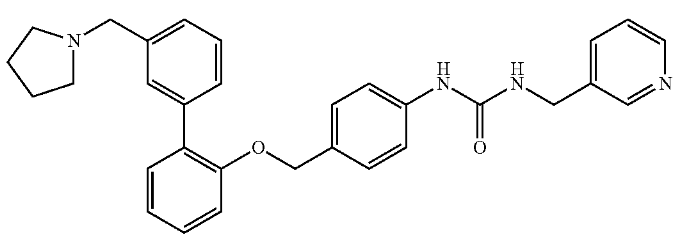 [SMILES: O=C(NCc1cccnc1)Nc1ccc(COc2ccccc2-c2cccc(CN3CCCC3)c2)cc1] | 1-(Pyridin-3-ylmethyl)-3-[4-({[3'-(pyrrolidin-1-ylmethyl)biphenyl-2-yl]oxy}methyl)phenyl]urea |
| 18 | 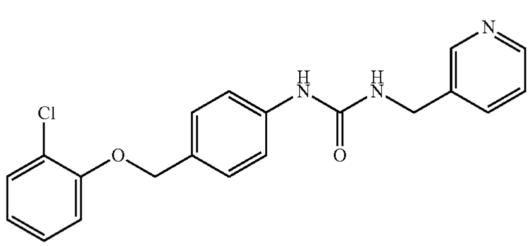 [SMILES: O=C(NCc1cccnc1)Nc1ccc(COc2ccccc2Cl)cc1] | 1-{4-[(2-Chlorophenoxy)methyl]phenyl}-3-(pyridin-3-ylmethyl)urea |

TABLE 1-continued

| Example Number | Structure | ¹H NMR Data (400 MHz, DMSO-d6) |
|---|---|---|
| 19 | 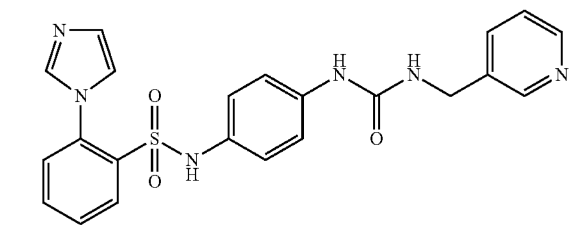 [SMILES: O=C(NCc1cccnc1)Nc1ccc(NS(=O)(=O)c2ccccc2-n2ccnc2)cc1] | 2-(1H-Imidazol-1-yl)-N-(4-{[(pyridin-3-ylmethyl)carbamoyl]amino}phenyl)benzenesulfonamide |
| 20 | 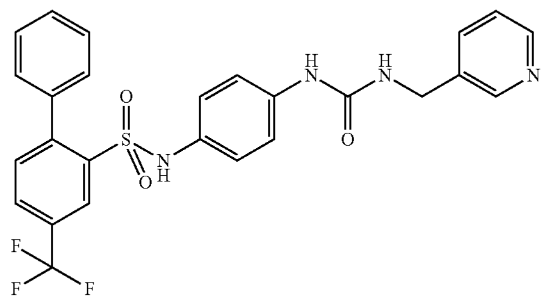 [SMILES: O=C(NCc1cccnc1)Nc1ccc(NS(=O)(=O)c2cc(C(F)(F)F)ccc2-c2ccccc2)cc1] | N-(4-{[(pyridin-3-ylmethyl)carbamoyl]amino}phenyl)-4-(trifluoromethyl)biphenyl-2-sulfonamide |
| 21 | 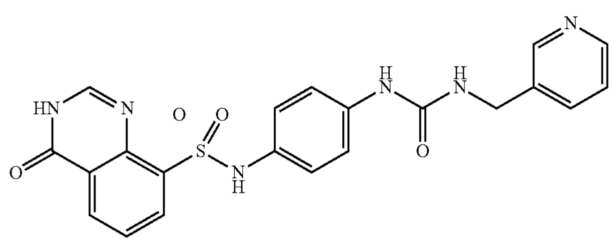 | 4-oxo-N-(4-{[(pyridin-3-ylmethyl)carbamoyl]amino}phenyl)-3,4-dihydroquinazoline-8-sulfonamide |
| 22 | 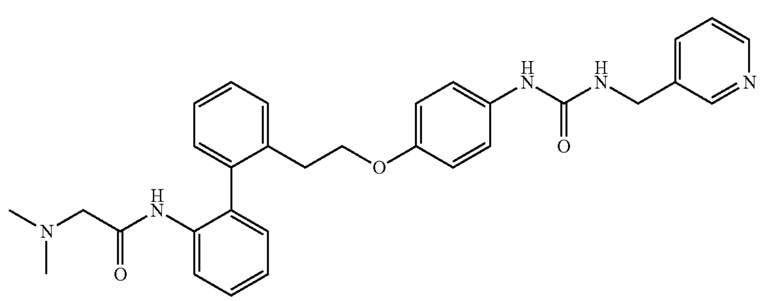 [SMILES: CN(C)CC(=O)Nc1ccccc1-c1ccccc1CCOc1ccc(NC(=O)NCc2cccnc2)cc1] | N~2~,N~2~-Dimethyl-N-{2'-[2-(4-{[(pyridin-3-ylmethyl)carbamoyl]amino}phenoxy)ethyl]biphenyl-2-yl}glycinamide |
| 23 | 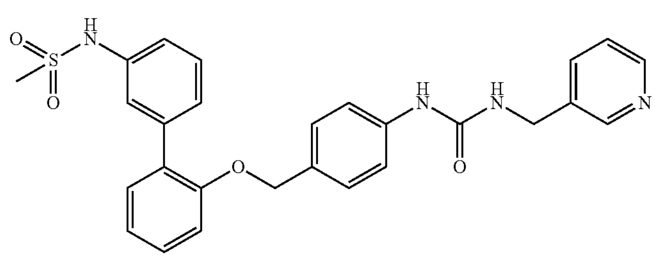 [SMILES: CS(=O)(=O)Nc1cccc(-c2ccccc2OCc2ccc(NC(=O)NCc3cccnc3)cc2)c1] | N-{2'-[(4-{[(Pyridin-3-ylmethyl)carbamoyl]amino}benzyl)oxy]biphenyl-3-yl}methanesulfonamide |

TABLE 1-continued

| Example Number | Structure | ¹H NMR Data (400 MHz, DMSO-d6) |
|---|---|---|
| 24 | 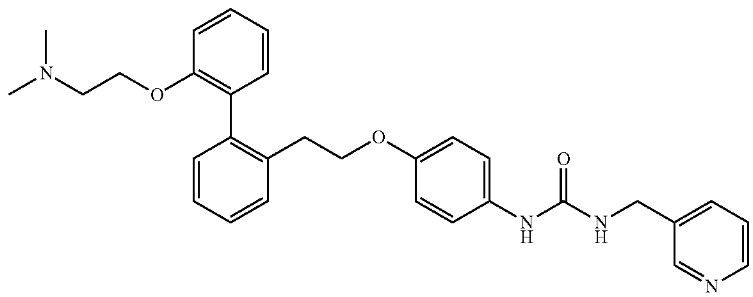 [SMILES: CN(C)CCOc1ccccc1-c1ccccc1CCOc1ccc(NC(=O)NCc2cccnc2)cc1] | 1-[4-(2-{2'-[2-(Dimethylamino)ethoxy]biphenyl-2-yl}ethoxy)phenyl]-3-(pyridin-3-ylmethyl)urea |
| 25 | 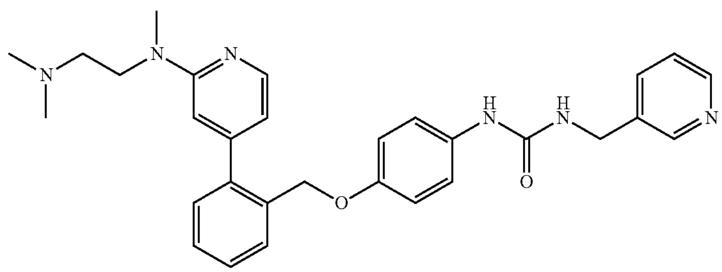 [SMILES: CN(C)CCN(C)c1cc(-c2ccccc2COc2ccc(NC(=O)NCc3cccnc3)cc2)ccn1] | 1-(4-{[2-(2-{[2-(Dimethylamino)ethyl](methyl)amino}pyridin-4-yl)benzyl]oxy}phenyl)-3-(pyridin-3-ylmethyl)urea |
| 26 | 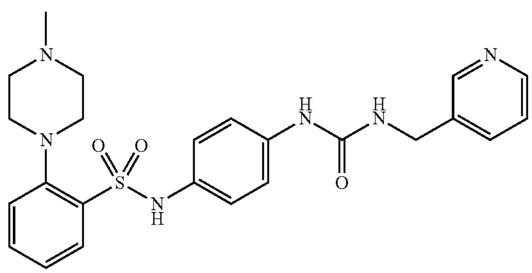 [SMILES: CN1CCN(c2ccccc2S(=O)(=O)Nc2ccc(NC(=O)NCc3cccnc3)cc2)CC1] | 2-(4-methylpiperazin-1-yl)-N-(4-{[(pyridin-3-ylmethyl)carbamoyl]amino}phenyl)benzenesulfonamide |
| 27 | 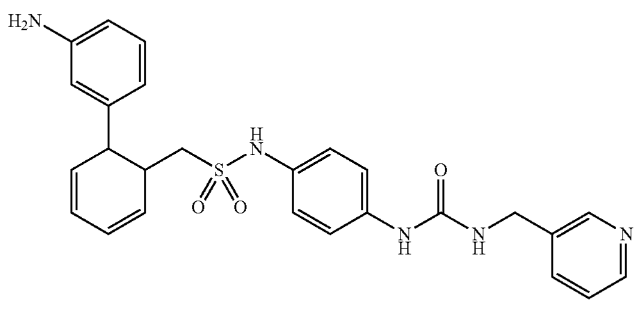 [SMILES: Nc1cccc(C2C=CC=CC2CS(=O)(=O)Nc2ccc(NC(=O)NCc3cccnc3)cc2)c1] | 1-[6-(3-Aminophenyl)cyclohexa-2,4-dien-1-yl]-N-(4-{[(pyridin-3-ylmethyl)carbamoyl]amino}phenyl)methanesulfonamide |
| 28 | 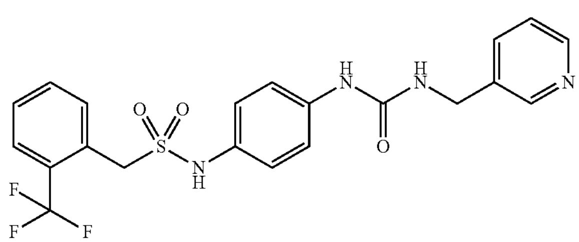 [SMILES: O=C(NCc1cccnc1)Nc1ccc(NS(=O)(=O)Cc2ccccc2C(F)(F)F)cc1] | N-(4-{[(Pyridin-3-ylmethyl)carbamoyl]amino}phenyl)-1-[2-(trifluoromethyl)phenyl]methanesulfonamide |

TABLE 1-continued

| Example Number | Structure | ¹H NMR Data (400 MHz, DMSO-d6) |
|---|---|---|
| 29 | 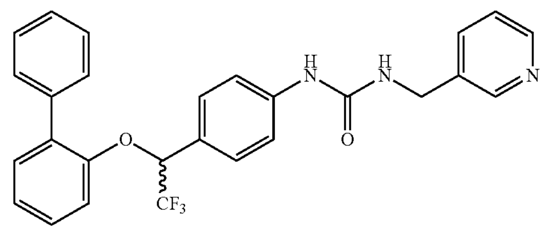 [SMILES: O=C(NCc1cccnc1)Nc1ccc(C(Oc2ccccc2-c2ccccc2)C(F)(F)F)cc1] | 1-{4-[1-(Biphenyl-2-yloxy)-2,2,2-trifluoroethyl]phenyl}-3-(pyridin-3-ylmethyl)urea |
| 30 | 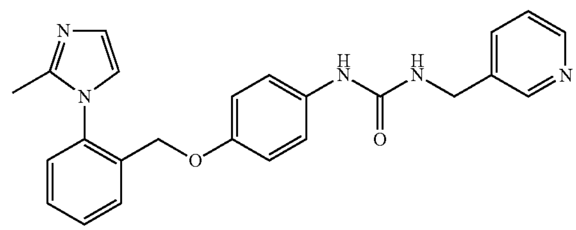 [SMILES: Cc1nccn1-c1ccccc1COc1ccc(NC(=O)NCc2cccnc2)cc1] | 1-(4-{[2-(2-Methyl-1H-imidazol-1-yl)benzyl]oxy}phenyl)-3-(pyridin-3-ylmethyl)urea |
| 31 | 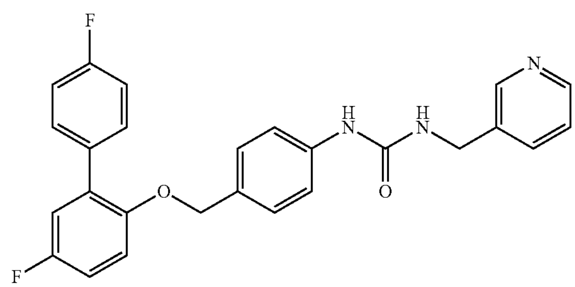 [SMILES: O=C(NCc1cccnc1)Nc1ccc(COc2ccc(F)cc2-c2ccc(F)cc2)cc1] | 1-(4-{[(4',5-Difluorobiphenyl-2-yl)oxy]methyl}phenyl)-3-(pyridin-3-ylmethyl)urea |
| 32 | 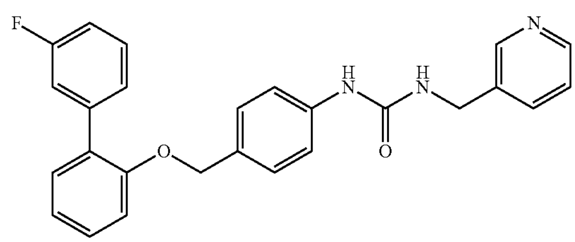 [SMILES: O=C(NCc1cccnc1)Nc1ccc(COc2ccccc2-c2cccc(F)c2)cc1] | 1-(4-{[(3'-Fluorobiphenyl-2-yl)oxy]methyl}phenyl)-3-(pyridin-3-ylmethyl)urea |
| 33 | 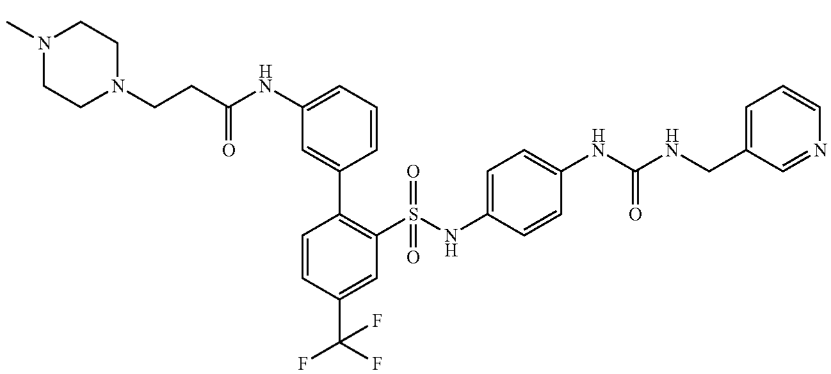 [SMILES: CN1CCN(CCC(=O)Nc2cccc(-c3ccc(C(F)(F)F)cc3S(=O)(=O)Nc3ccc(NC(=O)NCc4cccnc4)cc3)c2)CC1] | 3-(4-Methylpiperazin-1-yl)-N-{2'-[(4-{[(pyridin-3-ylmethyl)carbamoyl]amino}phenyl)sulfamoyl]-4'-(trifluoromethyl)biphenyl-3-yl}propanamide |

TABLE 1-continued

| Example Number | Structure | ¹H NMR Data (400 MHz, DMSO-d6) |
|---|---|---|
| 34 | 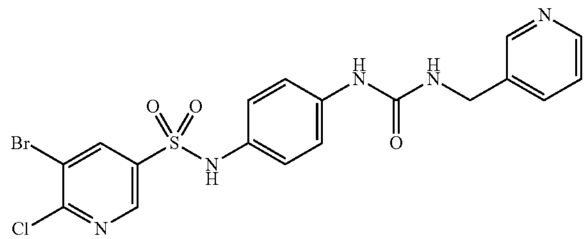 [SMILES: O=C(NCc1cccnc1)Nc1ccc(NS(=O)(=O)c2cnc(Cl)c(Br)c2)cc1] | 5-bromo-6-chloro-N-(4-{[(pyridin-3-ylmethyl)carbamoyl]amino}phenyl)pyridine-3-sulfonamide |
| 35 | 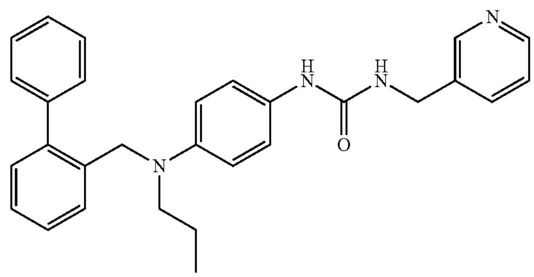 [SMILES: CCCN(Cc1ccccc1-c1ccccc1)c1ccc(NC(=O)NCc2cccnc2)cc1] | 1-{4-[(Biphenyl-2-ylmethyl)(propyl)amino]phenyl}-3-(pyridin-3-ylmethyl)urea |
| 36 | 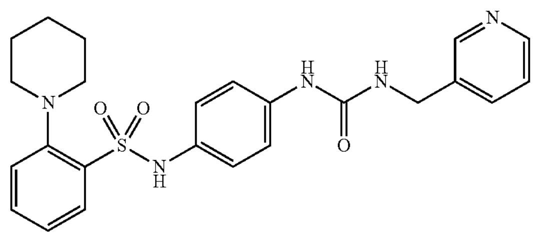 [SMILES: O=C(NCc1cccnc1)Nc1ccc(NS(=O)(=O)c2ccccc2N2CCCCC2)cc1] | 2-(piperidin-1-yl)-N-(4-{[(pyridin-3-ylmethyl)carbamoyl]amino}phenyl)benzenesulfonamide |
| 37 | 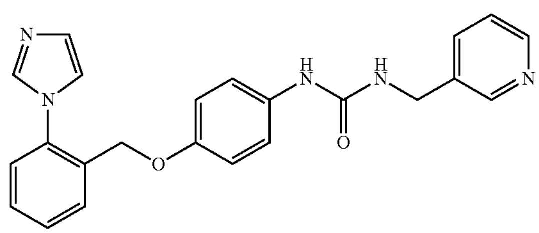 [SMILES: O=C(NCc1cccnc1)Nc1ccc(OCc2ccccc2-n2ccnc2)cc1] | 1-(4-{[2-(1H-Imidazol-1-yl)benzyl]oxy}phenyl)-3-(pyridin-3-ylmethyl)urea |
| 38 | 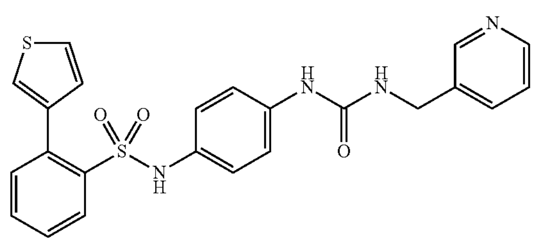 [SMILES: O=C(NCc1cccnc1)Nc1ccc(NS(=O)(=O)c2ccccc2-c2ccsc2)cc1] | N-(4-{[(pyridin-3-ylmethyl)carbamoyl]amino}phenyl)-2-(thiophen-3-yl)benzenesulfonamide |
| 39 | 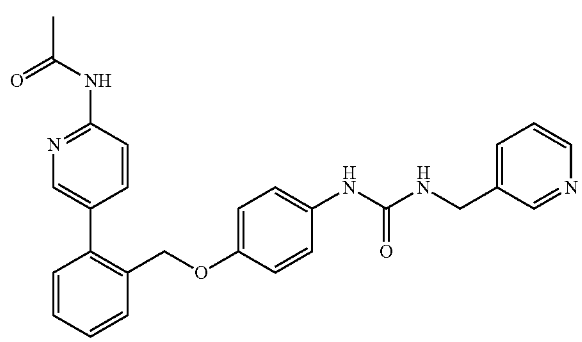 [SMILES: CC(=O)Nc1ccc(-c2ccccc2COc2ccc(NC(=O)NCc3cccnc3)cc2)cn1] | N-(5-{2-[(4-{[(Pyridin-3-ylmethyl)carbamoyl]amino}phenoxy)methyl]phenyl}pyridin-2-yl)acetamide |

TABLE 1-continued

| Example Number | Structure | ¹H NMR Data (400 MHz, DMSO-d6) |
|---|---|---|
| 40 | 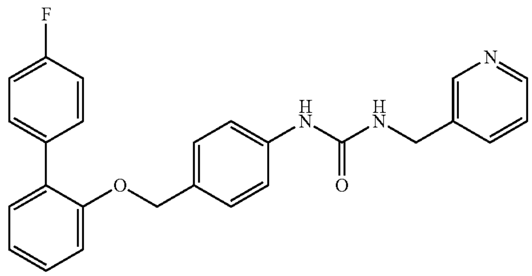 [SMILES: O=C(NCc1cccnc1)Nc1ccc(COc2ccccc2-c2ccc(F)cc2)cc1] | 1-(4-{[(4'-Fluorobiphenyl-2-yl)oxy]methyl}phenyl)-3-(pyridin-3-ylmethyl)urea |
| 41 | 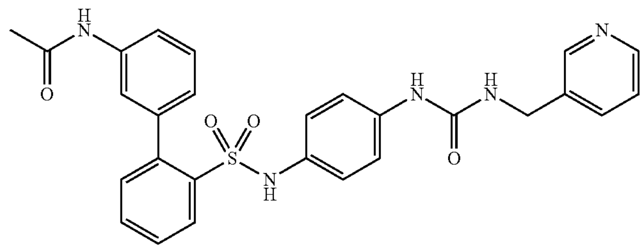 [SMILES: CC(=O)Nc1cccc(-c2ccccc2S(=O)(=O)Nc2ccc(NC(=O)NCc3cccnc3)cc2)c1] | N-{2'-[(4-{[(pyridin-3-ylmethyl)carbamoyl]amino}phenyl)sulfamoyl]biphenyl-3-yl}acetamide |
| 42 | 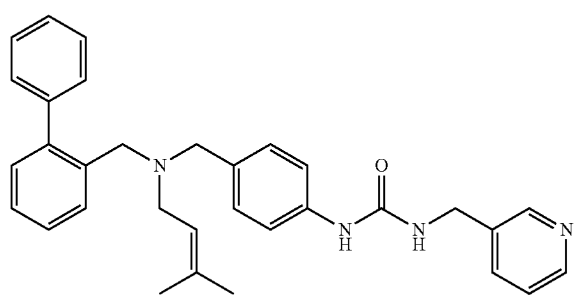 [SMILES: CC(C)=CCN(Cc1ccc(NC(=O)NCc2cccnc2)cc1)Cc1ccccc1-c1ccccc1] | 1-(4-{[(Biphenyl-2-ylmethyl)(3-methylbut-2-en-1-yl)amino]methyl}phenyl)-3-(pyridin-3-ylmethyl)urea |
| 43 | 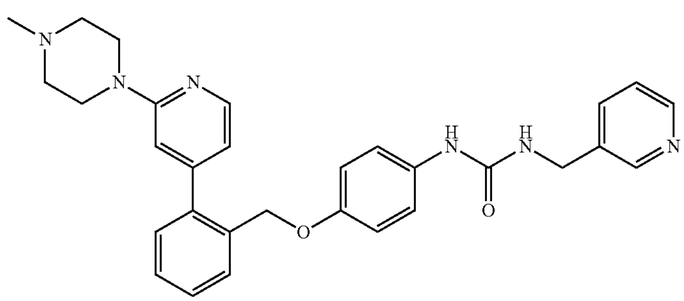 [SMILES: CN1CCN(c2cc(-c3ccccc3COc3ccc(NC(=O)NCc4cccnc4)cc3)ccn2)CC1] | 1-[4-({2-[2-(4-Methylpiperazin-1-yl)pyridin-4-yl]benzyl}oxy)phenyl]-3-(pyridin-3-ylmethyl)urea |
| 44 | 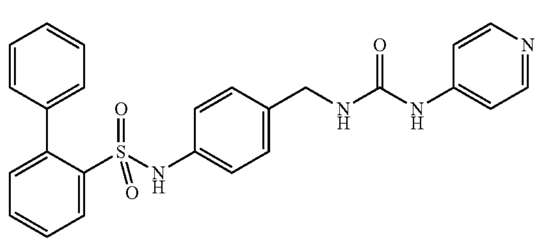 [SMILES: O=C(NCc1ccc(NS(=O)(=O)c2ccccc2-c2ccccc2)cc1)Nc1ccncc1] | N-(4-{[(pyridin-4-ylcarbamoyl)amino]methyl}phenyl)biphenyl-2-sulfonamide |

TABLE 1-continued

| Example Number | Structure | $^1$H NMR Data (400 MHz, DMSO-d6) |
|---|---|---|
| 45 | 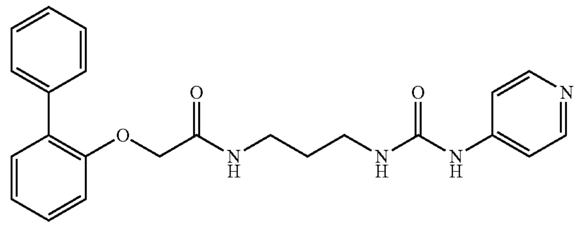 [SMILES: O=C(COc1ccccc1-c1ccccc1)NCCCNC(=O)Nc1ccncc1] | 2-(Biphenyl-2-yloxy)-N-{3-[(pyridin-4-ylcarbamoyl)amino]propyl}acetamide |
| 46 | 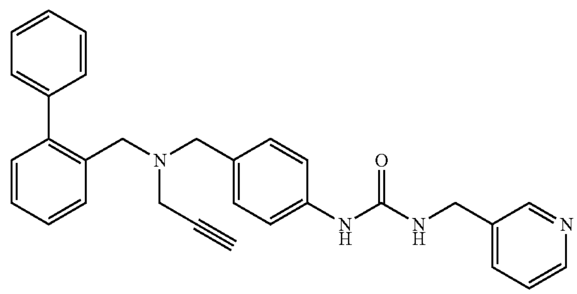 [SMILES: C#CCN(Cc1ccc(NC(=O)NCc2cccnc2)cc1)Cc1ccccc1-c1ccccc1] | 1-(4-{[(Biphenyl-2-ylmethyl)(prop-2-yn-1-yl)amino]methyl}phenyl)-3-(pyridin-3-ylmethyl)urea |
| 47 | 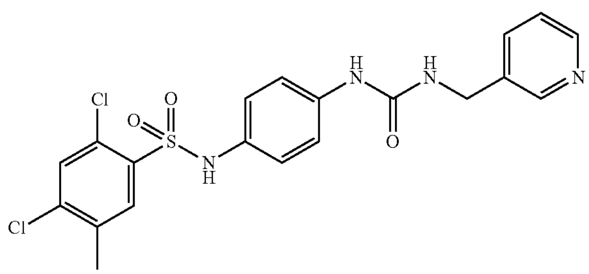 [SMILES: Cc1cc(S(=O)(=O)Nc2ccc(NC(=O)NCc3cccnc3)cc2)c(Cl)cc1Cl] | 2,4-dichloro-5-methyl-N-(4-{[(pyridin-3-ylmethyl)carbamoyl]amino}phenyl)benzenesulfonamide |
| 48 | 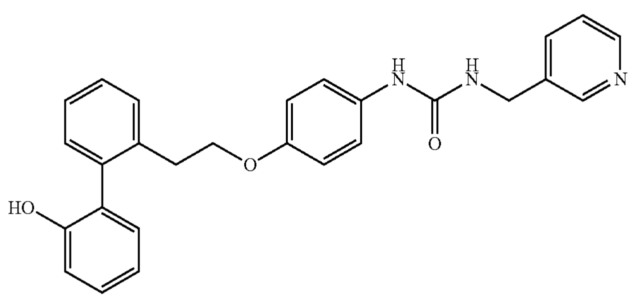 | 1-{4-[2-(2'-Hydroxybiphenyl-2-yl)ethoxy]phenyl}-3-(pyridin-3-ylmethyl)urea |
| 49 | 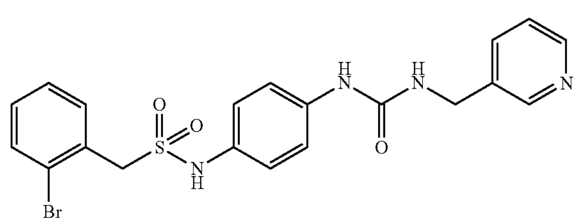 [SMILES: O=C(NCc1cccnc1)Nc1ccc(NS(=O)(=O)Cc2ccccc2Br)cc1] | 1-(2-Bromophenyl)-N-(4-{[(pyridin-3-ylmethyl)carbamoyl]amino}phenyl)methanesulfonamide |
| 50 | 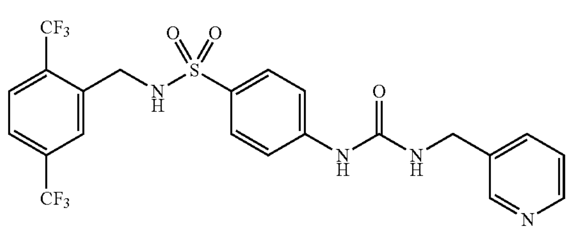 [SMILES: O=C(NCc1cccnc1)Nc1ccc(S(=O)(=O)NCc2cc(C(F)(F)F)ccc2C(F)(F)F)cc1] | N-[2,5-Bis(trifluoromethyl)benzyl]-4-{[(pyridin-3-ylmethyl)carbamoyl]amino}benzenesulfonamide |

TABLE 1-continued

| Example Number | Structure | ¹H NMR Data (400 MHz, DMSO-d6) |
|---|---|---|
| 51 | 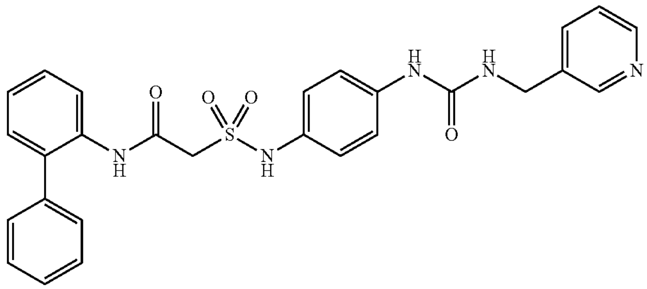 [SMILES: O=C(CS(=O)(=O)Nc1ccc(NC(=O)NCc2cccnc2)cc1)Nc1ccccc1-c1ccccc1] | N-(Biphenyl-2-yl)-2-[(4-{[(pyridin-3-ylmethyl)carbamoyl]amino}phenyl)sulfamoyl]acetamide |
| 52 | 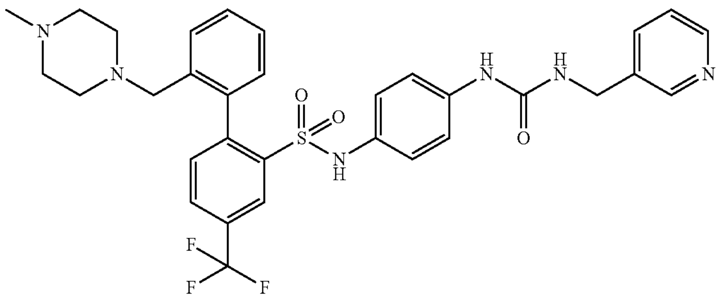 [SMILES: CN1CCN(Cc2ccccc2-c2ccc(C(F)(F)F)cc2S(=O)(=O)Nc2ccc(NC(=O)NCc3cccnc3)cc2)CC1] | 2'-[(4-Methylpiperazin-1-yl)methyl]-N-(4-{[(pyridin-3-ylmethyl)carbamoyl]amino}phenyl)-4-(trifluoromethyl)biphenyl-2-sulfonamide |
| 53 | 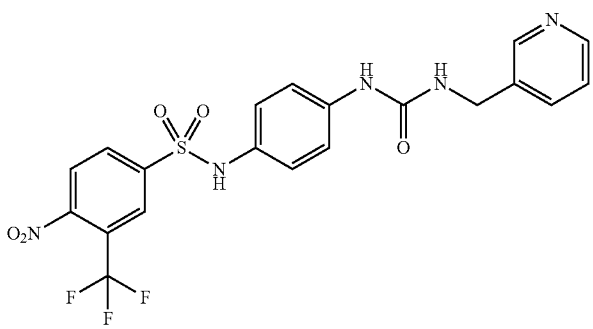 [SMILES: O=C(NCc1cccnc1)Nc1ccc(NS(=O)(=O)c2ccc([N+](=O)[O-])c(C(F)(F)F)c2)cc1] | 4-Nitro-N-(4-{[(pyridin-3-ylmethyl)carbamoyl]amino}phenyl)-3-(trifluoromethyl)benzenesulfonamide |
| 54 | 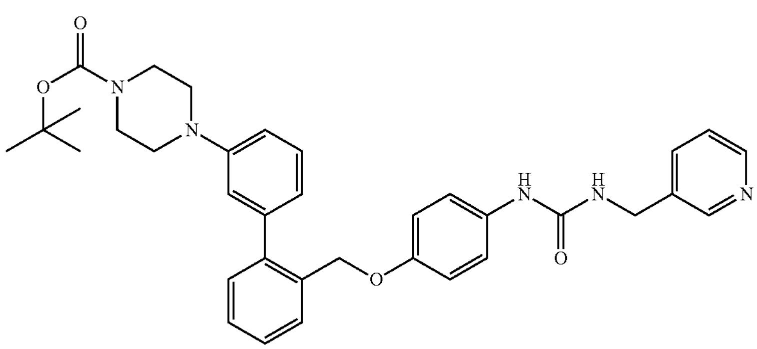 [SMILES: CC(C)(C)OC(=O)N1CCN(c2cccc(-c3ccccc3COc3ccc(NC(=O)NCc4cccnc4)cc3)c2)CC1] | tert-Butyl 4-{2'-[(4-{[(pyridin-3-ylmethyl)carbamoyl]amino}phenoxy)methyl]biphenyl-3-yl}piperazine-1-carboxylate |
| 55 | 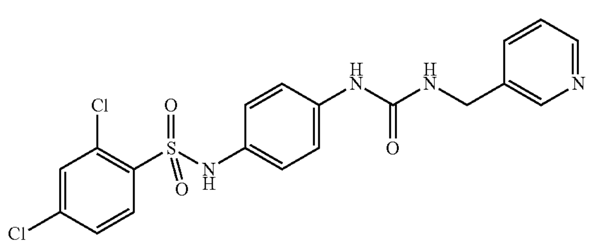 [SMILES: O=C(NCc1cccnc1)Nc1ccc(NS(=O)(=O)c2ccc(Cl)cc2Cl)cc1] | 2,4-dichloro-N-(4-{[(pyridin-3-ylmethyl)carbamoyl]amino}phenyl)benzenesulfonamide |

TABLE 1-continued

| Example Number | Structure | ¹H NMR Data (400 MHz, DMSO-d6) |
|---|---|---|
| 56 | 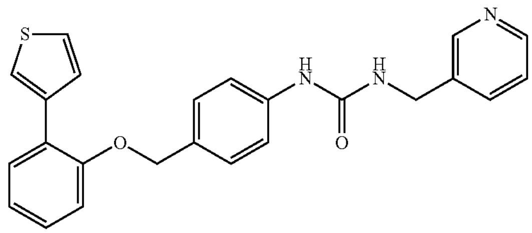 [SMILES: O=C(NCc1cccnc1)Nc1ccc(COc2ccccc2-c2ccsc2)cc1] | 1-(Pyridin-3-ylmethyl)-3-(4-{[2-(thiophen-3-yl)phenoxy]methyl}phenyl)urea |
| 57 | 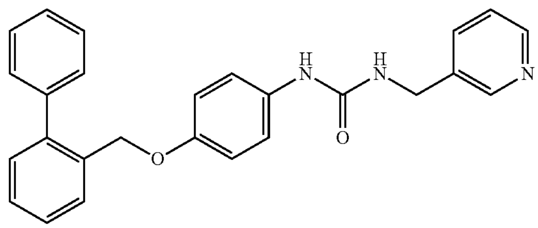 | 1-[4-(biphenyl-2-ylmethoxy)phenyl]-3-(pyridin-3-ylmethyl)urea |
| 58 | 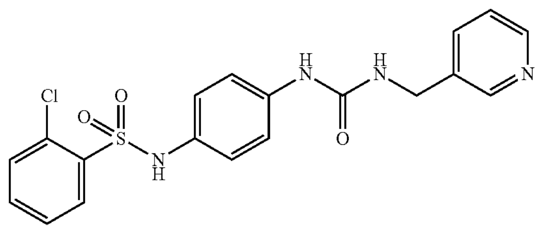 [SMILES: O=C(NCc1cccnc1)Nc1ccc(NS(=O)(=O)c2ccccc2Cl)cc1] | 2-chloro-N-(4-{[(pyridin-3-ylmethyl)carbamoyl]amino}phenyl)benzenesulfonamide |
| 59 | 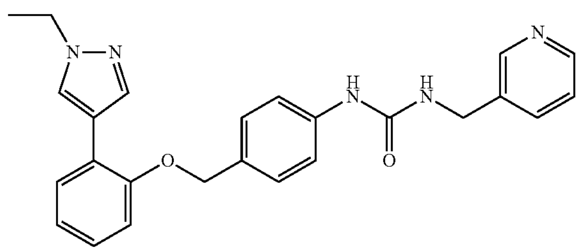 [SMILES: CCn1cc(-c2ccccc2OCc2ccc(NC(=O)NCc3cccnc3)cc2)cn1] | 1-(4-{[2-(1-Ethyl-1H-pyrazol-4-yl)phenoxy]methyl}phenyl)-3-(pyridin-3-ylmethyl)urea |
| 60 | 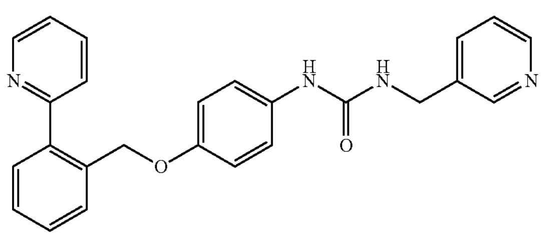 [SMILES: O=C(NCc1cccnc1)Nc1ccc(OCc2ccccc2-c2ccccn2)cc1] | 1-(4-{[2-(Pyridin-2-yl)benzyl]oxy}phenyl)-3-(pyridin-3-ylmethyl)urea |
| 61 | 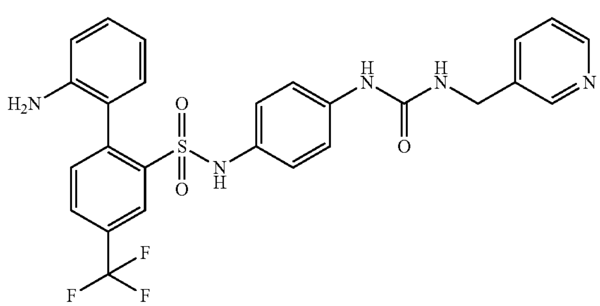 [SMILES: Nc1ccccc1-c1ccc(C(F)(F)F)cc1S(=O)(=O)Nc1ccc(NC(=O)NCc2cccnc2)cc1] | 2'-Amino-N-(4-{[(pyridin-3-ylmethyl)carbamoyl]amino}phenyl)-4-(trifluoromethyl)biphenyl-2-sulfonamide |

TABLE 1-continued

| Example Number | Structure | ¹H NMR Data (400 MHz, DMSO-d6) |
|---|---|---|
| 62 | 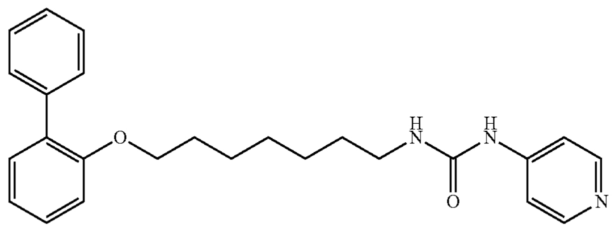 [SMILES: O=C(NCCCCCCCOc1ccccc1-c1ccccc1)Nc1ccncc1] | 1-[7-(Biphenyl-2-yloxy)heptyl]-3-pyridin-4-ylurea |
| 63 | 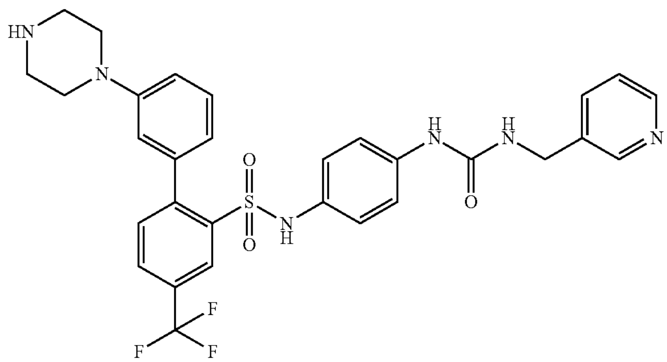 [SMILES: O=C(NCc1cccnc1)Nc1ccc(NS(=O)(=O)c2cc(C(F)(F)F)ccc2-c2cccc(N3CCNCC3)c2)cc1] | 3'-(Piperazin-1-yl)-N-(4-{[(pyridin-3-ylmethyl)carbamoyl]amino}phenyl)-4-(trifluoromethyl)biphenyl-2-sulfonamide |
| 64 | 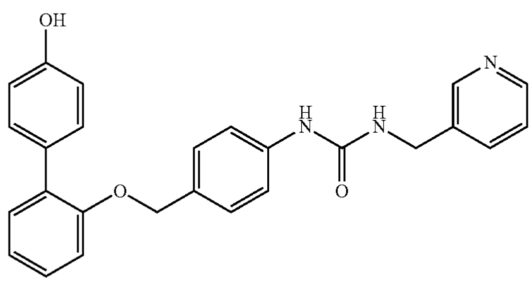 | 1-(4-{[(4'-Hydroxybiphenyl-2-yl)oxy]methyl}phenyl)-3-(pyridin-3-ylmethyl)urea |
| 65 | 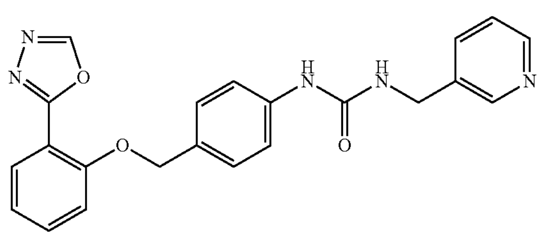 [SMILES: O=C(NCc1cccnc1)Nc1ccc(COc2ccccc2-c2nnco2)cc1] | 1-(4-{[2-(1,3,4-Oxadiazol-2-yl)phenoxy]methyl}phenyl)-3-(pyridin-3-ylmethyl)urea |
| 66 | 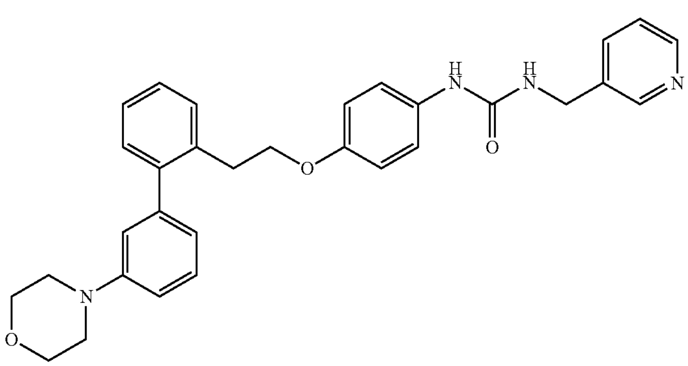 [SMILES: O=C(NCc1cccnc1)Nc1ccc(OCCc2ccccc2-c2cccc(N3CCOCC3)c2)cc1] | 1-(4-{2-[3'-(Morpholin-4-yl)biphenyl-2-yl]ethoxy}phenyl)-3-(pyridin-3-ylmethyl)urea |

TABLE 1-continued

| Example Number | Structure | ¹H NMR Data (400 MHz, DMSO-d6) |
|---|---|---|
| 67 | 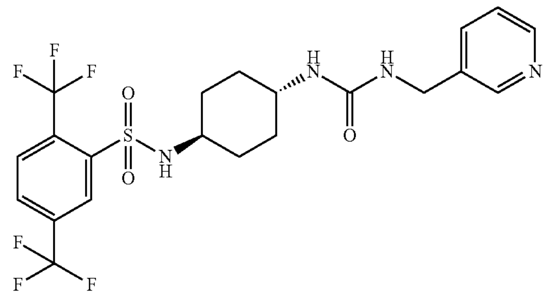 [SMILES: O=C(NCc1cccnc1)N[C@H]1CC[C@H](NS(=O)(=O)c2cc(C(F)(F)F)ccc2C(F)(F)F)CC1] | N-(trans-4-{[(Pyridin-3-ylmethyl)carbamoyl]amino}cyclohexyl)-2,5-bis(trifluoromethyl)benzenesulfonamide |
| 68 | 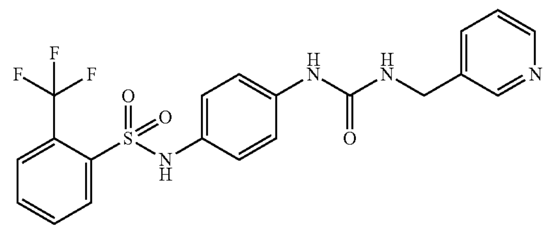 [SMILES: O=C(NCc1cccnc1)Nc1ccc(NS(=O)(=O)c2ccccc2C(F)(F)F)cc1] | N-(4-{[(Pyridin-3-ylmethyl)carbamoyl]amino}phenyl)-2-(trifluoromethyl)benzenesulfonamide |
| 69 | 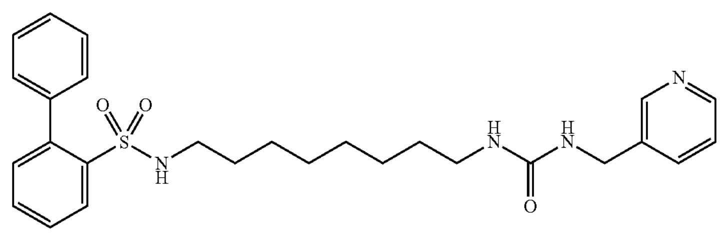 [SMILES: O=C(NCCCCCCCCNS(=O)(=O)c1ccccc1-c1ccccc1)NCc1cccnc1] | N-(8-{[(Pyridin-3-ylmethyl)carbamoyl]amino}octyl)biphenyl-2-sulfonamide |
| 70 | 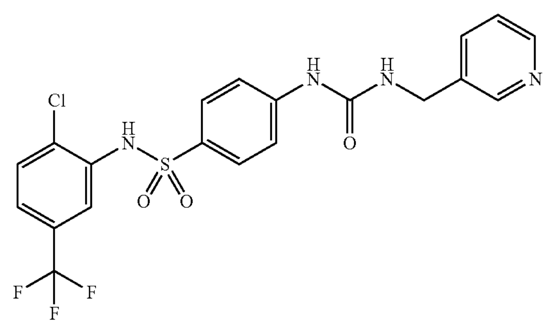 [SMILES: O=C(NCc1cccnc1)Nc1ccc(S(=O)(=O)Nc2cc(C(F)(F)F)ccc2Cl)cc1] | N-[2-Chloro-5-(trifluoromethyl)phenyl]-4-{[(pyridin-3-ylmethyl)carbamoyl]amino}benzenesulfonamide |
| 71 | 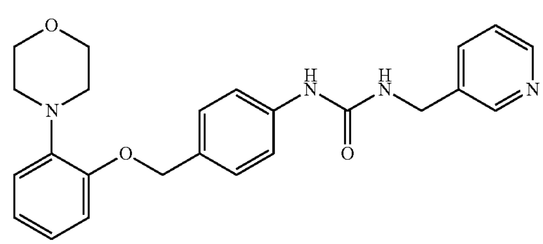 [SMILES: O=C(NCc1cccnc1)Nc1ccc(COc2ccccc2N2CCOCC2)cc1] | 1-(4-{[2-(Morpholin-4-yl)phenoxy]methyl}phenyl)-3-(pyridin-3-ylmethyl)urea |
| 72 | 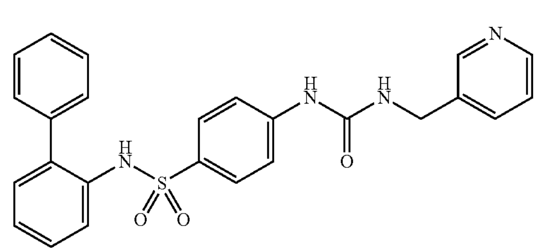 [SMILES: O=C(NCc1cccnc1)Nc1ccc(S(=O)(=O)Nc2ccccc2-c2ccccc2)cc1] | N-(biphenyl-2-yl)-4-{[(pyridin-3-ylmethyl)carbamoyl]amino}benzenesulfonamide |

TABLE 1-continued

| Example Number | Structure | ¹H NMR Data (400 MHz, DMSO-d6) |
|---|---|---|
| 73 | 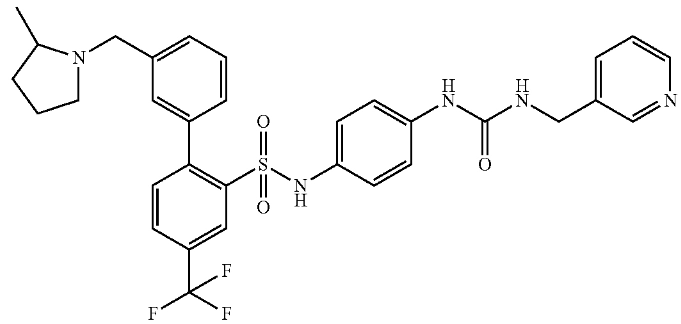 [SMILES: CC1CCCN1Cc1cccc(-c2ccc(C(F)(F)F)cc2S(=O)(=O)Nc2ccc(NC(=O)NCc3cccnc3)cc2)c1] | 3'-[(2-Methyl-pyrrolidin-1-yl)methyl]-N-(4-{[(pyridin-3-ylmethyl)carbamoyl]amino}phenyl)-4-(trifluoromethyl)biphenyl-2-sulfonamide |
| 74 | 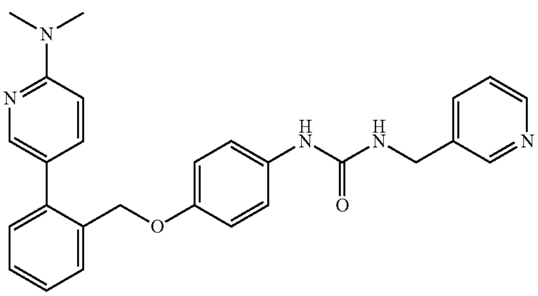 [SMILES: CN(C)c1ccc(-c2ccccc2COc2ccc(NC(=O)NCc3cccnc3)cc2)cn1] | 1-[4-({2-[6-(Dimethylamino)pyridin-3-yl]benzyl}oxy)phenyl]-3-(pyridin-3-ylmethyl)urea |
| 75 | 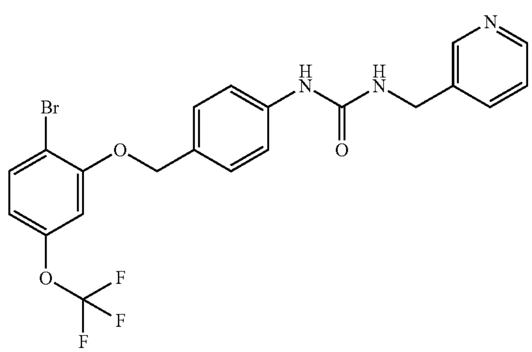 [SMILES: O=C(NCc1cccnc1)Nc1ccc(COc2cc(OC(F)(F)F)ccc2Br)cc1] | 1-(4-{[2-Bromo-5-(trifluoromethoxy)phenoxy]methyl}phenyl)-3-(pyridin-3-ylmethyl)urea |
| 76 | 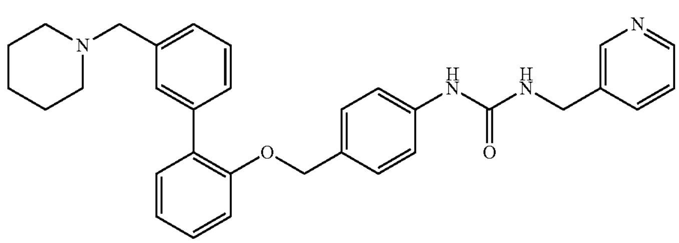 [SMILES: O=C(NCc1cccnc1)Nc1ccc(COc2ccccc2-c2cccc(CN3CCCCC3)c2)cc1] | 1-[4-({[3'-(Piperidin-1-ylmethyl)biphenyl-2-yl]oxy}methyl)phenyl]-3-(pyridin-3-ylmethyl)urea |

TABLE 1-continued

| Example Number | Structure | ¹H NMR Data (400 MHz, DMSO-d6) |
|---|---|---|
| 77 | 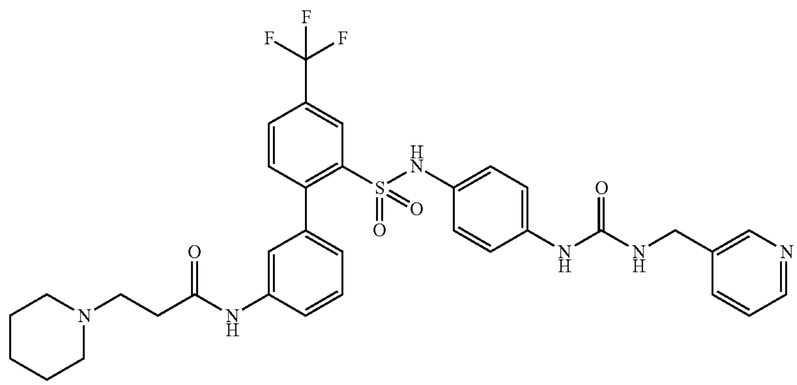 [SMILES: O=C(CCN1CCCCC1)Nc1cccc(-c2ccc(C(F)(F)F)cc2S(=O)(=O)Nc2ccc(NC(=O)NCc3cccnc3)cc2)c1] | 3-(Piperidin-1-yl)-N-{2'-[(4-{[(pyridin-3-ylmethyl)carbamoyl]amino}phenyl)sulfamoyl]-4'-(trifluoromethyl)biphenyl-3-yl}propanamide |
| 78 | 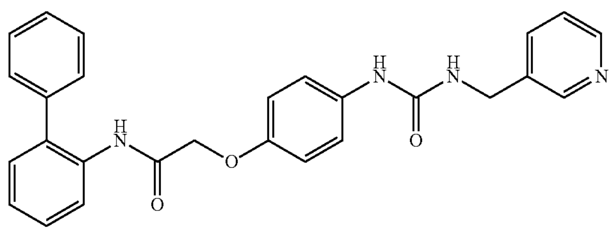 [SMILES: O=C(COc1ccc(NC(=O)NCc2cccnc2)cc1)Nc1ccccc1-c1ccccc1] | N-(Biphenyl-2-yl)-2-(4-{[(pyridin-3-ylmethyl)carbamoyl]amino}phenoxy)acetamide |
| 79 | 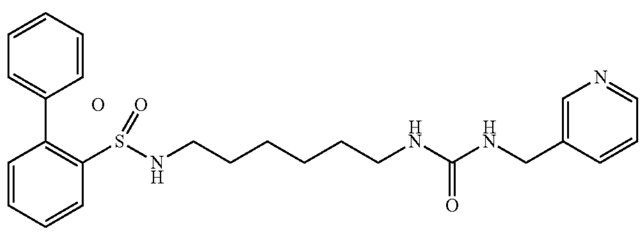 | N-(6-{[(Pyridin-3-ylmethyl)carbamoyl]amino}hexyl)biphenyl-2-sulfonamide |
| 80 | 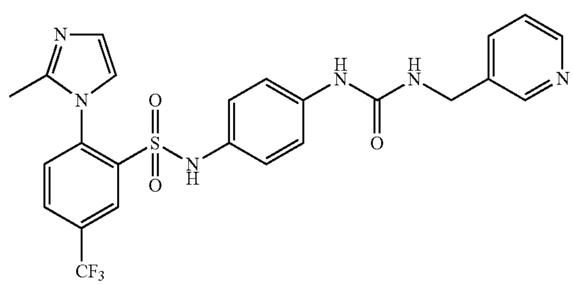 [SMILES: Cc1nccn1-c1ccc(C(F)(F)F)cc1S(=O)(=O)Nc1ccc(NC(=O)NCc2cccnc2)cc1] | 2-(2-Methyl-1H-imidazol-1-yl)-N-(4-{[(pyridin-3-ylmethyl)carbamoyl]amino}phenyl)-5-(trifluoromethyl)benzenesulfonamide |
| 81 | 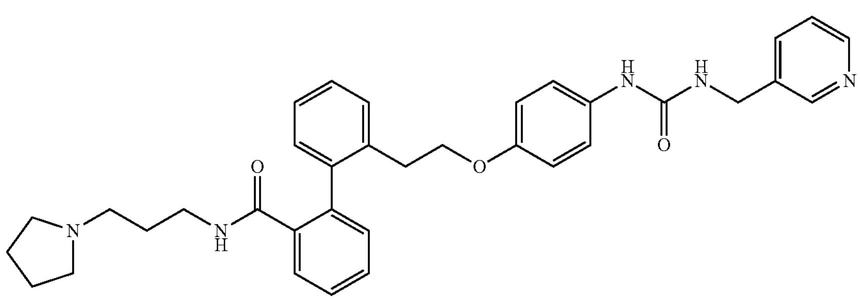 [SMILES: O=C(NCc1cccnc1)Nc1ccc(OCCc2ccccc2-c2ccccc2C(=O)NCCCN2CCCC2)cc1] | 2'-[2-(4-{[(Pyridin-3-ylmethyl)carbamoyl]amino}phenoxy)ethyl]-N-[3-(pyrrolidin-1-yl)propyl]biphenyl-2-carboxamide |

TABLE 1-continued

| Example Number | Structure | 1H NMR Data (400 MHz, DMSO-d6) |
| --- | --- | --- |
| 82 | 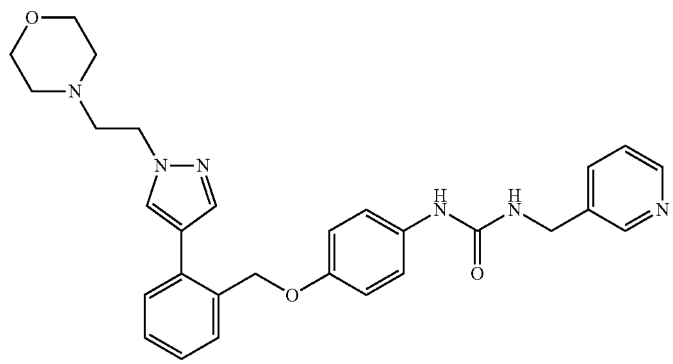 [SMILES: O=C(NCc1cccnc1)Nc1ccc(OCc2ccccc2-c2cnn(CCN3CCOCC3)c2)cc1] | 1-{4-[(2-{1-[2-(Morpholin-4-yl)ethyl]-1H-pyrazol-4-yl}benzyl)oxy]phenyl}-3-(pyridin-3-ylmethyl)urea |
| 83 | 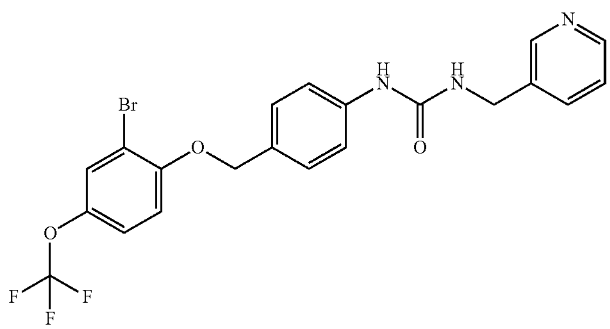 [SMILES: O=C(NCc1cccnc1)Nc1ccc(COc2ccc(OC(F)(F)F)cc2Br)cc1] | 1-(4-{[2-Bromo-4-(trifluoromethoxy)phenoxy]methyl}phenyl)-3-(pyridin-3-ylmethyl)urea |
| 84 | 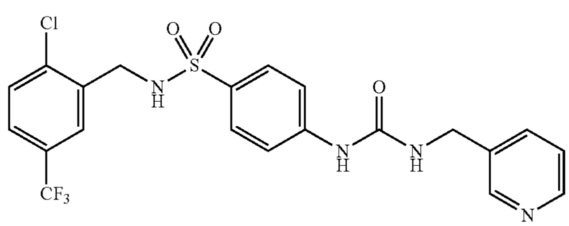 [SMILES: O=C(NCc1cccnc1)Nc1ccc(S(=O)(=O)NCc2cc(C(F)(F)F)ccc2Cl)cc1] | N-[2-Chloro-5-(trifluoromethyl)benzyl]-4-{[(pyridin-3-ylmethyl)carbamoyl]amino}benzenesulfonamide |
| 85 | 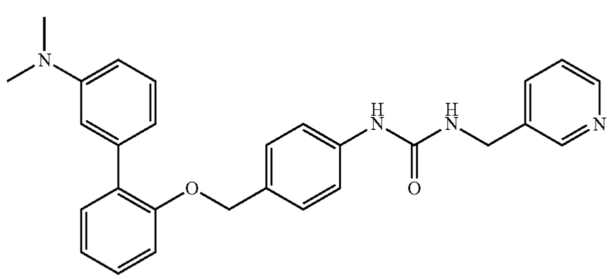 [SMILES: CN(C)c1cccc(-c2ccccc2OCc2ccc(NC(=O)NCc3cccnc3)cc2)c1] | 1-[4-({[3'-(Dimethylamino)biphenyl-2-yl]oxy}methyl)phenyl]-3-(pyridin-3-ylmethyl)urea |
| 86 | 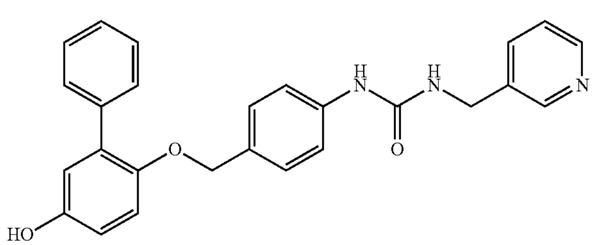 [SMILES: O=C(NCc1cccnc1)Nc1ccc(COc2ccc(O)cc2-c2ccccc2)cc1] | 1-(4-{[(5-Hydroxybiphenyl-2-yl)oxy]methyl}phenyl)-3-(pyridin-3-ylmethyl)urea |

TABLE 1-continued

| Example Number | Structure | ¹H NMR Data (400 MHz, DMSO-d6) |
|---|---|---|
| 87 | 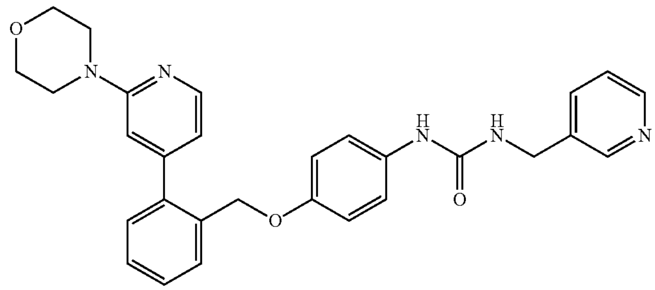 [SMILES: O=C(NCc1cccnc1)Nc1ccc(OCc2ccccc2-c2ccnc(N3CCOCC3)c2)cc1] | 1-[4-({2-[2-(Morpholin-4-yl)pyridin-4-yl]benzyl}oxy)phenyl]-3-(pyridin-3-ylmethyl)urea |
| 88 | 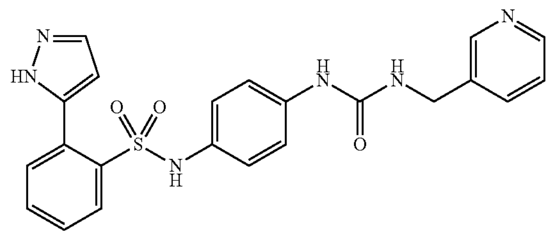 [SMILES: O=C(NCc1cccnc1)Nc1ccc(NS(=O)(=O)c2ccccc2-c2ccn[nH]2)cc1] | 2-(1H-Pyrazol-5-yl)-N-(4-{[(pyridin-3-ylmethyl)carbamoyl]amino}phenyl)benzenesulfonamide |
| 89 | 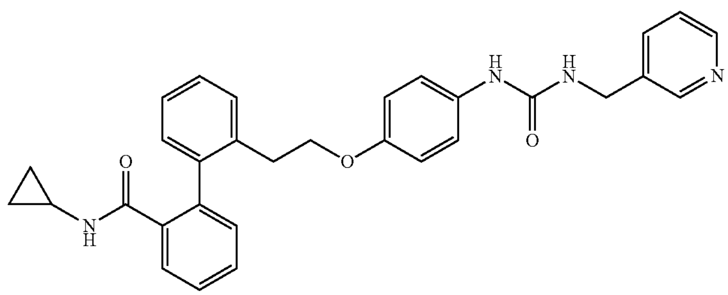 [SMILES: O=C(NCc1cccnc1)Nc1ccc(OCCc2ccccc2-c2ccccc2C(=O)NC2CC2)cc1] | N-Cyclopropyl-2'-[2-(4-{[(pyridin-3-ylmethyl)carbamoyl]amino}phenoxy)ethyl]biphenyl-2-carboxamide |
| 90 | 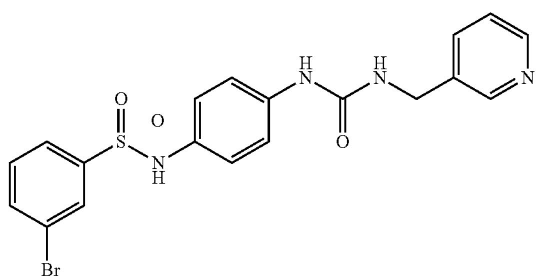 | 3-Bromo-N-(4-{[(pyridin-3-ylmethyl)carbamoyl]amino}phenyl)benzenesulfonamide |
| 91 | 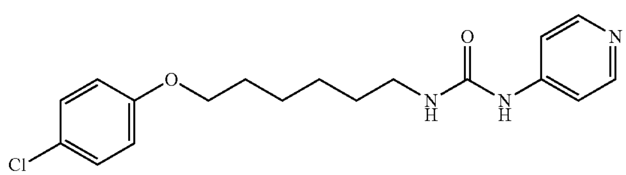 [SMILES: O=C(NCCCCCCOc1ccc(Cl)cc1)Nc1ccncc1] | 1-[6-(4-Chlorophenoxy)hexyl]-3-pyridin-4-ylurea |
| 92 | 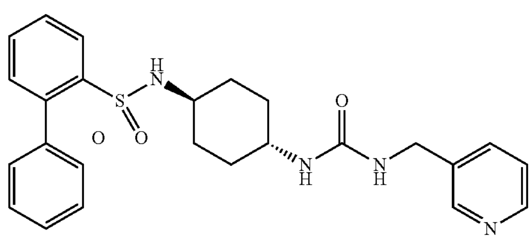 | N-(trans-4-{[(Pyridin-3-ylmethyl)carbamoyl]amino}cyclohexyl)biphenyl-2-sulfonamide |

TABLE 1-continued

| Example Number | Structure | ¹H NMR Data (400 MHz, DMSO-d6) |
|---|---|---|
| 93 | 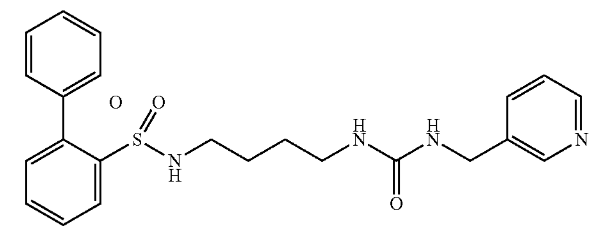 | N-(4-{[(pyridin-3-ylmethyl)carbamoyl]amino}butyl)biphenyl-2-sulfonamide |
| 94 | 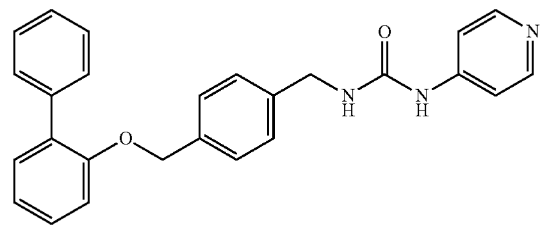 [SMILES: O=C(NCc1ccc(COc2ccccc2-c2ccccc2)cc1)Nc1ccncc1] | 1-{4-[(biphenyl-2-yloxy)methyl]benzyl}-3-pyridin-4-ylurea |
| 95 | 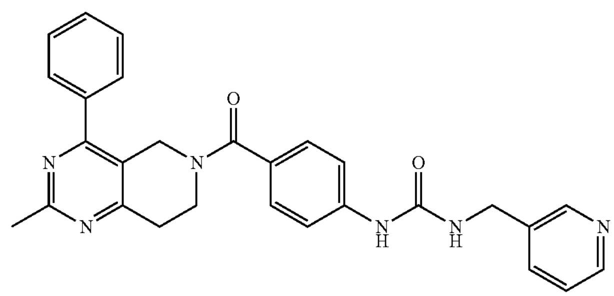 [SMILES: Cc1nc2c(c(-c3ccccc3)n1)CN(C(=O)c1ccc(NC(=O)NCc3cccnc3)cc1)CC2] | 1-{4-[(2-Methyl-4-phenyl-7,8-dihydropyrido[4,3-d]pyrimidin-6(5H)-yl)carbonyl]phenyl}-3-(pyridin-3-ylmethyl)urea |
| 96 | 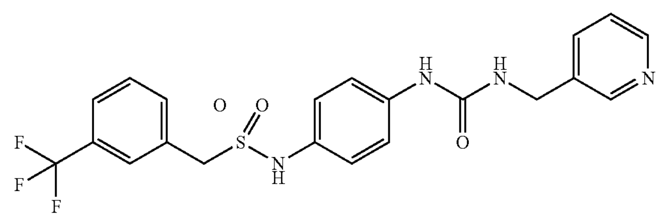 | N-(4-{[(Pyridin-3-ylmethyl)carbamoyl]amino}phenyl)-1-[3-(trifluoromethyl)phenyl]methanesulfonamide |
| 97 | 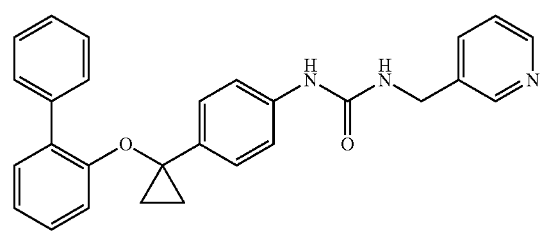 [SMILES: O=C(NCc1cccnc1)Nc1ccc(C2(Oc3ccccc3-c3ccccc3)CC2)cc1] | 1-{4-[1-(Biphenyl-2-yloxy)cyclopropyl]phenyl}-3-(pyridin-3-ylmethyl)urea |
| 98 | 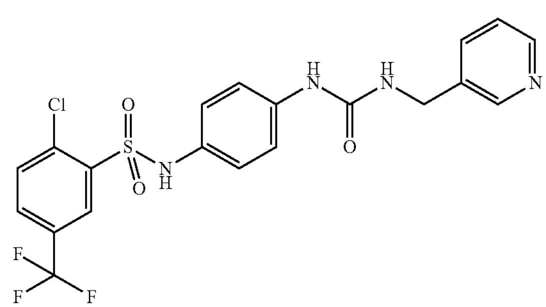 [SMILES: O=C(NCc1cccnc1)Nc1ccc(NS(=O)(=O)c2cc(C(F)(F)F)ccc2Cl)cc1] | 2-chloro-N-(4-{[(pyridin-3-ylmethyl)carbamoyl]amino}phenyl)-5-(trifluoromethyl)benzenesulfonamide |

TABLE 1-continued

| Example Number | Structure | $^1$H NMR Data (400 MHz, DMSO-d6) |
|---|---|---|
| 99 | 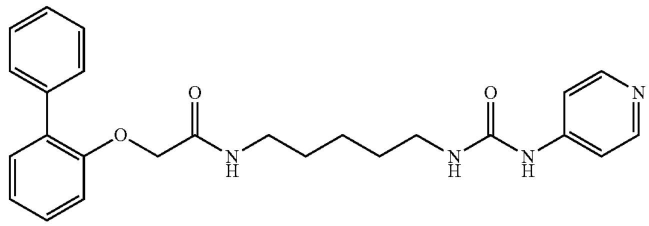 [SMILES: O=C(COc1ccccc1-c1ccccc1)NCCCCCNC(=O)Nc1ccncc1] | 2-(Biphenyl-2-yloxy)-N-{5-[(pyridin-4-ylcarbamoyl)amino]pentyl}acetamide |
| 100 | 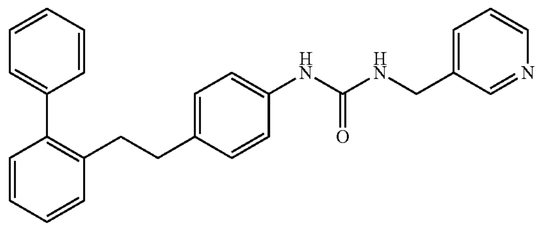 [SMILES: O=C(NCc1cccnc1)Nc1ccc(CCc2ccccc2-c2ccccc2)cc1] | 1-{4-[2-(Biphenyl-2-yl)ethyl]phenyl}-3-(pyridin-3-ylmethyl)urea |
| 101 | 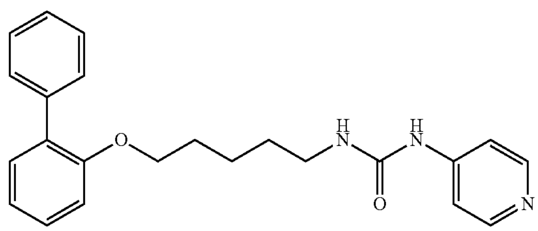 [SMILES: O=C(NCCCCCOc1ccccc1-c1ccccc1)Nc1ccncc1] | 1-[5-(biphenyl-2-yloxy)pentyl]-3-pyridin-4-ylurea |
| 102 | 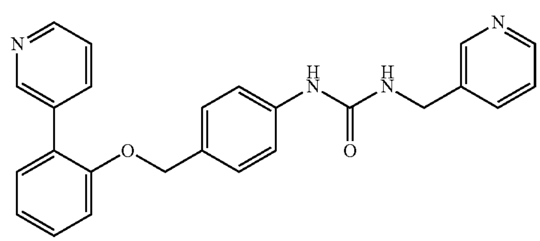 [SMILES: O=C(NCc1cccnc1)Nc1ccc(COc2ccccc2-c2cccnc2)cc1] | 1-(Pyridin-3-ylmethyl)-3-(4-{[2-(pyridin-3-yl)phenoxy]methyl}phenyl)urea |
| 103 | 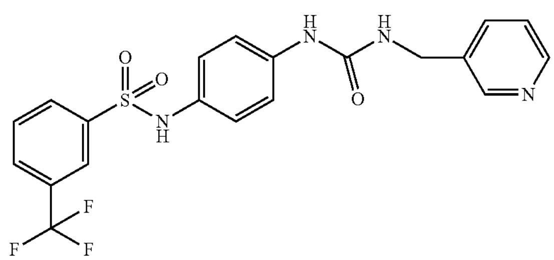 [SMILES: O=C(NCc1cccnc1)Nc1ccc(NS(=O)(=O)c2cccc(C(F)(F)F)c2)cc1] | N-(4-{[(Pyridin-3-ylmethyl)carbamoyl]amino}phenyl)-3-(trifluoromethyl)benzenesulfonamide |
| 104 | 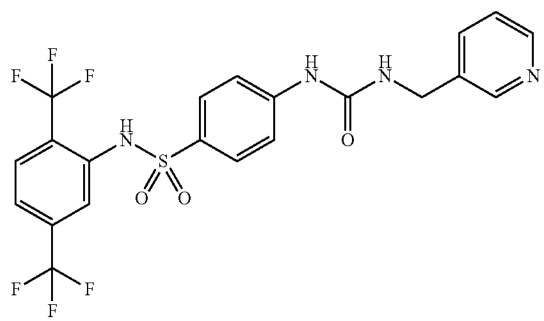 [SMILES: O=C(NCc1cccnc1)Nc1ccc(S(=O)(=O)Nc2cc(C(F)(F)F)ccc2C(F)(F)F)cc1] | N-[2,5-Bis(trifluoromethyl)phenyl]-4-{[(pyridin-3-ylmethyl)carbamoyl]amino}benzenesulfonamide |

TABLE 1-continued

| Example Number | Structure | ¹H NMR Data (400 MHz, DMSO-d6) |
|---|---|---|
| 105 | 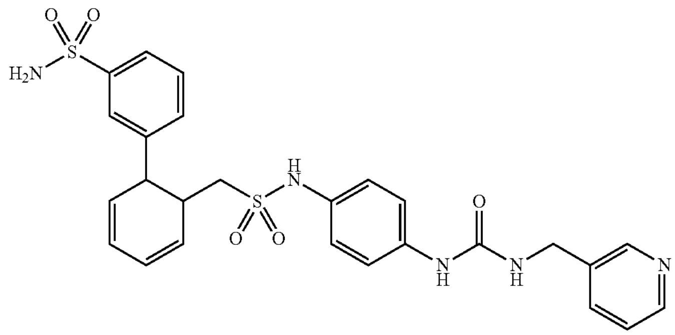 [SMILES: NS(=O)(=O)c1cccc(C2C=CC=CC2CS(=O)(=O)Nc2ccc(NC(=O)NCc3cccnc3)cc2)c1] | 3-(6-{[(4-{[(Pyridin-3-ylmethyl)carbamoyl]amino}phenyl)sulfamoyl]methyl}cyclohexa-2,4-dien-1-yl)benzenesulfonamide |
| 106 | 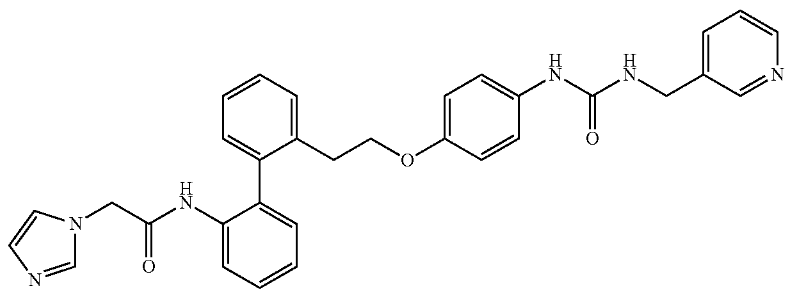 [SMILES: O=C(Cn1ccnc1)Nc1ccccc1-c1ccccc1CCOc1ccc(NC(=O)NCc2cccnc2)cc1] | 2-(1H-Imidazol-1-yl)-N-{2'-[2-(4-{[(pyridin-3-ylmethyl)carbamoyl]amino}phenoxy)ethyl]biphenyl-2-yl}acetamide |
| 107 | 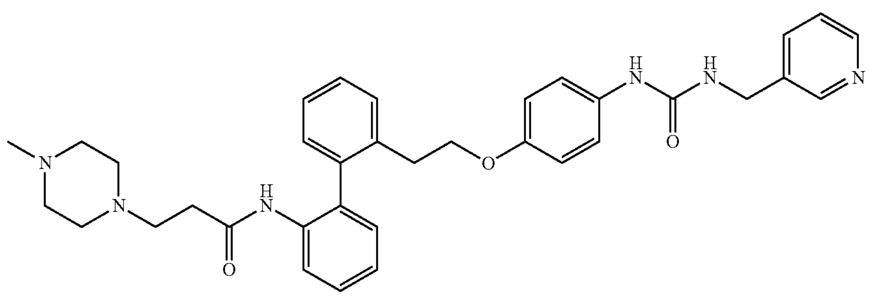 [SMILES: CN1CCN(CCC(=O)Nc2ccccc2-c2ccccc2CCOc2ccc(NC(=O)NCc3cccnc3)cc2)CC1] | 3-(4-Methylpiperazin-1-yl)-N-{2'-[2-(4-{[(pyridin-3-ylmethyl)carbamoyl]amino}phenoxy)ethyl]biphenyl-2-yl}propanamide |
| 108 | 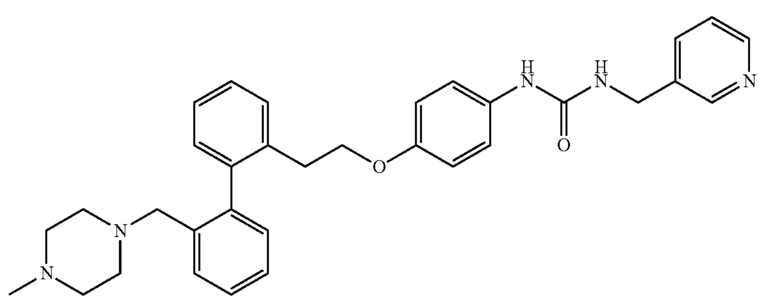 [SMILES: CN1CCN(Cc2ccccc2-c2ccccc2CCOc2ccc(NC(=O)NCc3cccnc3)cc2)CC1] | 1-[4-(2-{2'-[(4-Methylpiperazin-1-yl)methyl]biphenyl-2-yl}ethoxy)phenyl]-3-(pyridin-3-ylmethyl)urea |
| 109 | 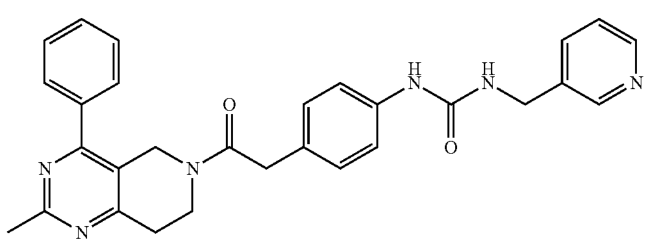 [SMILES: Cc1nc2c(c(-c3ccccc3)n1)CN(C(=O)Cc1ccc(NC(=O)NCc3cccnc3)cc1)CC2] | 1-{4-[2-(2-Methyl-4-phenyl-7,8-dihydropyrido[4,3-d]pyrimidin-6(5H)-yl)-2-oxoethyl]phenyl}-3-(pyridin-3-ylmethyl)urea |

TABLE 1-continued

| Example Number | Structure | $^1$H NMR Data (400 MHz, DMSO-d6) |
|---|---|---|
| 110 | 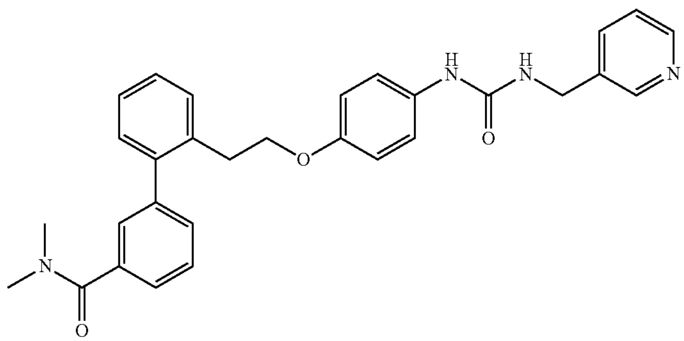 [SMILES: CN(C)C(=O)c1cccc(-c2ccccc2CCOc2ccc(NC(=O)NCc3cccnc3)cc2)c1] | N,N-Dimethyl-2'-[2-(4-{[(pyridin-3-ylmethyl)carbamoyl]amino}phenoxy)ethyl]biphenyl-3-carboxamide |
| 111 | 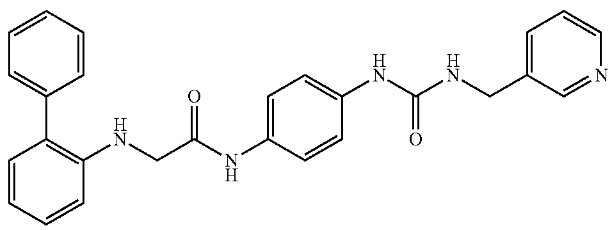 [SMILES: O=C(CNc1ccccc1-c1ccccc1)Nc1ccc(NC(=O)NCc2cccnc2)cc1] | N~2~-Biphenyl-2-yl-N-(4-{[(pyridin-3-ylmethyl)carbamoyl]amino}phenyl)glycinamide |
| 112 | 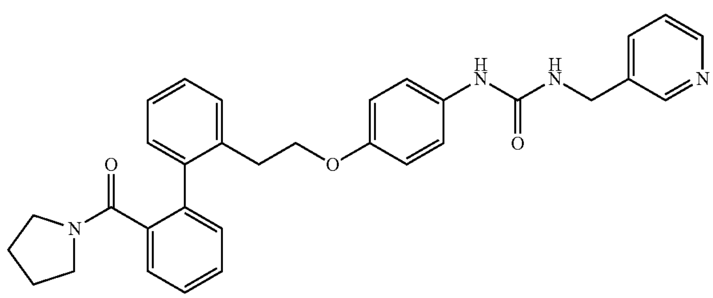 [SMILES: O=C(NCc1cccnc1)Nc1ccc(OCCc2ccccc2-c2ccccc2C(=O)N2CCCC2)cc1] | 1-(Pyridin-3-ylmethyl)-3-(4-{2-[2'-(pyrrolidin-1-ylcarbonyl)biphenyl-2-yl]ethoxy}phenyl)urea |
| 113 | 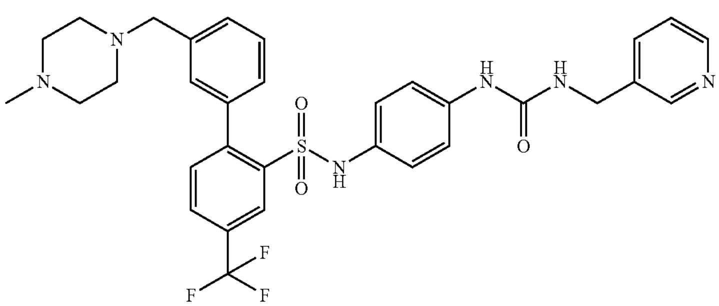 [SMILES: CN1CCN(Cc2cccc(-c3ccc(C(F)(F)F)cc3S(=O)(=O)Nc3ccc(NC(=O)NCc4cccnc4)cc3)c2)CC1] | 3'-[(4-Methylpiperazin-1-yl)methyl]-N-(4-{[(pyridin-3-ylmethyl)carbamoyl]amino}phenyl)-4-(trifluoromethyl)biphenyl-2-sulfonamide |
| 114 | 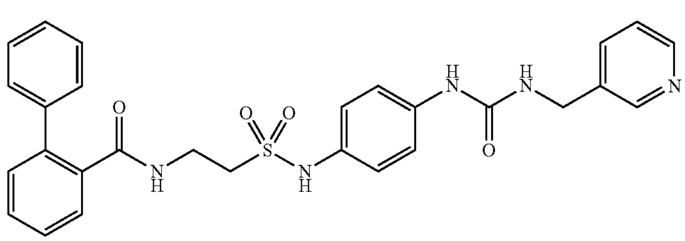 [SMILES: O=C(NCc1cccnc1)Nc1ccc(NS(=O)(=O)CCNC(=O)c2ccccc2-c2ccccc2)cc1] | N-{2-[(4-{[(Pyridin-3-ylmethyl)carbamoyl]amino}phenyl)sulfamoyl]ethyl}biphenyl-2-carboxamide |

TABLE 1-continued

| Example Number | Structure | ¹H NMR Data (400 MHz, DMSO-d6) |
|---|---|---|
| 115 | 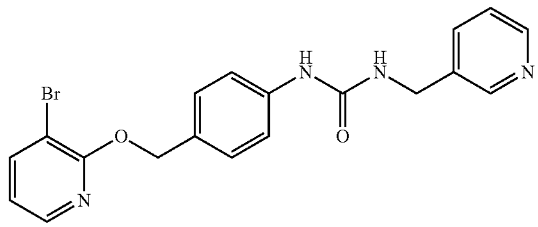 [SMILES: O=C(NCc1cccnc1)Nc1ccc(COc2ncccc2Br)cc1] | 1-(4-{[(3-Bromopyridin-2-yl)oxy]methyl}phenyl)-3-(pyridin-3-ylmethyl)urea |
| 116 | 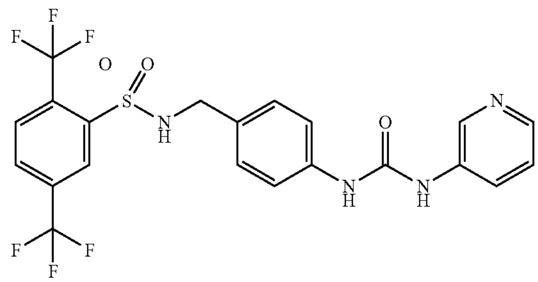 | N-{4-[(Pyridin-3-ylcarbamoyl)amino]benzyl}-2,5-bis(trifluoromethyl)benzenesulfonamide |
| 117 | 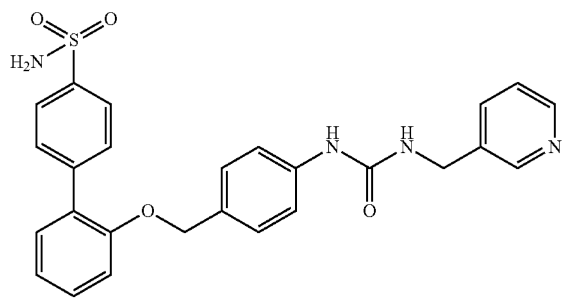 [SMILES: NS(=O)(=O)c1ccc(-c2ccccc2OCc2ccc(NC(=O)NCc3cccnc3)cc2)cc1] | 2'-[(4-{[(Pyridin-3-ylmethyl)carbamoyl]amino}benzyl)oxy]biphenyl-4-sulfonamide |
| 118 | 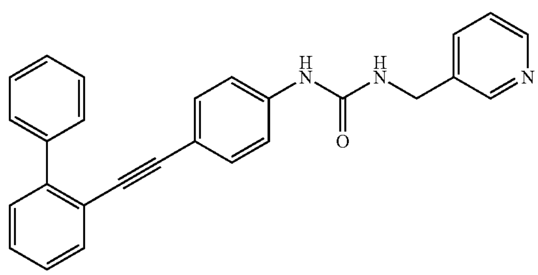 [SMILES: O=C(NCc1cccnc1)Nc1ccc(C#Cc2ccccc2-c2ccccc2)cc1] | 1-[4-(Biphenyl-2-ylethynyl)phenyl]-3-(pyridin-3-ylmethyl)urea |
| 119 | 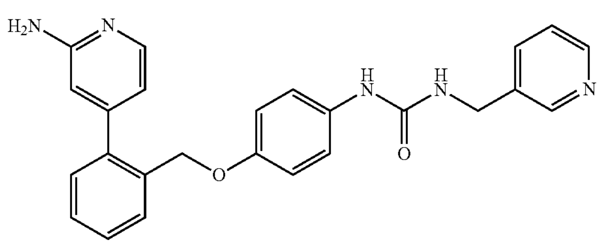 [SMILES: Nc1cc(-c2ccccc2COc2ccc(NC(=O)NCc3cccnc3)cc2)ccn1] | 1-(4-{[2-(2-Aminopyridin-4-yl)benzyl]oxy}phenyl)-3-(pyridin-3-ylmethyl)urea |
| 120 | 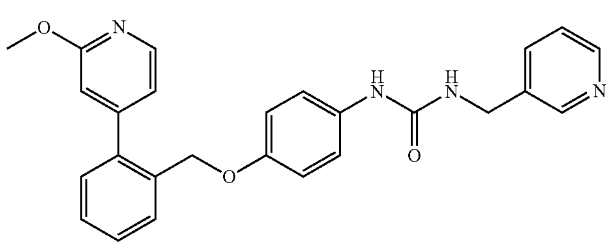 [SMILES: COc1cc(-c2ccccc2COc2ccc(NC(=O)NCc3cccnc3)cc2)ccn1] | 1-(4-{[2-(2-Methoxypyridin-4-yl)benzyl]oxy}phenyl)-3-(pyridin-3-ylmethyl)urea |

TABLE 1-continued

| Example Number | Structure | ¹H NMR Data (400 MHz, DMSO-d6) |
|---|---|---|
| 121 | 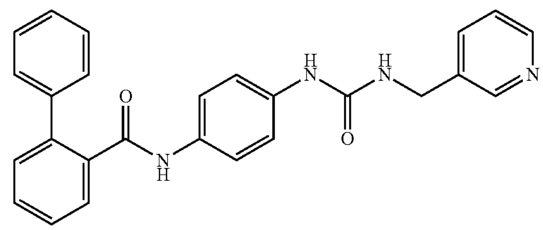 [SMILES: O=C(NCc1cccnc1)Nc1ccc(NC(=O)c2ccccc2-c2ccccc2)cc1] | N-(4-{[(Pyridin-3-ylmethyl)carbamoyl]amino}benzyl)biphenyl-2-carboxamide |
| 122 | 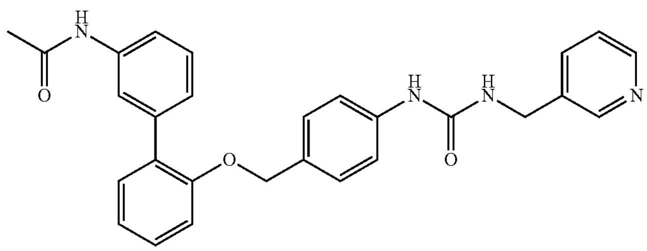 [SMILES: CC(=O)Nc1cccc(-c2ccccc2OCc2ccc(NC(=O)NCc3cccnc3)cc2)c1] | N-{2'-[(4-{[(Pyridin-3-ylmethyl)carbamoyl]amino}benzyl)oxy]biphenyl-3-yl}acetamide |
| 123 | 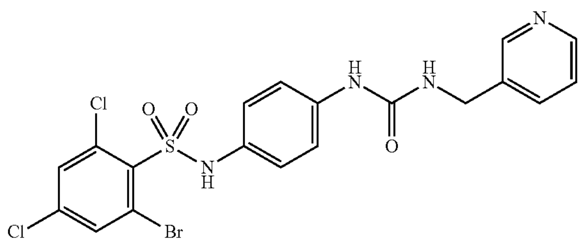 [SMILES: O=C(NCc1cccnc1)Nc1ccc(NS(=O)(=O)c2c(Cl)cc(Cl)cc2Br)cc1] | 2-bromo-4,6-dichloro-N-(4-{[(pyridin-3-ylmethyl)carbamoyl]amino}phenyl)benzenesulfonamide |
| 124 | 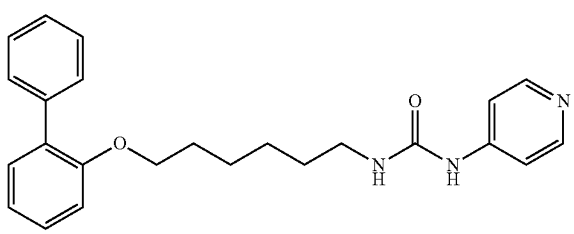 [SMILES: O=C(NCCCCCCOc1ccccc1-c1ccccc1)Nc1ccncc1] | 1-[6-(biphenyl-2-yloxy)hexyl]-3-pyridin-4-ylurea |
| 125 | 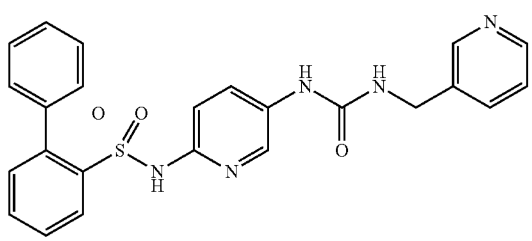 | N-(5-{[(Pyridin-3-ylmethyl)carbamoyl]amino}pyridin-2-yl)biphenyl-2-sulfonamide |
| 126 | 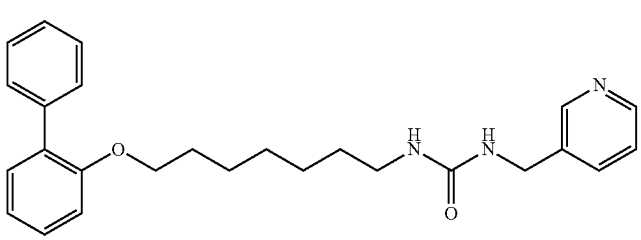 [SMILES: O=C(NCCCCCCCOc1ccccc1-c1ccccc1)NCc1cccnc1] | 1-[7-(Biphenyl-2-yloxy)heptyl]-3-(pyridin-3-ylmethyl)urea |

TABLE 1-continued

| Example Number | Structure | $^1$H NMR Data (400 MHz, DMSO-d6) |
|---|---|---|
| 127 | 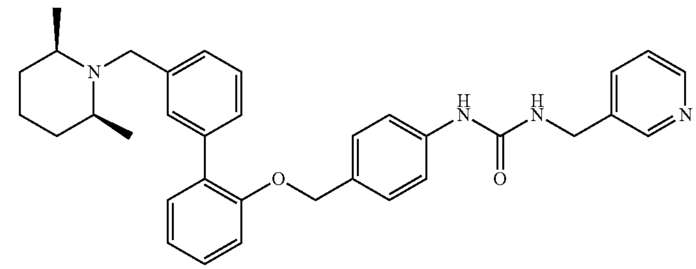 [SMILES: C[C@@H]1CCC[C@H](C)N1Cc1cccc(-c2ccccc2OCc2ccc(NC(=O)NCc3cccnc3)cc2)c1] | 1-(4-{[(3'-{[(2R,6S)-2,6-Dimethylpiperidin-1-yl]methyl}biphenyl-2-yl)oxy]methyl}phenyl)-3-(pyridin-3-ylmethyl)urea |
| 128 | 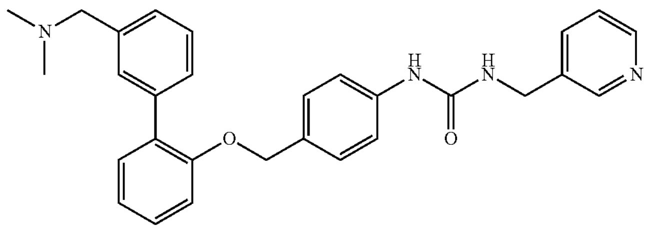 [SMILES: CN(C)Cc1cccc(-c2ccccc2OCc2ccc(NC(=O)NCc3cccnc3)cc2)c1] | 1-{4-[({3'-[(Dimethylamino)methyl]biphenyl-2-yl}oxy)methyl]phenyl}-3-(pyridin-3-ylmethyl)urea |
| 129 | 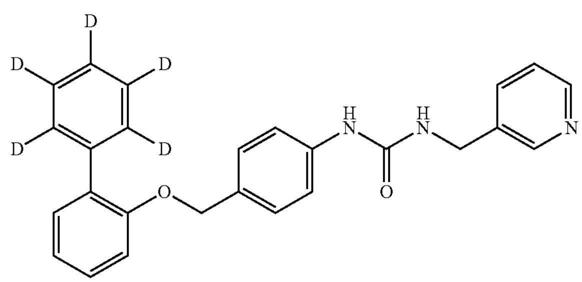 [SMILES: [2H]c1c([2H])c([2H])c(-c2ccccc2OCc2ccc(NC(=O)NCc3cccnc3)cc2)c([2H])c1[2H]] | 1-(4-{[(2',3',4',5',6'-~2~H_5_)Biphenyl-2-yloxy]methyl}phenyl)-3-(pyridin-3-ylmethyl)urea |
| 130 | 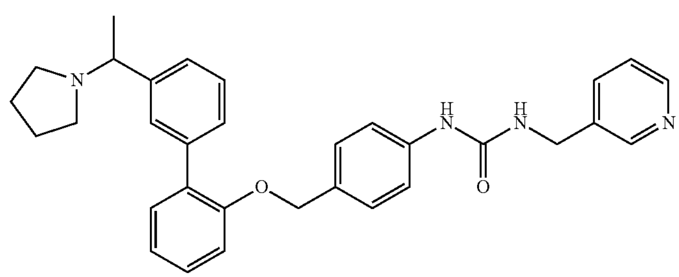 [SMILES: CC(c1cccc(-c2ccccc2OCc2ccc(NC(=O)NCc3cccnc3)cc2)c1)N1CCCC1] | 1-(Pyridin-3-ylmethyl)-3-[4-({3'-[1-(pyrrolidin-1-yl)ethyl]biphenyl-2-yl}methoxy)phenyl]urea |
| 131 | 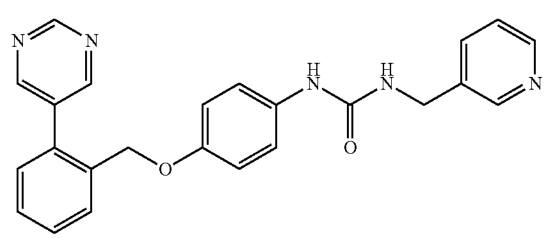 [SMILES: O=C(NCc1cccnc1)Nc1ccc(OCc2ccccc2-c2cncnc2)cc1] | 1-(Pyridin-3-ylmethyl)-3-(4-{[2-(pyrimidin-5-yl)benzyl]oxy}phenyl)urea |

TABLE 1-continued

| Example Number | Structure | ¹H NMR Data (400 MHz, DMSO-d6) |
|---|---|---|
| 132 | 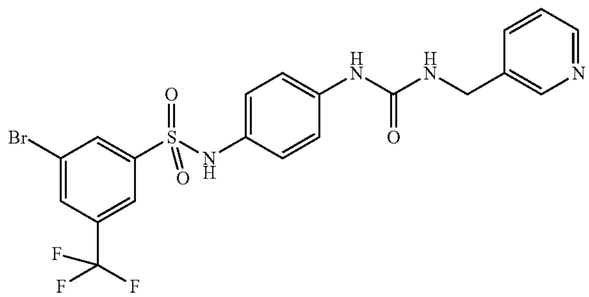 [SMILES: O=C(NCc1cccnc1)Nc1ccc(NS(=O)(=O)c2cc(Br)cc(C(F)(F)F)c2)cc1] | 3-bromo-N-(4-{[(pyridin-3-ylmethyl)carbamoyl]amino}phenyl)-5-(trifluoromethyl)benzenesulfonamide |
| 133 | 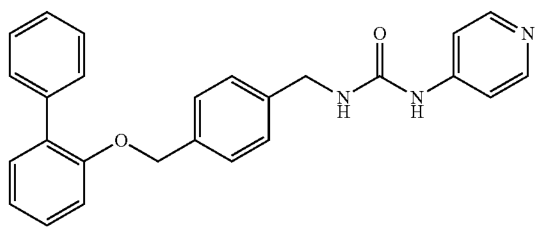 [SMILES: O=C(NCc1ccc(COc2ccccc2-c2ccccc2)cc1)Nc1ccncc1] | 1-{4-[(Biphenyl-2-yloxy)methyl]benzyl}-3-(pyridin-4-ylmethyl)urea |
| 134 | 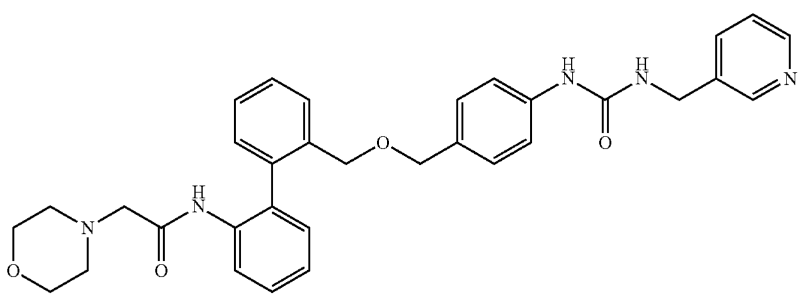 [SMILES: O=C(CN1CCOCC1)Nc1ccccc1-c1ccccc1COCc1ccc(NC(=O)NCc2cccnc2)cc1] | 2-(Morpholin-4-yl)-N-{2'-[2-(4-{[(pyridin-3-ylmethyl)carbamoyl]amino}phenoxy)ethyl]biphenyl-2-yl}acetamide |
| 135 | 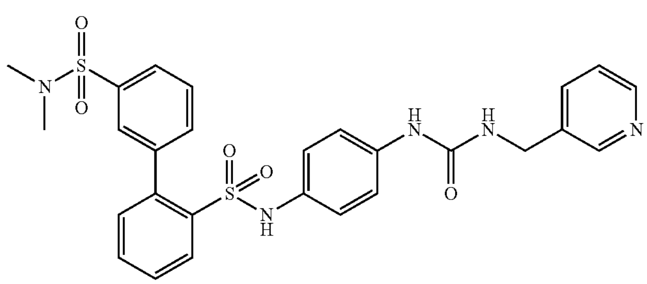 [SMILES: CN(C)S(=O)(=O)c1cccc(-c2ccccc2S(=O)(=O)Nc2ccc(NC(=O)NCc3cccnc3)cc2)c1] | N~3~',N~3~'-Dimethyl-N~2~-(4-{[(pyridin-3-ylmethyl)carbamoyl]amino}phenyl)biphenyl-2,3'-disulfonamide |
| 136 | 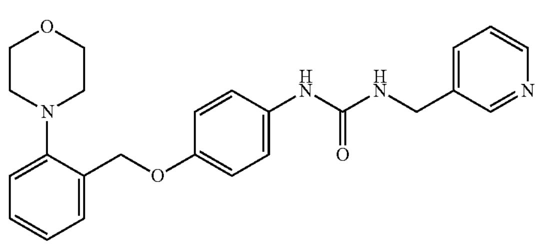 [SMILES: O=C(NCc1cccnc1)Nc1ccc(OCc2ccccc2N2CCOCC2)cc1] | 1-(4-{[2-(Morpholin-4-yl)benzyl]oxy}phenyl)-3-(pyridin-3-ylmethyl)urea |

TABLE 1-continued

| Example Number | Structure | $^1$H NMR Data (400 MHz, DMSO-d6) |
|---|---|---|
| 137 | 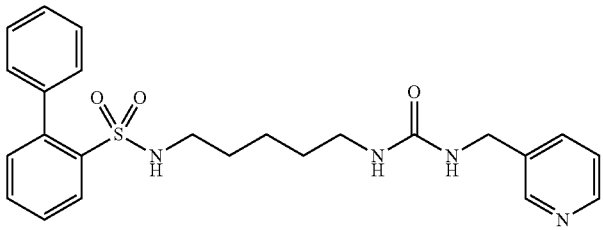 [SMILES: O=C(NCCCCCNS(=O)(=O)c1ccccc1-c1ccccc1)NCc1cccnc1] | N-(5-{[(pyridin-3-ylmethyl)carbamoyl]amino}pentyl)biphenyl-2-sulfonamide |
| 138 | 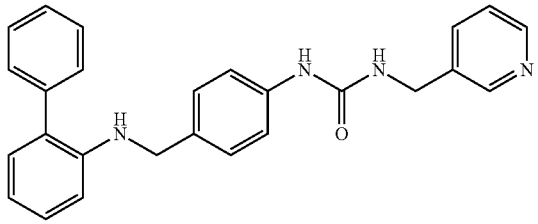 [SMILES: O=C(NCc1cccnc1)Nc1ccc(CNc2ccccc2-c2ccccc2)cc1] | 1-{4-[(Biphenyl-2-ylamino)methyl]phenyl}-3-(pyridin-3-ylmethyl)urea |
| 139 | 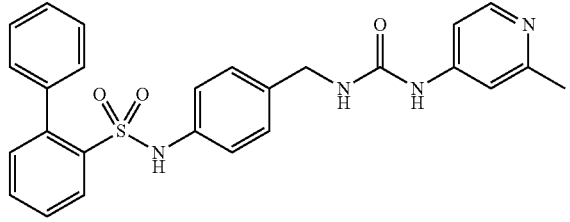 [SMILES: Cc1cc(NC(=O)NCc2ccc(NS(=O)(=O)c3ccccc3-c3ccccc3)cc2)ccn1] | N-[4-({[(2-Methylpyridin-4-yl)carbamoyl]amino}methyl)phenyl]biphenyl-2-sulfonamide |
| 140 | 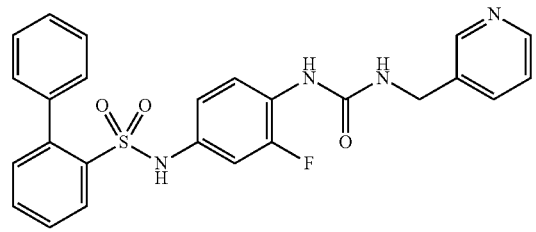 [SMILES: O=C(NCc1cccnc1)Nc1ccc(NS(=O)(=O)c2ccccc2-c2ccccc2)cc1F] | N-(3-fluoro-4-{[(pyridin-3-ylmethyl)carbamoyl]amino}phenyl)biphenyl-2-sulfonamide |
| 141 | 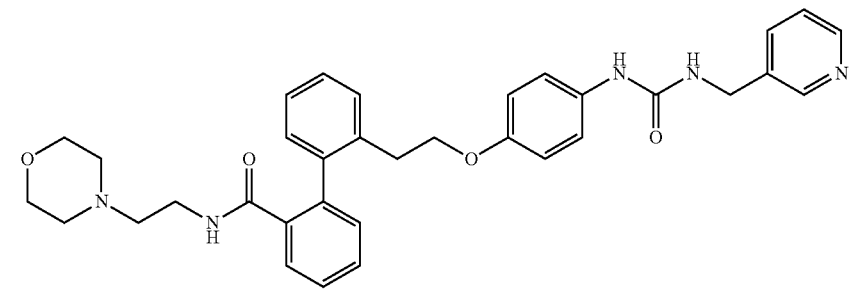 [SMILES: O=C(NCc1cccnc1)Nc1ccc(OCCc2ccccc2-c2ccccc2C(=O)NCCN2CCOCC2)cc1] | N-[2-(Morpholin-4-yl)ethyl]-2'-[2-(4-{[(pyridin-3-ylmethyl)carbamoyl]amino}phenoxy)ethyl]biphenyl-2-carboxamide |
| 142 | 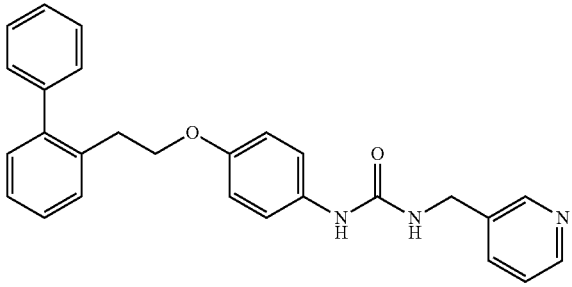 [SMILES: O=C(NCc1cccnc1)Nc1ccc(OCCc2ccccc2-c2ccccc2)cc1] | 1-{4-[2-(Biphenyl-2-yl)ethoxy]phenyl}-3-(pyridin-3-ylmethyl)urea |

TABLE 1-continued

| Example Number | Structure | ¹H NMR Data (400 MHz, DMSO-d6) |
|---|---|---|
| 143 | 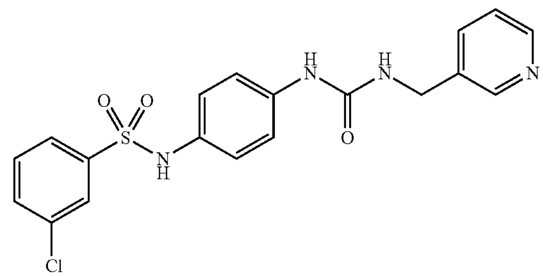 [SMILES: O=C(NCc1cccnc1)Nc1ccc(NS(=O)(=O)c2cccc(Cl)c2)cc1] | 1-(2-Chlorophenyl)-N-(4-{[(pyridin-3-ylmethyl)carbamoyl]amino}phenyl)methanesulfonamide |
| 144 | 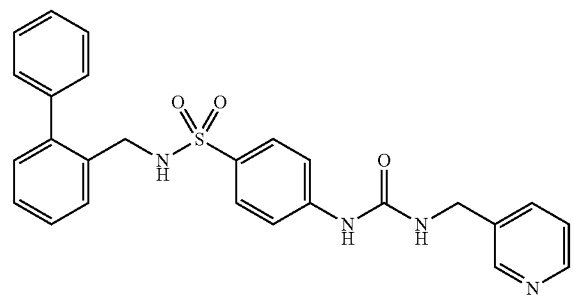 [SMILES: O=C(NCc1cccnc1)Nc1ccc(S(=O)(=O)NCc2ccccc2-c2ccccc2)cc1] | N-(Biphenyl-2-ylmethyl)-4-{[(pyridin-3-ylmethyl)carbamoyl]amino}benzenesulfonamide |
| 145 | 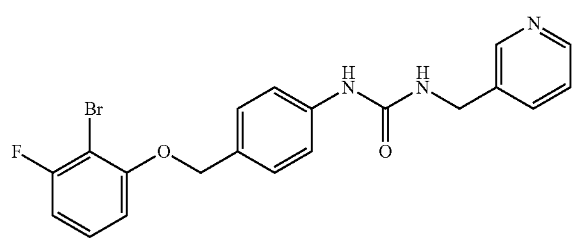 [SMILES: O=C(NCc1cccnc1)Nc1ccc(COc2cccc(F)c2Br)cc1] | 1-{4-[(2-Bromo-3-fluorophenoxy)methyl]phenyl}-3-(pyridin-3-ylmethyl)urea |
| 146 | 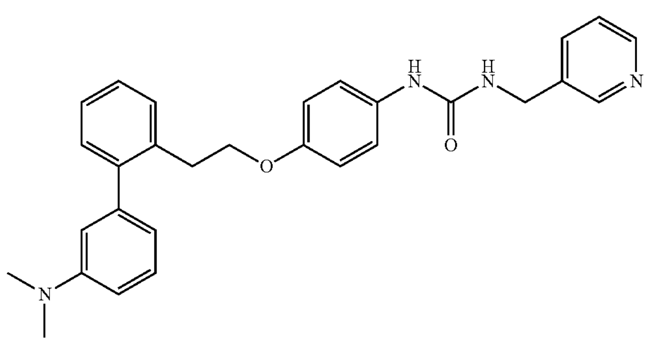 [SMILES: CN(C)c1cccc(-c2ccccc2CCOc2ccc(NC(=O)NCc3cccnc3)cc2)c1] | 1-(4-{2-[3'-(Dimethylamino)biphenyl-2-yl]ethoxy}phenyl)-3-(pyridin-3-ylmethyl)urea |
| 147 | 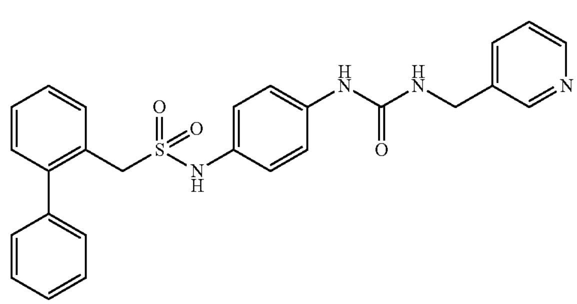 [SMILES: O=C(NCc1cccnc1)Nc1ccc(NS(=O)(=O)Cc2ccccc2-c2ccccc2)cc1] | 1-(Biphenyl-2-yl)-N-(4-{[(pyridin-3-ylmethyl)carbamoyl]amino}phenyl)methanesulfonamide |

TABLE 1-continued

| Example Number | Structure | ¹H NMR Data (400 MHz, DMSO-d6) |
|---|---|---|
| 148 | 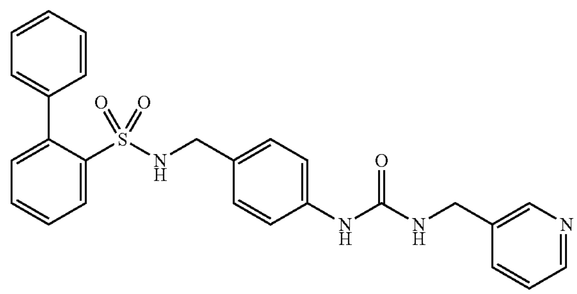 [SMILES: O=C(NCc1cccnc1)Nc1ccc(CNS(=O)(=O)c2ccccc2-c2ccccc2)cc1] | N-(4-{[(Pyridin-3-ylmethyl)carbamoyl]amino}benzyl)biphenyl-2-sulfonamide |
| 149 | 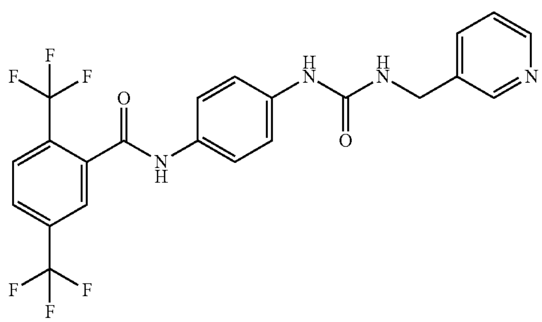 [SMILES: O=C(NCc1cccnc1)Nc1ccc(NC(=O)c2cc(C(F)(F)F)ccc2C(F)(F)F)cc1] | N-(4-{[(Pyridin-3-ylmethyl)carbamoyl]amino}phenyl)-2,5-bis(trifluoromethyl)benzamide |
| 150 | 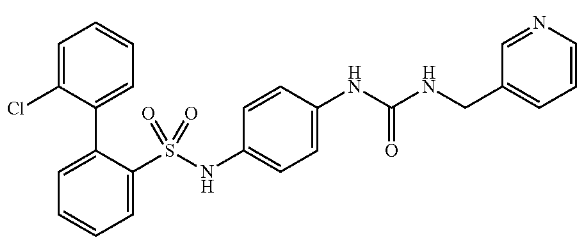 [SMILES: O=C(NCc1cccnc1)Nc1ccc(NS(=O)(=O)c2ccccc2-c2ccccc2Cl)cc1] | 2'-chloro-N-(4-{[(pyridin-3-ylmethyl)carbamoyl]amino}phenyl)biphenyl-2-sulfonamide |
| 151 | 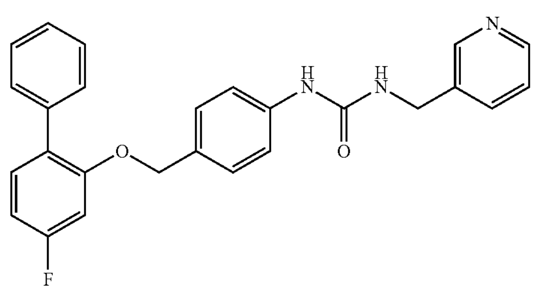 [SMILES: O=C(NCc1cccnc1)Nc1ccc(COc2cc(F)ccc2-c2ccccc2)cc1] | 1-(4-{[(4-Fluoro-biphenyl-2-yl)oxy]methyl}phenyl)-3-(pyridin-3-ylmethyl)urea |
| 152 | 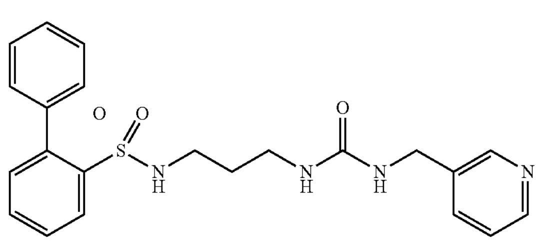 | N-(3-{[(pyridin-3-ylmethyl)carbamoyl]amino}propyl)biphenyl-2-sulfonamide |

TABLE 1-continued

| Example Number | Structure | ¹H NMR Data (400 MHz, DMSO-d6) |
|---|---|---|
| 153 | 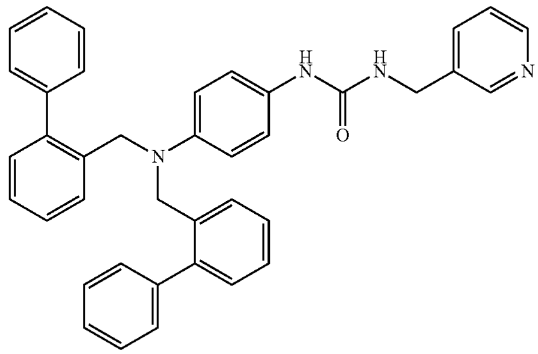 [SMILES: O=C(NCc1cccnc1)Nc1ccc(N(Cc2ccccc2-c2ccccc2)Cc2ccccc2-c2ccccc2)cc1] | 1-{4-[Bis(biphenyl-2-ylmethyl)amino]phenyl}-3-(pyridin-3-ylmethyl)urea |
| 154 | 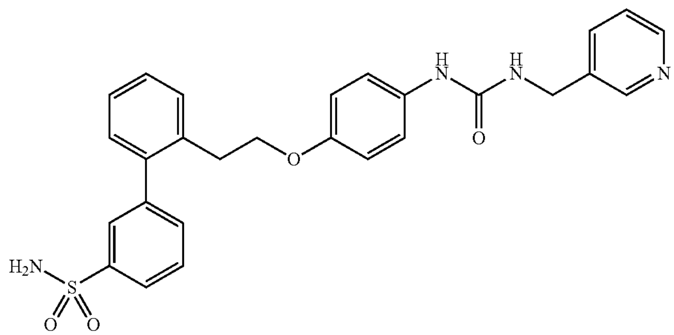 [SMILES: NS(=O)(=O)c1cccc(-c2ccccc2CCOc2ccc(NC(=O)NCc3cccnc3)cc2)c1] | 2'-[2-(4-{[(Pyridin-3-ylmethyl)carbamoyl]amino}phenoxy)ethyl]biphenyl-3-sulfonamide |
| 155 | 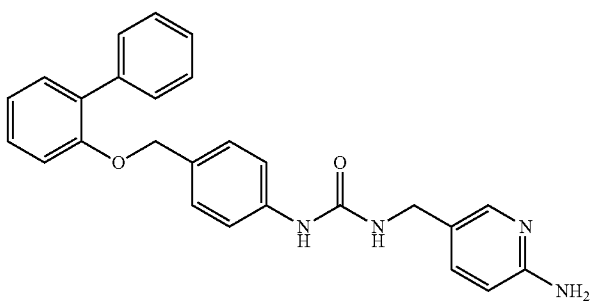 [SMILES: Nc1ccc(CNC(=O)Nc2ccc(COc3ccccc3-c3ccccc3)cc2)cn1] | 1-[(6-Aminopyridin-3-yl)methyl]-3-{4-[(biphenyl-2-yloxy)methyl]phenyl}urea |
| 156 | 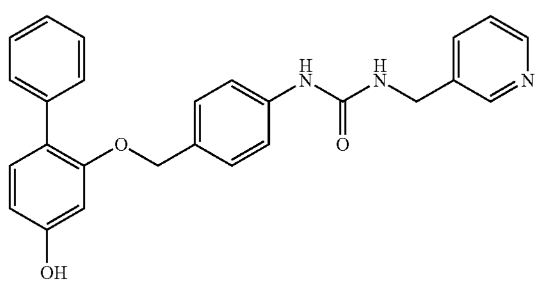 [SMILES: O=C(NCc1cccnc1)Nc1ccc(COc2cc(O)ccc2-c2ccccc2)cc1] | 1-(4-{[(4-Hydroxybiphenyl-2-yl)oxy]methyl}phenyl)-3-(pyridin-3-ylmethyl)urea |
| 157 | 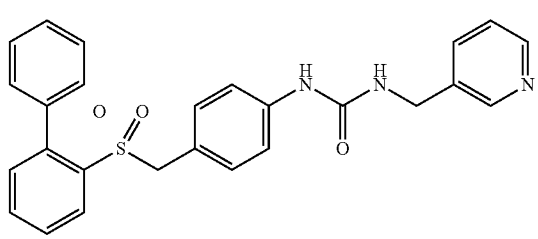 | 1-{4-[(biphenyl-2-ylsulfonyl)methyl]phenyl}-3-(pyridin-3-ylmethyl)urea |

TABLE 1-continued

| Example Number | Structure | $^1$H NMR Data (400 MHz, DMSO-d6) |
|---|---|---|
| 158 | 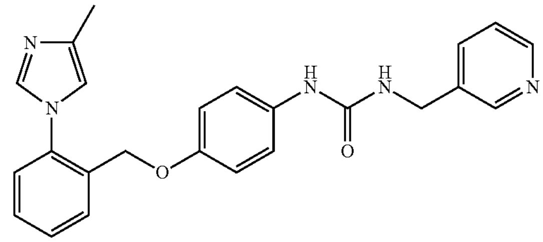 [SMILES: Cc1cn(-c2ccccc2COc2ccc(NC(=O)NCc3cccnc3)cc2)cn1] | 1-(4-{[2-(4-Methyl-1H-imidazol-1-yl)benzyl]oxy}phenyl)-3-(pyridin-3-ylmethyl)urea |
| 159 | 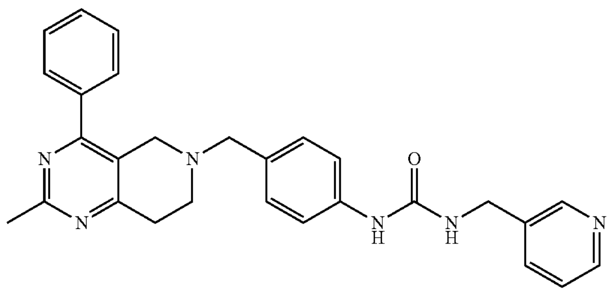 [SMILES: Cc1nc2c(c(-c3ccccc3)n1)CN(Cc1ccc(NC(=O)NCc3cccnc3)cc1)CC2] | 1-{4-[(2-Methyl-4-phenyl-7,8-dihydropyrido[4,3-d]pyrimidin-6(5H)-yl)methyl]phenyl}-3-(pyridin-3-ylmethyl)urea |
| 160 | 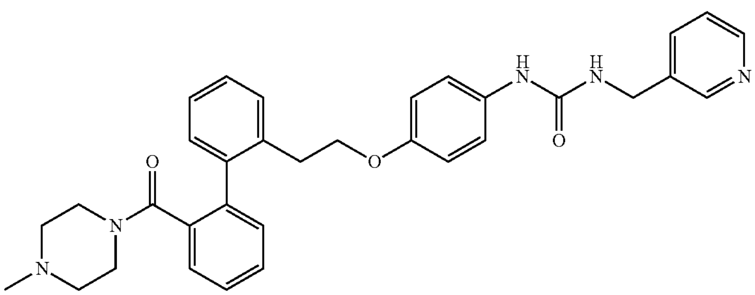 [SMILES: CN1CCN(C(=O)c2ccccc2-c2ccccc2CCOc2ccc(NC(=O)NCc3cccnc3)cc2)CC1] | 1-[4-(2-{2'-[(4-Methylpiperazin-1-yl)carbonyl]biphenyl-2-yl}ethoxy)phenyl]-3-(pyridin-3-ylmethyl)urea |
| 161 | 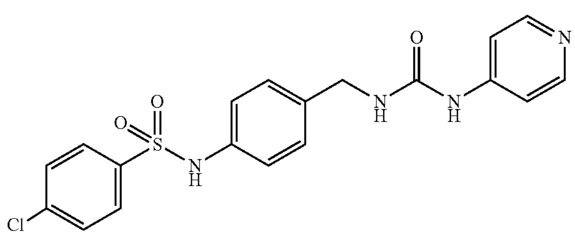 [SMILES: O=C(NCc1ccc(NS(=O)(=O)c2ccc(Cl)cc2)cc1)Nc1ccncc1] | 4-Chloro-N-(4-{[(pyridin-4-ylcarbamoyl)amino]methyl}phenyl)benzenesulfonamide |
| 162 | 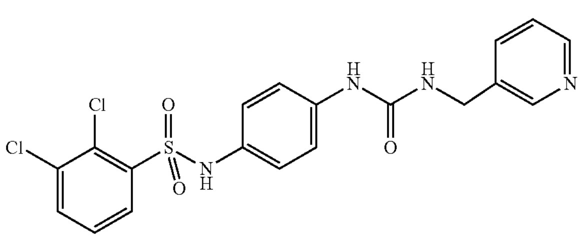 [SMILES: O=C(NCc1cccnc1)Nc1ccc(NS(=O)(=O)c2cccc(Cl)c2Cl)cc1] | 2,3-dichloro-N-(4-{[(pyridin-3-ylmethyl)carbamoyl]amino}phenyl)benzenesulfonamide |

TABLE 1-continued

| Example Number | Structure | ¹H NMR Data (400 MHz, DMSO-d6) |
|---|---|---|
| 163 | 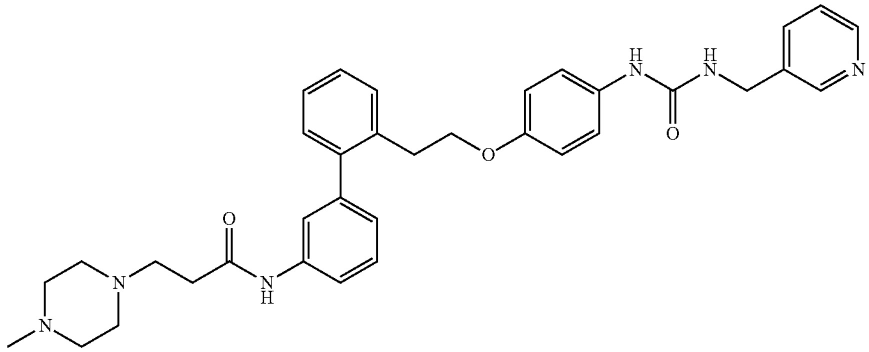 [SMILES: CN1CCN(CCC(=O)Nc2cccc(-c3ccccc3CCOc3ccc(NC(=O)NCc4cccnc4)cc3)c2)CC1] | 3-(4-Methylpiperazin-1-yl)-N-{2'-[2-(4-{[(pyridin-3-ylmethyl)carbamoyl]amino}phenoxy)ethyl]biphenyl-3-yl}propanamide |
| 164 | 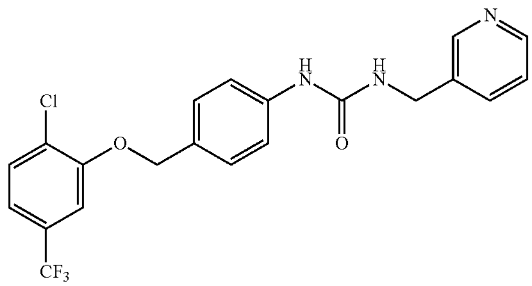 [SMILES: O=C(NCc1cccnc1)Nc1ccc(COc2cc(C(F)(F)F)ccc2Cl)cc1] | 1-(4-{[2-Chloro-5-(trifluoromethyl)phenoxy]methyl}phenyl)-3-(pyridin-3-ylmethyl)urea |
| 165 | 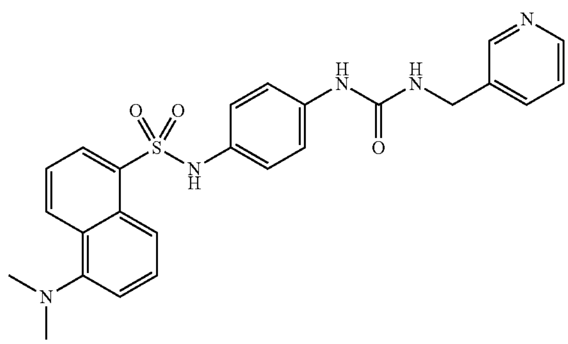 [SMILES: CN(C)c1cccc2c(S(=O)(=O)Nc3ccc(NC(=O)NCc4cccnc4)cc3)cccc12] | 5-(Dimethylamino)-N-(4-{[(pyridin-3-ylmethyl)carbamoyl]amino}phenyl)naphthalene-1-sulfonamide |
| 166 | 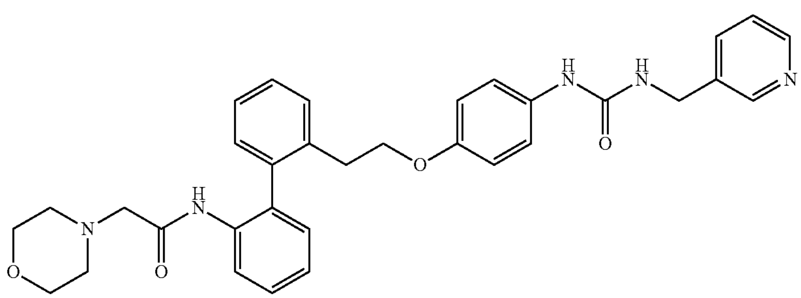 [SMILES: O=C(CN1CCOCC1)Nc1ccccc1-c1ccccc1CCOc1ccc(NC(=O)NCc2cccnc2)cc1] | 2-(Morpholin-4-yl)-N-{2'-[2-(4-{[(pyridin-3-ylmethyl)carbamoyl]amino}phenoxy)ethyl]biphenyl-2-yl}acetamide |
| 167 | 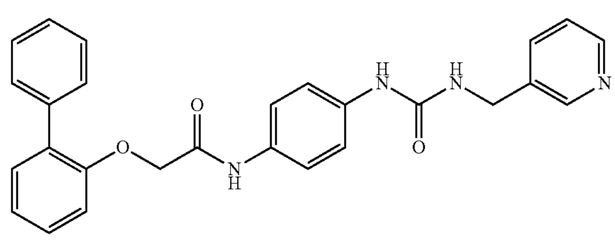 [SMILES: O=C(COc1ccccc1-c1ccccc1)Nc1ccc(NC(=O)NCc2cccnc2)cc1] | 2-(Biphenyl-2-yloxy)-N-(4-{[(pyridin-3-ylmethyl)carbamoyl]amino}phenyl)acetamide |

TABLE 1-continued

| Example Number | Structure | ¹H NMR Data (400 MHz, DMSO-d6) |
|---|---|---|
| 168 | 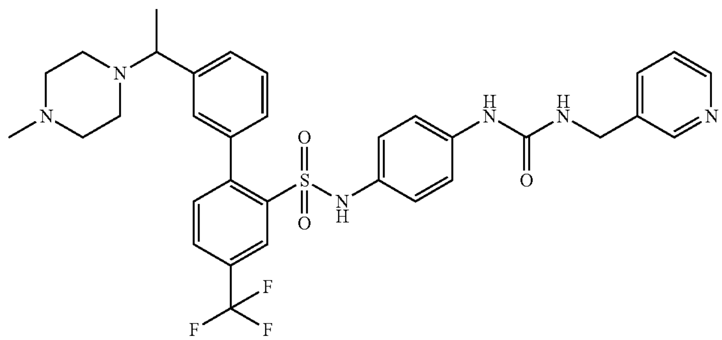 [SMILES: CC(c1cccc(-c2ccc(C(F)(F)F)cc2S(=O)(=O)Nc2ccc(NC(=O)NCc3cccnc3)cc2)c1)N1CCN(C)CC1] | 3'-[1-(4-Methylpiperazin-1-yl)ethyl]-N-(4-{[(pyridin-3-ylmethyl)carbamoyl]amino}phenyl)-4-(trifluoromethyl)biphenyl-2-sulfonamide |
| 169 | 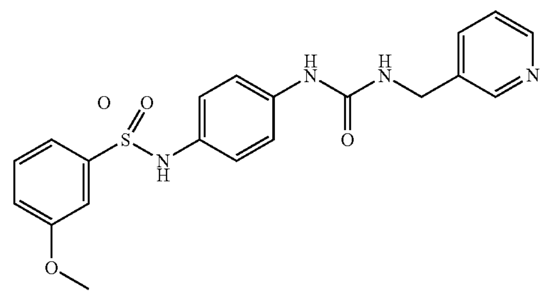 | 3-Methoxy-N-(4-{[(pyridin-3-ylmethyl)carbamoyl]amino}phenyl)benzenesulfonamide |
| 170 | 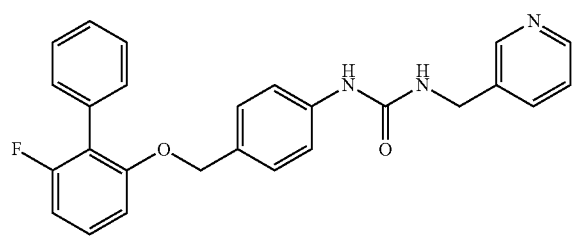 [SMILES: O=C(NCc1cccnc1)Nc1ccc(COc2cccc(F)c2-c2ccccc2)cc1] | 1-(4-{[(6-Fluorobiphenyl-2-yl)oxy]methyl}phenyl)-3-(pyridin-3-ylmethyl)urea |
| 171 | 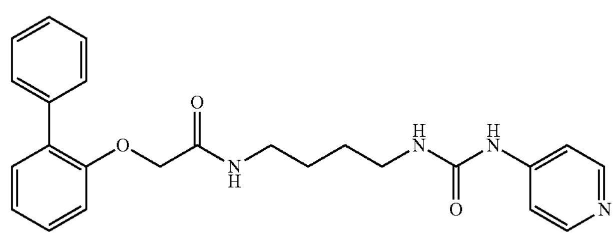 [SMILES: O=C(COc1ccccc1-c1ccccc1)NCCCCNC(=O)Nc1ccncc1] | 2-(Biphenyl-2-yloxy)-N-{4-[(pyridin-4-ylcarbamoyl)amino]butyl}acetamide |
| 172 | 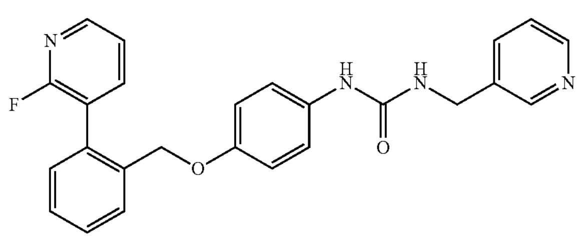 [SMILES: O=C(NCc1cccnc1)Nc1ccc(OCc2ccccc2-c2cccnc2F)cc1] | 1-(4-{[2-(2-Fluoropyridin-3-yl)benzyl]oxy}phenyl)-3-(pyridin-3-ylmethyl)urea |

TABLE 1-continued

| Example Number | Structure | ¹H NMR Data (400 MHz, DMSO-d6) |
|---|---|---|
| 173 | 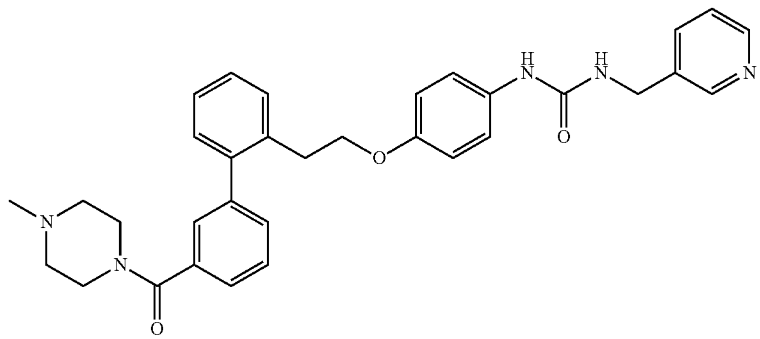 [SMILES: CN1CCN(C(=O)c2cccc(-c3ccccc3CCOc3ccc(NC(=O)NCc4cccnc4)cc3)c2)CC1] | 1-[4-(2-{3'-[(4-Methylpiperazin-1-yl)carbonyl]biphenyl-2-yl}ethoxy)phenyl]-3-(pyridin-3-ylmethyl)urea |
| 174 | 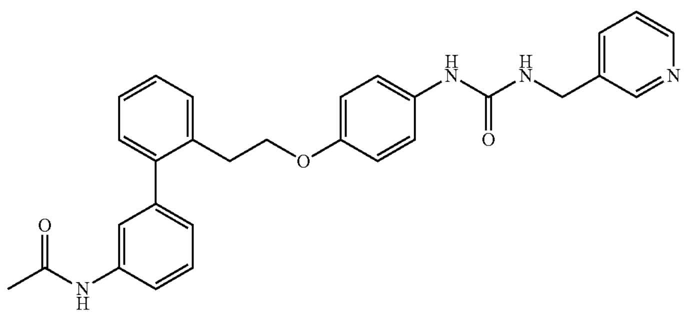 [SMILES: CC(=O)Nc1cccc(-c2ccccc2CCOc2ccc(NC(=O)NCc3cccnc3)cc2)c1] | N-{2'-[2-(4-{[(Pyridin-3-ylmethyl)carbamoyl]amino}phenoxy)ethyl]biphenyl-3-yl}acetamide |
| 175 | 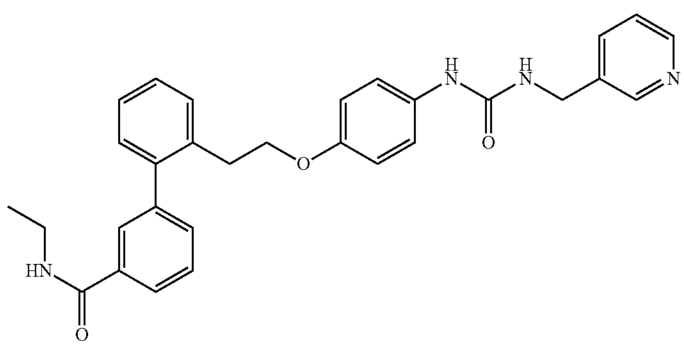 [SMILES: CCNC(=O)c1cccc(-c2ccccc2CCOc2ccc(NC(=O)NCc3cccnc3)cc2)c1] | N-Ethyl-2'-[2-(4-{[(pyridin-3-ylmethyl)carbamoyl]amino}phenoxy)ethyl]biphenyl-3-carboxamide |
| 176 | 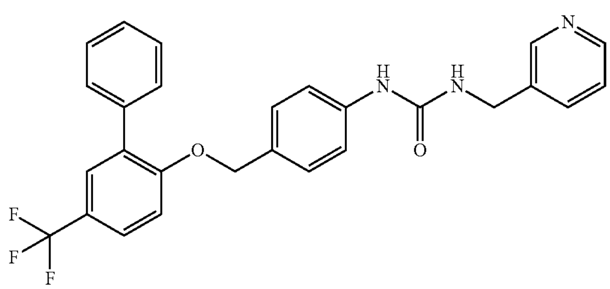 [SMILES: O=C(NCc1cccnc1)Nc1ccc(COc2ccc(C(F)(F)F)cc2-c2ccccc2)cc1] | 1-(Pyridin-3-ylmethyl)-3-[4-({[5-(trifluoromethyl)biphenyl-2-yl]oxy}methyl)phenyl]urea |
| 177 | 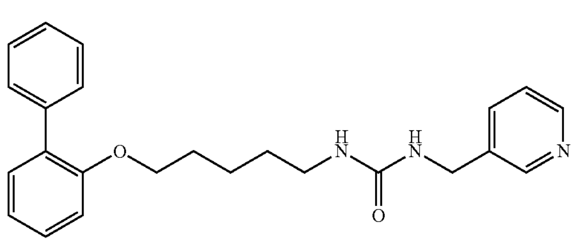 [SMILES: O=C(NCCCCCOc1ccccc1-c1ccccc1)NCc1cccnc1] | 1-[5-(Biphenyl-2-yloxy)pentyl]-3-(pyridin-3-ylmethyl)urea |

TABLE 1-continued

| Example Number | Structure | ¹H NMR Data (400 MHz, DMSO-d6) |
|---|---|---|
| 178 | 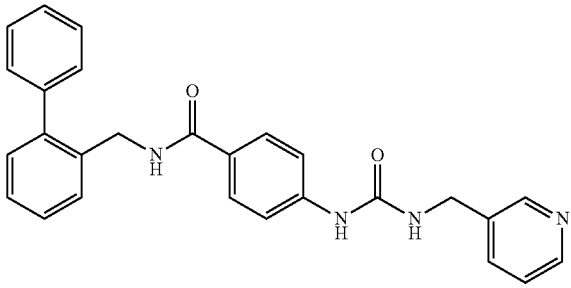 [SMILES: O=C(NCc1cccnc1)Nc1ccc(C(=O)NCc2ccccc2-c2ccccc2)cc1] | N-(Biphenyl-2-ylmethyl)-4-{[(pyridin-3-ylmethyl)carbamoyl]amino}benzamide |
| 179 | 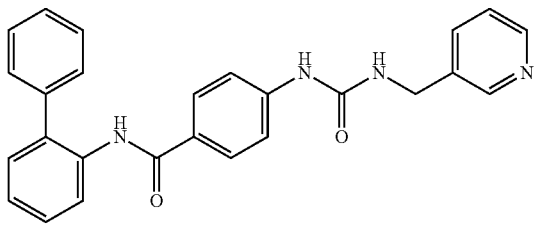 [SMILES: O=C(NCc1cccnc1)Nc1ccc(C(=O)Nc2ccccc2-c2ccccc2)cc1] | N-(biphenyl-2-yl)-4-{[(pyridin-3-ylmethyl)carbamoyl]amino}benzamide |
| 180 | 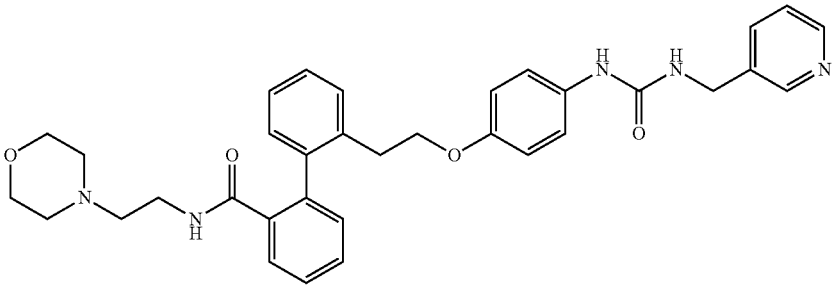 [SMILES: O=C(NCc1cccnc1)Nc1ccc(OCCc2ccccc2-c2ccccc2C(=O)NCCN2CCOCC2)cc1] | N-[2-(Morpholin-4-yl)ethyl]-2'-[2-(4-{[(pyridin-3-ylmethyl)carbamoyl]amino}phenoxy)ethyl]biphenyl-2-carboxamide |
| 181 | 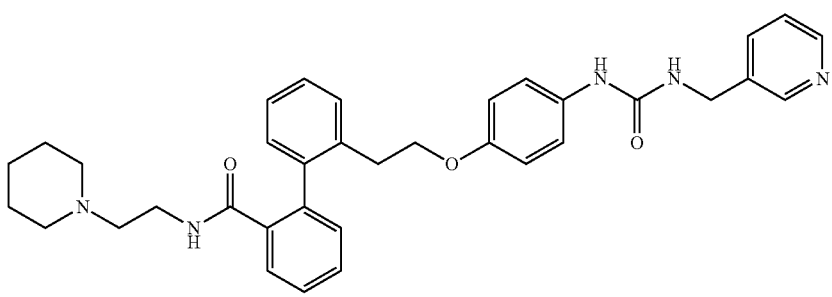 [SMILES: O=C(NCc1cccnc1)Nc1ccc(OCCc2ccccc2-c2ccccc2C(=O)NCCN2CCCCC2)cc1] | N-[2-(Piperidin-1-yl)ethyl]-2'-[2-(4-{[(pyridin-3-ylmethyl)carbamoyl]amino}phenoxy)ethyl]biphenyl-2-carboxamide |
| 182 | 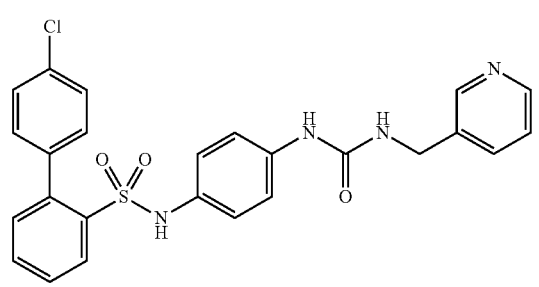 | 4'-chloro-N-(4-{[(pyridin-3-ylmethyl)carbamoyl]amino}phenyl)biphenyl-2-sulfonamide |

TABLE 1-continued

| Example Number | Structure | ¹H NMR Data (400 MHz, DMSO-d6) |
|---|---|---|
| 183 | 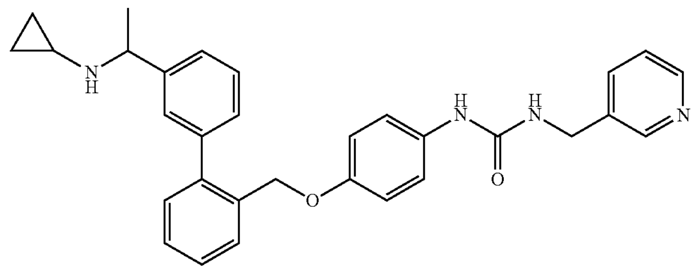 [SMILES: CC(NC1CC1)c1cccc(-c2ccccc2COc2ccc(NC(=O)NCc3cccnc3)cc2)c1] | 1-[4-({3'-[1-(Cyclopropylamino)ethyl]biphenyl-2-yl}methoxy)phenyl]-3-(pyridin-3-ylmethyl)urea |
| 184 | 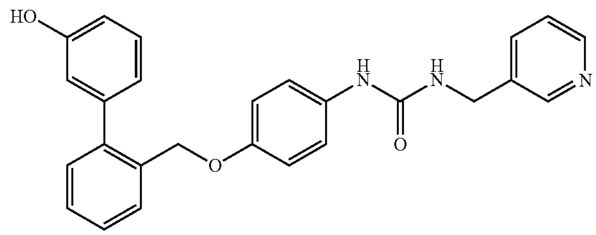 [SMILES: O=C(NCc1cccnc1)Nc1ccc(OCc2ccccc2-c2cccc(O)c2)cc1] | 1-(4-{[(3'-Hydroxybiphenyl-2-yl)oxy]methyl}phenyl)-3-(pyridin-3-ylmethyl)urea |
| 185 | 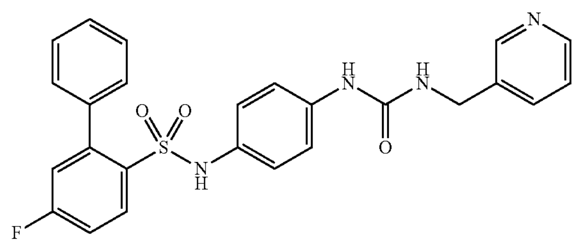 [SMILES: O=C(NCc1cccnc1)Nc1ccc(NS(=O)(=O)c2ccc(F)cc2-c2ccccc2)cc1] | 5-fluoro-N-4-{[(pyridin-3-ylmethyl)carbamoyl]amino}phenyl)biphenyl-2-sulfonamide |
| 186 | 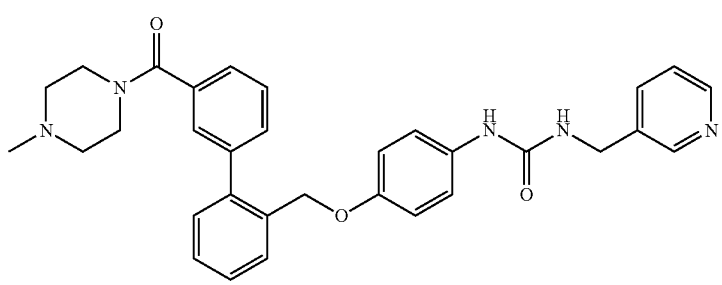 [SMILES: CN1CCN(C(=O)c2cccc(-c3ccccc3COc3ccc(NC(=O)NCc4cccnc4)cc3)c2)CC1] | 1-[4-({3'-[(4-Methylpiperazin-1-yl)carbonyl]biphenyl-2-yl}methoxy)phenyl]-3-(pyridin-3-ylmethyl)urea |
| 187 | 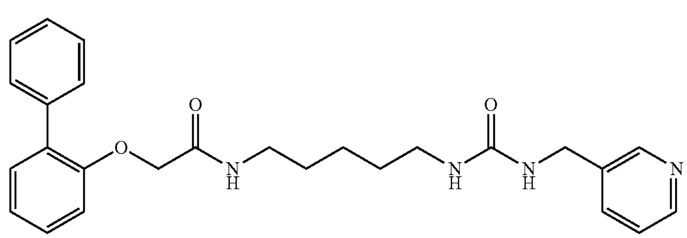 [SMILES: O=C(COc1ccccc1-c1ccccc1)NCCCCCNC(=O)NCc1cccnc1] | 2-(Biphenyl-2-yloxy)-N-(5-{[(pyridin-3-ylmethyl)carbamoyl]amino}pentyl)acetamide |
| 188 | 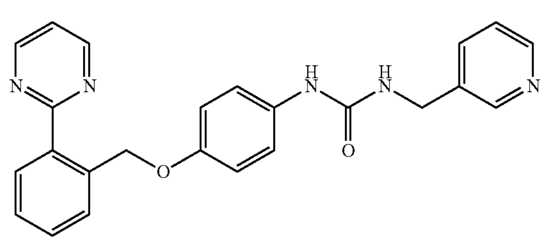 [SMILES: O=C(NCc1cccnc1)Nc1ccc(OCc2ccccc2-c2ncccn2)cc1] | 1-(Pyridin-3-ylmethyl)-3-(4-{[2-(pyrimidin-2-yl)benzyl]oxy}phenyl)urea |

TABLE 1-continued

| Example Number | Structure | ¹H NMR Data (400 MHz, DMSO-d6) |
|---|---|---|
| 189 | 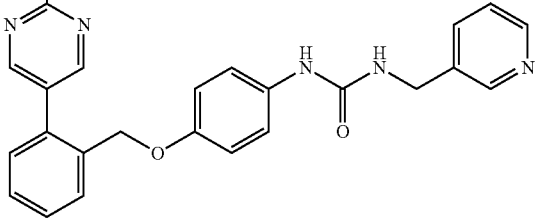 | 1-(4-{[2-(2-Amino-pyrimidin-5-yl)ben-zyl]oxy}phenyl)-3-(pyridin-3-ylmethyl)urea |
| 190 | 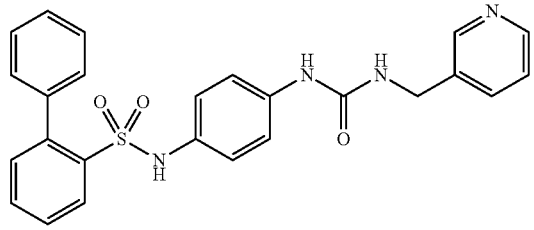 [SMILES: O=C(NCc1cccnc1)Nc1ccc(NS(=O)(=O)c2ccccc2-c2ccccc2)cc1] | N-(4-{[(Pyridin-3-ylmethyl)carbamoyl]a-mino}phenyl)biphenyl-2-sulfonamide |
| 191 | 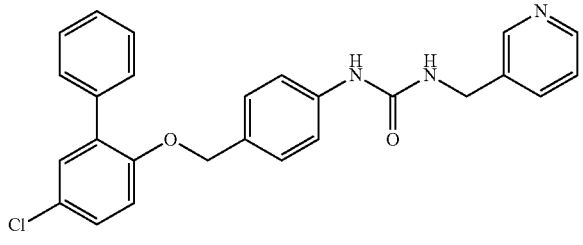 [SMILES: O=C(NCc1cccnc1)Nc1ccc(COc2ccc(Cl)cc2-c2ccccc2)cc1] | 1-(4-{[(5-Chlorobiphenyl-2-yl)oxy]meth-yl}phenyl)-3-(pyridin-3-ylmethyl)urea |
| 192 | 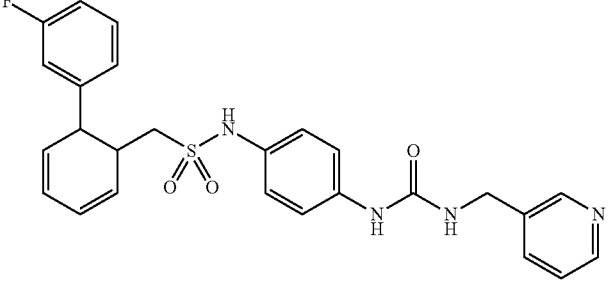 | 1-[6-(3-Fluorophenyl)cyclo-hexa-2,4-dien-1-yl]-N-(4-{[(pyridin-3-ylmethyl)carbamoyl]a-mino}phenyl)methane-sulfonamide |
| 193 | 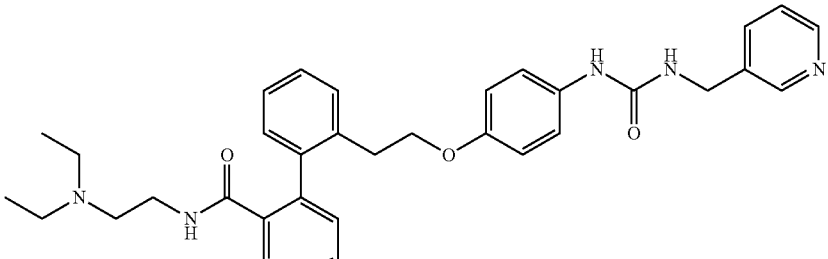 | N-[2-(Diethylamino)ethyl]-2'-[2-(4-{[(pyridin-3-ylmethyl)carbamoyl]a-mino}phenoxy)ethyl]bi-phenyl-2-carboxamide |

TABLE 1-continued

| Example Number | Structure | ¹H NMR Data (400 MHz, DMSO-d6) |
|---|---|---|
| 194 | 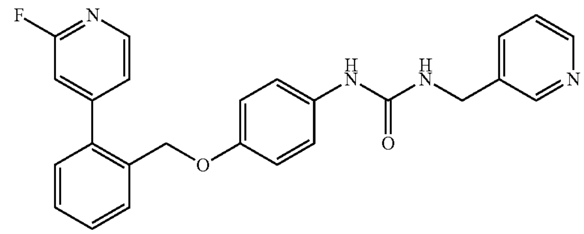 [SMILES: O=C(NCc1cccnc1)Nc1ccc(OCc2ccccc2-c2ccnc(F)c2)cc1] | 1-(4-{[2-(2-Fluoropyridin-4-yl)benzyl]oxy}phenyl)-3-(pyridin-3-ylmethyl)urea |
| 195 | 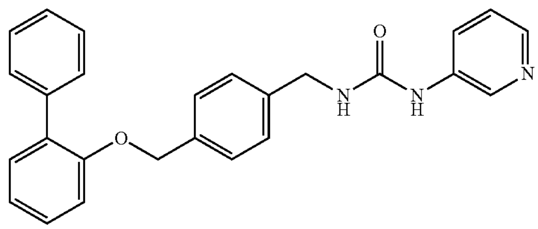 [SMILES: O=C(NCc1ccc(COc2ccccc2-c2ccccc2)cc1)Nc1cccnc1] | 1-{4-[(biphenyl-2-yloxy)methyl]benzyl}-3-pyridin-3-ylurea |
| 196 | 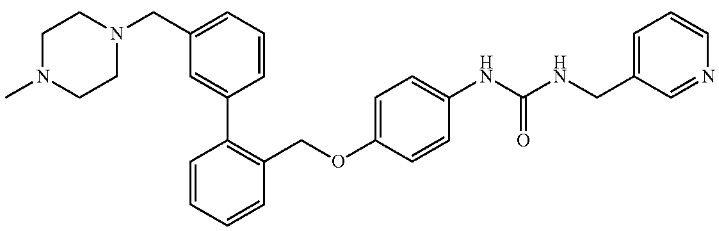 [SMILES: CN1CCN(Cc2cccc(-c3ccccc3COc3ccc(NC(=O)NCc4cccnc4)cc3)c2)CC1] | 1-{4-[({3'-[(4-Methylpiperazin-1-yl)methyl]biphenyl-2-yl}oxy)methyl]phenyl}-3-(pyridin-3-ylmethyl)urea |
| 197 | 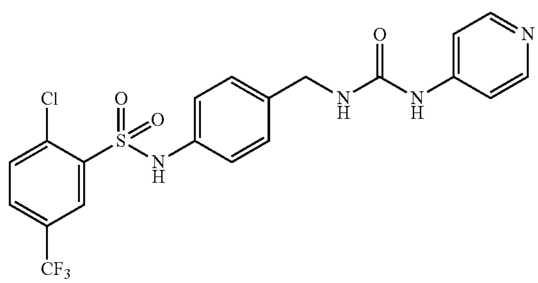 [SMILES: O=C(NCc1ccc(NS(=O)(=O)c2cc(C(F)(F)F)ccc2Cl)cc1)Nc1ccncc1] | 2-Chloro-N-(4-{[(pyridin-4-ylcarbamoyl)amino]methyl}phenyl)-5-(trifluoromethyl)benzenesulfonamide |
| 198 | 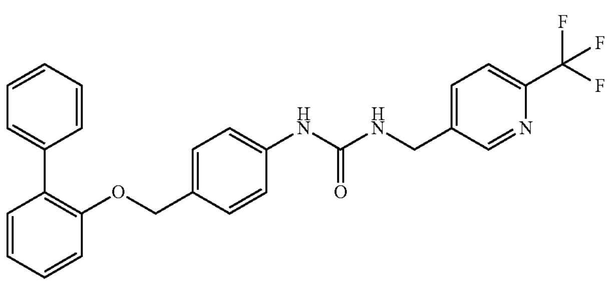 [SMILES: O=C(NCc1ccc(C(F)(F)F)nc1)Nc1ccc(COc2ccccc2-c2ccccc2)cc1] | 1-{4-[(Biphenyl-2-yloxy)methyl]phenyl}-3-{[6-(trifluoromethyl)pyridin-3-yl]methyl}urea |
| 199 | 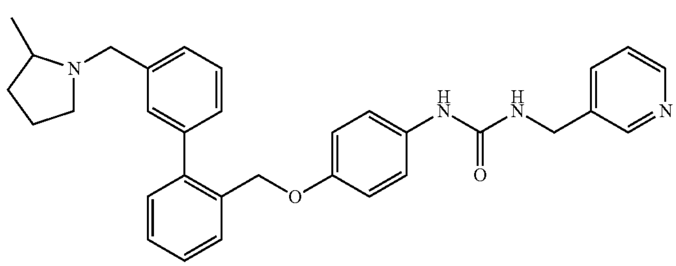 [SMILES: CC1CCCN1Cc1cccc(-c2ccccc2COc2ccc(NC(=O)NCc3cccnc3)cc2)c1] | 1-[4-({3'-[(2-Methylpyrrolidin-1-yl)methyl]biphenyl-2-yl}methoxy)phenyl]-3-(pyridin-3-ylmethyl)urea |

TABLE 1-continued

| Example Number | Structure | ¹H NMR Data (400 MHz, DMSO-d6) |
| --- | --- | --- |
| 200 | 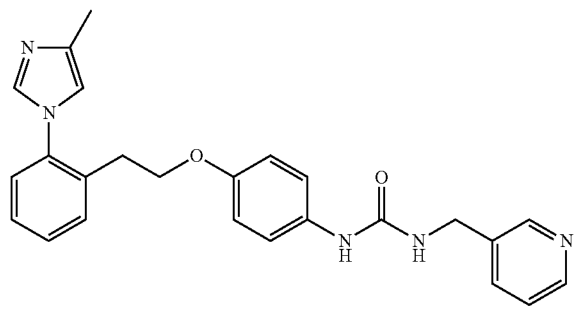 [SMILES: Cc1cn(-c2ccccc2CCOc2ccc(NC(=O)NCc3cccnc3)cc2)cn1] | 1-(4-{2-[2-(4-Methyl-1H-imidazol-1-yl)phenyl]ethoxy}phenyl)-3-(pyridin-3-ylmethyl)urea |
| 201 | 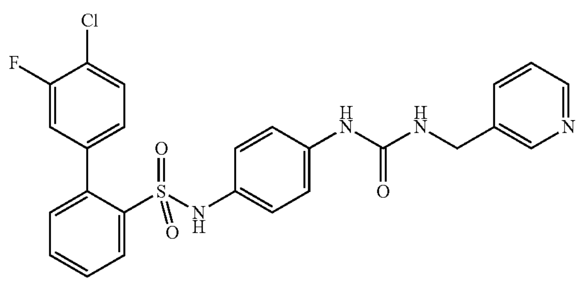 [SMILES: O=C(NCc1cccnc1)Nc1ccc(NS(=O)(=O)c2ccccc2-c2ccc(Cl)c(F)c2)cc1] | 4'-chloro-3'-fluoro-N-(4-{[(pyridin-3-ylmethyl)carbamoyl]amino}phenyl)biphenyl-2-sulfonamide |
| 202 | 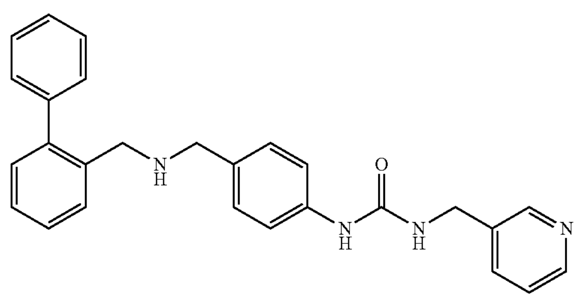 [SMILES: O=C(NCc1cccnc1)Nc1ccc(CNCc2ccccc2-c2ccccc2)cc1] | 1-(4-{[(Biphenyl-2-ylmethyl)amino]methyl}phenyl)-3-(pyridin-3-ylmethyl)urea |
| 203 | 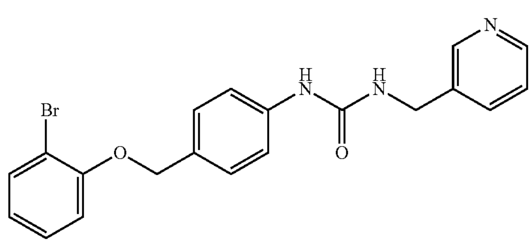 [SMILES: O=C(NCc1cccnc1)Nc1ccc(COc2ccccc2Br)cc1] | 1-{4-[(2-bromophenoxy)methyl]phenyl}-3-(pyridin-3-ylmethyl)urea |
| 204 | 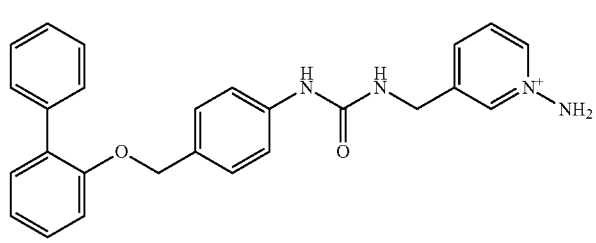 [SMILES: N[n+]1cccc(CNC(=O)Nc2ccc(COc3ccccc3-c3ccccc3)cc2)c1] | 1-Amino-3-{[({4-[(biphenyl-2-yloxy)methyl]phenyl}carbamoyl)amino]methyl}pyridinium |

TABLE 1-continued

| Example Number | Structure | ¹H NMR Data (400 MHz, DMSO-d6) |
|---|---|---|
| 205 | 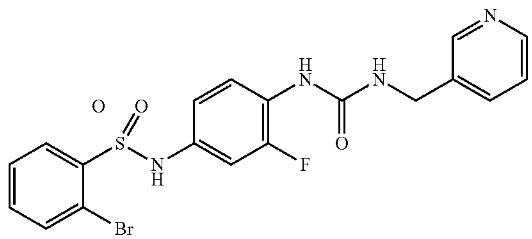 | 2-bromo-N-(3-fluoro-4-{[(pyridin-3-ylmethyl)carbamoyl]amino}phenyl)benzenesulfonamide |
| 206 | 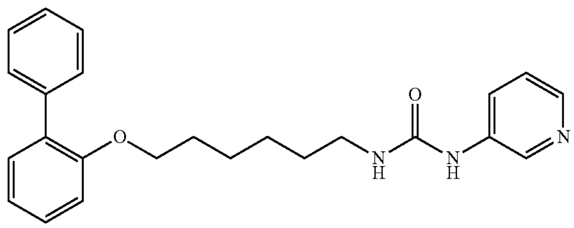 | 1-[6-(Biphenyl-2-yloxy)hexyl]-3-pyridin-3-ylurea |
| 207 | 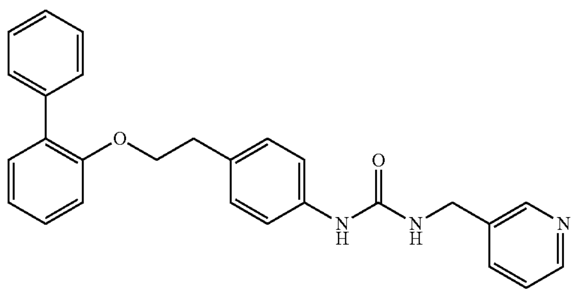 [SMILES: O=C(NCc1cccnc1)Nc1ccc(CCOc2ccccc2-c2ccccc2)cc1] | 1-{4-[2-(Biphenyl-2-yloxy)ethyl]phenyl}-3-(pyridin-3-ylmethyl)urea |
| 208 | 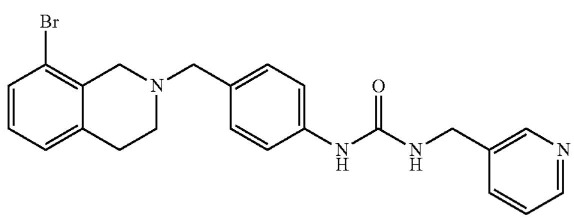 [SMILES: O=C(NCc1cccnc1)Nc1ccc(CN2CCc3cccc(Br)c3C2)cc1] | 1-{4-[(8-Bromo-3,4-dihydroisoquinolin-2(1H)-yl)methyl]phenyl}-3-(pyridin-3-ylmethyl)urea |
| 209 | 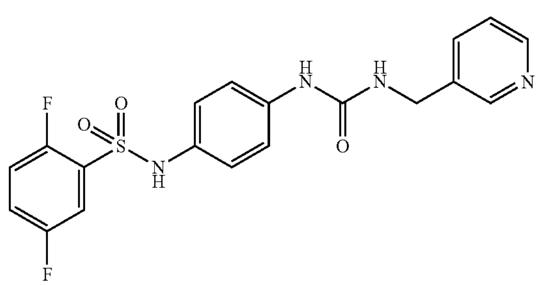 [SMILES: O=C(NCc1cccnc1)Nc1ccc(NS(=O)(=O)c2cc(F)ccc2F)cc1] | 2,5-Difluoro-N-(4-{[(pyridin-3-ylmethyl)carbamoyl]amino}phenyl)benzenesulfonamide |
| 210 | 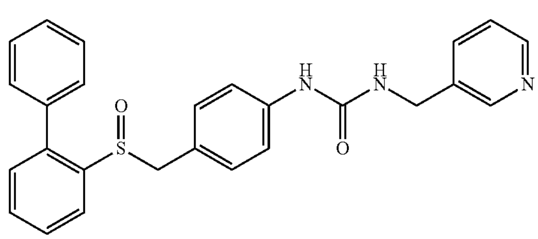 [SMILES: O=C(NCc1cccnc1)Nc1ccc(CS(=O)c2ccccc2-c2ccccc2)cc1] | 1-{4-[(biphenyl-2-ylsulfinyl)methyl]phenyl}-3-(pyridin-3-ylmethyl)urea |

TABLE 1-continued

| Example Number | Structure | ¹H NMR Data (400 MHz, DMSO-d6) |
|---|---|---|
| 211 | 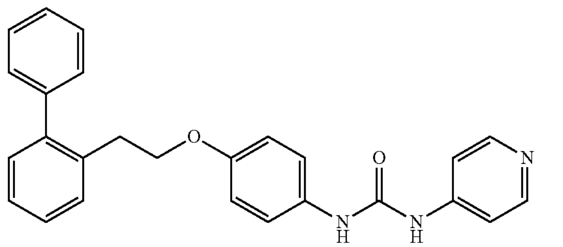 [SMILES: O=C(Nc1ccncc1)Nc1ccc(OCCc2ccccc2-c2ccccc2)cc1] | 1-{4-[2-(Biphenyl-2-yl)ethoxy]phenyl}-3-pyridin-4-ylurea |
| 212 | 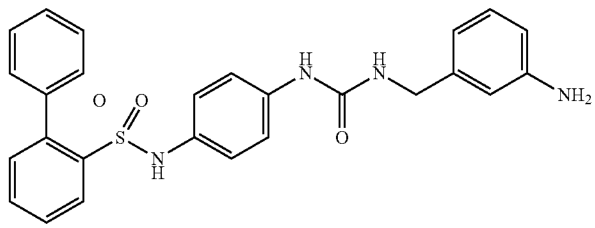 | N-(4-{[(3-aminobenzyl)carbamoyl]amino}phenyl)biphenyl-2-sulfonamide |
| 213 | 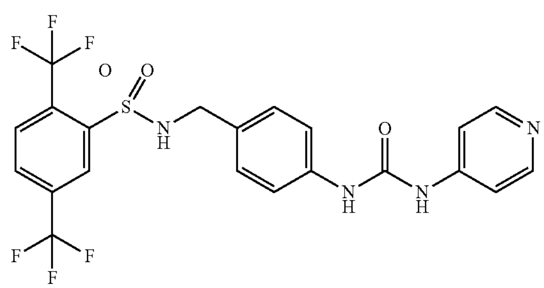 | N-{4-[(Pyridin-4-ylcarbamoyl)amino]benzyl}-2,5-bis(trifluoromethyl)benzenesulfonamide |
| 214 | 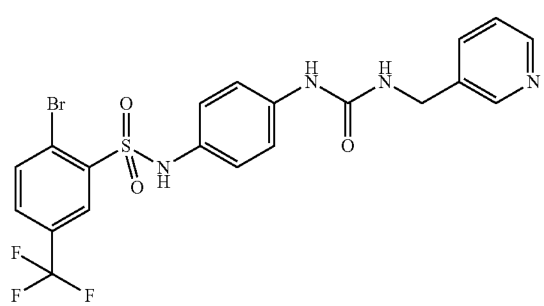 [SMILES: O=C(NCc1cccnc1)Nc1ccc(NS(=O)(=O)c2cc(C(F)(F)F)ccc2Br)cc1] | 2-Bromo-N-(4-{[(pyridin-3-ylmethyl)carbamoyl]amino}phenyl)-5-(trifluoromethyl)benzenesulfonamide |
| 215 | 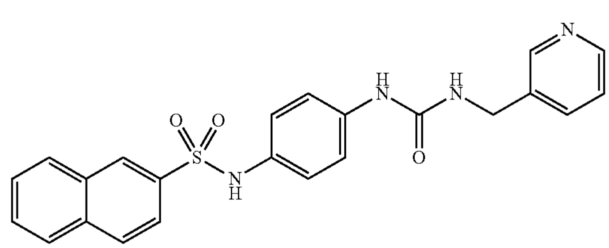 [SMILES: O=C(NCc1cccnc1)Nc1ccc(NS(=O)(=O)c2ccc3ccccc3c2)cc1] | N-(4-{[(Pyridin-3-ylmethyl)carbamoyl]amino}phenyl)naphthalene-2-sulfonamide |

TABLE 1-continued

| Example Number | Structure | ¹H NMR Data (400 MHz, DMSO-d6) |
| --- | --- | --- |
| 216 | 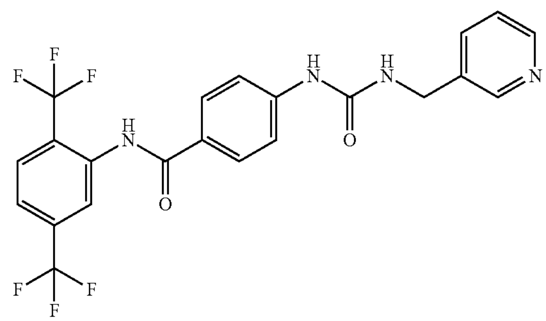 [SMILES: O=C(NCc1cccnc1)Nc1ccc(C(=O)Nc2cc(C(F)(F)F)ccc2C(F)(F)F)cc1] | N-[2,5-Bis(trifluoromethyl)phenyl]-4-{[(pyridin-3-ylmethyl)carbamoyl]amino}benzamide |
| 217 | 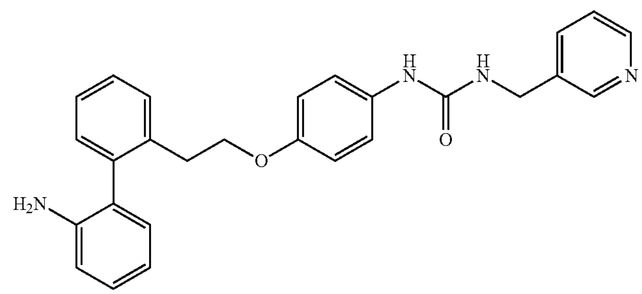 [SMILES: Nc1ccccc1-c1ccccc1CCOc1ccc(NC(=O)NCc2cccnc2)cc1] | 1-{4-[2-(2'-Aminobiphenyl-2-yl)ethoxy]phenyl}-3-(pyridin-3-ylmethyl)urea |
| 218 | 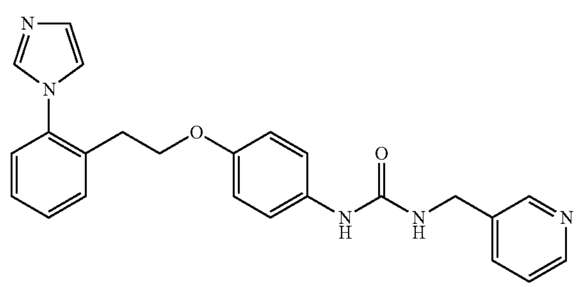 [SMILES: O=C(NCc1cccnc1)Nc1ccc(OCCc2ccccc2-n2ccnc2)cc1] | 1-(4-{2-[2-(1H-Imidazol-1-yl)phenyl]ethoxy}phenyl)-3-(pyridin-3-ylmethyl)urea |
| 219 | 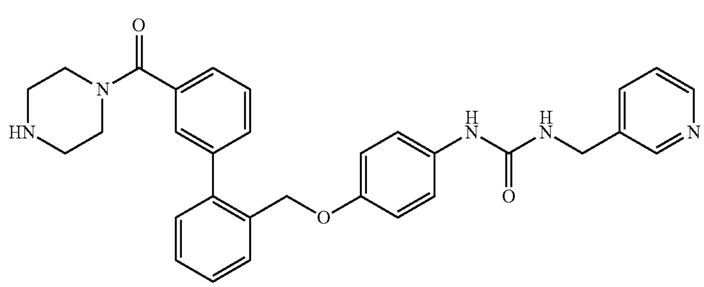 [SMILES: O=C(NCc1cccnc1)Nc1ccc(OCc2ccccc2-c2cccc(C(=O)N3CCNCC3)c2)cc1] | 1-(4-{[3'-(Piperazin-1-ylcarbonyl)biphenyl-2-yl]methoxy}phenyl)-3-(pyridin-3-ylmethyl)urea |
| 220 | 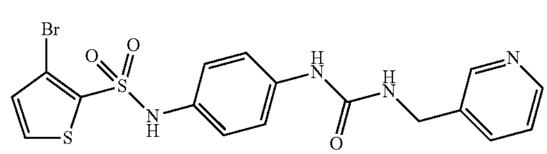 [SMILES: O=C(NCc1cccnc1)Nc1ccc(NS(=O)(=O)c2sccc2Br)cc1] | 3-bromo-N-(4-{[(pyridin-3-ylmethyl)carbamoyl]amino}phenyl)thiophene-2-sulfonamide |

TABLE 1-continued

| Example Number | Structure | ¹H NMR Data (400 MHz, DMSO-d6) |
| --- | --- | --- |
| 221 | 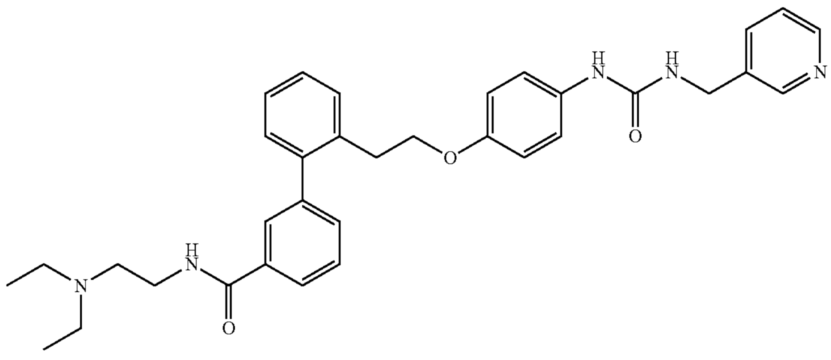 [SMILES: CCN(CC)CCNC(=O)c1cccc(-c2ccccc2CCOc2ccc(NC(=O)NCc3cccnc3)cc2)c1] | N-[2-Diethyl-amino)ethyl]-2'-[2-(4-{[(pyridin-3-ylmethyl)carbamoyl]amino}phenoxy)ethyl]biphenyl-3-carboxamide |
| 222 | 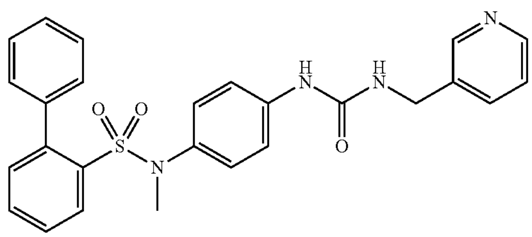 [SMILES: CN(c1ccc(NC(=O)NCc2cccnc2)cc1)S(=O)(=O)c1ccccc1-c1ccccc1] | N-methyl-N-(4-{[(pyridin-3-ylmethyl)carbamoyl]amino}phenyl)biphenyl-2-sulfonamide |
| 223 | 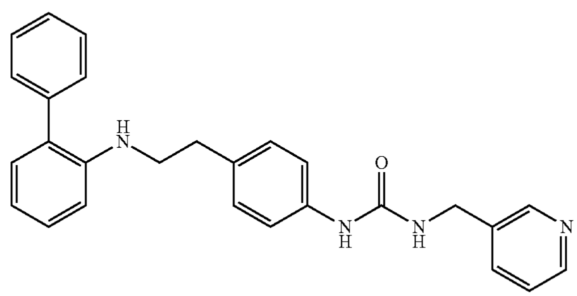 [SMILES: O=C(NCc1cccnc1)Nc1ccc(CCNc2ccccc2-c2ccccc2)cc1] | 1-{4-[2-(Biphenyl-2-ylamino)ethyl]phenyl}-3-(pyridin-3-ylmethyl)urea |
| 224 | 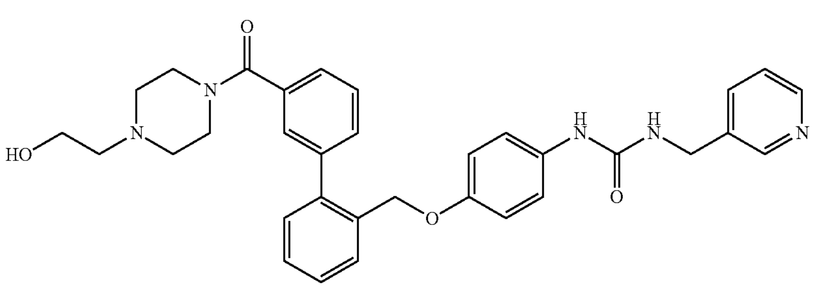 [SMILES: O=C(NCc1cccnc1)Nc1ccc(OCc2ccccc2-c2cccc(C(=O)N3CCN(CCO)CC3)c2)cc1] | 1-{4-[(3'-{[4-(2-Hydroxyethyl)piperazin-1-yl]carbonyl}biphenyl-2-yl)methoxy]phenyl}-3-(pyridin-3-ylmethyl)urea |
| 225 | 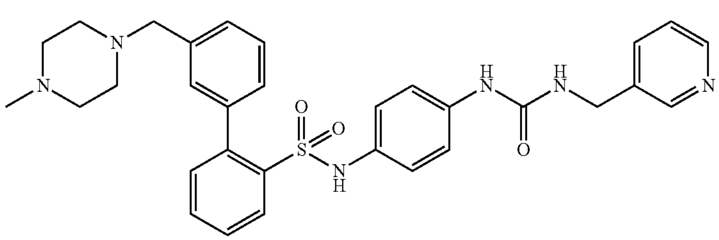 [SMILES: CN1CCN(Cc2cccc(-c3ccccc3S(=O)(=O)Nc3ccc(NC(=O)NCc4cccnc4)cc3)c2)CC1] | 3'-[(4-Methylpiperazin-1-yl)methyl]-N-(4-{[(pyridin-3-ylmethyl)carbamoyl]amino}phenyl)biphenyl-2-sulfonamide |

TABLE 1-continued

| Example Number | Structure | ¹H NMR Data (400 MHz, DMSO-d6) |
|---|---|---|
| 226 | 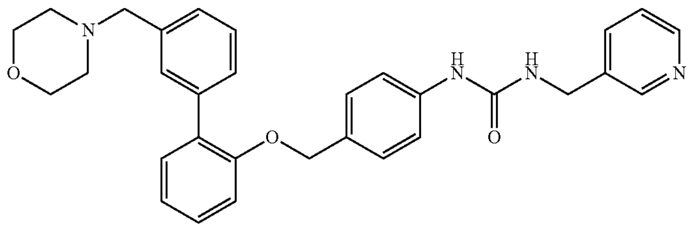 [SMILES: O=C(NCc1cccnc1)Nc1ccc(COc2ccccc2-c2cccc(CN3CCOCC3)c2)cc1] | 1-[4-({[3'-(Morpholin-4-ylmethyl)biphenyl-2-yl]oxy}methyl)phenyl]-3-(pyridin-3-ylmethyl)urea |
| 227 | 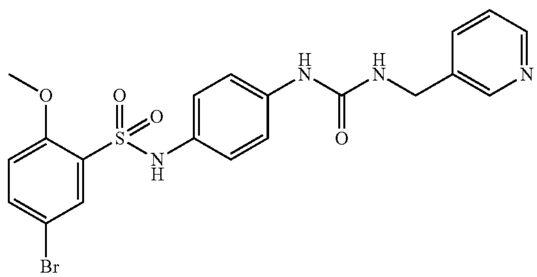 [SMILES: COc1ccc(Br)cc1S(=O)(=O)Nc1ccc(NC(=O)NCc2cccnc2)cc1] | 5-Bromo-2-methoxy-N-(4-{[(pyridin-3-ylmethyl)carbamoyl]amino}phenyl)benzenesulfonamide |
| 228 | 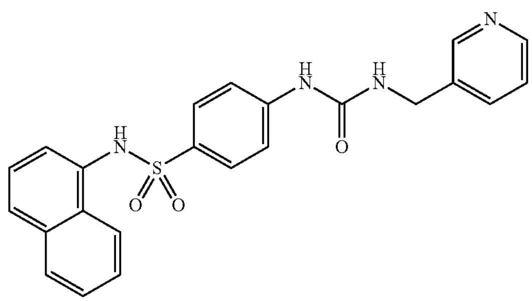 [SMILES: O=C(NCc1cccnc1)Nc1ccc(S(=O)(=O)Nc2cccc3ccccc23)cc1] | N-(naphthalen-1-yl)-4-{[(pyridin-3-ylmethyl)carbamoyl]amino}benzenesulfonamide |
| 229 | 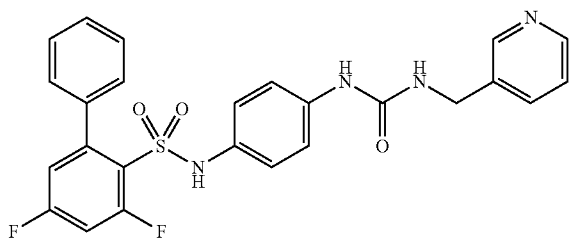 [SMILES: O=C(NCc1cccnc1)Nc1ccc(NS(=O)(=O)c2c(F)cc(F)cc2-c2ccccc2)cc1] | 3,5-difluoro-N-(4-{[(pyridin-3-ylmethyl)carbamoyl]amino}phenyl)biphenyl-2-sulfonamide |
| 230 | 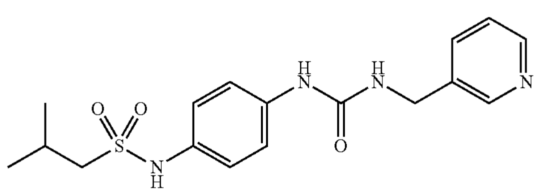 [SMILES: CC(C)CS(=O)(=O)Nc1ccc(NC(=O)NCc2cccnc2)cc1] | 2-methyl-N-(4-{[(pyridin-3-ylmethyl)carbamoyl]amino}phenyl)propane-1-sulfonamide |
| 231 | 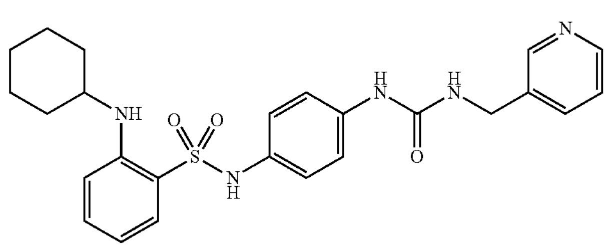 [SMILES: O=C(NCc1cccnc1)Nc1ccc(NS(=O)(=O)c2ccccc2NC2CCCCC2)cc1] | 2-(cyclohexylamino)-N-(4-{[(pyridin-3-ylmethyl)carbamoyl]amino}phenyl)benzenesulfonamide |

TABLE 1-continued

| Example Number | Structure | ¹H NMR Data (400 MHz, DMSO-d6) |
|---|---|---|
| 232 | 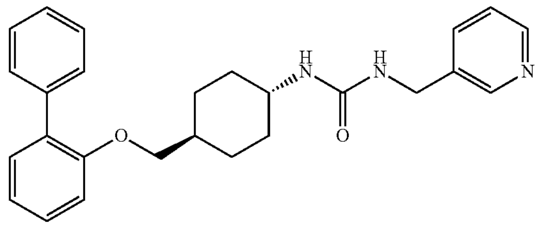 [SMILES: O=C(NCc1cccnc1)N[C@H]1CC[C@H](COc2ccccc2-c2ccccc2)CC1] | 1-{trans-4-[(Biphenyl-2-yloxy)methyl]cyclohexyl}-3-(pyridin-3-ylmethyl)urea |
| 233 | 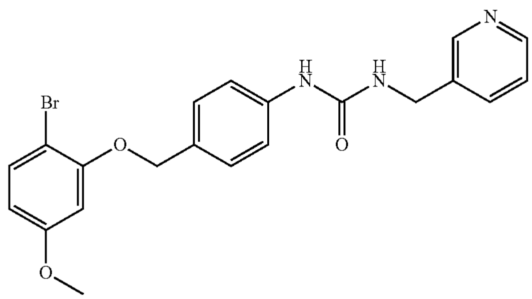 [SMILES: COc1ccc(Br)c(OCc2ccc(NC(=O)NCc3cccnc3)cc2)c1] | 1-{4-[(2-Bromo-5-methoxyphenoxy)methyl]phenyl}-3-(pyridin-3-ylmethyl)urea |
| 234 | 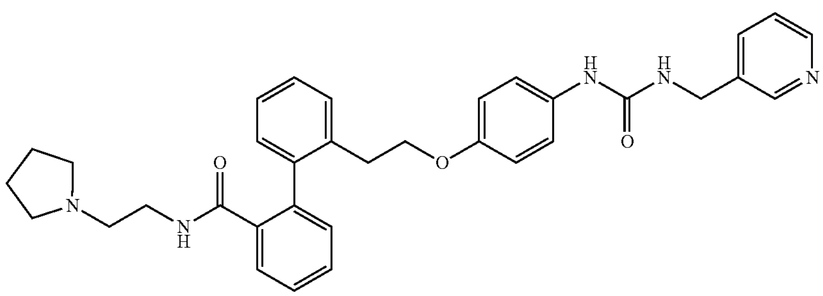 [SMILES: O=C(NCc1cccnc1)Nc1ccc(OCCc2ccccc2-c2ccccc2C(=O)NCCN2CCCC2)cc1] | 2'-[2-(4-{[(Pyridin-3-ylmethyl)carbamoyl]amino}phenoxy)ethyl]-N-[2-(pyrrolidin-1-yl)ethyl]biphenyl-2-carboxamide |
| 235 | 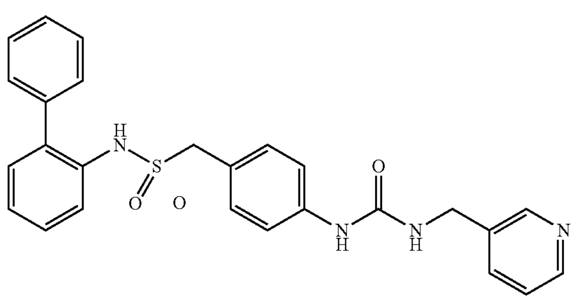 | N-(Biphenyl-2-yl)-1-(4-{[(pyridin-3-ylmethyl)carbamoyl]amino}phenyl)methanesulfonamide |
| 236 | 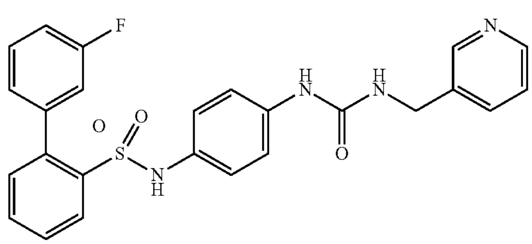 | 3'-fluoro-N-(4-{[(pyridin-3-ylmethyl)carbamoyl]amino}phenyl)biphenyl-2-sulfonamide |

TABLE 1-continued

| Example Number | Structure | ¹H NMR Data (400 MHz, DMSO-d6) |
|---|---|---|
| 237 | 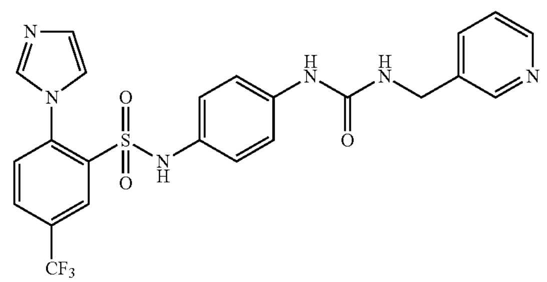 [SMILES: O=C(NCc1cccnc1)Nc1ccc(NS(=O)(=O)c2cc(C(F)(F)F)ccc2-n2ccnc2)cc1] | 2-(1H-Imidazol-1-yl)-N-(4-{[(pyridin-3-ylmethyl)carbamoyl]amino}phenyl)-5-(trifluoromethyl)benzenesulfonamide |
| 238 | 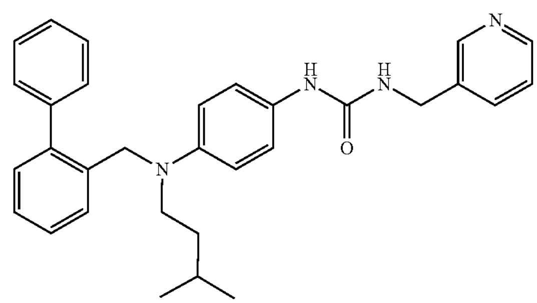 [SMILES: CC(C)CCN(Cc1ccccc1-c1ccccc1)c1ccc(NC(=O)NCc2cccnc2)cc1] | 1-{4-[(Biphenyl-2-ylmethyl)(3-methylbutyl)amino]phenyl}-3-(pyridin-3-ylmethyl)urea |
| 239 | 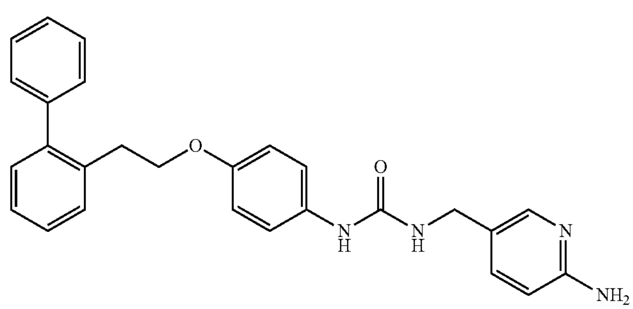 [SMILES: Nc1ccc(CNC(=O)Nc2ccc(OCCc3ccccc3-c3ccccc3)cc2)cn1] | 1-[(6-Aminopyridin-3-yl)methyl]-3-{4-[2-(biphenyl-2-yl)ethoxy]phenyl}urea |
| 240 | 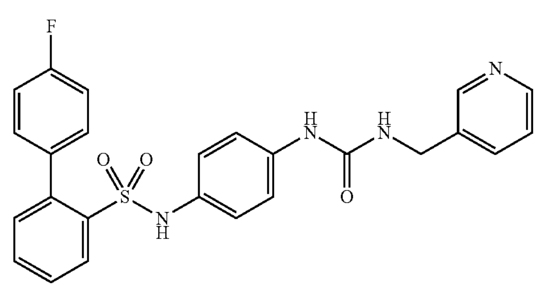 [SMILES: O=C(NCc1cccnc1)Nc1ccc(NS(=O)(=O)c2ccccc2-c2ccc(F)cc2)cc1] | 4'-fluoro-N-(4-{[(pyridin-3-ylmethyl)carbamoyl]amino}phenyl)biphenyl-2-sulfonamide |
| 241 | 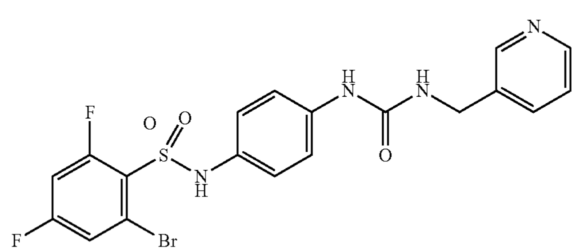 | 2-bromo-4,6-difluoro-N-(4-{[(pyridin-3-ylmethyl)carbamoyl]amino}phenyl)benzenesulfonamide |

| Example Number | Structure | ¹H NMR Data (400 MHz, DMSO-d6) |
|---|---|---|
| 242 | 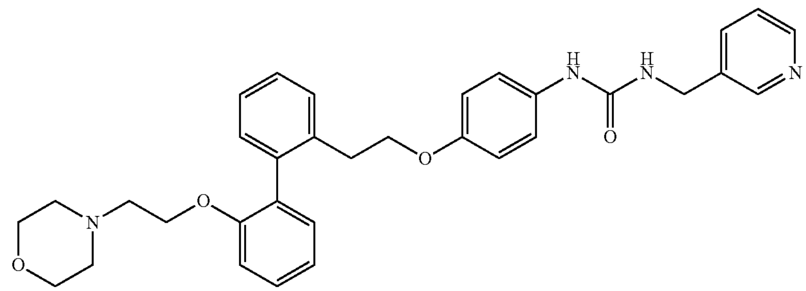 [SMILES: O=C(NCc1cccnc1)Nc1ccc(OCCc2ccccc2-c2ccccc2OCCN2CCOCC2)cc1] | 1-[4-(2-{2'-[2-(Morpholin-4-yl)ethoxy]biphenyl-2-yl}ethoxy)phenyl]-3-(pyridin-3-ylmethyl)urea |
| 243 | 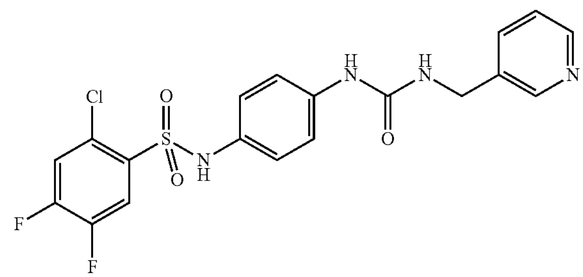 [SMILES: O=C(NCc1cccnc1)Nc1ccc(NS(=O)(=O)c2cc(F)c(F)cc2Cl)cc1] | 2-chloro-4,5-difluoro-N-(4-{[(pyridin-3-ylmethyl)carbamoyl]amino}phenyl)benzenesulfonamide |
| 244 | 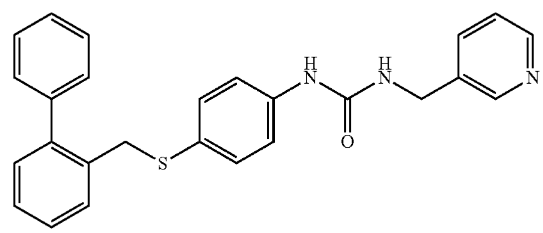 [SMILES: O=C(NCc1cccnc1)Nc1ccc(SCc2ccccc2-c2ccccc2)cc1] | 1-{4-[(biphenyl-2-ylmethyl)sulfanyl]phenyl}-3-(pyridin-3-ylmethyl)urea |
| 245 | 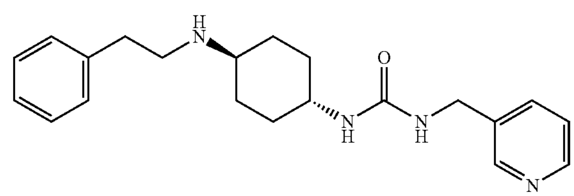 [SMILES: O=C(NCc1cccnc1)N[C@H]1CC[C@H](NCCc2ccccc2)CC1] | 1-{trans-4-[(2-Phenylethyl)amino]cyclohexyl}-3-(pyridin-3-ylmethyl)urea |
| 246 | 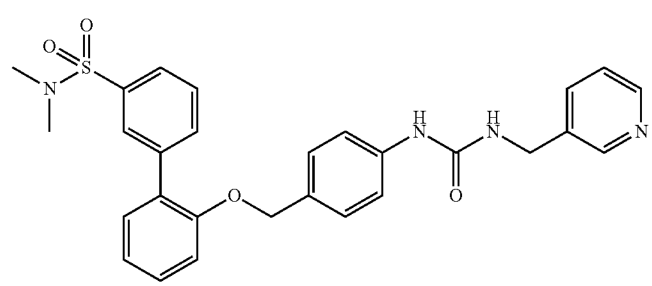 [SMILES: CN(C)S(=O)(=O)c1cccc(-c2ccccc2OCc2ccc(NC(=O)NCc3cccnc3)cc2)c1] | N,N-Dimethyl-2'-[(4-{[(pyridin-3-ylmethyl)carbamoyl]amino}benzyl)oxy]biphenyl-3-sulfonamide |
| 247 | 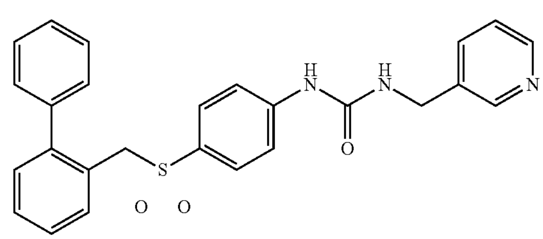 | 1-{4-[(biphenyl-2-ylmethyl)sulfonyl]phenyl}-3-(pyridin-3-ylmethyl)urea |

TABLE 1-continued

| Example Number | Structure | ¹H NMR Data (400 MHz, DMSO-d6) |
|---|---|---|
| 248 | 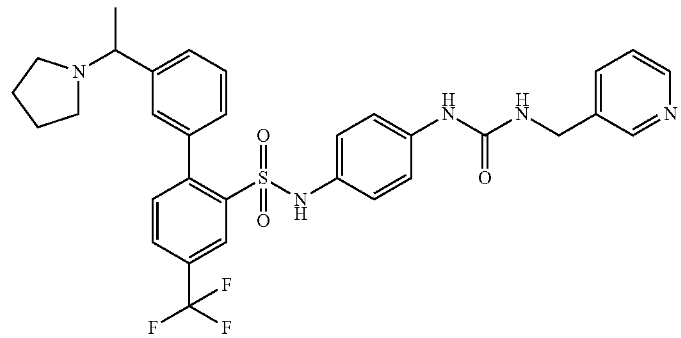 [SMILES: CC(c1cccc(-c2ccc(C(F)(F)F)cc2S(=O)(=O)Nc2ccc(NC(=O)NCc3cccnc3)cc2)c1)N1CCCC1] | N-(4-{[(Pyridin-3-ylmethyl)carbamoyl]amino}phenyl)-3'-[1-(pyrrolidin-1-yl)ethyl]-4-(trifluoromethyl)biphenyl-2-sulfonamide |
| 249 | 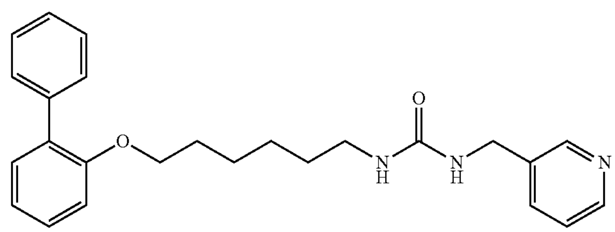 [SMILES: O=C(NCCCCCCOc1ccccc1-c1ccccc1)NCc1cccnc1] | 1-[6-(biphenyl-2-yloxy)hexyl]-3-(pyridin-3-ylmethyl)urea |
| 250 | 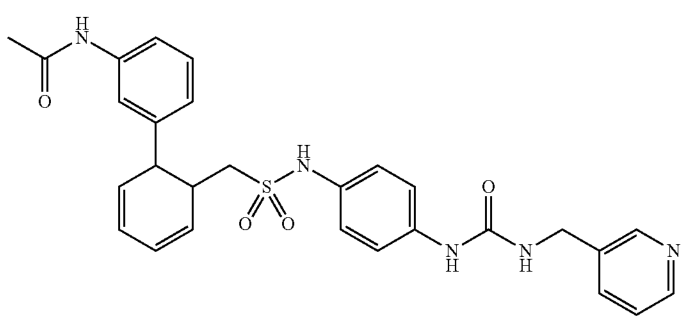 [SMILES: CC(=O)Nc1cccc(C2C=CC=CC2CS(=O)(=O)Nc2ccc(NC(=O)NCc3cccnc3)cc2)c1] | N-[3-(6-{[(4-{[(Pyridin-3-ylmethyl)carbamoyl]amino}phenyl)sulfamoyl]methyl}cyclohexa-2,4-dien-1-yl)phenyl]acetamide |
| 251 | 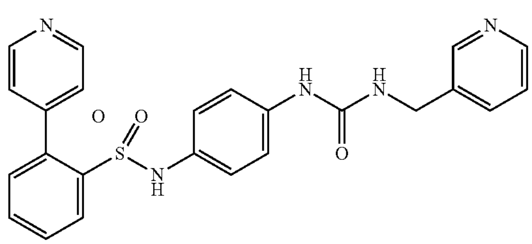 | 2-(pyridin-4-yl)-N-(4-{(pyridin-3-ylmethyl)carbamoyl]amino}phenyl)benzenesulfonamide |
| 252 | 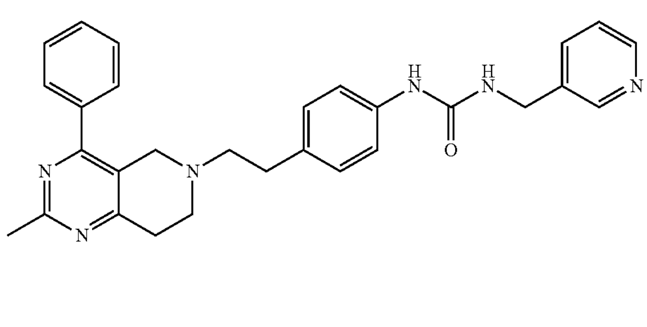 [SMILES: Cc1nc2c(c(-c3ccccc3)n1)CN(CCc1ccc(NC(=O)NCc3cccnc3)cc1)CC2] | 1-{4-[2-(2-Methyl-4-phenyl-7,8-dihydropyrido[4,3-d]pyrimidin-6(5H)-yl)ethyl]phenyl}-3-(pyridin-3-ylmethyl)urea |

TABLE 1-continued

| Example Number | Structure | ¹H NMR Data (400 MHz, DMSO-d6) |
|---|---|---|
| 253 | 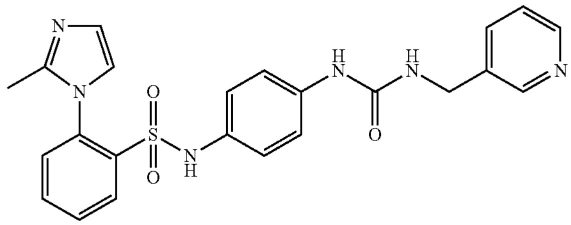 [SMILES: Cc1nccn1-c1ccccc1S(=O)(=O)Nc1ccc(NC(=O)NCc2cccnc2)cc1] | 2-(2-Methyl-1H-imidazol-1-yl)-N-(4-{[(pyridin-3-ylmethyl)carbamoyl]amino}phenyl)benzenesulfonamide |
| 254 | 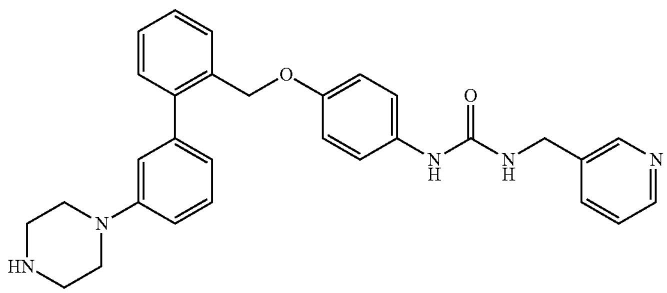 [SMILES: O=C(NCc1cccnc1)Nc1ccc(OCc2ccccc2-c2cccc(N3CCNCC3)c2)cc1] | 1-(4-{[3'-(Piperazin-1-yl)biphenyl-2-yl]methoxy}phenyl)-3-(pyridin-3-ylmethyl)urea |
| 255 | 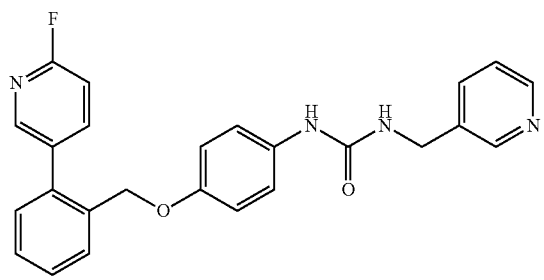 [SMILES: O=C(NCc1cccnc1)Nc1ccc(OCc2ccccc2-c2ccc(F)nc2)cc1] | 1-(4-{[2-(6-Fluoropyridin-3-yl)benzyl]oxy}phenyl)-3-(pyridin-3-ylmethyl)urea |
| 256 | 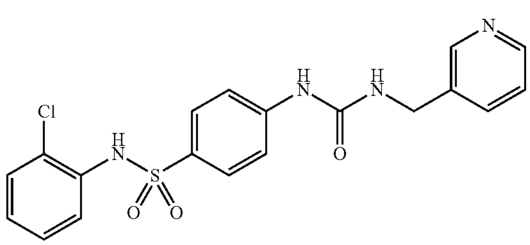 [SMILES: O=C(NCc1cccnc1)Nc1ccc(S(=O)(=O)Nc2ccccc2Cl)cc1] | N-(2-chlorophenyl)-4-{[(pyridin-3-ylmethyl)carbamoyl]amino}benzenesulfonamide |
| 257 | 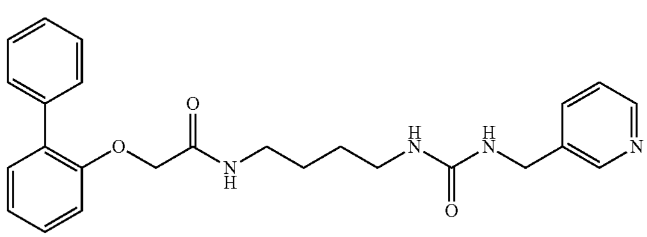 [SMILES: O=C(COc1ccccc1-c1ccccc1)NCCCCNC(=O)NCc1cccnc1] | 2-(Biphenyl-2-yloxy)-N-(4-{[(pyridin-3-ylmethyl)carbamoyl]amino}butyl)acetamide |

TABLE 1-continued

| Example Number | Structure | ¹H NMR Data (400 MHz, DMSO-d6) |
|---|---|---|
| 258 | 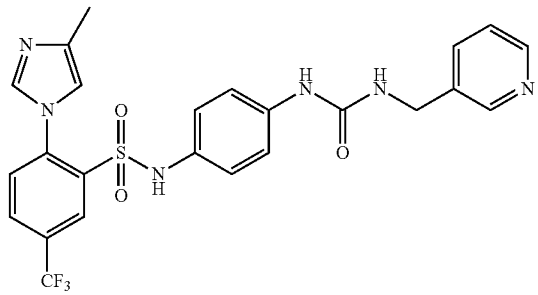 [SMILES: Cc1cn(-c2ccc(C(F)(F)F)cc2S(=O)(=O)Nc2ccc(NC(=O)NCc3cccnc3)cc2)cn1] | 2-(4-Methyl-1H-imidazol-1-yl)-N-(4-{[(pyridin-3-ylmethyl)carbamoyl]amino}phenyl)-5-(trifluoromethyl)benzenesulfonamide |
| 259 | 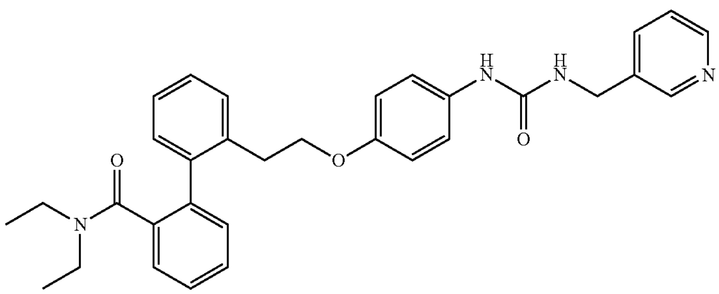 [SMILES: CCN(CC)C(=O)c1ccccc1-c1ccccc1CCOc1ccc(NC(=O)NCc2cccnc2)cc1] | N,N-Diethyl-2'-[2-(4-{[(pyridin-3-ylmethyl)carbamoyl]amino}phenoxy)ethyl]biphenyl-2-carboxamide |
| 260 | 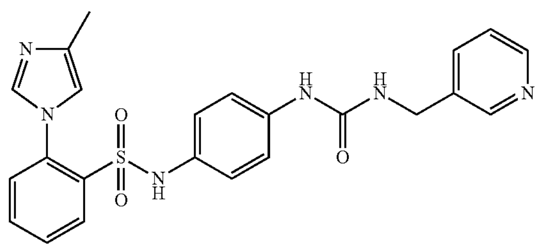 [SMILES: Cc1cn(-c2ccccc2S(=O)(=O)Nc2ccc(NC(=O)NCc3cccnc3)cc2)cn1] | 2-(4-Methyl-1H-imidazol-1-yl)-N-(4-{[(pyridin-3-ylmethyl)carbamoyl]amino}phenyl)benzenesulfonamide |
| 261 | 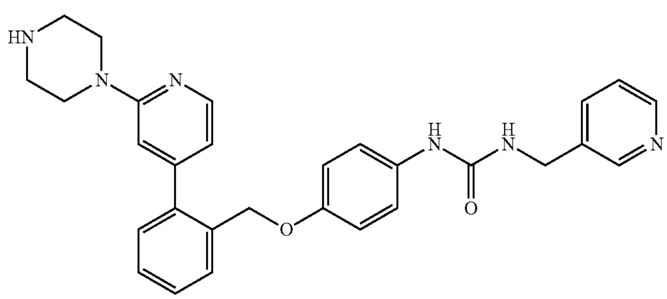 [SMILES: O=C(NCc1cccnc1)Nc1ccc(OCc2ccccc2-c2ccnc(N3CCNCC3)c2)cc1] | 1-[4-({2-[2-(Piperazin-1-yl)pyridin-4-yl]benzyl}oxy)phenyl]-3-(pyridin-3-ylmethyl)urea |
| 262 | 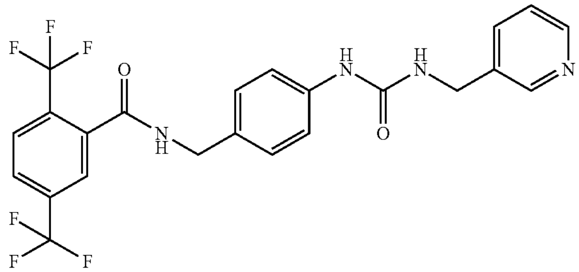 [SMILES: O=C(NCc1cccnc1)Nc1ccc(CNC(=O)c2cc(C(F)(F)F)ccc2C(F)(F)F)cc1] | N-(4-{[(Pyridin-3-ylmethyl)carbamoyl]amino}benzyl)-2,5-bis(trifluoromethyl)benzamide |

TABLE 1-continued

| Example Number | Structure | ¹H NMR Data (400 MHz, DMSO-d6) |
|---|---|---|
| 263 | 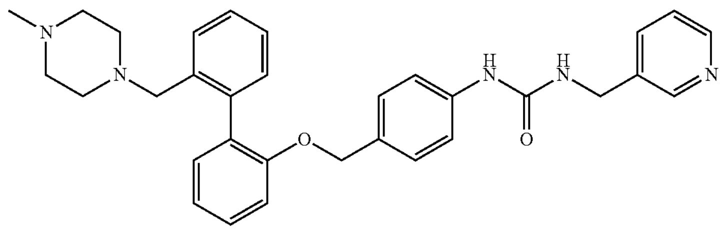 [SMILES: CN1CCN(Cc2ccccc2-c2ccccc2OCc2ccc(NC(=O)NCc3cccnc3)cc2)CC1] | 1-{4-[({2'-[(4-Methylpiperazin-1-yl)methyl]biphenyl-2-yl}oxy)methyl]phenyl}-3-(pyridin-3-ylmethyl)urea |
| 264 | 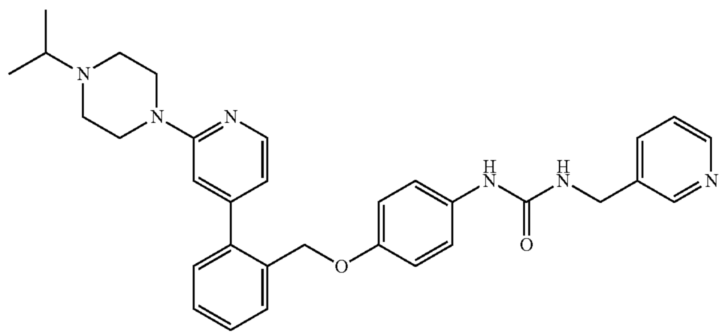 [SMILES: CC(C)N1CCN(c2cc(-c3ccccc3COc3ccc(NC(=O)NCc4cccnc4)cc3)ccn2)CC1] | 1-{4-[(2-{2-[4-(Propan-2-yl)piperazin-1-yl]pyridin-4-yl}benzyl)oxy]phenyl}-3-(pyridin-3-ylmethyl)urea |
| 265 | 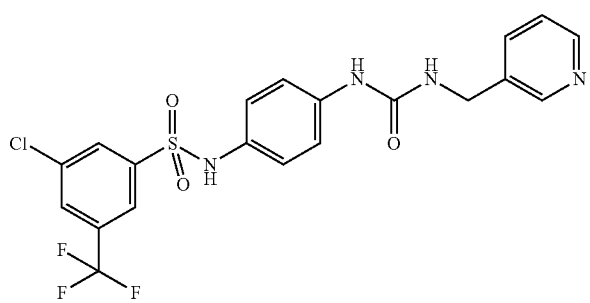 [SMILES: O=C(NCc1cccnc1)Nc1ccc(NS(=O)(=O)c2cc(Cl)cc(C(F)(F)F)c2)cc1] | 3-chloro-N-(4-{[(pyridin-3-ylmethyl)carbamoyl]amino}phenyl)-5-(trifluoromethyl)benzenesulfonamide |
| 266 | 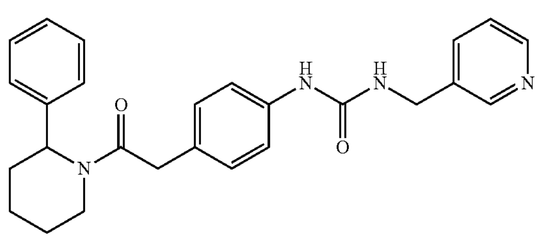 [SMILES: O=C(NCc1cccnc1)Nc1ccc(CC(=O)N2CCCCC2c2ccccc2)cc1] | 1-{4-[2-Oxo-2-(2-phenylpiperidin-1-yl)ethyl]phenyl}-3-(pyridin-3-ylmethyl)urea |
| 267 | 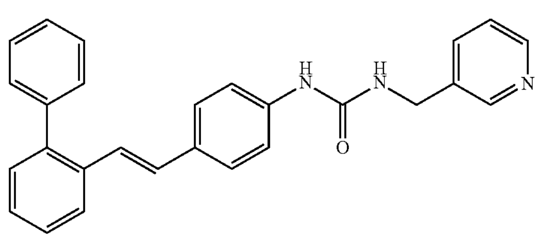 [SMILES: O=C(NCc1cccnc1)Nc1ccc(/C=C/c2ccccc2-c2ccccc2)cc1] | 1-{4-[(E)-2-(Biphenyl-2-yl)ethenyl]phenyl}-3-(pyridin-3-ylmethyl)urea |

TABLE 1-continued

| Example Number | Structure | $^1$H NMR Data (400 MHz, DMSO-d6) |
| --- | --- | --- |
| 268 | 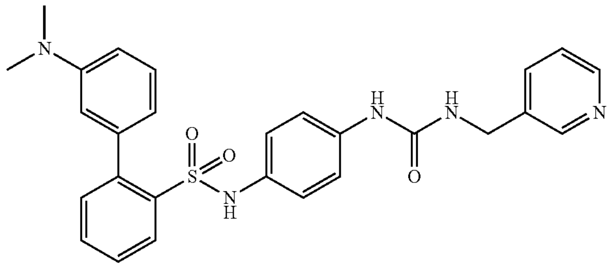 [SMILES: CN(C)c1cccc(-c2ccccc2S(=O)(=O)Nc2ccc(NC(=O)NCc3cccnc3)cc2)c1] | 3'-(Dimethylamino)-N-(4-{[(pyridin-3-ylmethyl)carbamoyl]amino}phenyl)biphenyl-2-sulfonamide |
| 269 | 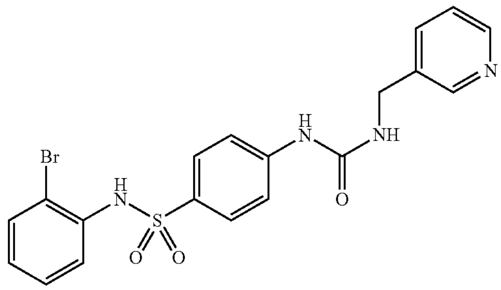 [SMILES: O=C(NCc1cccnc1)Nc1ccc(S(=O)(=O)Nc2ccccc2Br)cc1] | N-(2-Bromophenyl)-4-{[(pyridin-3-ylmethyl)carbamoyl]amino}benzenesulfonamide |
| 270 | 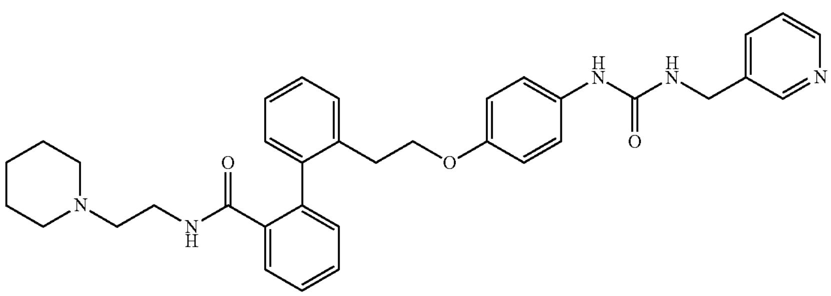 [SMILES: O=C(NCc1cccnc1)Nc1ccc(OCCc2ccccc2-c2ccccc2C(=O)NCCN2CCCCC2)cc1] | N-[2-(Piperidin-1-yl)ethyl]-2'-[2-(4-{[(pyridin-3-ylmethyl)carbamoyl]amino}phenoxy)ethyl]biphenyl-2-carboxamide |
| 271 | 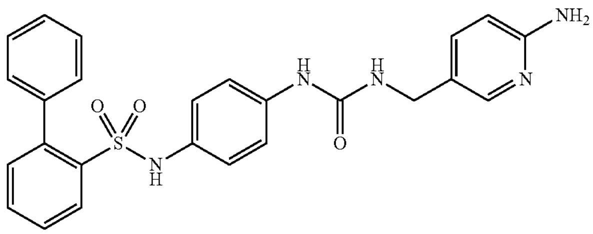 [SMILES: Nc1ccc(CNC(=O)Nc2ccc(NS(=O)(=O)c3ccccc3-c3ccccc3)cc2)cn1] | N-[4-({[(6-Aminopyridin-3-yl)methyl]carbamoyl}amino)phenyl]biphenyl-2-sulfonamide |
| 272 | 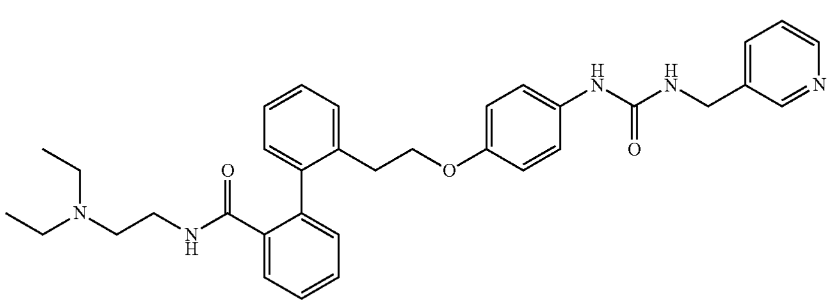 [SMILES: CCN(CC)CCNC(=O)c1ccccc1-c1ccccc1CCOc1ccc(NC(=O)NCc2cccnc2)cc1] | N-[2-(Diethylamino)ethyl]-2'-[2-(4-{[(pyridin-3-ylmethyl)carbamoyl]amino}phenoxy)ethyl]biphenyl-2-carboxamide |

TABLE 1-continued

| Example Number | Structure | ¹H NMR Data (400 MHz, DMSO-d6) |
|---|---|---|
| 273 | 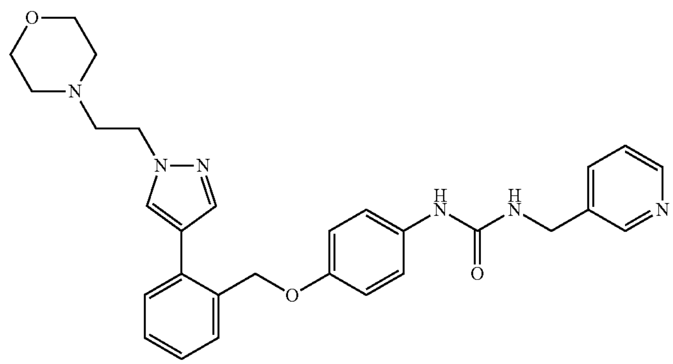 [SMILES: O=C(NCc1cccnc1)Nc1ccc(OCc2ccccc2-c2cnn(CCN3CCOCC3)c2)cc1] | 1-{4-[(2-{1-[2-(Morpholin-4-yl)ethyl]-1H-pyrazol-4-yl}benzyl)oxy]phenyl}-3-(pyridin-3-ylmethyl)urea |
| 274 | 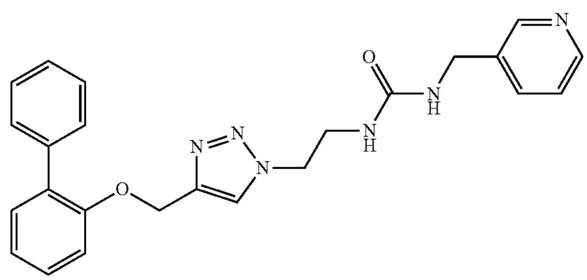 [SMILES: O=C(NCCn1cc(COc2ccccc2-c2ccccc2)nn1)NCc1cccnc1] | 1-(2-{4-[(Biphenyl-2-yloxy)methyl]-1H-1,2,3-triazol-1-yl}ethyl)-3-(pyridin-3-ylmethyl)urea |
| 275 | 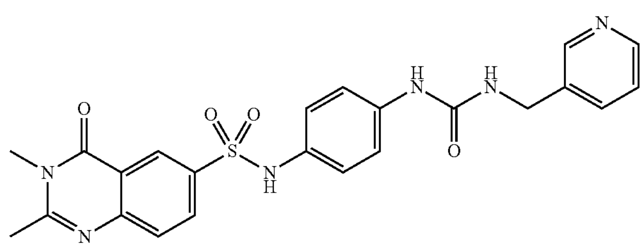 [SMILES: Cc1nc2ccc(S(=O)(=O)Nc3ccc(NC(=O)NCc4cccnc4)cc3)cc2c(=O)n1C] | 2,3-Dimethyl-4-oxo-N-(4-{[(pyridin-3-ylmethyl)carbamoyl]amino}phenyl)-3,4-dihydroquinazoline-6-sulfonamide |
| 276 | 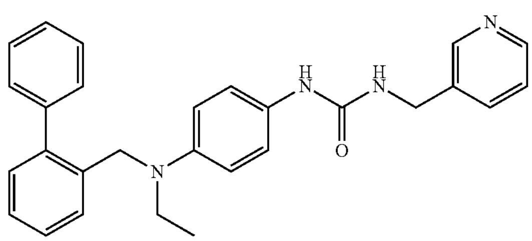 [SMILES: CCN(Cc1ccccc1-c1ccccc1)c1ccc(NC(=O)NCc2cccnc2)cc1] | 1-{4-[(Biphenyl-2-ylmethyl)(ethyl)amino]phenyl}-3-(pyridin-3-ylmethyl)urea |
| 277 | 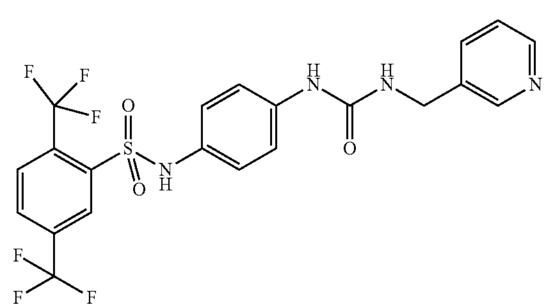 [SMILES: O=C(NCc1cccnc1)Nc1ccc(NS(=O)(=O)c2cc(C(F)(F)F)ccc2C(F)(F)F)cc1] | N-(4-{[(pyridin-3-ylmethyl)carbamoyl]amino}phenyl)-2,5-bis(trifluoromethyl)benzenesulfonamide |

TABLE 1-continued

| Example Number | Structure | ¹H NMR Data (400 MHz, DMSO-d6) |
|---|---|---|
| 278 | 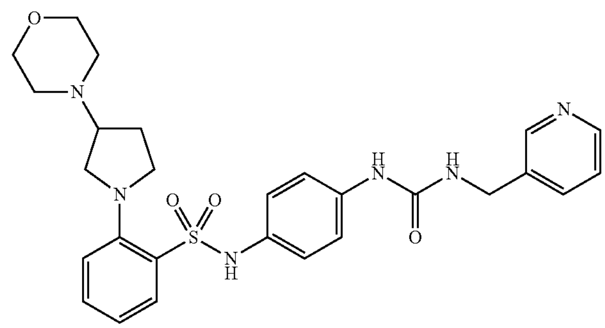 [SMILES: O=C(NCc1cccnc1)Nc1ccc(NS(=O)(=O)c2ccccc2N2CCC(N3CCOCC3)C2)cc1] | 2-[3-(morpholin-4-yl)pyrrolidin-1-yl]-N-(4-{[(pyridin-3-ylmethyl)carbamoyl]amino}phenyl)benzenesulfonamide |
| 279 | 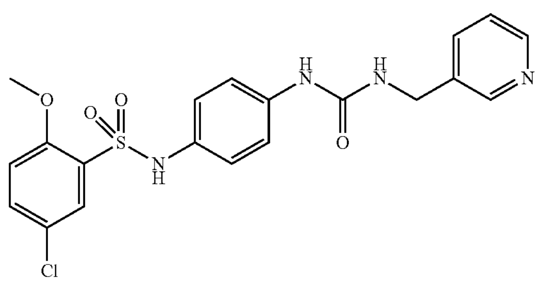 [SMILES: COc1ccc(Cl)cc1S(=O)(=O)Nc1ccc(NC(=O)NCc2cccnc2)cc1] | 5-Chloro-2-methoxy-N-(4-{[(pyridin-3-ylmethyl)carbamoyl]amino}phenyl)benzenesulfonamide |
| 280 | 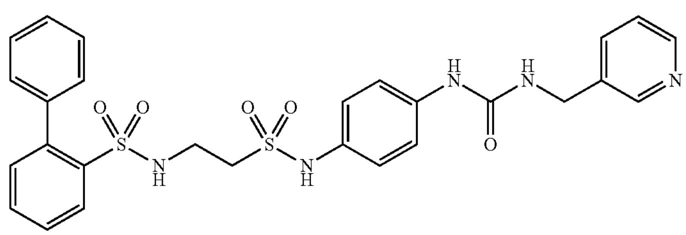 [SMILES: O=C(NCc1cccnc1)Nc1ccc(NS(=O)(=O)CCNS(=O)(=O)c2ccccc2-c2ccccc2)cc1] | N-{2-[(4-{[(Pyridin-3-ylmethyl)carbamoyl]amino}phenyl)sulfamoyl]ethyl}biphenyl-2-sulfonamide |
| 281 | 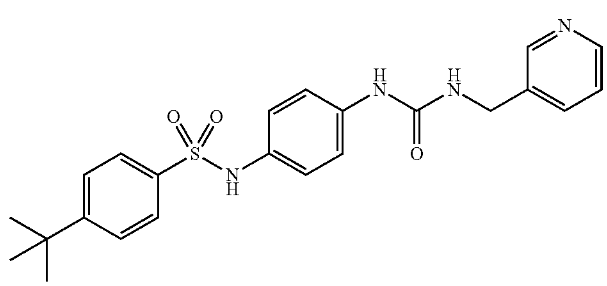 [SMILES: CC(C)(C)c1ccc(S(=O)(=O)Nc2ccc(NC(=O)NCc3cccnc3)cc2)cc1] | 4-tert-Butyl-N-(4-{[(pyridin-3-ylmethyl)carbamoyl]amino}phenyl)benzenesulfonamide |
| 282 | 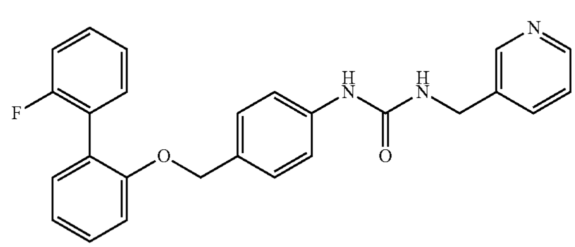 [SMILES: O=C(NCc1cccnc1)Nc1ccc(COc2ccccc2-c2ccccc2F)cc1] | 1-(4-{[(2'-Fluorobiphenyl-2-yl)oxy]methyl}phenyl)-3-(pyridin-3-ylmethyl)urea |

TABLE 1-continued

| Example Number | Structure | $^1$H NMR Data (400 MHz, DMSO-d6) |
|---|---|---|
| 283 | 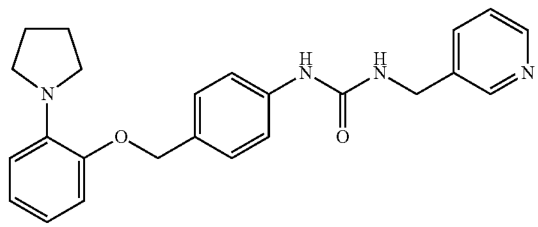 [SMILES: O=C(NCc1cccnc1)Nc1ccc(COc2ccccc2N2CCCC2)cc1] | 1-(Pyridin-3-ylmethyl)-3-(4-{[2-(pyrrolidin-1-yl)phenoxy]methyl}phenyl)urea |
| 284 | 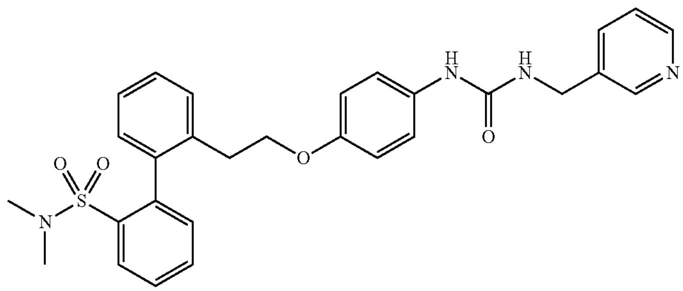 [SMILES: CN(C)S(=O)(=O)c1ccccc1-c1ccccc1CCOc1ccc(NC(=O)NCc2cccnc2)cc1] | N,N-Dimethyl-2'-[2-(4-{[(pyridin-3-ylmethyl)carbamoyl]amino}phenoxy)ethyl]biphenyl-2-sulfonamide |
| 285 | 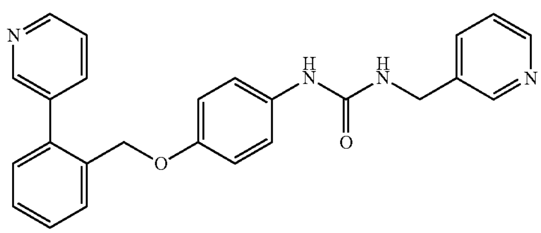 [SMILES: O=C(NCc1cccnc1)Nc1ccc(OCc2ccccc2-c2cccnc2)cc1] | 1-(4-{[2-(Pyridin-3-yl)benzyl]oxy}phenyl)-3-(pyridin-3-ylmethyl)urea |
| 286 | 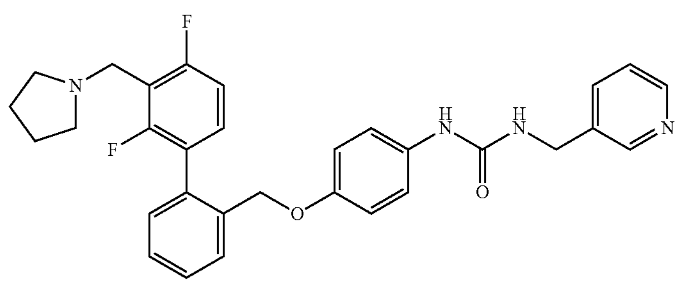 [SMILES: O=C(NCc1cccnc1)Nc1ccc(OCc2ccccc2-c2ccc(F)c(CN3CCCC3)c2F)cc1] | 1-(4-{[2',4'-Difluoro-3'-(pyrrolidin-1-ylmethyl)biphenyl-2-yl]methoxy}phenyl)-3-(pyridin-3-ylmethyl)urea |
| 287 | 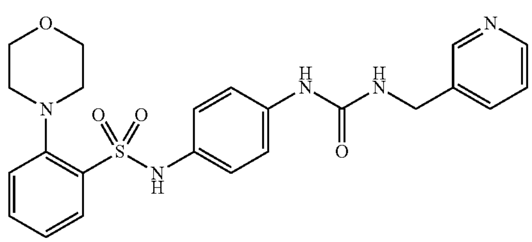 [SMILES: O=C(NCc1cccnc1)Nc1ccc(NS(=O)(=O)c2ccccc2N2CCOCC2)cc1] | 2-(morpholin-4-yl)-N-(4-{[(pyridin-3-ylmethyl)carbamoyl]amino}phenyl)benzenesulfonamide |
| 288 | 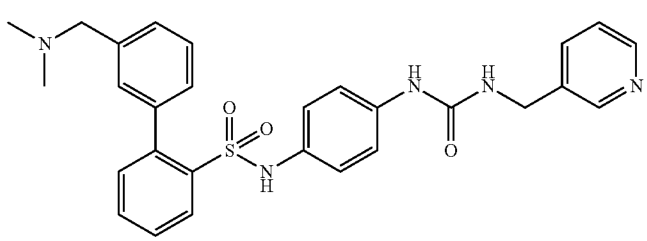 [SMILES: CN(C)Cc1cccc(-c2ccccc2S(=O)(=O)Nc2ccc(NC(=O)NCc3cccnc3)cc2)c1] | 3'-[(Dimethylamino)methyl]-N-(4-{[(pyridin-3-ylmethyl)carbamoyl]amino}phenyl)biphenyl-2-sulfonamide |

TABLE 1-continued

| Example Number | Structure | ¹H NMR Data (400 MHz, DMSO-d6) |
|---|---|---|
| 289 | 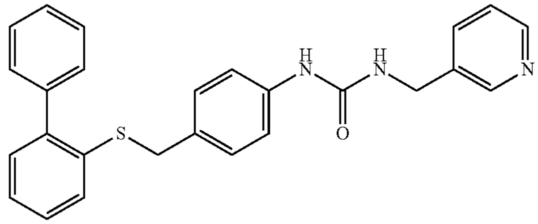 | 2-Bromo-N-(4-{[(pyridin-3-ylmethyl)carbamoyl]amino}phenyl)benzenesulfonamide |
| 290 | 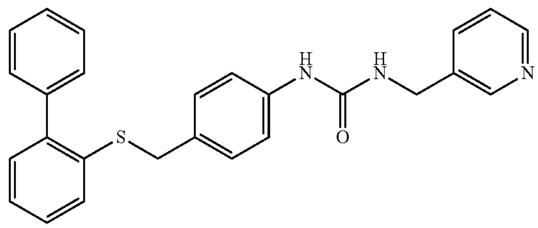 | 1-{4-[(biphenyl-2-ylsulfanyl)methyl]phenyl}-3-(pyridin-3-ylmethyl)urea |
| 291 | 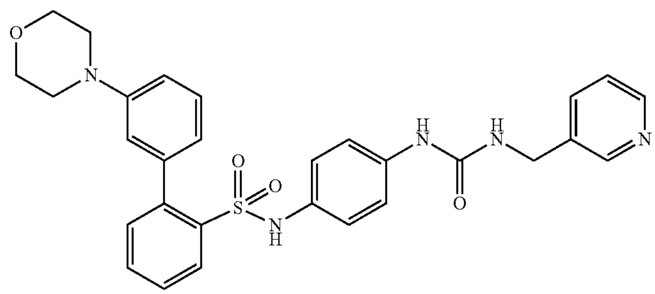 [SMILES: O=C(NCc1cccnc1)Nc1ccc(NS(=O)(=O)c2ccccc2-c2cccc(N3CCOCC3)c2)cc1] | 3'-(Morpholin-4-yl)-N-(4-{[(pyridin-3-ylmethyl)carbamoyl]amino}phenyl)biphenyl-2-sulfonamide |
| 292 | 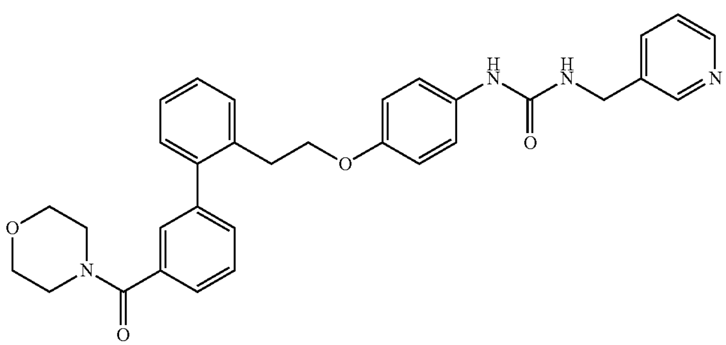 [SMILES: O=C(NCc1cccnc1)Nc1ccc(OCCc2ccccc2-c2cccc(C(=O)N3CCOCC3)c2)cc1] | 1-(4-{2-[3'-(Morpholin-4-ylcarbonyl)biphenyl-2-yl]ethoxy}phenyl)-3-(pyridin-3-ylmethyl)urea |
| 293 | 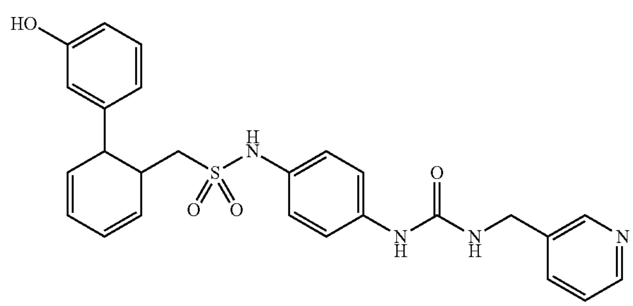 [SMILES: O=C(NCc1cccnc1)Nc1ccc(NS(=O)(=O)CC2C=CC=CC2c2cccc(O)c2)cc1] | 1-[6-(3-Hydroxyphenyl)cyclohexa-2,4-dien-1-yl]-N-(4-{[(pyridin-3-ylmethyl)carbamoyl]amino}phenyl)methanesulfonamide |

TABLE 1-continued

| Example Number | Structure | $^1$H NMR Data (400 MHz, DMSO-d6) |
|---|---|---|
| 294 | 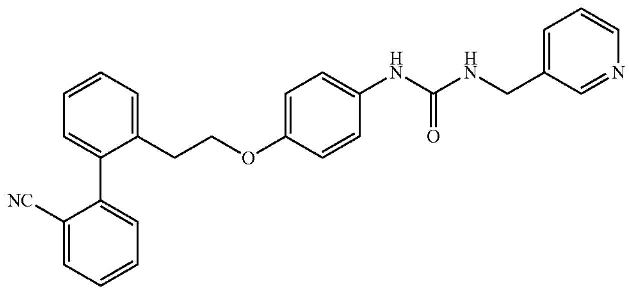 [SMILES: N#Cc1ccccc1-c1ccccc1CCOc1ccc(NC(=O)NCc2cccnc2)cc1] | 1-{4-[2-(2'-Cyano-biphenyl-2-yl)ethoxy]phenyl}-3-(pyridin-3-ylmethyl)urea |
| 295 | 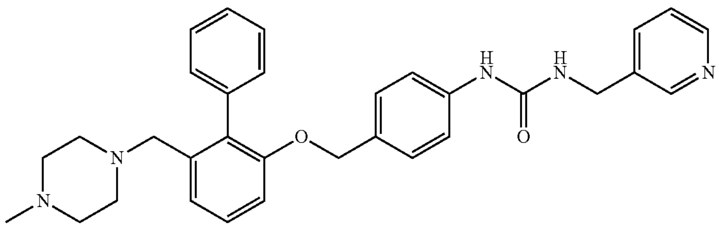 [SMILES: CN1CCN(Cc2cccc(OCc3ccc(NC(=O)NCc4cccnc4)cc3)c2-c2ccccc2)CC1] | 1-{4-[({6-[(4-Methylpiperazin-1-yl)methyl]biphenyl-2-yl}oxy)methyl]phenyl}-3-(pyridin-3-ylmethyl)urea |
| 296 | 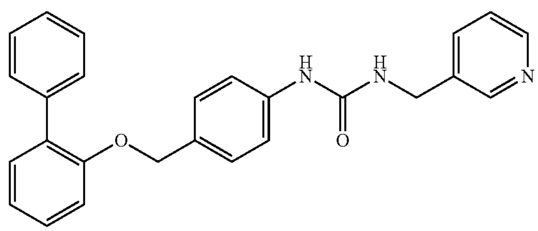 [SMILES: O=C(NCc1cccnc1)Nc1ccc(COc2ccccc2-c2ccccc2)cc1] | 1-{4-[(Biphenyl-2-yloxy)methyl]phenyl}-3-(pyridin-3-ylmethyl)urea |
| 297 | 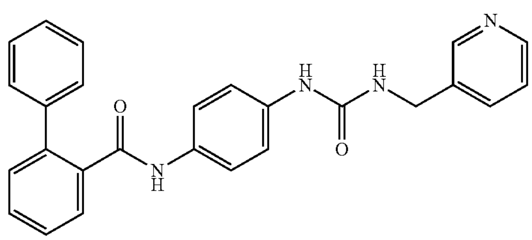 [SMILES: O=C(NCc1cccnc1)Nc1ccc(NC(=O)c2ccccc2-c2ccccc2)cc1] | N-(4-{[(pyridin-3-ylmethyl)carbamoyl]amino}phenyl)biphenyl-2-carboxamide |
| 298 | 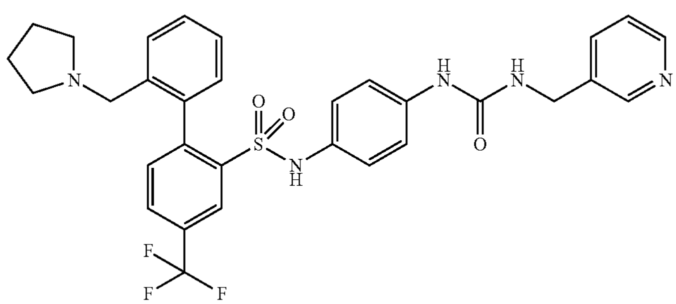 [SMILES: O=C(NCc1cccnc1)Nc1ccc(NS(=O)(=O)c2cc(C(F)(F)F)ccc2-c2ccccc2CN2CCCC2)cc1] | N-(4-{[(Pyridin-3-ylmethyl)carbamoyl]amino}phenyl)-2'-(pyrrolidin-1-ylmethyl)-4-(trifluoromethyl)biphenyl-2-sulfonamide |
| 299 | 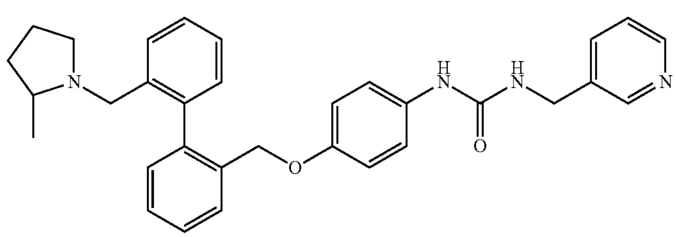 [SMILES: CC1CCCN1Cc1ccccc1-c1ccccc1COc1ccc(NC(=O)NCc2cccnc2)cc1] | 1-[4-({2'-[(2-Methylpyrrolidin-1-yl)methyl]biphenyl-2-yl}methoxy)phenyl]-3-(pyridin-3-ylmethyl)urea |

TABLE 1-continued

| Example Number | Structure | ¹H NMR Data (400 MHz, DMSO-d6) |
|---|---|---|
| 300 | 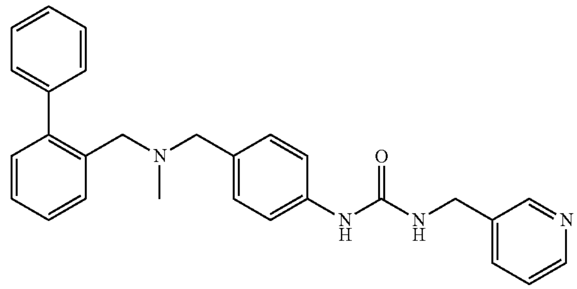 [SMILES: CN(Cc1ccc(NC(=O)NCc2cccnc2)cc1)Cc1ccccc1-c1ccccc1] | 1-(4-{[(Biphenyl-2-ylmethyl)(methyl)amino]methyl}phenyl)-3-(pyridin-3-ylmethyl)urea |
| 301 | 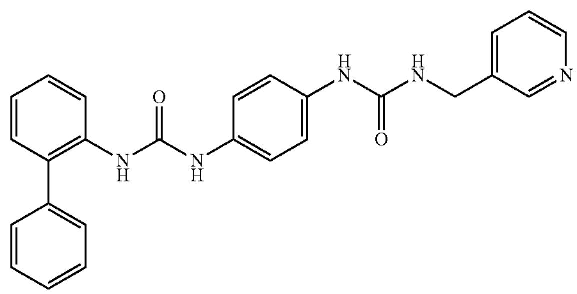 [SMILES: O=C(NCc1cccnc1)Nc1ccc(NC(=O)Nc2ccccc2-c2ccccc2)cc1] | 3-Biphenyl-2-yl-3-(4-{[(pyridin-3-ylmethyl)carbamoyl]amino}phenyl)urea (non-preferred name) |
| 302 | 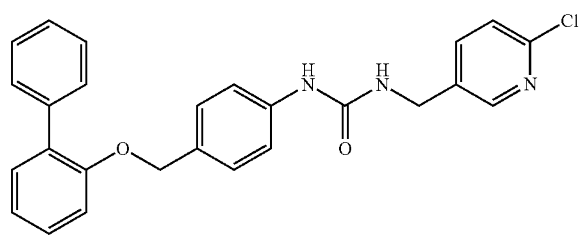 [SMILES: O=C(NCc1ccc(Cl)nc1)Nc1ccc(COc2ccccc2-c2ccccc2)cc1] | 1-{4-[(Biphenyl-2-yloxy)methyl]phenyl}-3-[(6-chloropyridin-3-yl)methyl]urea |
| 303 | 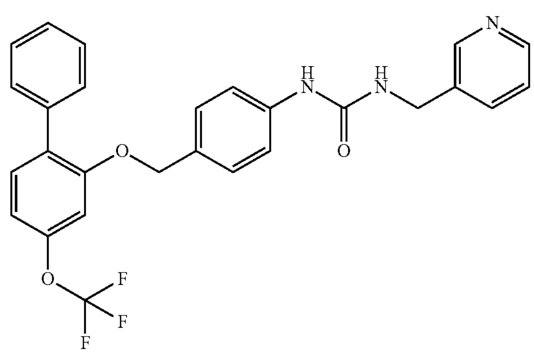 [SMILES: O=C(NCc1cccnc1)Nc1ccc(COc2cc(OC(F)(F)F)ccc2-c2ccccc2)cc1] | 1-(Pyridin-3-ylmethyl)-3-[4-({[4-(trifluoromethoxy)biphenyl-2-yl]oxy}methyl)phenyl]urea |
| 304 | 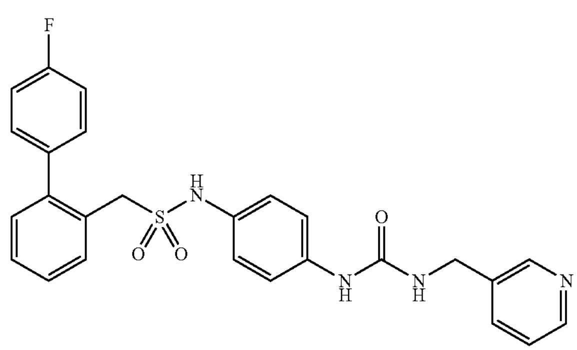 [SMILES: O=C(NCc1cccnc1)Nc1ccc(NS(=O)(=O)Cc2ccccc2-c2ccc(F)cc2)cc1] | 1-(4'-Fluorobiphenyl-2-yl)-N-(4-{[(pyridin-3-ylmethyl)carbamoyl]amino}phenyl)methanesulfonamide |

| Example Number | Structure | ¹H NMR Data (400 MHz, DMSO-d6) |
|---|---|---|
| 305 | 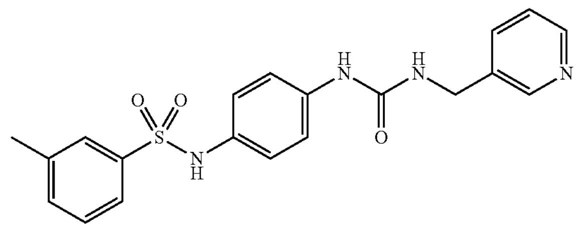 [SMILES: Cc1cccc(S(=O)(=O)Nc2ccc(NC(=O)NCc3cccnc3)cc2)c1] | 3-methyl-N-(4-{[(pyridin-3-ylmethyl)carbamoyl]amino}phenyl)benzenesulfonamide |
| 306 | 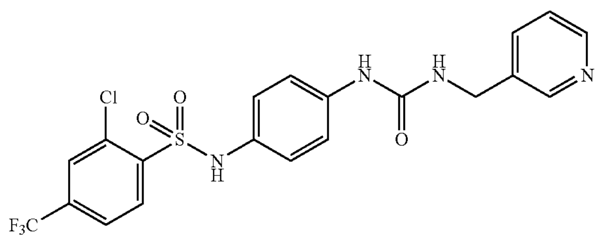 [SMILES: O=C(NCc1cccnc1)Nc1ccc(NS(=O)(=O)c2ccc(C(F)(F)F)cc2Cl)cc1] | 2-chloro-N-(4-{[(pyridin-3-ylmethyl)carbamoyl]amino}phenyl)-4-(trifluoromethyl)benzenesulfonamide |
| 307 | 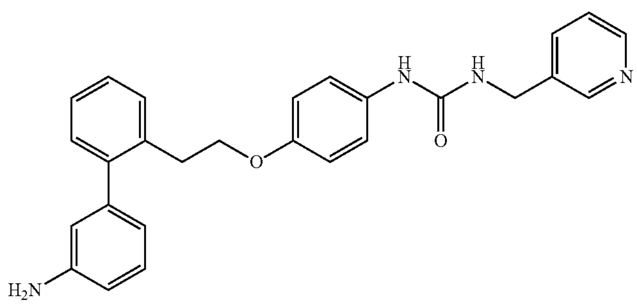 [SMILES: Nc1cccc(-c2ccccc2CCOc2ccc(NC(=O)NCc3cccnc3)cc2)c1] | 1-{4-[2-(3'-Aminobiphenyl-2-yl)ethoxy]phenyl}-3-(pyridin-ylmethyl)urea |
| 308 | 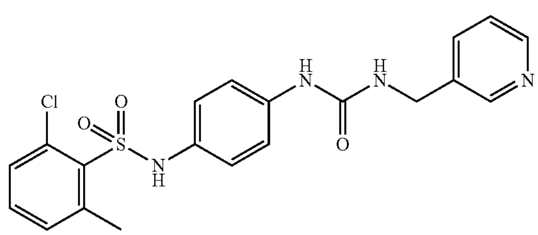 [SMILES: Cc1cccc(Cl)c1S(=O)(=O)Nc1ccc(NC(=O)NCc2cccnc2)cc1] | 2-chloro-6-methyl-N-(4-{[(pyridin-3-ylmethyl)carbamoyl]amino}phenyl)benzenesulfonamide |
| 309 | 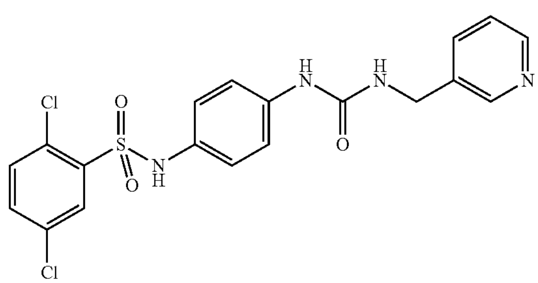 [SMILES: O=C(NCc1cccnc1)Nc1ccc(NS(=O)(=O)c2cc(Cl)ccc2Cl)cc1] | 2,5-dichloro-N-(4-{[(pyridin-3-ylmethyl)carbamoyl]amino}phenyl)benzenesulfonamide |
| 310 | 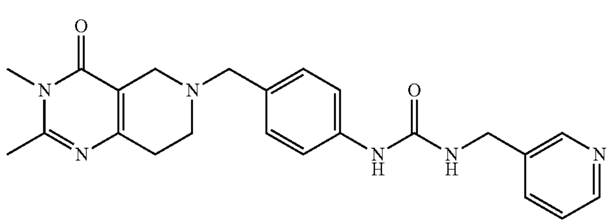 [SMILES: Cc1nc2c(c(=O)n1C)CN(Cc1ccc(NC(=O)NCc3cccnc3)cc1)CC2] | 1-{4-[(2,3-Dimethyl-4-oxo-3,5,7,8-tetrahydropyrido[4,3-d]pyrimidin-6(4H)-yl)methyl]phenyl}-3-(pyridin-3-ylmethyl)urea |

TABLE 1-continued

| Example Number | Structure | ¹H NMR Data (400 MHz, DMSO-d6) |
|---|---|---|
| 311 | 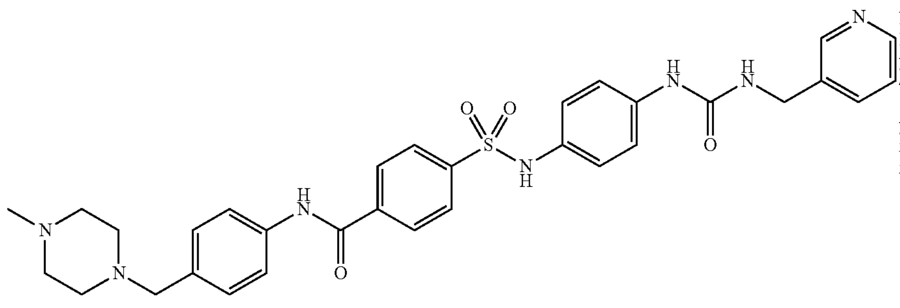 [SMILES: CN1CCN(Cc2ccc(NC(=O)c3ccc(S(=O)(=O)Nc4ccc(NC(=O)NCc5cccnc5)cc4)cc3)cc2)CC1] | N-{4-[(4-Methylpiperazin-1-yl)methyl]phenyl}-4-[(4-{[(pyridin-3-ylmethyl)carbamoyl]amino}phenyl)sulfamoyl]benzamide |
| 312 | 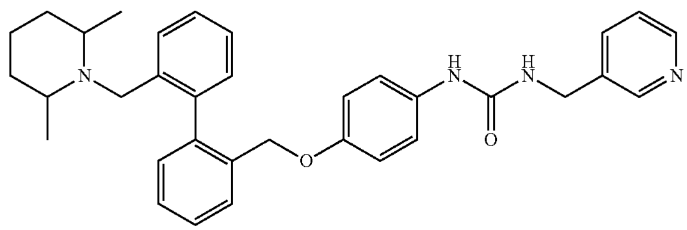 [SMILES: CC1CCCC(C)N1Cc1ccccc1-c1ccccc1COc1ccc(NC(=O)NCc2cccnc2)cc1] | 1-[4-({2'-[(2,6-Dimethylpiperidin-1-yl)methyl]biphenyl-2-yl}methoxy)phenyl]-3-(pyridin-3-ylmethyl)urea |
| 313 | 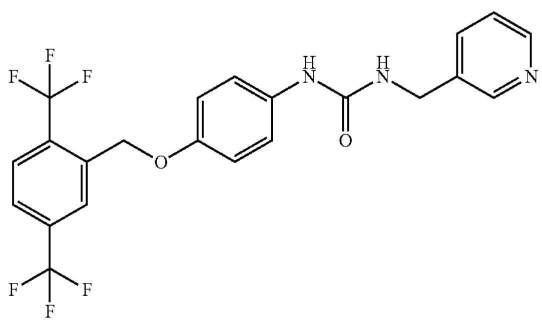 [SMILES: O=C(NCc1cccnc1)Nc1ccc(OCc2cc(C(F)(F)F)ccc2C(F)(F)F)cc1] | 1-(4-{[2,5-Bis(trifluoromethyl)benzyl]oxy}phenyl)-3-(pyridin-3-ylmethyl)urea |
| 314 | 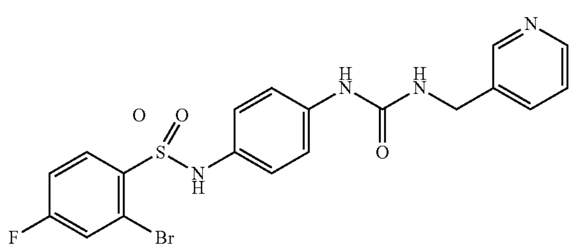 | 2-bromo-4-fluoro-N-(4-{[(pyridin-3-ylmethyl)carbamoyl]amino}phenyl)benzenesulfonamide |
| 315 | 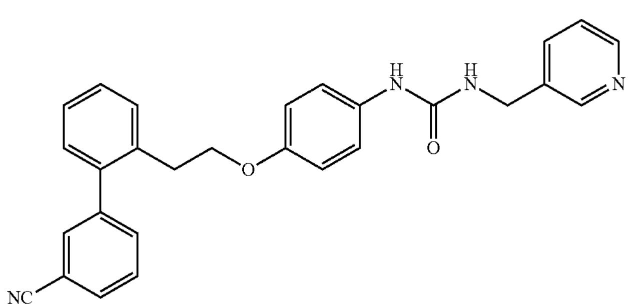 [SMILES: N#Cc1cccc(-c2ccccc2CCOc2ccc(NC(=O)NCc3cccnc3)cc2)c1] | 1-{4-[2-(3'-Cyanobiphenyl-2-yl)ethoxy]phenyl}-3-(pyridin-3-ylmethyl)urea |

TABLE 1-continued

| Example Number | Structure | ¹H NMR Data (400 MHz, DMSO-d6) |
|---|---|---|
| 316 | 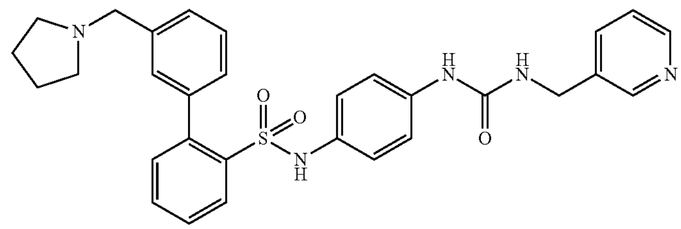 [SMILES: O=C(NCc1cccnc1)Nc1ccc(NS(=O)(=O)c2ccccc2-c2cccc(CN3CCCC3)c2)cc1] | N-(4-{[(Pyridin-3-ylmethyl)carbamoyl]amino}phenyl)-3'-(pyrrolidin-1-ylmethyl)biphenyl-2-sulfonamide |
| 317 | 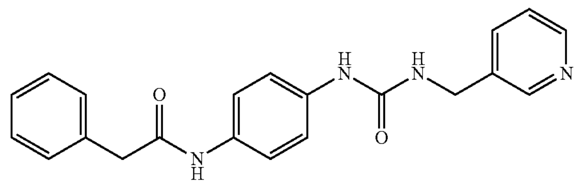 [SMILES: O=C(Cc1ccccc1)Nc1ccc(NC(=O)NCc2cccnc2)cc1] | 2-phenyl-N-(4-{[(pyridin-3-ylmethyl)carbamoyl]amino}phenyl)acetamide |
| 318 | 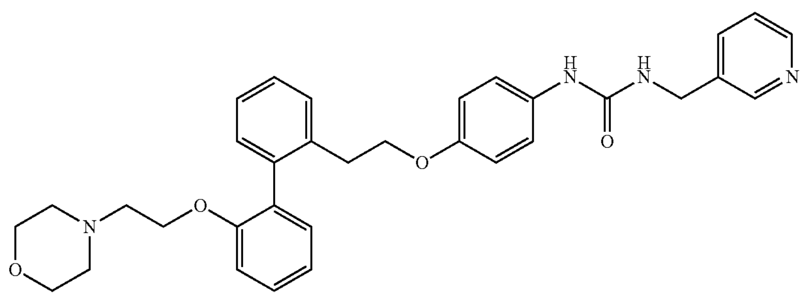 [SMILES: O=C(NCc1cccnc1)Nc1ccc(OCCc2ccccc2-c2ccccc2OCCN2CCOCC2)cc1] | 1-[4-(2-{2'-[2-(Morpholin-4-yl)ethoxy]biphenyl-2-yl}ethoxy)phenyl]-3-(pyridin-3-ylmethyl)urea |
| 319 | 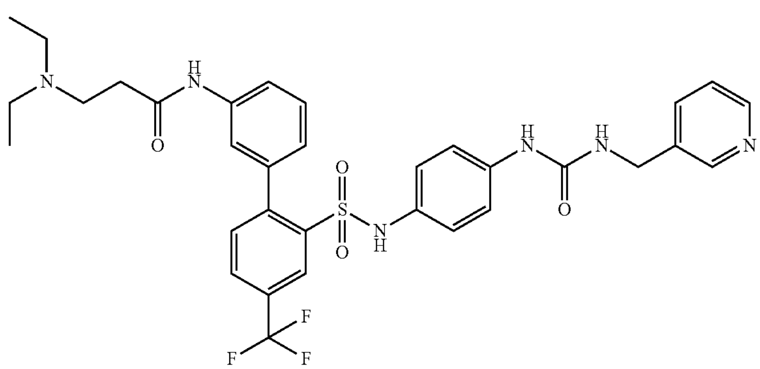 [SMILES: CCN(CC)CCC(=O)Nc1cccc(-c2ccc(C(F)(F)F)cc2S(=O)(=O)Nc2ccc(NC(=O)NCc3cccnc3)cc2)c1] | N~3~,N~3~-Diethyl-N-{2'-[(4-{[(pyridin-3-ylmethyl)carbamoyl]amino}phenyl)sulfamoyl]-4'-(trifluoromethyl)biphenyl-3-yl}-beta-alaninamide |
| 320 | 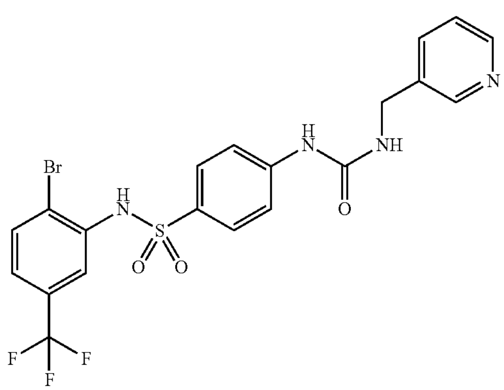 [SMILES: O=C(NCc1cccnc1)Nc1ccc(S(=O)(=O)Nc2cc(C(F)(F)F)ccc2Br)cc1] | N-[2-Bromo-5-(trifluoromethyl)phenyl]-4-{[(pyridin-3-ylmethyl)carbamoyl]amino}benzenesulfonamide |

TABLE 1-continued

| Example Number | Structure | ¹H NMR Data (400 MHz, DMSO-d6) |
|---|---|---|
| 321 | 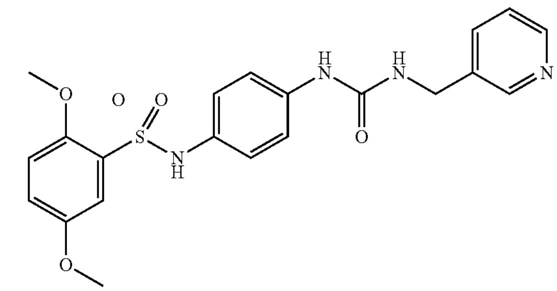 | 2,5-Dimethoxy-N-(4-{[(pyridin-3-ylmethyl)carbamoyl]amino}phenyl)benzenesulfonamide |
| 322 | 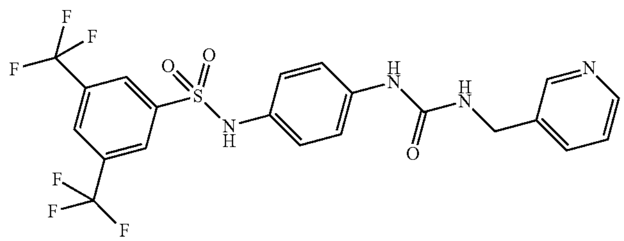 [SMILES: O=C(NCc1cccnc1)Nc1ccc(NS(=O)(=O)c2cc(C(F)(F)F)cc(C(F)(F)F)c2)cc1] | N-(4-{[(pyridin-3-ylmethyl)carbamoyl]amino}phenyl)-3,5-bis(trifluoromethyl)benzenesulfonamide |
| 323 | 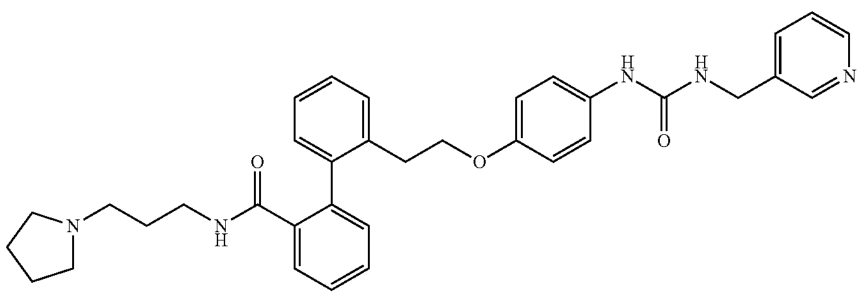 [SMILES: O=C(NCc1cccnc1)Nc1ccc(OCCc2ccccc2-c2ccccc2C(=O)NCCCN2CCCC2)cc1] | 2'-[2-(4-{[(Pyridin-3-ylmethyl)carbamoyl]amino}phenoxy)ethyl]-N-[3-(pyrrolidin-1-yl)propyl]biphenyl-2-carboxamide |
| 324 | 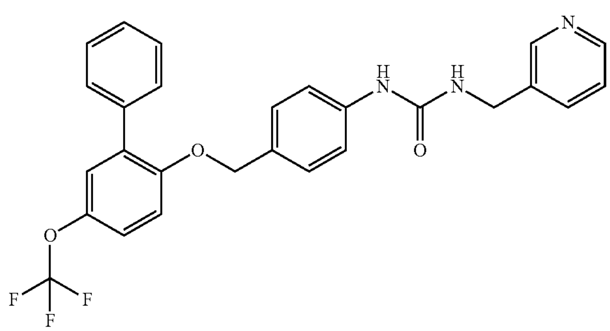 [SMILES: O=C(NCc1cccnc1)Nc1ccc(COc2ccc(OC(F)(F)F)cc2-c2ccccc2)cc1] | 1-(Pyridin-3-ylmethyl)-3-[4-({[5-(trifluoromethoxy)biphenyl-2-yl]oxy}methyl)phenyl]urea |
| 325 | 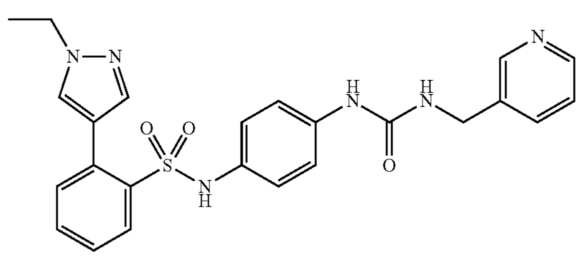 [SMILES: CCn1cc(-c2ccccc2S(=O)(=O)Nc2ccc(NC(=O)NCc3cccnc3)cc2)cn1] | 2-(1-Ethyl-1H-pyrazol-4-yl)-N-(4-{[(pyridin-3-ylmethyl)carbamoyl]amino}phenyl)benzenesulfonamide |

TABLE 1-continued

| Example Number | Structure | $^1$H NMR Data (400 MHz, DMSO-d6) |
|---|---|---|
| 326 | 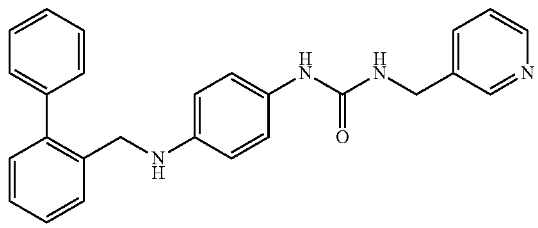 [SMILES: O=C(NCc1cccnc1)Nc1ccc(NCc2ccccc2-c2ccccc2)cc1] | 1-{4-[(Biphenyl-2-ylmethyl)amino]phenyl}-3-(pyridin-3-ylmethyl)urea |
| 327 | 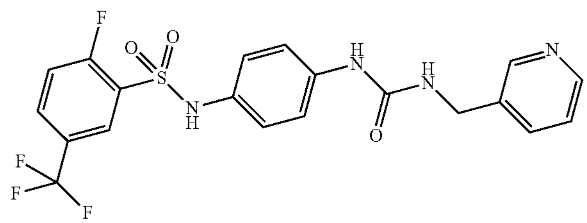 [SMILES: O=C(NCc1cccnc1)Nc1ccc(NS(=O)(=O)c2cc(C(F)(F)F)ccc2F)cc1] | 2-fluoro-N-(4-{[(pyridin-3-ylmethyl)carbamoyl]amino}phenyl)-5-(trifluoromethyl)benzenesulfonamide |
| 328 | 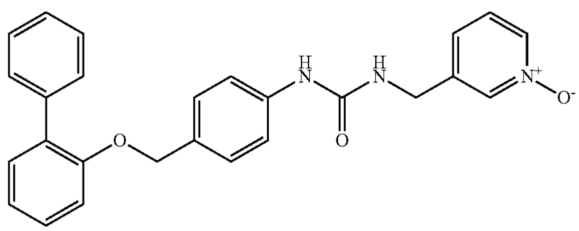 [SMILES: O=C(NCc1ccc[n+]([O-])c1)Nc1ccc(COc2ccccc2-c2ccccc2)cc1] | 1-{4-[(Biphenyl-2-yloxy)methyl]phenyl}-3-[(1-oxidopyridin-3-yl)methyl]urea |
| 329 | 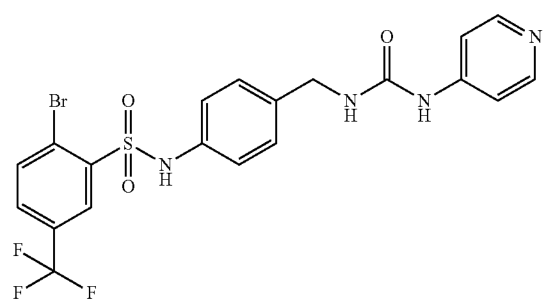 [SMILES: O=C(NCc1ccc(NS(=O)(=O)c2cc(C(F)(F)F)ccc2Br)cc1)Nc1ccncc1] | 2-bromo-N-(4-{[(pyridin-4-ylcarbamoyl)amino]methyl}phenyl)-5-(trifluoromethyl)benzenesulfonamide |
| 330 | 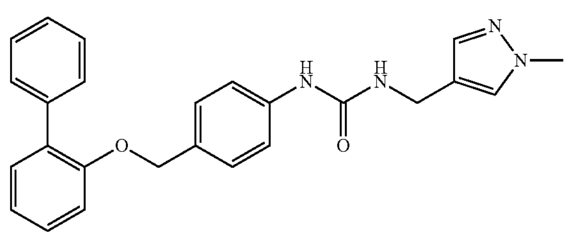 [SMILES: Cn1cc(CNC(=O)Nc2ccc(COc3ccccc3-c3ccccc3)cc2)cn1] | 1-{4-[(Biphenyl-2-yloxy)methyl]phenyl}-3-[(1-methyl-1H-pyrazol-4-yl)methyl]urea |
| 331 | 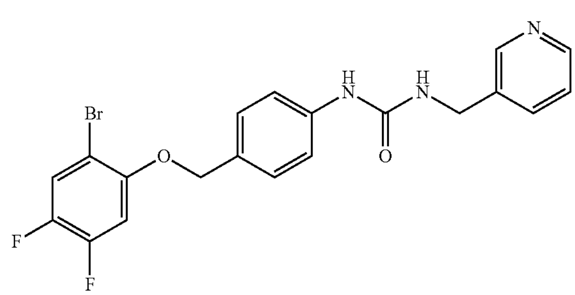 [SMILES: O=C(NCc1cccnc1)Nc1ccc(COc2cc(F)c(F)cc2Br)cc1] | 1-{4-[(2-Bromo-4,5-difluorophenoxy)methyl]phenyl}-3-(pyridin-3-ylmethyl)urea |

Table 2, below, depicts several exemplary Nampt-inhibiting compound of Formula IV that can be used in the therapeutic methods of the present invention. All of the compounds depicted have been found in the 72-hour HCT116 cytotoxitity assay described below to have an IC$_{50}$ of less than 100 nM.

TABLE 2

| Example Number | Structure | $^1$H NMR Data (400 MHz, DMSO-d6) |
|---|---|---|
| 595 | 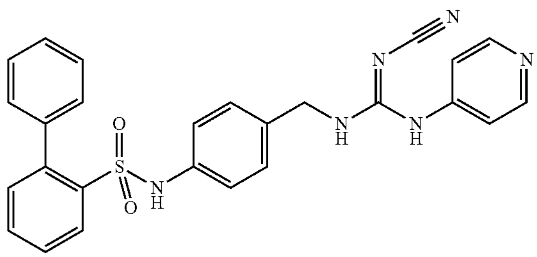 [SMILES: N#C/N=C(/NCc1ccc(NS(=O)(=O)c2ccccc2-c2ccccc2)cc1)Nc1ccncc1] | N-[4-({[(Z)-(Cyanoamino)(pyridazin-4-ylamino)methylidene]amino}methyl)phenyl]biphenyl-2-sulfonamide |
| 596 | 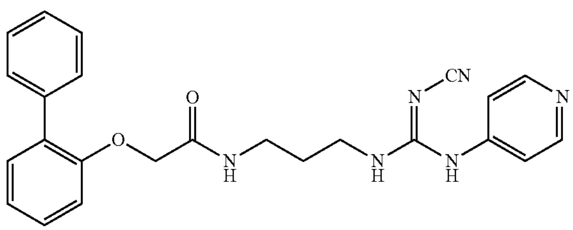 [SMILES: N#C/N=C(/NCCCNC(=O)COc1ccccc1-c1ccccc1)Nc1ccncc1] | 2-(Biphenyl-2-yloxy)-N-(3-{[(Z)-(cyanoamino)(pyridin-4-ylamino)methylidene]amino}propyl)acetamide |
| 597 | 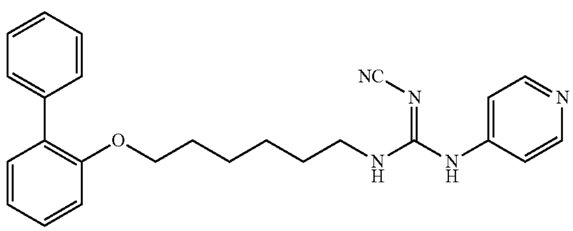 [SMILES: N#C/N=C(\NCCCCCCOc1ccccc1-c1ccccc1)Nc1ccncc1] | 1-[6-(Biphenyl-2-yloxy)hexyl]-2-cyano-3-pyridin-4-ylguanidine |
| 598 | 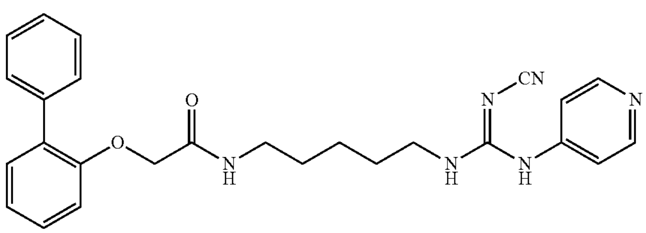 [SMILES: N#C/N=C(/NCCCCCNC(=O)COc1ccccc1-c1ccccc1)Nc1ccncc1] | 2-(Biphenyl-2-yloxy)-N-(5-{[(Z)-(cyanoamino)(pyridin-4-ylamino)methylidene]amino}pentyl)acetamide |
| 599 | 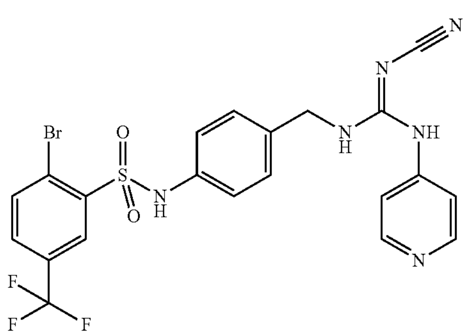 [SMILES: N#C/N=C(/NCc1ccc(NS(=O)(=O)c2cc(C(F)(F)F)ccc2Br)cc1)Nc1ccncc1] | 2-Bromo-N-[4-({[(Z)-(cyanoamino)(pyridin-4-ylamino)methylidene]amino}methyl)phenyl]-5-(trifluoromethyl)benzenesulfonamide |

TABLE 2-continued

| Example Number | Structure | ¹H NMR Data (400 MHz, DMSO-d6) |
|---|---|---|
| 600 | 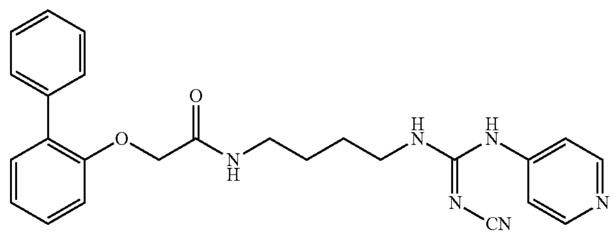 [SMILES: N#C/N=C(/NCCCCNC(=O)COc1ccccc1-c1ccccc1)Nc1ccncc1] | 2-(Biphenyl-2-yloxy)-N-(4-{[(Z)-(cyanoamino)(pyridin-4-ylamino)methylidene]amino}butyl)acetamide |
| 601 | 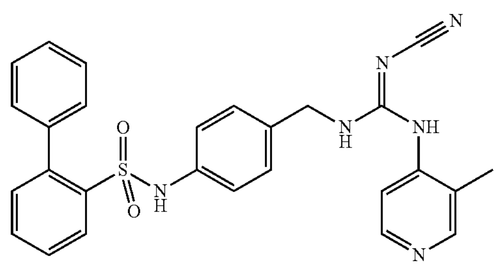 [SMILES: Cc1cnccc1N/C(=N\C#N)NCc1ccc(NS(=O)(=O)c2ccccc2-c2ccccc2)cc1] | N-{4-[({(Z)-(Cyanoamino)[(3-methylpyridin-4-yl)amino]methylidene}amino)methyl]phenyl}biphenyl-2-sulfonamide |
| 602 | 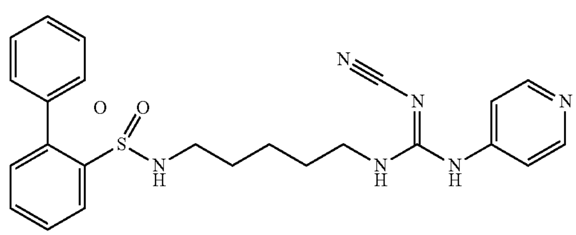 | N-(5-{[(Z)-(Cyanoamino)(pyridin-4-ylamino)methylidene]amino}pentyl)biphenyl-2-sulfonamide |
| 603 | 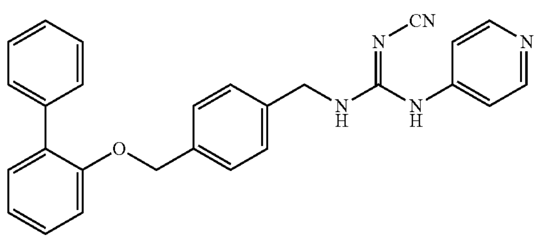 [SMILES: N#C/N=C(/NCc1ccc(COc2ccccc2-c2ccccc2)cc1)Nc1ccncc1] | 1-{4-[(Biphenyl-2-yloxy)methyl]benzyl}-2-cyano-3-pyridin-3-ylguanidine |
| 604 | 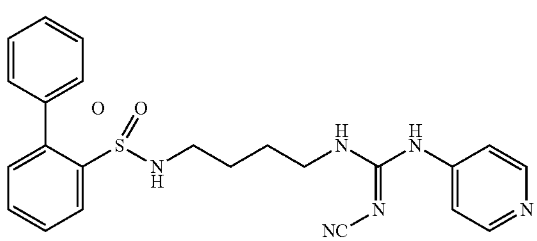 | N-(4-{[(Z)-(Cyanoamino)(pyridin-4-ylamino)methylidene]amino}butyl)biphenyl-2-sulfonamide |
| 605 | 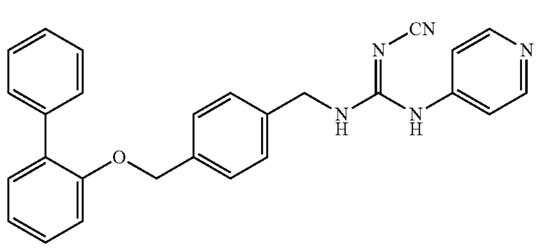 [SMILES: N#C/N=C(/NCc1ccc(COc2ccccc2-c2ccccc2)cc1)Nc1ccncc1] | 1-{4-[(Biphenyl-2-yloxy)methyl]benzyl}-2-cyano-3-pyridin-4-ylguanidine |

TABLE 2-continued

| Example Number | Structure | ¹H NMR Data (400 MHz, DMSO-d6) |
|---|---|---|
| 606 | 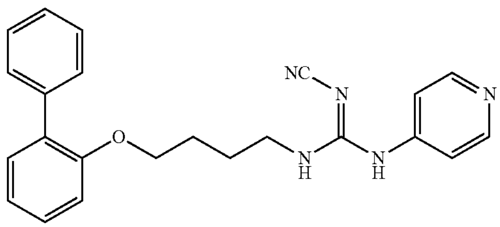 [SMILES: N#C/N=C(\NCCCCOc1ccccc1-c1ccccc1)Nc1ccncc1] | 1-[4-(Biphenyl-2-yloxy)butyl]-2-cyano-3-pyridin-4-ylguanidine |
| 607 | 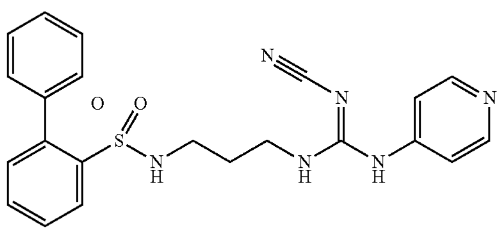 | N-(3-{[(Z)-(Cyanoamino)(pyridin-4-ylamino)methylidene]amino}propyl)biphenyl-2-sulfonamide |
| 608 | 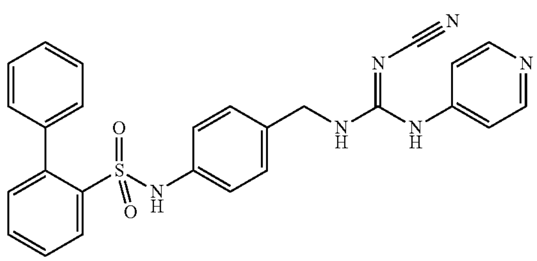 [SMILES: N#C/N=C(/NCc1ccc(NS(=O)(=O)c2ccccc2-c2ccccc2)cc1)Nc1ccncc1] | N-[4-({[(Z)-(Cyanoamino)(pyridin-3-ylamino)methylidene]amino}methyl)phenyl]biphenyl-2-sulfonamide |
| 609 | 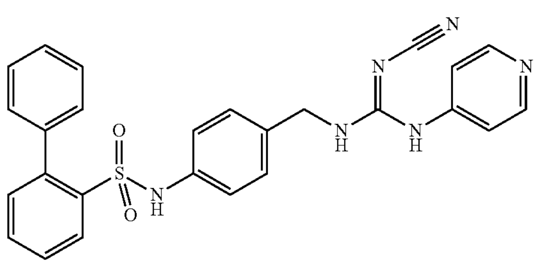 [SMILES: N#C/N=C(/NCc1ccc(NS(=O)(=O)c2ccccc2-c2ccccc2)cc1)Nc1ccncc1] | N-[4-({[(Z)-(Cyanoamino)(pyridin-4-ylamino)methylidene]amino}methyl)phenyl]biphenyl-2-sulfonamide |
| 610 | 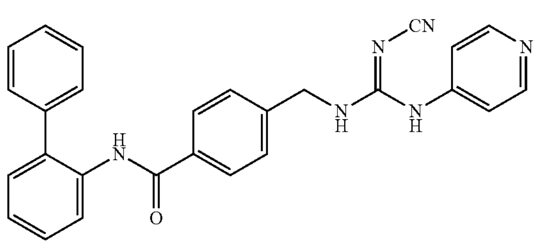 [SMILES: N#C/N=C(/NCc1ccc(C(=O)Nc2ccccc2-c2ccccc2)cc1)Nc1ccncc1] | N-(Biphenyl-2-yl)-4-({[(Z)-(cyanoamino)(pyridin-4-ylamino)methylidene]amino}methyl)benzamide |
| 611 | 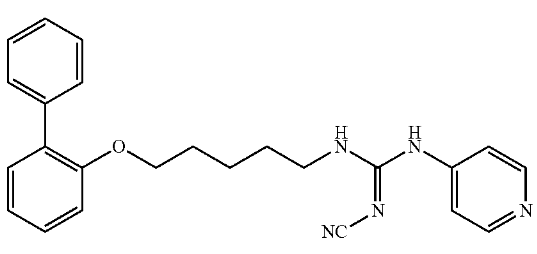 [SMILES: N#C/N=C(\NCCCCCOc1ccccc1-c1ccccc1)Nc1ccncc1] | 1-[5-(Biphenyl-2-yloxy)pentyl]-2-cyano-3-pyridin-4-ylguanidine |

TABLE 2-continued

| Example Number | Structure | $^1$H NMR Data (400 MHz, DMSO-d6) |
|---|---|---|
| 612 | 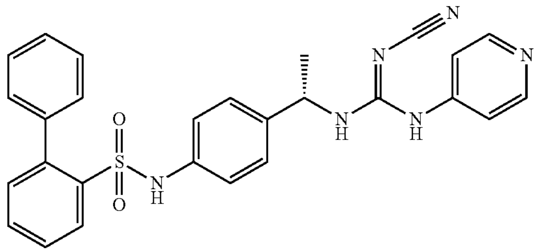 [SMILES: C[C@H](N/C(=N/C#N)Nc1ccncc1)c1ccc(NS(=O)(=O)c2ccccc2-c2ccccc2)cc1] | N-{4-[(1S)-1-{[(Z)-(Cyanoamino)(pyridin-4-ylamino)methylidene]amino}ethyl]phenyl}biphenyl-2-sulfonamide |

Biochemical and Biological Examples

Nampt Activity Assays

Figure 2:
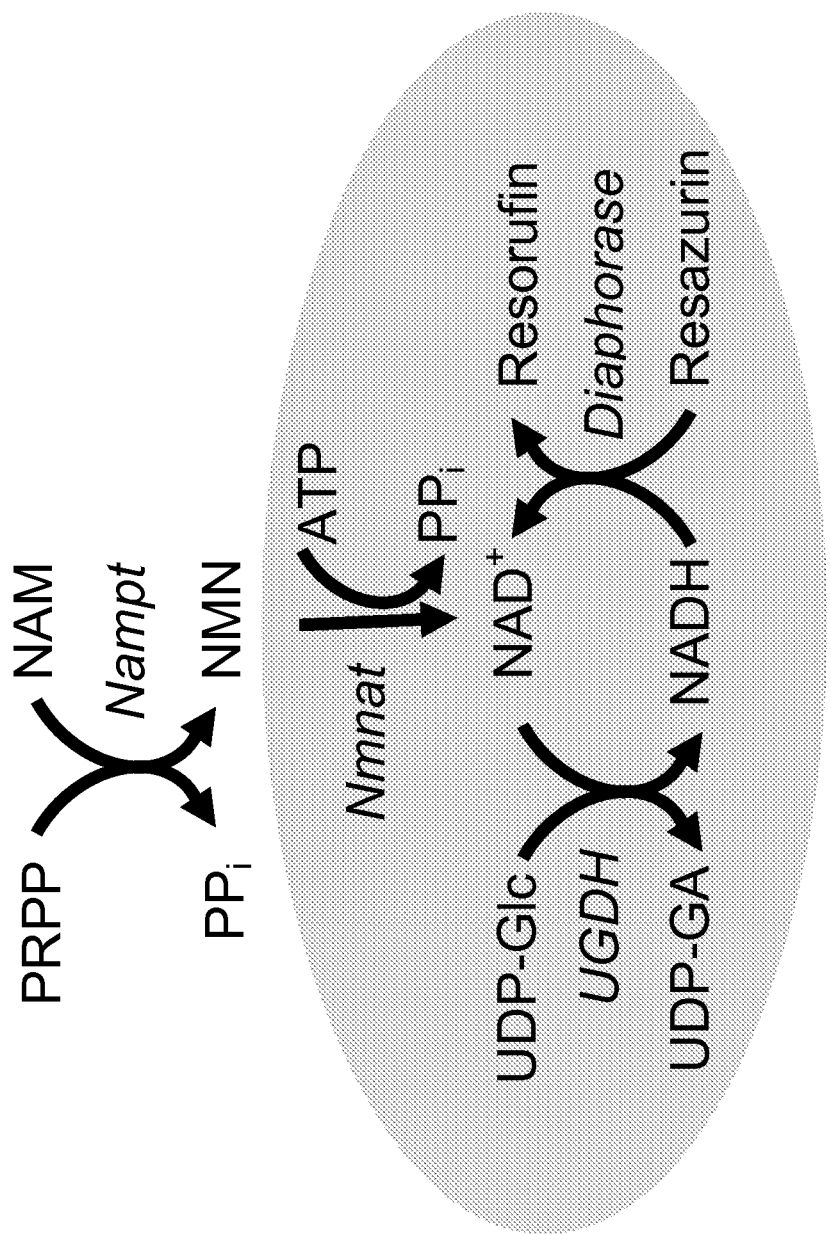
FIG. 2 schematically depicts the coupled biochemical assay used in determining the degree to which specific compounds inhibit Nampt.

The assay for Nampt enzymatic activity (depicted schematically in FIG. 2) was constructed based on a previously published coupled enzyme fluorometric technique, which employs NADH as ultimate analyte (Revollo, J. R. et al. *Biol. Chem.* 279, 50754-50763 (2004)). A substantial improvement in assay sensitivity was achieved by switching from direct detection to a coupled resazurin/diaphorase-based fluorometric detection system for NADH (Guilbault, G. G., and Kramer, D. N. *Anal. Chem.* 37, 1219-1221 (1965)).

5-phosphoribosyl-1-pyrophosphate (PRPP), ATP, Nam, NaMN, Triton X-100, UDP-glucose and diaphorase were purchased from Sigma-Aldrich, St. Louis, Mo. Human Nampt, NMN adenylyltransferase (NMNAT1) and UDP-glucose dehydrogenase (UGDH) encoding DNAs were each inserted into a house-modified *E. Coli* expression vector such that the expressed proteins carried an N-terminal 6xHis tag. The His-tagged proteins were expressed in the BL21-AI *E. Coli* expression strain (Invitrogen Corporation, Carlsbad, Calif.) following induction by 0.2% L-arabinose and 0.5 mM IPTG at 30° C. Proteins were purified on Ni-NTA resin (Qiagen, Inc., Valencia, Calif.).

The standard inhibition analyses were performed in a real-time mode in 96-well microtiter plates using 50 mM Tris-HCl, pH 7.5, 1% DMSO (v/v), 0.01% Triton X-100 (v/v), 10 mM MgCl$_2$, 2 mM ATP, 3 µM NAM, 8 µM PRPP, 50 µM Nampt, as well as the following detection reagents: 5 nM Nmnat, 200 nM Ugdh, 200 µM UDP-glucose, 0.02 U/mL diaphorase and 0.25 µM resazurin. Incubation of samples at room temperature for up to 3 hours was followed by quantification of fluorescence intensities at excitation and emission wavelengths of 510 nm and 590 nm, respectively, using Gemini XS plate reader (Molecular Devices, Sunnyvale, Calif.). The counter-assay intended to disqualify false positives, such as inhibitors of detection enzymes or fluorescence quenchers, was carried out essentially as described above with an exception that 1 µM NaMN was substituted for Nampt. A preparation of catalytically inactive Nampt-D313A mutant enzyme was used as a negative control for assay development.

Figure 3:
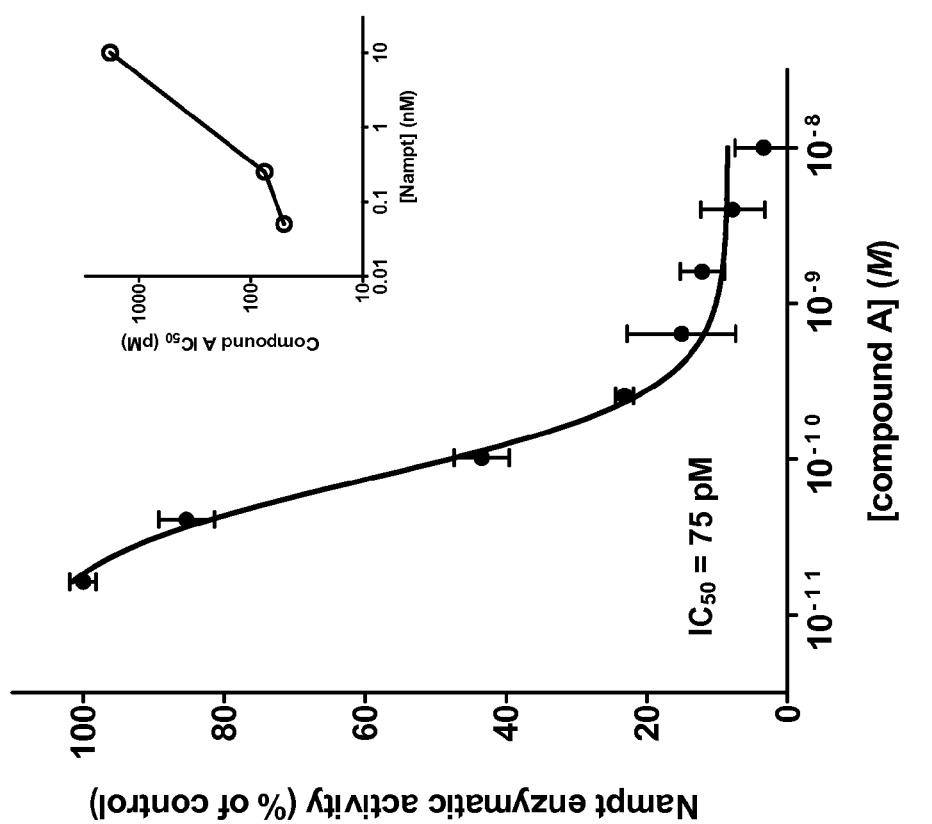
FIG. 3 shows the dose response of a particularly active compound (Exemplary Compound A (i.e., Example 296, or 1-{4-[(biphenyl-2-yloxy)methyl]phenyl}-3-(pyridin-3-ylmethyl)urea); $IC_{50}$=75 µM) obtained with the Assay depicted in FIG. 2, while the inset shows $IC_{50}$ values derived for Exemplary Compound A at multiple enzyme concentrations.

Using this assay, Exemplary Compound A (i.e., 1-{4-[(biphenyl-2-yloxy)methyl]phenyl}-3-(pyridin-3-ylmethyl)urea) exhibited an IC$_{50}$ of 75 µM. See FIG. 3.

Assay to Measure NAD and ATP in Cellular Lysates

NAD in cells was measured by modification of existing protocols (Lee, H. I., et al. *Exp. Mol. Med.* 40, 246-253 (2008)). MCF-10A cells stably transduced with the PIK3CA (H1047R) oncogene were seeded in 96 well plates at very high density (100% confluence) and allowed to settle overnight. Test compound dissolved in DMSO was added and drug incubation proceeded for 20-24 hours. Cells were washed with PBS and harvested by incubation in 25 µL 0.5 M perchloric acid (HClO$_4$) followed by vigorous shaking at 4° C. for 15 minutes. Acidic cell lysates were neutralized by adding 8 µL of 2 M KOH/0.2 M K$_2$HPO$_4$. The entire lysate volume was transferred to a centrifuge plate and spun at 3000 rpm in a table top centrifuge (4° C.) for 5 minutes to clear the precipitate. Lysate was assayed for both NAD and ATP. For NAD measurement, 10 µL lysate from the centrifuged plate was added to 90 µL of reaction solution in Costar 96 half-well plates (Corning, Corning, N.Y.). The final concentration of the reaction mixture was 120 µM Tris-HCl, pH 7.5, 0.01% Triton X-100, 35 µM UDP-Glucose, 50 nM UGDH, 0.5 M resazurin, and 0.1 unit/mL Diaphorase. Reactions were allowed to proceed for 1 hour at room temperature, after which time fluorescence was read on a Gemini plate reader as described above.

For ATP measurement, 5 µL of cleared lysate was added to 195 µL PBS. 50 µL CellTiter-Glo reagent (Promega Corporation, Madison, Wis.) was added and ATP measured as described in the cytotoxicity assay methods.

Figure 4:
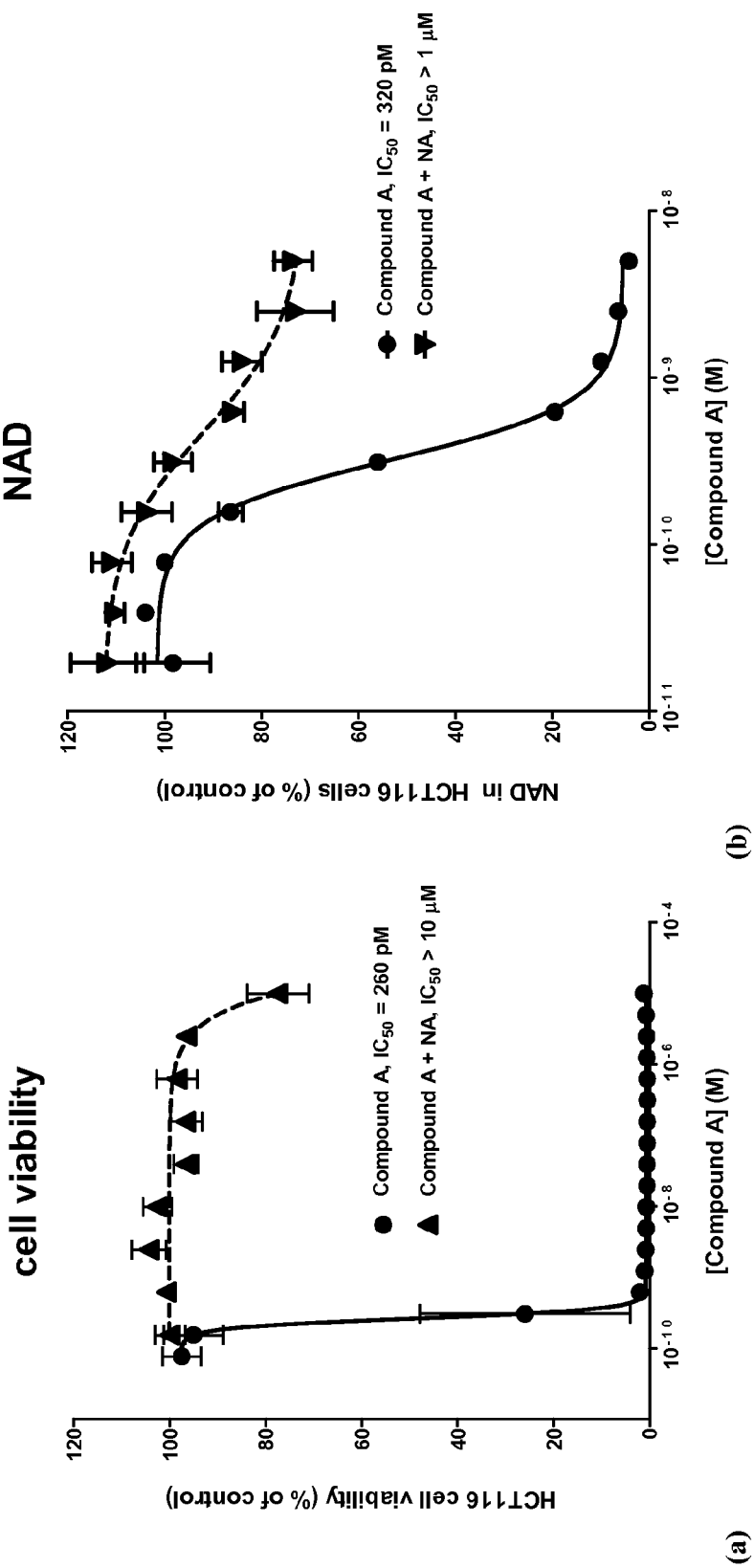
FIG. 4 shows that exemplary Exemplary Compound A potently decreases cell viability (a) and NAD depletion (b) in Naprt1-proficient HCT116 cells.

Using such methods NAD Depeletion was followed in lysates of Naprt-proficient HCT116 cells, exposed to Exemplary Compound A, as shown in FIG. 4 (*a*). For these assays the HCT116 cells were treated with the indicated concentrations of Exemplary Compound A for 24 h in the presence (IC50>1 µM) or absence (IC50=260 pM) of 10 µM NA. Importantly, the observed Exemplary Compound A-induced NAD depletion was completely abolished in presence of NA, which feeds into the alternative de novo NAD synthetic pathway, the first step of which is catalyzed by Naprt1 (FIG. 1). These results suggest that exposure to Exemplary Compound A results in NAD depletion as a result of the specific inhibition of Nampt, and the "Nam salvage pathway." See FIG. 1.

72 Hour HCT116 Cytotoxicity Assay

HCT116 cells were seeded in 96 well plates (Greiner Bio-One, Monroe, N.C.) and allowed to settle overnight. Test compound dissolved in dimethyl sulfoxide (DMSO) was added and drug incubation proceeded for 72 hours. When applicable, a 1000x solution of nicotinic acid (NA; Sigma-Aldrich, St. Louis, Mo.) dissolved in water was generated, and 1x NA (10 M final concentration) was added at the same time as the test compound. After 72 hour, 50 µL of CellTiter-Glo Luminescent Cell Viability Assay reagent (Promega Corporation, Madison, Wis.) was added to cells in 200 µL of cellular media. After a proscribed incubation period, luminescence was measured using a TopCount NXT plate reader (PerkinElmer, Waltham, Mass.).

The example compounds listed in Tables 1 and 2 exhibited an HCT116 cell cytotoxicity with an IC$_{50}$ of less than 100 nM.

For example, example compound number 152 exhibited an IC$_{50}$ of about 55 nM, example compound number 164 exhibited an IC$_{50}$ of about 74 nM, example compound number 210 exhibited an IC$_{50}$ of about 39 nM, and example compound number 605 exhibited an IC$_{50}$ of about 1.1 nM.

Using such methods the cytotoxicity of Exemplary Compound A to Naprt-proficient HCT116 cells was studied at increasing concentrations of Exemplary Compound A. See FIG. 4(b). Specifically, HCT116 cells were treated with the indicated concentrations of Exemplary Compound A for 72 h in the presence (IC50>10 μM) or absence (IC50=260 pM) of 10 M NA. Notably, Exemplary Compound A-induced cell death was completely abolished in presence of NA (FIG. 4b), indicating that the cytotoxic effects of Exemplary Compound A were the result of NAD depletion caused by the inhibition of Nampt.

Standard Cytotoxicity Assay for Other Cancer Cell Types

Exponentially growing cells were plated at an appropriate density (generally 5000 cells/well for 72 hour assay or 500 cells/well for 7-10 day assays) in 96 well plates (Greiner Bio-One, Monroe, N.C., Packard Instrument Co., Meriden, Conn. or PerkinElmer, Waltham, Mass.) in 100 μL of fresh media. Approximately 24 hours later, test compound was added from serial dilutions prepared in DMSO from DMSO stock solutions. After the appropriate time of continuous compound exposure (in most cases 3 days, but in some cases 7 and/or 10 days), 100 μL of 1× CellTiter-Glo Luminescent Cell Viability Assay reagent (Promega Corporation, Madison, Wis.) was added, plates were incubated at room temperature for 15 minutes, and luminescence data was collected using a TopCount NXT plate reader. Values were normalized to solvent controls and plotted versus compound concentration to determine the concentration required for a 50% reduction in cell viability (TC$_{50}$).

Figure 5:
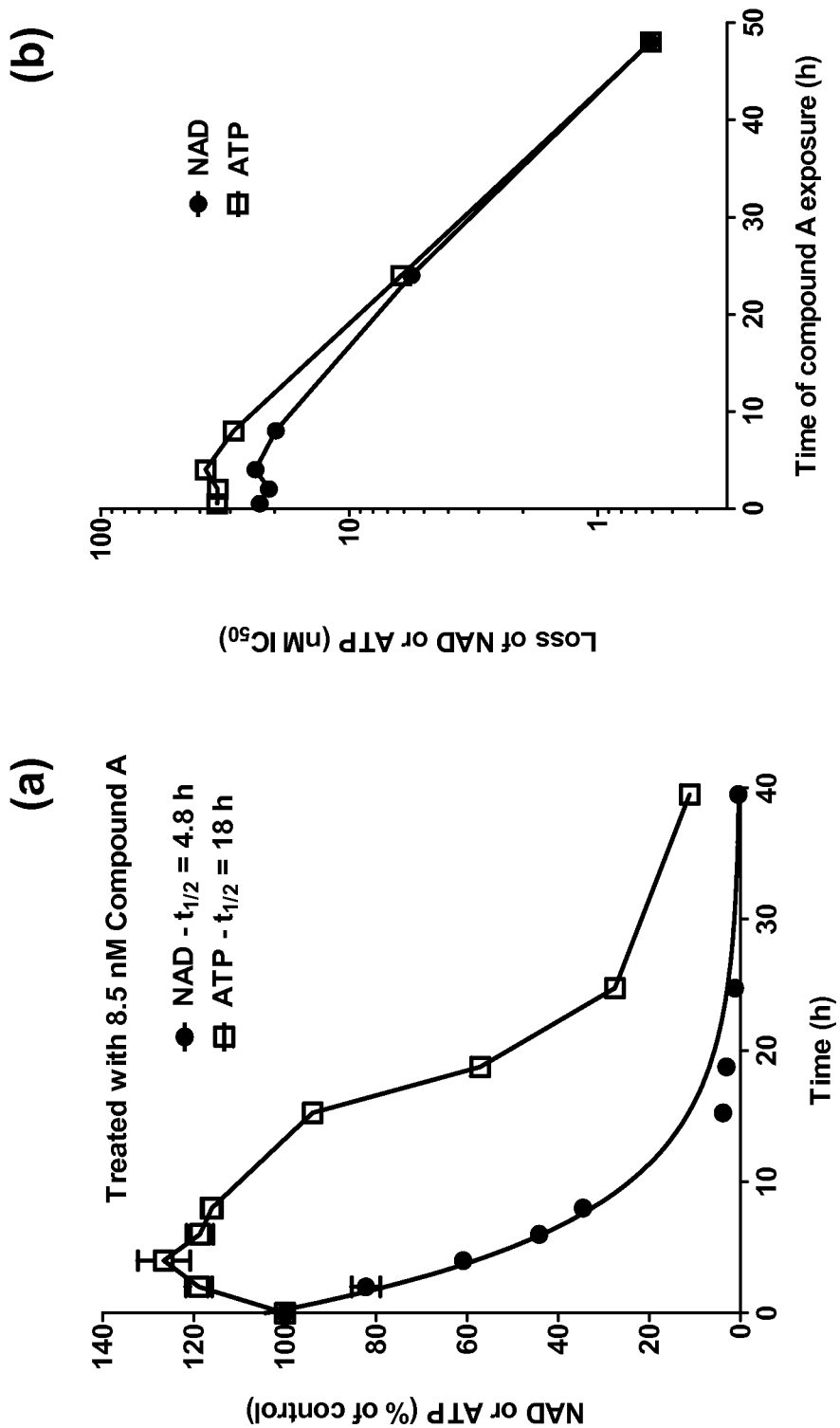
FIG. 5 depicts Exemplary Compound A-induced NAD and ATP depletion kinetics and potency as a function of exposure time.

Nampt Inhibitor-Induced NAD- and ATP-Depletion Kinetics and Potency as a Function of Exposure Time Kinetics of NAD and ATP depletion in Naprt1-proficient HCT116 cells induced by Exemplary Compound A was studied using the assays described above. HCT116 cells were treated with 8.5 nM Exemplary Compound A and cellular NAD and ATP were measured at various times. The results are shown in FIG. 5(a). It should be noted that loss of ATP did not initiate until NAD depletion was in excess of 90%.

Potency of Exemplary Compound A as a function of time of exposure was also studied using the assays described above. Cells were treated with a range of Exemplary Compound A concentration for varying times of exposure, and IC$_{50}$ values for NAD and ATP depletion were determined. The results are shown in FIG. 5(b). Exemplary Compound A exposure for as little as 30 min resulted in NAD and ATP depletion with potencies of 23 and 33 nM respectively. After 48 h, potencies for depletion of both had increased to about 600 μM.

Nicotinic Acid Rescue Cytotoxicity Assays

Cell lines were treated with a fixed dose of Exemplary Compound A and screened for NA rescue and Naprt1 expression by immunoblotting and qRT-PCR (Table 3). Of 176 cell lines tested, 47 did not rescue, 16 partially rescued and 113 completely rescued. The 176 cell lines included 5 normal (non-cancerous) cell lines and 3 primary cell lines (italicized in the table), all of which rescued. Naprt1 was quantified by western blotting and qRT-PCR in 164 and 123 of the 176 cell lines, respectively. Naprt1 levels were low or undetectable in cell lines that did not rescue. A statistically significant (p value <0.0001) correlation existed between a NA rescue phenotype and Naprt1 protein or mRNA expression levels.

For quantification by western blot, human tumor cell proteins were prepared from frozen cell pellets. Cell pellets were thawed and lysed in 0.5% Triton X-100, 50 mM HEPES [pH 7.4], 150 mM NaCl, 1 mM EDTA, 10% glycerol, and 1 mM DTT for 30 minutes at 4° C. After centrifugation to remove cellular debris, protein concentration was determined using the BCA (BCA1-1KT; Sigma-Aldrich, St. Louis, Mo.) or CBQCA protein assay kits (Molecular Probes #C-6667; Life Technologies, Inc., Carlsbad, Calif.). Ruby Red staining of SDS-PAGE gels was used to confirm protein loading.

For immunoblot detection, equivalent protein amounts were resolved by electrophoresis and transferred to nitrocellulose membrane. Membranes were blocked in Starting Block T20 (TBS) (#37543; Thermo Scientific, Rockford, Ill.) and were probed with anti-Naprt (13549-1-AP; Proteintech Group, Inc., Chicago, Ill.) or anti-Gapdh (#CB1001; Calbiochem, EMD4Biosciences, San Diego, Calif.) antibodies. HRP-conjugated secondary antibodies (Santa Cruz Biotechnology, Inc., Santa Cruz, Calif.) and Super Signal West Dura Extended Duration Substrate (#34075; Thermo Scientific, Rockford, Ill.) were used for detection. Protein signals were quantified by imaging using an EC3 imaging system and VisionWorksSL software (UVP Bioimaging Systems; UVP, LLC, Upland, Calif.). The dynamic range of signal detection was enhanced by utilizing multiple exposure times. Naprt protein levels were calculated as a percentage of the cognate signal detected in the HCT116 cell lysate.

For quantification by qRT-PCR, untreated cell pellets were collected lysed in RLT buffer with 1% β-mercaptoethanol. RNA was isolated using an RNeasy spin column kit (74104; Qiagen, Inc., Valencia, Calif.), loaded in triplicate to a 96-well plate at 11 ng total RNA/well, and probed for NAPRT1 with the TaqMan primer set Hs00292993_ml (Life Technologies, Inc., Carlsbad, Calif.), using the QuantiTect probe RT-PCR kit (204443; Qiagen, Inc., Valencia, Calif.), with a final sample volume of 25 ul/well. Relative NAPRT expression was assayed on the Applied Biosystems 7300 Real-Time PCR system thermal cycler (Life Technologies, Inc., Carlsbad, Calif.). The plate was heated to 50° C. for 30 minutes, followed by 95° C. for 15 minutes, followed by 40 cycles alternating between 95° C. for 15 seconds and 60° C. for 1 minute. Data was collected during the 60° C. step of each cycle, and cycle threshold values were interpolated onto a dilution curve of total RNA from the cell line SK-BR-3 to give relative values of the initial NAPRT mRNA concentration for each sample. The average RNA concentration for each cell line was then presented relative to the expression seen in the cell line SK-BR-3 as a percentage.

TABLE 3

| Cell line | Tissue | NA rescue | Cell line | Tissue | NA rescue |
|---|---|---|---|---|---|
| T24 | bladder | yes | NCI-H1993 | lung (NSCLC) | yes |
| KINGS-1 | brain; anaplastic astrocytoma (glioma) | no | NCI-H2030 | lung (NSCLC) | yes |

TABLE 3-continued

| Cell line | Tissue | NA rescue | Cell line | Tissue | NA rescue |
|---|---|---|---|---|---|
| CCF-STTG1 | brain; astrocytoma | yes | NCI-H2110 | lung (NSCLC) | yes |
| SNB-75 | brain; astrocytoma | yes | NCI-H2228 | lung (NSCLC) | yes |
| SW1088 | brain; astrocytoma | yes | NCI-H226 | lung (NSCLC) | yes |
| SW1783 | brain; astrocytoma | yes | NCI-H23 | lung (NSCLC) | yes |
| SF-268 | brain; astrocytoma, anaplastic | no | NCI-H441 | lung (NSCLC) | yes |
| SNB-19 | brain; glioblastoma | no | NCI-H596 | lung (NSCLC) | partial |
| U251 | brain; glioblastoma | no | NCI-H69 | lung (small cell) | no |
| DBTRG-05MG | brain; glioblastoma | yes | NCI-H146 | lung (small cell) | yes |
| KNS-42 | brain; glioma | no | NCI-H209 | lung (small cell) | yes |
| Hs683 | brain; glioma | yes | NCI-H345 | lung (small cell) | yes |
| no.10 | brain; glioma, anaplastic | no | SHP-77 | lung (small cell) | yes |
| no.11 | brain; glioma, anaplastic | partial | KARPAS-299 | lymphocytic leukemia | no |
| SF-539 | brain; gliosarcoma | yes | CCRF-CEM | lymphocytic leukemia | yes |
| M059J | brain; malignant glioblastoma; glioma | no | Jurkat | lymphocytic leukemia | yes |
| PFSK-1 | brain; malignant neuroectodermal tumor | partial | MOLT4 | lymphocytic leukemia | yes |
| Daoy | brain; medulloblastoma | yes | THP-1 | lymphocytic leukemia | yes |
| CHLA-90 | brain; neuroblastoma | no | MONO-MAC-6 | lymphocytic leukemia | partial |
| IMR-32 | brain; neuroblastoma | no | Daudi | lymphoma | no |
| LA-N-6 | brain; neuroblastoma | yes | H9 | lymphoma | no |
| SMS-KCNR | brain; neuroblastoma, ALK (R1275Q). | yes | NAMALWA | lymphoma | no |
| SK-N-SH | brain; neuroblastoma, metastatic | no | SR-786 | lymphoma | no |
| SH-SY5Y | brain; neuroblastoma; bone marrow met. | no | SU-DHL-1 | lymphoma | no |
| SK-N-FI | brain; neuroblastoma; bone marrow met. | no | L-82 | lymphoma | yes |
| SK-N-MC | brain; neuroepithelioma; supra-orbital met. | no | Ramos | lymphoma | yes |
| H4 | brain; neuroglioma | partial | SU-DHL-10 | lymphoma | yes |
| KELLY | brain; oligodendroglioma | no | U-937 | lymphoma | yes |
| BT-474 | breast | yes | DEL | lymphoma | partial |
| DU4475 | breast | yes | SR | lymphoma | partial |
| HCC1937 | breast | yes | SU-DHL-8 | lymphoma | partial |
| MCF7 | breast | yes | SUP-M2 | lymphoma | partial |
| MDA-MB-231 | breast | yes | UACC-257 | melanoma | yes |
| MDA-MB-436 | breast | yes | MALME-3M | melanoma (lung metastasis) | yes |
| SK-BR-3 | breast | yes | A2058 | melanoma (lymph node metastasis) | yes |
| COLO320DM | colorectal | no | NIH-3T3 | mouse; fibroblast | no |
| COLO320HSR | colorectal | no | Hepa1-6 | mouse; hepatoma | partial |
| DLD-1 | colorectal | yes | RAW264.7 | mouse; leukemia | no |
| HCC2998 | colorectal | yes | MLE-12 | mouse; lung | no |
| HCT-15 | colorectal | yes | KU812 | myelogenous leukemia | no |
| HCT-8 | colorectal | yes | HL-60 | myelogenous leukemia | yes |
| KM12 | colorectal | yes | K562 | myelogenous leukemia | yes |
| LS174T | colorectal | yes | MOLM-13 | myelogenous leukemia | yes |
| RKO | colorectal | yes | MV-4-11 | myelogenous leukemia | yes |

TABLE 3-continued

| Cell line | Tissue | NA rescue | Cell line | Tissue | NA rescue |
|---|---|---|---|---|---|
| SK-CO-1 | colorectal | yes | NB-4 | myelogenous leukemia | yes |
| SNU-C2B | colorectal | yes | NOMO-1 | myelogenous leukemia | partial |
| SW-48 | colorectal | yes | SKM-1 | myelogenous leukemia | partial |
| SW480 | colorectal | yes | K562 | myelogenous leukemia (CML) | yes |
| SW620 | colorectal | yes | MEG-01 | myelogenous leukemia (CML) | yes |
| Hs414.T | fibrosarcoma | yes | AMO-1 | myeloma | no |
| Hs93.T | fibrosarcoma | yes | U266 | myeloma | no |
| SW684 | fibrosarcoma | yes | KMS-11 | myeloma | yes |
| SW872 | fibrosarcoma | yes | MC/CAR | myeloma | yes |
| HepG2 | hepatocellular carcinoma | no | MM.1S | myeloma | yes |
| Huh7 | hepatocellular carcinoma | yes | MOLP-8 | myeloma | partial |
| SNU182 | hepatocellular carcinoma | yes | RPMI-8226 | myeloma | partial |
| SNU449 | hepatocellular carcinoma | yes | JJN3 | myeloma (plasma cell leukemia) | yes |
| ACHN | kidney | yes | HOS | osteosarcoma | no |
| BEAS-2B | lung (normal) | yes | MG-63 | osteosarcoma | no |
| IMR-90 | lung (normal) | yes | U-2 OS | osteosarcoma | no |
| MRC-5 | lung (normal) | yes | Saos-2 | osteosarcoma | yes |
| Wi-38 | lung (normal) | yes | SJSA1 | osteosarcoma | yes |
| HCC78 | lung (NSCLC) | no | SK-ES-1 | osteosarcoma | yes |
| NCI-H322 | lung (NSCLC) | no | OVCAR-3 | ovary | yes |
| A549 | lung (NSCLC) | yes | UWB1.289 | ovary | yes |
| Calu-1 | lung (NSCLC) | yes | AsPC-1 | pancreas | yes |
| Calu-6 | lung (NSCLC) | yes | BxPC-3 | pancreas | yes |
| EKVX | lung (NSCLC) | yes | Capan-1 | pancreas | yes |
| HOP18 | lung (NSCLC) | yes | CFPAC-1 | pancreas | yes |
| HOP62 | lung (NSCLC) | yes | Hs766T | pancreas | yes |
| HOP92 | lung (NSCLC) | yes | Panc-1 | pancreas | yes |
| NCI-H1299 | lung (NSCLC) | yes | PBMC | primary blood | yes |
| NCI-H1437 | lung (NSCLC) | yes | SAEC | primary lung | yes |
| NCI-H1568 | lung (NSCLC) | yes | keratinocytes | primary skin | yes |
| NCI-H1792 | lung (NSCLC) | yes | DU145 | prostate | yes |
| NCI-H1944 | lung (NSCLC) | yes | LNCAP | prostate | yes |
|  |  |  | MALME-3 | skin (normal) | yes |

Additional cancer cell lines were treated with Exemplary Compounds A, C, D, E, F, G and H (identified below) (Table 4). The NA rescue phenotype of a particular cancer cell line was maintained for all Nampt inhibitors tested.

TABLE 4

| Cell line | Tissue | Ex. Comp. A Rescuable by NA? | Ex. Comp. C Rescuable by NA? | Ex. Comp. D Rescuable by NA? | Ex. Comp. E Rescuable by NA? | Ex. Comp. F Rescuable by NA? | Ex. Comp. G Rescuable by NA? | Ex. Comp. H Rescuable by NA? |
|---|---|---|---|---|---|---|---|---|
| HCT-116 | colorectal | yes | yes | yes | yes | yes | yes | yes |
| HT-1080 | fibrosarcoma | no | no | no | no | no | no | no |
| NCI-N87 | gastric | yes | yes | yes | yes | yes | yes | yes |
| MiaPaCa2 | pancreatic | no | no | no | no | no | no | no |
| HCC827 | NSCLC | no | no | no | no | no | no | no |
| NCI-H460 | NSCLC | no | no | no | no | no | no | no |
| COLO-205 | colorectal | yes | yes | yes | yes | yes | yes | yes |
| SU-DHL-4 | DLBCL (NHL) | partial | partial | partial | partial | partial | partial | partial |
| SU-DHL-5 | DLBCL (NHL) | no | no | no | no | no | no | no |
| DB | DLBCL (NHL) | partial | partial | partial | partial | partial | partial | partial |
| OCI-Ly19 | DLBCL (NHL) | yes | yes | yes | yes | yes | yes | yes |
| OPM-2 | multiple myeloma | no | no | no | no | no | no | no |

TABLE 4-continued

| Cell line | Tissue | Ex. Comp. A Rescuable by NA? | Ex. Comp. C Rescuable by NA? | Ex. Comp. D Rescuable by NA? | Ex. Comp. E Rescuable by NA? | Ex. Comp. F Rescuable by NA? | Ex. Comp. G Rescuable by NA? | Ex. Comp. H Rescuable by NA? |
|---|---|---|---|---|---|---|---|---|
| NCI-H929 | multiple myeloma | no | no | no | no | no | no | no |
| U-87MG | glioma | no | no | no | no | no | no | no |
| A172 | glioma | no | no | no | no | no | no | no |
| SF-295 | glioma | no | no | no | no | no | no | no |
| NCI-H1650 | NSCLC | no | no | no | no | no | no | no |
| NCI-H522 | NSCLC | no | no | no | no | no | no | no |
| DMS-114 | SCLC | yes | yes | yes | yes | yes | yes | yes |
| NCI-H82 | SCLC | yes | yes | yes | yes | yes | yes | yes |
| OVCAR-8 | ovarian | yes | yes | yes | yes | yes | yes | yes |
| HT29 | colorectal | yes | yes | yes | yes | yes | yes | yes |

Additionally, Nicotinic Acid (NA) rescue of cytotoxicity of Nampt inhibitors was assessed by two distinct methods. In the first method, Nampt1 inhibitor cytotoxicity was evaluated in the presence and absence of exogenous nicotinic acid (NA) at a fixed concentration. A loss of cytotoxicity in the presence of NA indicates that the Naprt1 pathway is active in that cell line, and that NA-mediated activity of the Naprt1-catlyzed de novo synthesis pathway can overcome the effects of Nampt inhibition. For this method, the following modifications were made to the standard cytotoxicity assay. Twenty four hours after cells were plated, the media was removed and replaced with media containing 10 µM nicotinic acid. Compounds were then immediately added. Cell viability was then assessed at 72 h. Comparison of the cytotoxic potency for the Nampt1 inhibitor in the absence and presence of NA revealed whether NA was effective at rescuing Nampt1 inhibitor-mediated cytotoxicity.

In the second method, cells were exposed to varying concentrations of NA in the presence of a fixed, toxic concentration of Nampt1 inhibitor. This allows determination of the relative effectiveness of NA at rescuing Nampt1 inhibitor-mediated cytotoxicity across cell lines. For this method, the following modifications were made to the standard cytotoxicity assay. Twenty four hours after cell were plated, a serial dilution of nicotinic acid, dissolved in water, was generated and added to the cells. Nampt1 inhibitor at a single concentration, generally a final concentration of 50 nM, was then immediately added. Cell viability was then assessed at 72 h. Cell viability (after normalization to controls lacking Nampt1 inhibitor) was plotted against NA concentration.

Cell lines that displayed a complete or nearly complete recovery of viability in the presence of NA were deemed to be rescued by NA. In cases where the high asymptote of the NA rescue curve corresponded to 75% or less recovery in cell viability, the cell line was deemed to be partially rescued. Cell lines that displayed little or no increase in viability in the presence of NA were deemed to be not rescued. The $EC_{50}$ values for NA rescue were determined as the concentration of NA that yielded a 50% recovery in cell viability compared to controls lacking Nampt1 inhibitor.

Using the first of the two assays described above, the 90 compounds shown in Table 5, below, were tested for cytotoxicity towards Naprt1-proficient HCT116 cells, and for the ability of NA to block the observed cytotoxicity (or "rescue" the cells from the cytotoxic activity of the tested compound). The compounds listed are referred to by a unique rescue analysis example number (i.e., R1, R2 . . . R90) that is used as a reference number in Table 4, in which the results of the cytotoxicity and rescue assays are presented.

TABLE 5

Compounds Tested for Cytotoxicity to HCT116 Cells, and for the Rescue of that Cytotoxicity by 10 µM Nicotinic Acid

| Example Number | Structure | IUPAC Name |
|---|---|---|
| R1 | 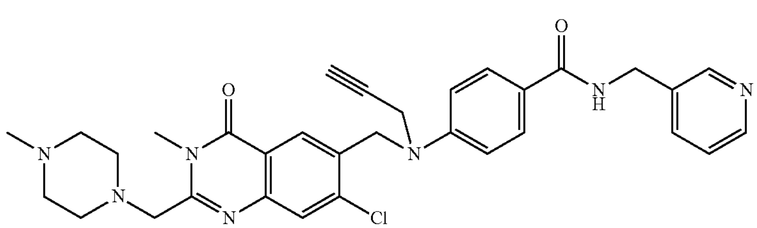 | 4-[({7-Chloro-3-methyl-2-[(4-methylpiperazin-1-yl)methyl]-4-oxo-3,4-dihydroquinazolin-6-yl}{methyl)(prop-2-yn-1-yl)amino]-N-(pyridin-3-ylmethyl)benzamide |

TABLE 5-continued

Compounds Tested for Cytotoxicity to HCT116 Cells, and for the Rescue of that Cytoxicity by 10 μM Nicotinic Acid

| Example Number | Structure | IUPAC Name |
|---|---|---|
| R2 | 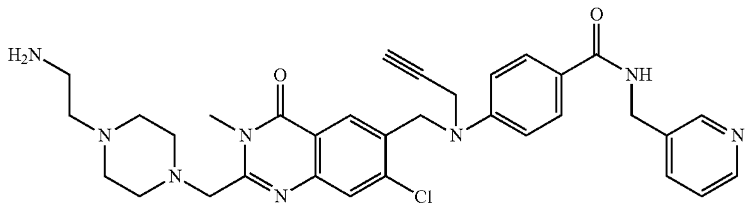 | 4-{[(2-{[4-(2-Aminoethyl)piperazin-1-yl]methyl}-7-chloro-3-methyl-4-oxo-3,4-dihydroquinazolin-6-yl)methyl](prop-2-yn-1-yl)amino}-N-(pyridin-3-ylmethyl)benzamide |
| R3 | 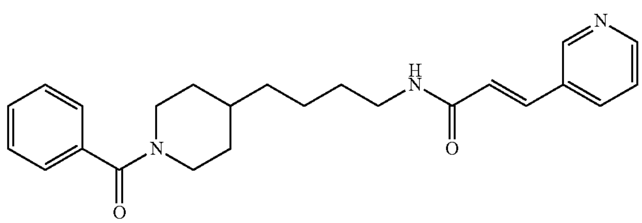 | (2E)-N-[4-(1-Benzoylpiperidin-4-yl)butyl]-3-(pyridin-3-yl)prop-2-enamide |
| R4 | 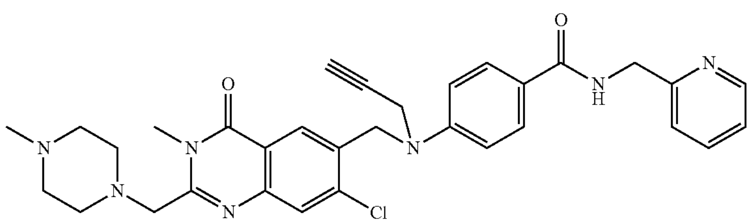 | 4-[({7-Chloro-3-methyl-2-[(4-methylpiperazin-1-yl)methyl]-4-oxo-3,4-dihydroquinazolin-6-yl}methyl)(prop-2-yn-1-yl)amino]-N-(pyridin-2-ylmethyl)benzamide |
| R5 | 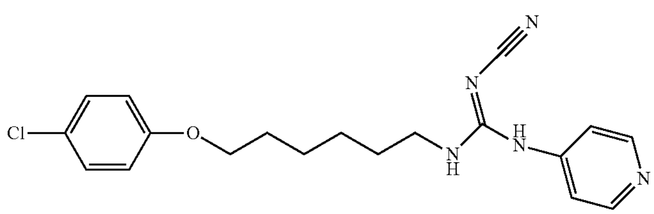 | 1-[6-(4-Chlorophenoxy)hexyl]-2-cyano-3-pyridin-4-ylguanidine |
| R6 | 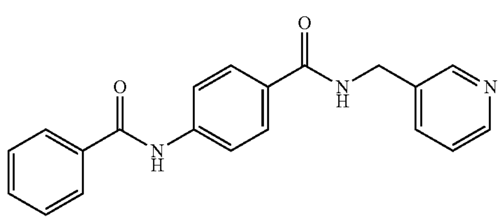 | 4-[(Phenylcarbonyl)amino]-N-(pyridin-3-ylmethyl)benzamide |
| R7 | 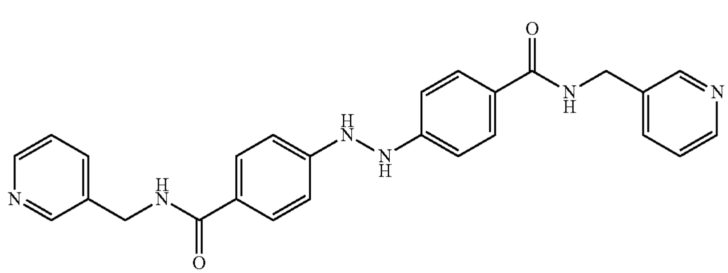 | 4,4'-Hydrazine-1,2-diylbis[N-(pyridin-3-ylmethyl)benzamide] |

TABLE 5-continued

Compounds Tested for Cytotoxicity to HCT116 Cells, and for the Rescue of that Cytoxicity by 10 μM Nicotinic Acid

| Example Number | Structure | IUPAC Name |
|---|---|---|
| R8 | 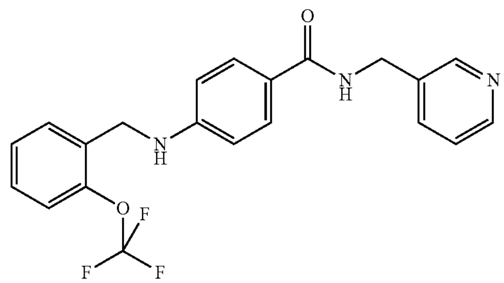 | N-(Pyridin-3-ylmethyl)-4-{[2-(trifluoromethoxy)benzyl]amino}benzamide |
| R9 | 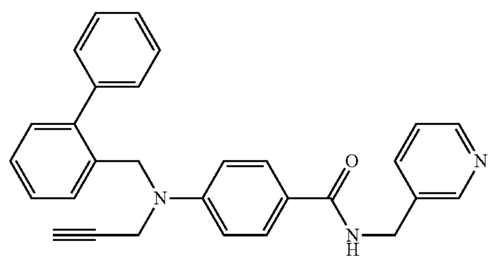 | 4-[(Biphenyl-2-ylmethyl)(prop-2-yn-1-yl)amino]-N-(pyridin-3-ylmethyl)benzamide |
| R10 | 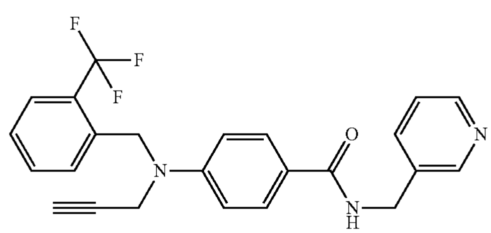 | 4-{Prop-2-yn-1-yl[2-(trifluoromethyl)benzyl]amino}-N-(pyridin-3-ylmethyl)benzamide |
| R11 | 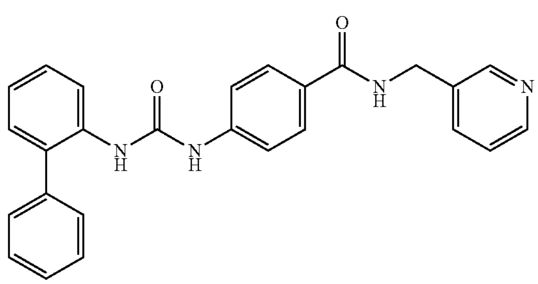 | 4-[(Biphenyl-2-ylcarbamoyl)amino]-N-(pyridin-3-ylmethyl)benzamide |
| R12 | 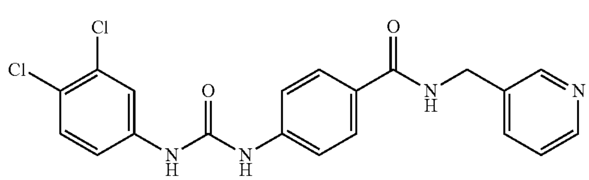 | 4-{[(3,4-Dichlorophenyl)carbamoyl]amino}-N-(pyridin-3-ylmethyl)benzamide |
| R13 | 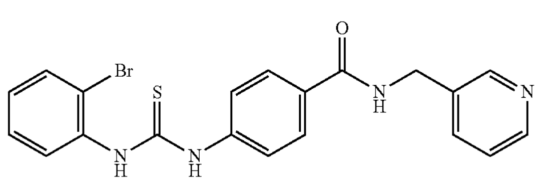 | 4-{[(2-Bromophenyl)carbamothioyl]amino}-N-(pyridin-3-ylmethyl)benzamide |

TABLE 5-continued

Compounds Tested for Cytotoxicity to HCT116 Cells, and for the Rescue of that Cytoxicity by 10 µM Nicotinic Acid

| Example Number | Structure | IUPAC Name |
|---|---|---|
| R14 | 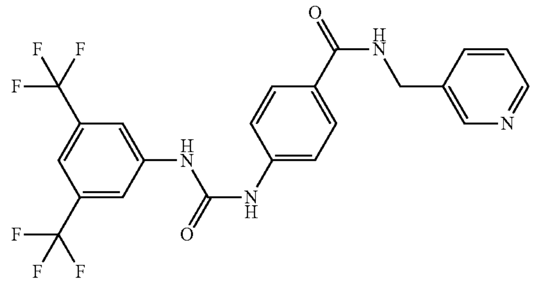 | 4-({[3,5-Bis(trifluoromethyl)phenyl]carbamoyl}amino)-N-(pyridin-3-ylmethyl)benzamide |
| R15 | 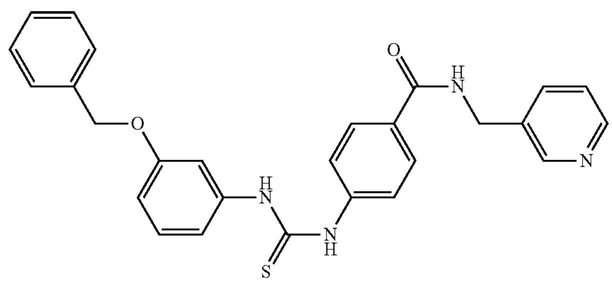 | 4-({[3-(Benzyloxy)phenyl]carbamothioyl}amino)-N-(pyridin-3-ylmethyl)benzamide |
| R16 | 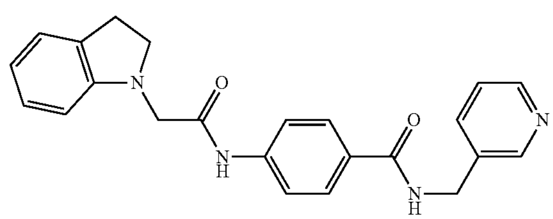 | 4-[(2,3-Dihydro-1H-indol-1-ylacetyl)amino]-N-(pyridin-3-ylmethyl)benzamide |
| R17 | 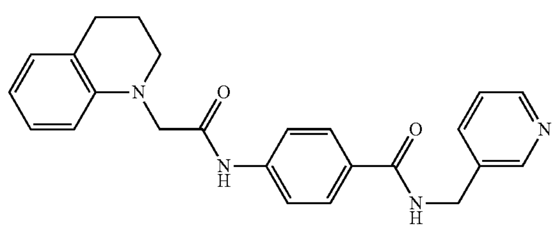 | 4-[(3,4-Dihydroquinolin-1(2H)-ylacetyl)amino]-N-(pyridin-3-ylmethyl)benzamide |
| R18 | 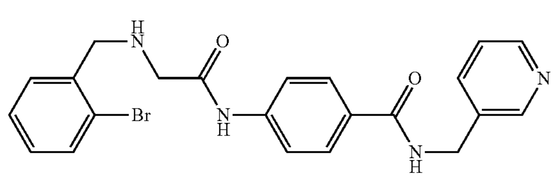 | 4-{[N-(2-Bromobenzyl)glycyl]amino}-N-(pyridin-3-ylmethyl)benzamide |
| R19 | 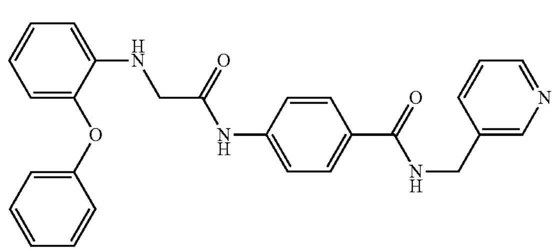 | 4-{[N-(2-Phenoxyphenyl)glycyl]amino}-N-(pyridin-3-ylmethyl)benzamide |

TABLE 5-continued

Compounds Tested for Cytotoxicity to HCT116 Cells, and for the Rescue of that Cytoxicity by 10 μM Nicotinic Acid

| Example Number | Structure | IUPAC Name |
|---|---|---|
| R20 | 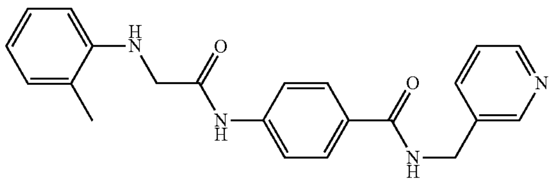 | 4-{[N-(2-Methylphenyl)glycyl]amino}-N-(pyridin-3-ylmethyl)benzamide |
| R21 | 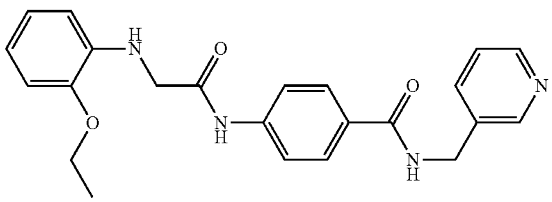 | 4-{[N-(2-Ethoxyphenyl)glycyl]amino}-N-(pyridin-3-ylmethyl)benzamide |
| R22 | 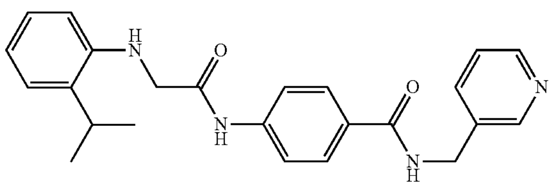 | 4-({N-[2-Propan-2-yl]phenyl]glycyl}amino)-N-(pyridin-3-ylmethyl)benzamide |
| R23 | 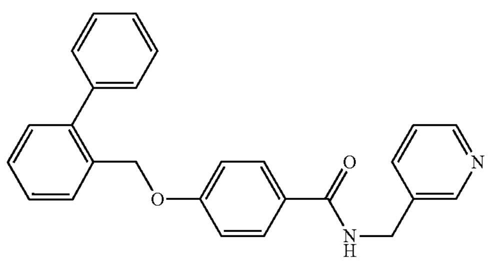 | 4-(Biphenyl-2-ylmethoxy)-N-(pyridin-3-ylmethyl)benzamide |
| R24 | 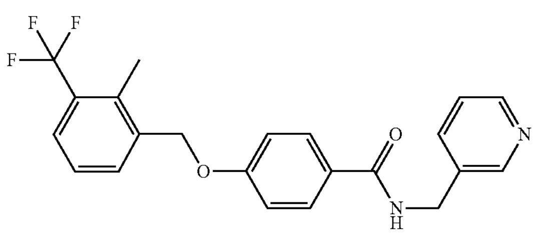 | 4-{[2-Methyl-3-(trifluoromethyl)benzyl]oxy}-N-(pyridin-3-ylmethyl)benzamide |
| R25 | 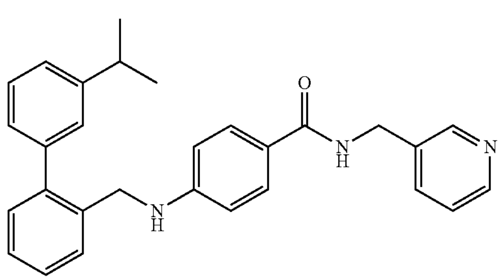 | 4-({[3'-(Propan-2-yl)biphenyl-2-yl]methyl}amino)-N-(pyridin-3-ylmethyl)benzamide |

TABLE 5-continued

Compounds Tested for Cytotoxicity to HCT116 Cells, and for the Rescue of that Cytoxicity by 10 μM Nicotinic Acid

| Example Number | Structure | IUPAC Name |
| --- | --- | --- |
| R26 | 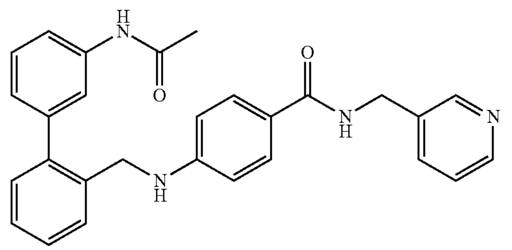 | 4-({[3'-(Acetylamino)biphenyl-2-yl]methyl}amino)-N-(pyridin-3-ylmethyl)benzamide |
| R27 | 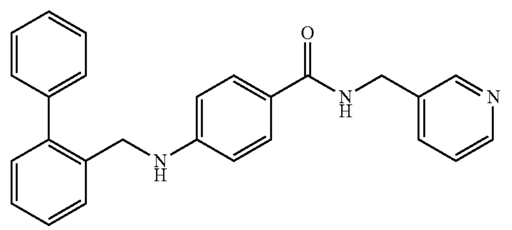 | 4-[(Biphenyl-2-ylmethyl)amino]-N-(pyridin-3-ylmethyl)benzamide |
| R28 | 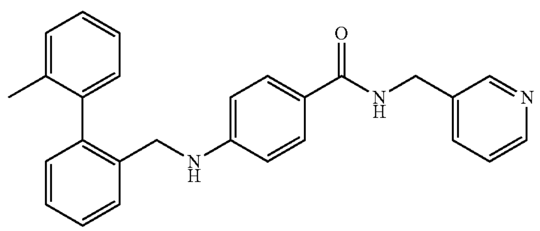 | 4-{[(2'-Methylbiphenyl-2-yl)methyl]amino}-N-(pyridin-3-ylmethyl)benzamide |
| R29 | 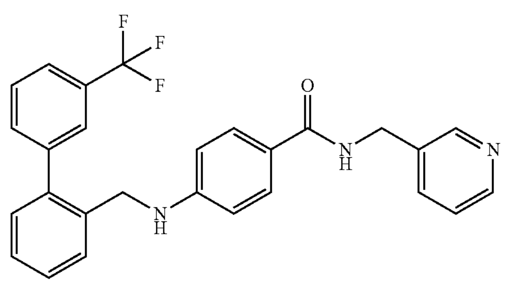 | N-(Pyridin-3-ylmethyl)-4-({[3'-(trifluoromethyl)biphenyl-2-yl]methyl}amino)benzamide |
| R30 | 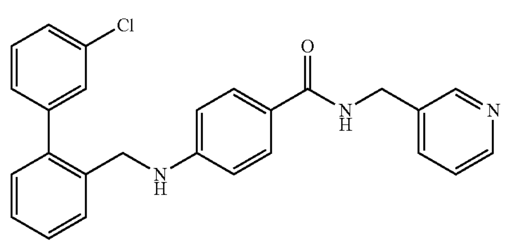 | 4-{[(3'-Chlorobiphenyl-2-yl)methyl]amino}-N-(pyridin-3-ylmethyl)benzamide |
| R31 | 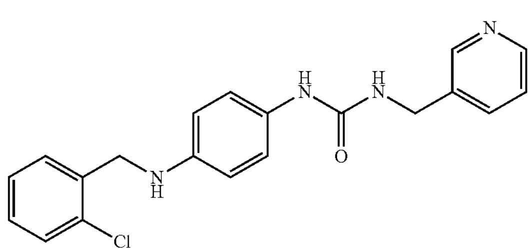 | 1-{4-[(2-Chlorobenzyl)amino]phenyl}-3-(pyridin-3-ylmethyl)urea |

TABLE 5-continued

Compounds Tested for Cytotoxicity to HCT116 Cells, and for the Rescue of that Cytoxicity by 10 μM Nicotinic Acid

| Example Number | Structure | IUPAC Name |
|---|---|---|
| R32 | 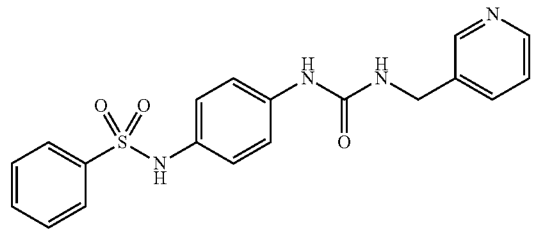 | N-(4-{[(Pyridin-3-ylmethyl)carbamoyl]amino}phenyl)benzene-sulfonamide |
| R33 | 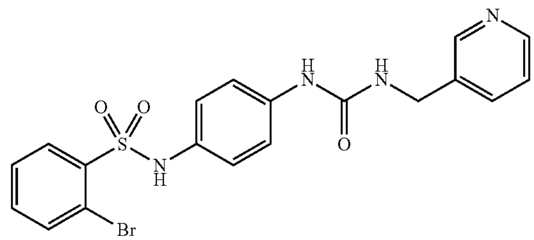 | 2-Bromo-N-(4-{[(pyridin-3-ylmethyl)carbamoyl]amino}phenyl)benzene-sulfonamide |
| R34 | 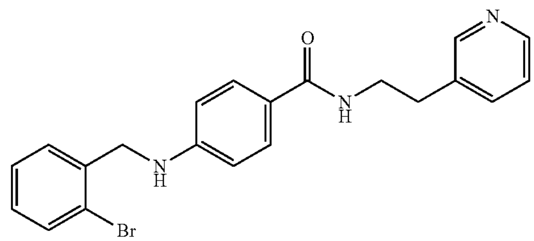 | 4-[(2-Bromobenzyl)amino]-N-[2-(pyridin-3-yl)ethyl]benzamide |
| R35 | 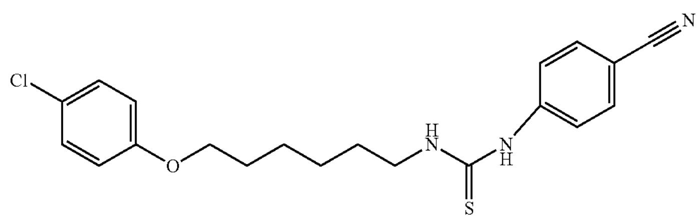 | 1-[6-(4-Chlorophenoxy)hexyl]-3-(4-cyanophenyl)thiourea |
| R36 | 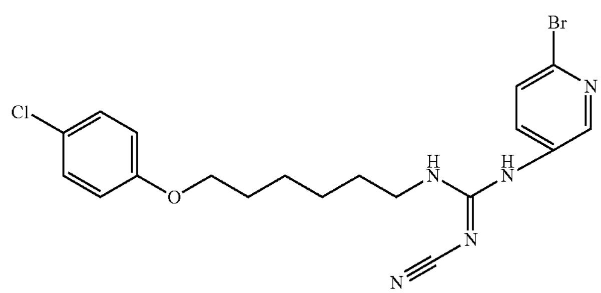 | 1-(6-Bromopyridin-3-yl)-2-[6-(4-chlorophenoxy)hexyl]-3-cyanoguanidine |
| R37 | 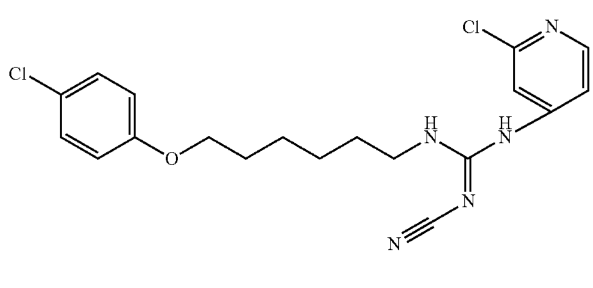 | 1-[6-(4-Chlorophenoxy)hexyl]-2-(2-chloropyridin-4-yl)-3-cyanoguanidine |

TABLE 5-continued

Compounds Tested for Cytotoxicity to HCT116 Cells, and for the Rescue of that Cytoxicity by 10 μM Nicotinic Acid

| Example Number | Structure | IUPAC Name |
| --- | --- | --- |
| R38 | 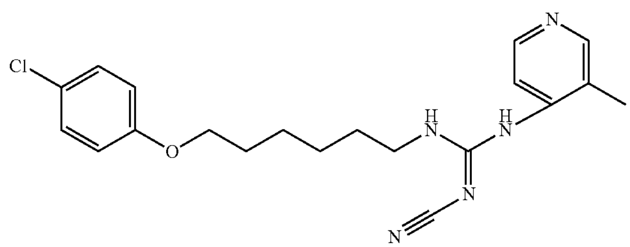 | 1-[6-(4-Chlorophenoxy)hexyl]-2-cyano-3-(3-methylpyridin-4-yl)guanidine |
| R39 | 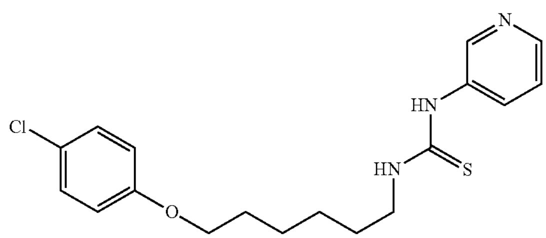 | 1-[6-(4-Chlorophenoxy)hexyl]-3-pyridin-3-ylthiourea |
| R40 | 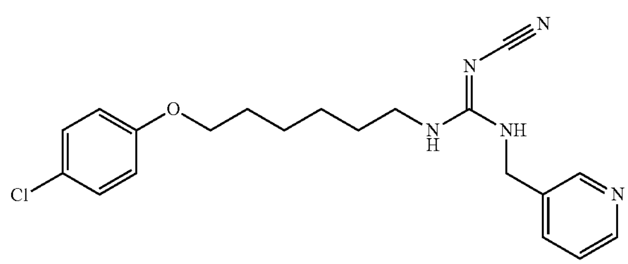 | 1-[6-(4-Chlorophenoxy)hexyl]-2-cyano-3-(pyridin-3-ylmethyl)guanidine |
| R41 | 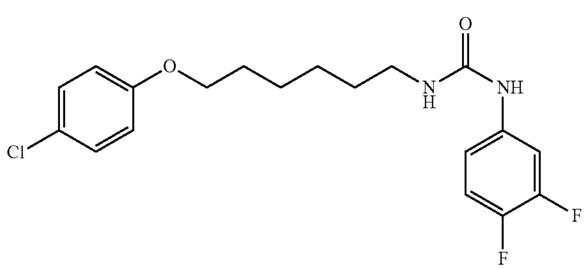 | 1-[6-(4-Chlorophenoxy)hexyl]-3-(3,4-difluorophenyl)urea |
| R42 | 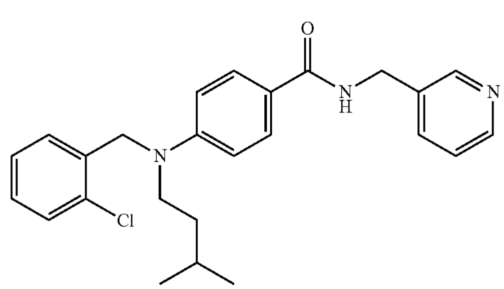 | 4-[(2-Chlorobenzyl)(3-methylbutyl)amino]-N-(pyridin-3-ylmethyl)benzamide |

TABLE 5-continued

Compounds Tested for Cytotoxicity to HCT116 Cells, and for the Rescue of that Cytoxicity by 10 μM Nicotinic Acid

| Example Number | Structure | IUPAC Name |
|---|---|---|
| R43 | 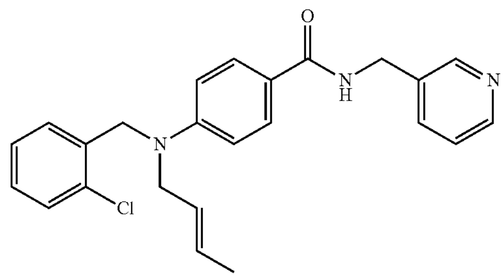 | 4-[(2E)-But-2-en-1-yl(2-chlorobenzyl)amino]-N-(pyridin-3-ylmethyl)benzamide |
| R44 | 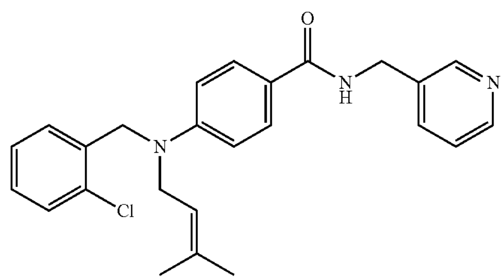 | 4-[(2-Chlorobenzyl)(3-methylbut-2-en-1-yl)amino]-N-(pyridin-3-ylmethyl)benzamide |
| R45 | 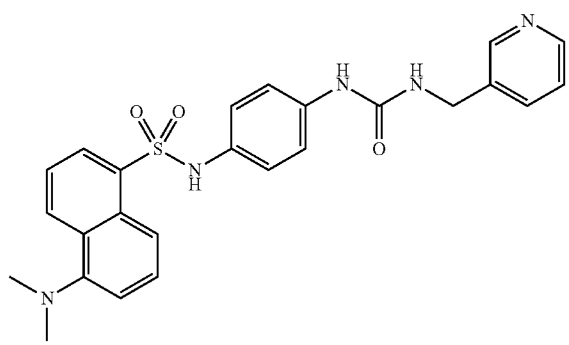 | 5-(Dimethylamino)-N-(4-{[(pyridin-3-ylmethyl)carbamoyl]amino}phenyl)naphthalene-1-sulfonamide |
| R46 | 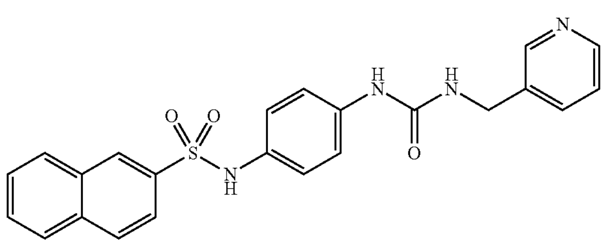 | N-(4-{[(Pyridin-3-ylmethyl)carbamoyl]amino}phenyl)naphthalene-2-sulfonamide |
| R47 | 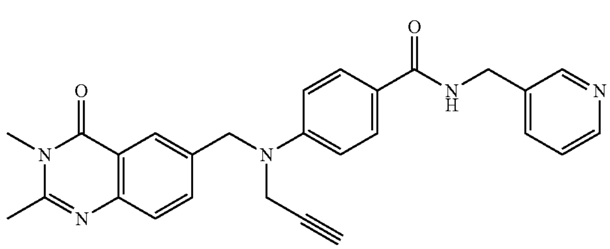 | 4-{[(2,3-Dimethyl-4-oxo-3,4-dihydroquinazolin-6-yl)methyl](prop-2-yn-1-yl)amino}-N-(pyridin-3-ylmethyl)benzamide |

TABLE 5-continued

Compounds Tested for Cytotoxicity to HCT116 Cells, and for the Rescue of that Cytoxicity by 10 μM Nicotinic Acid

| Example Number | Structure | IUPAC Name |
|---|---|---|
| R48 | 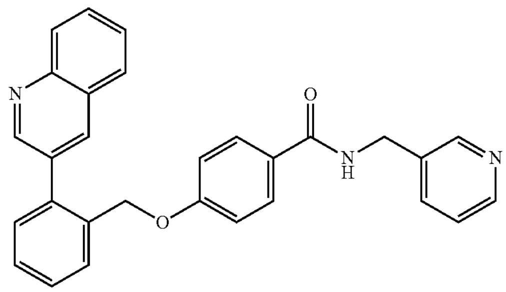 | N-(Pyridin-3-ylmethyl)-4-{[2-(quinolin-3-yl)benzyl]oxy}benzamide |
| R49 | 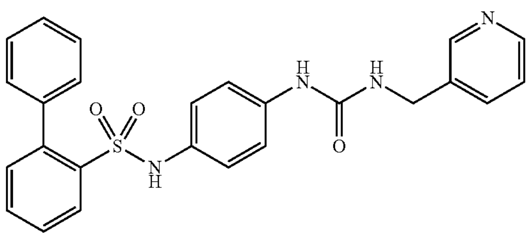 | N-(4-{[(Pyridin-3-ylmethyl)carbamoyl]amino}phenyl)biphenyl-2-sulfonamide |
| R50 | 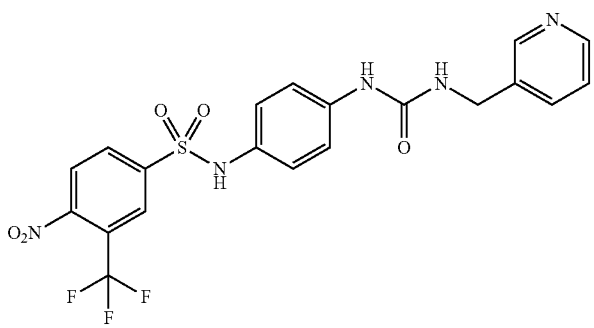 | 4-Nitro-N-(4-{[(pyridin-3-ylmethyl)carbamoyl]amino}phenyl)-3-(trifluoromethyl)benzenesulfonamide |
| R51 | 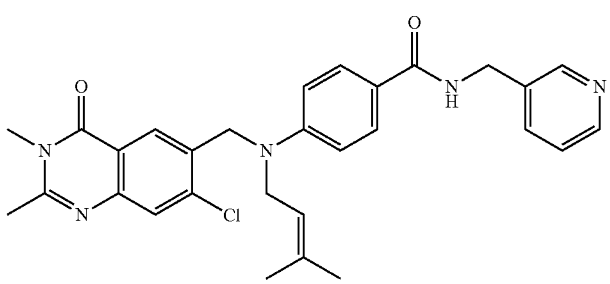 | 4-{[(7-Chloro-2,3-dimethyl-4-oxo-3,4-dihydroquinazolin-6-yl)methyl](3-methylbut-2-en-1-yl)amino}-N-(pyridin-3-ylmethyl)benzamide |
| R52 | 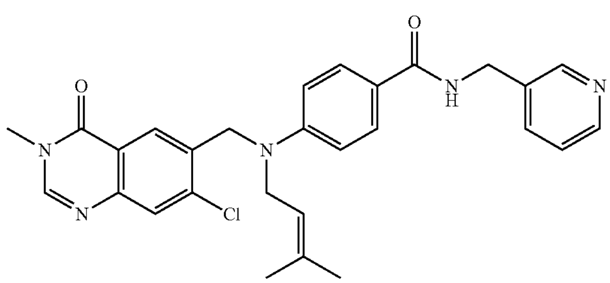 | 4-{[(7-Chloro-3-methyl-4-oxo-3,4-dihydroquinazolin-6-yl)methyl](3-methylbut-2-en-1-yl)amino}-N-(pyridin-3-ylmethyl)benzamide |

TABLE 5-continued

Compounds Tested for Cytotoxicity to HCT116 Cells, and for the Rescue of that Cytoxicity by 10 μM Nicotinic Acid

| Example Number | Structure | IUPAC Name |
| --- | --- | --- |
| R53 | 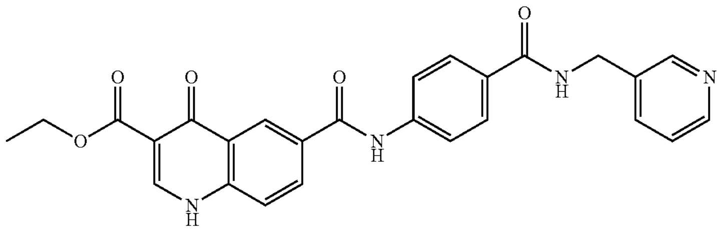 | ethyl 4-oxo-6-({4-[(pyridin-3-ylmethyl)carbamoyl]phenyl}carbamoyl)-1,4-dihydroquinoline-3-carboxylate |
| R54 | 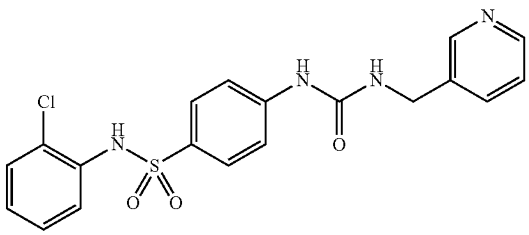 | N-(2-chlorophenyl)-4-{[(pyridin-3-ylmethyl)carbamoyl]amino}benzenesulfonamide |
| R55 | 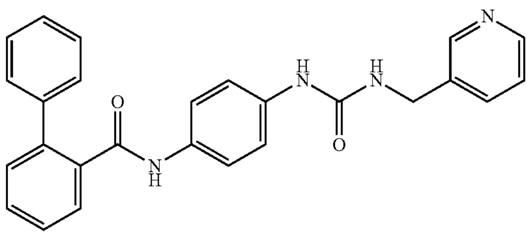 | N-(4-{[(pyridin-3-ylmethyl)carbamoyl]amino}phenyl)biphenyl-2-carboxamide |
| R56 | 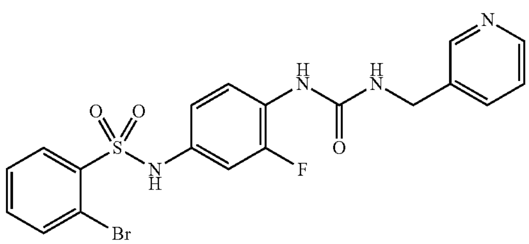 | 2-bromo-N-(3-fluoro-4-{[(pyridin-3-ylmethyl)carbamoyl]amino}phenyl)benzenesulfonamide |
| R57 | 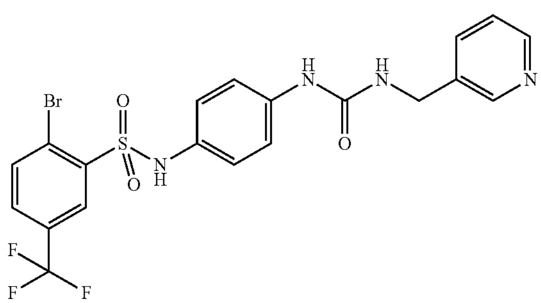 | 2-Bromo-N-(4-{[(pyridin-3-ylmethyl)carbamoyl]amino}phenyl)-5-(trifluoromethyl)benzenesulfonamide |
| R58 | 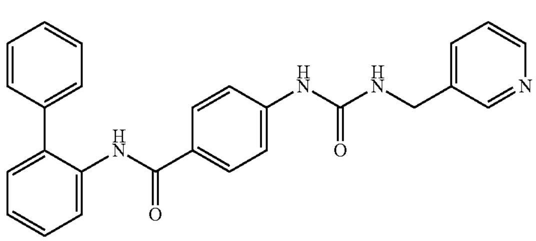 | N-(biphenyl-2-yl)-4-{[(pyridin-3-ylmethyl)carbamoyl]amino}benzamide |

TABLE 5-continued

Compounds Tested for Cytotoxicity to HCT116 Cells, and for the Rescue of that Cytoxicity by 10 µM Nicotinic Acid

| Example Number | Structure | IUPAC Name |
|---|---|---|
| R59 | 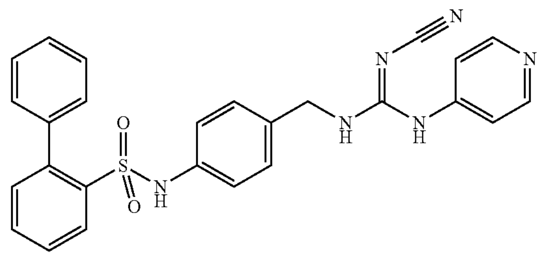 | N-(4-{[N''-cyano-N'-(pyridin-4-yl)carbamimidamido]methyl}phenyl)biphenyl-2-sulfonamide |
| R60 | 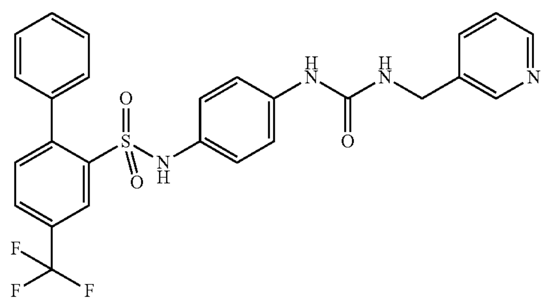 | N-(4-{[(pyridin-3-ylmethyl)carbamoyl]amino}phenyl)-4-(trifluoromethyl)biphenyl-2-sulfonamide |
| R61 | 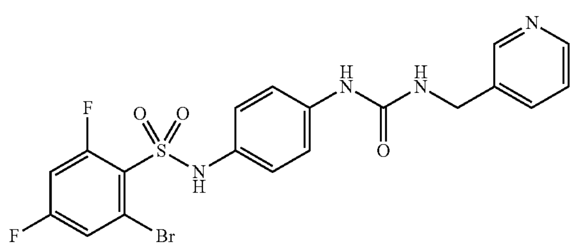 | 2-bromo-4,6-difluoro-N-(4-{[(pyridin-3-ylmethyl)carbamoyl]amino}phenyl)benzenesulfonamide |
| R62 | 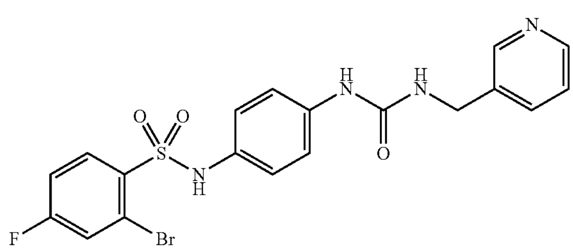 | 2-bromo-4-fluoro-N-(4-{[(pyridin-3-ylmethyl)carbamoyl]amino}phenyl)benzenesulfonamide |
| R63 | 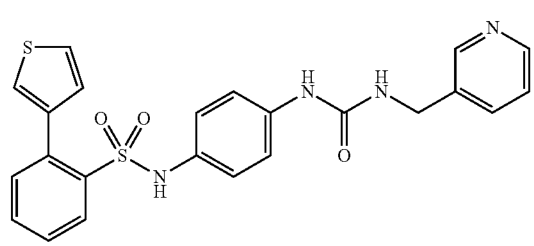 | N-(4-{[(pyridin-3-ylmethyl)carbamoyl]amino}phenyl)-2-(thiophen-3-yl)benzenesulfonamide |

TABLE 5-continued

Compounds Tested for Cytotoxicity to HCT116 Cells, and for the Rescue of that Cytoxicity by 10 μM Nicotinic Acid

| Example Number | Structure | IUPAC Name |
| --- | --- | --- |
| R64 | 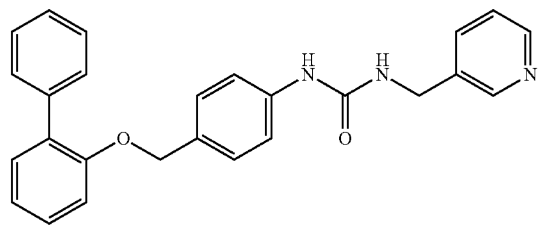 | 1-{4-[(Biphenyl-2-yloxy)methyl]phenyl}-3-(pyridin-3-ylmethyl)urea |
| R65 | 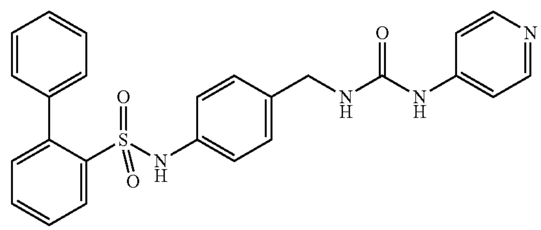 | N-(4-{[(pyridin-4-ylcarbamoyl)amino]methyl}phenyl)biphenyl-2-sulfonamide |
| R66 | 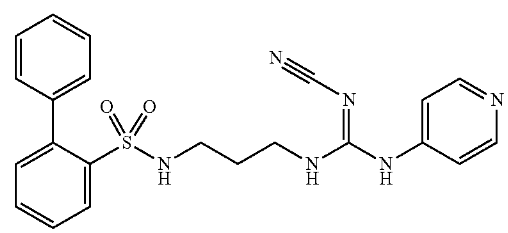 | N-{3-[N''-cyano-N'-(pyridin-4-yl)carbamimidamido]propyl}biphenyl-2-sulfonamide |
| R67 | 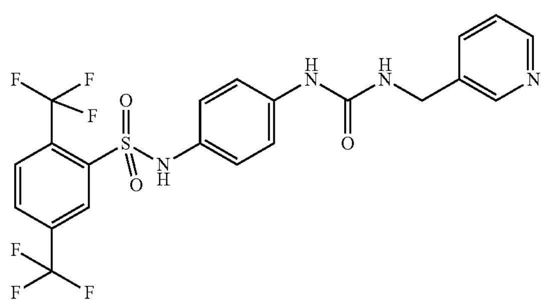 | N-(4-{(pyridin-3-ylmethyl)carbamoyl]amino}phenyl)-2,5-bis(trifluoromethyl)benzenesulfonamide |
| R68 | 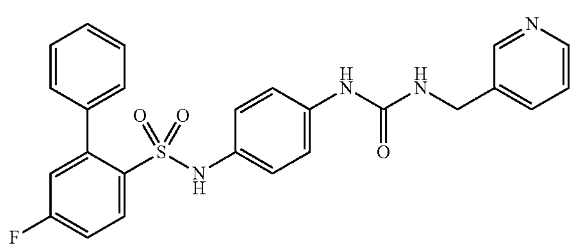 | 5-fluoro-N-(4-{[(pyridin-3-ylmethyl)carbamoyl]amino}phenyl)biphenyl-2-sulfonamide |

TABLE 5-continued

Compounds Tested for Cytotoxicity to HCT116 Cells, and for the Rescue of that Cytoxicity by 10 μM Nicotinic Acid

| Example Number | Structure | IUPAC Name |
| --- | --- | --- |
| R69 | 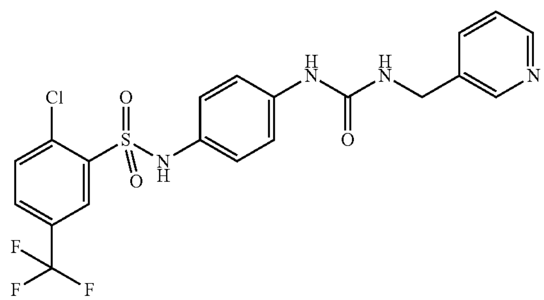 | 2-chloro-N-(4-{[(pyridin-3-ylmethyl)carbamoyl]amino}phenyl)-5-(trifluoromethyl)benzenesulfonamide |
| R70 | 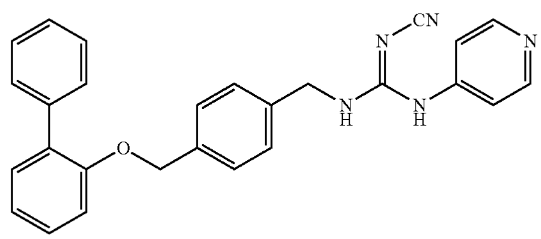 | 1-{4-[(biphenyl-2-yloxy)methyl]benzyl}-2-cyano-3-pyridin-4-ylguanidine |
| R71 | 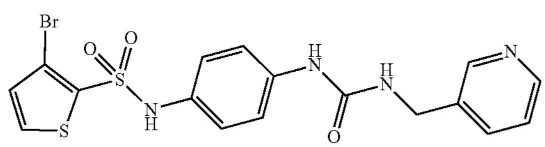 | 3-bromo-N-(4-{[(pyridin-3-ylmethyl)carbamoyl]amino}phenyl)thiophene-2-sulfonamide |
| R72 | 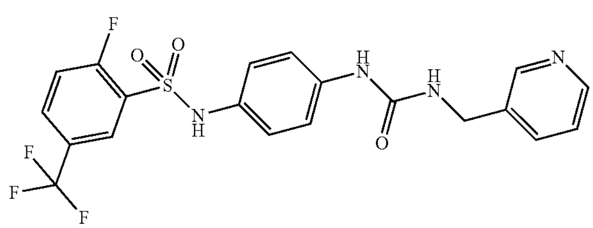 | 2-fluoro-N-(4-{[(pyridin-3-ylmethyl)carbamoyl]amino}phenyl)-5-(trifluoromethyl)benzenesulfonamide |
| R73 | 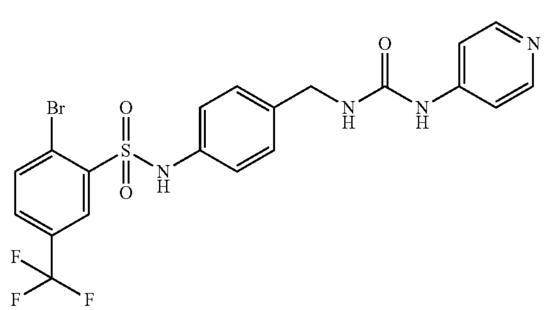 | 2-bromo-N-(4-{[(pyridin-4-ylcarbamoyl)amino]methyl}phenyl)-5-(trifluoromethyl)benzenesulfonamide |

TABLE 5-continued

Compounds Tested for Cytotoxicity to HCT116 Cells, and for the Rescue of that Cytoxicity by 10 µM Nicotinic Acid

| Example Number | Structure | IUPAC Name |
|---|---|---|
| R74 | 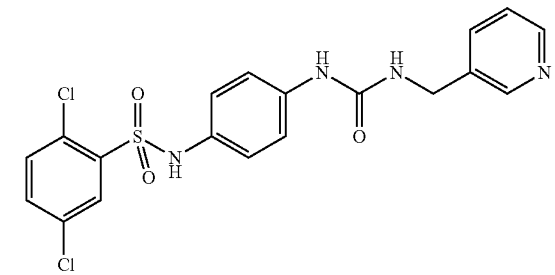 | 2,5-dichloro-N-(4-{[(pyridin-3-ylmethyl)carbamoyl]amino}phenyl)benzene-sulfonamide |
| R75 | 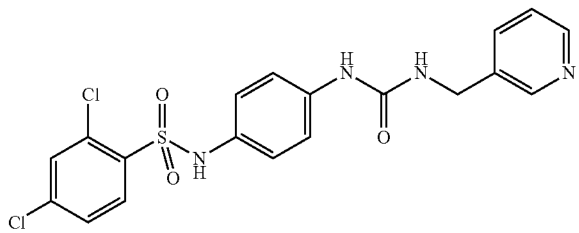 | 2,4-dichloro-N-(4-{[(pyridin-3-ylmethyl)carbamoyl]amino}phenyl)benzene-sulfonamide |
| R76 | 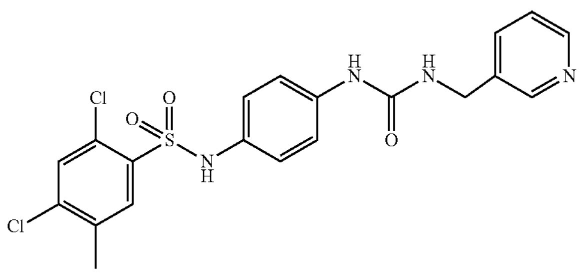 | 2,4-dichloro-5-methyl-N-(4-{[(pyridin-3-ylmethyl)carbamoyl]amino}phenyl)benzene-sulfonamide |
| R77 | 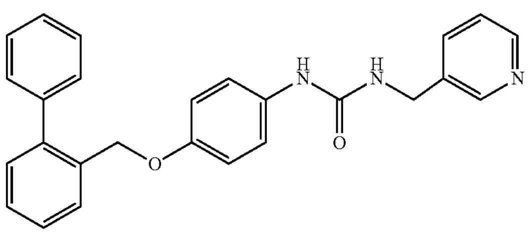 | 1-[4-(biphenyl-2-ylmethoxy)phenyl]-3-(pyridin-3-ylmethyl)urea |
| R78 | 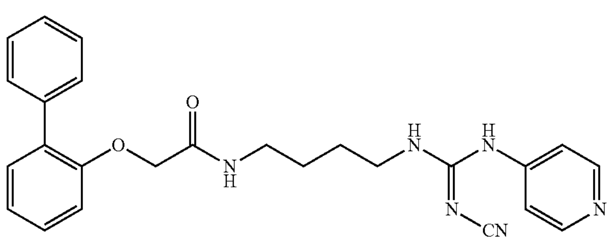 | 2-(Biphenyl-2-yloxy)-N-(4-{[(Z)-(cyanoamino)(pyridin-4-ylamino)methylidene]amino}butyl)acetamide |
| R79 | 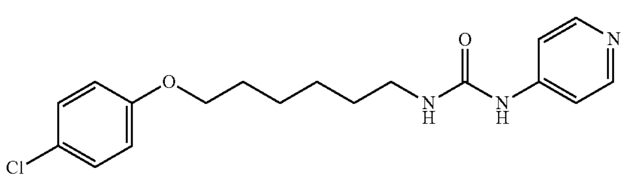 | 1-[6-(4-Chlorophenoxy)hexyl]-3-pyridin-4-ylurea |

TABLE 5-continued

Compounds Tested for Cytotoxicity to HCT116 Cells, and for the Rescue of that Cytoxicity by 10 μM Nicotinic Acid

| Example Number | Structure | IUPAC Name |
|---|---|---|
| R80 | 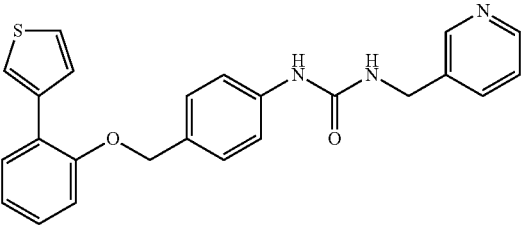 | 1-(Pyridin-3-ylmethyl)-3-(4-{[2-(thiophen-3-yl)phenoxy]methyl}phenyl)urea |
| R81 | 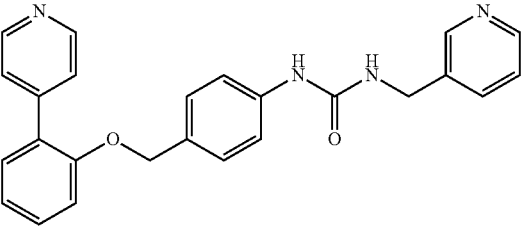 | 1-(Pyridin-3-ylmethyl)-3-(4-{[2-(pyridin-4-yl)phenoxy]methyl}phenyl)urea |
| R82 | 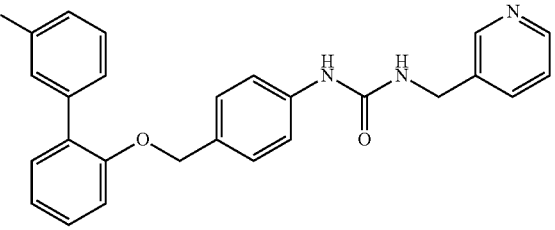 | 1-(4-{[(3'-Fluorobiphenyl-2-yl)oxy]methyl}phenyl)-3-(pyridin-3-ylmethyl)urea |
| R83 | 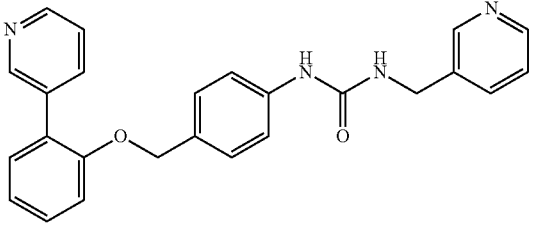 | 1-(Pyridin-3-ylmethyl)-3-(4-{[2-(pyridin-3-yl)phenoxy]methyl}phenyl)urea |
| R84 | 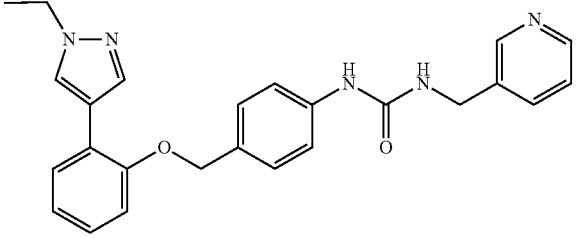 | 1-(4-{[2-(1-Ethyl-1H-pyrazol-4-yl)phenoxy]methyl}phenyl)-3-(pyridin-3-ylmethyl)urea |
| R85 | 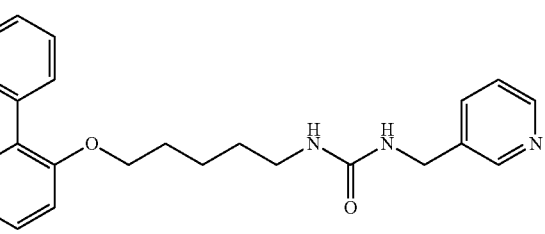 | 1-[5-(Biphenyl-2-yloxy)pentyl]-3-(pyridin-3-ylmethyl)urea |

TABLE 5-continued

Compounds Tested for Cytotoxicity to HCT116 Cells, and for the Rescue of that Cytoxicity by 10 μM Nicotinic Acid

| Example Number | Structure | IUPAC Name |
|---|---|---|
| R86 | 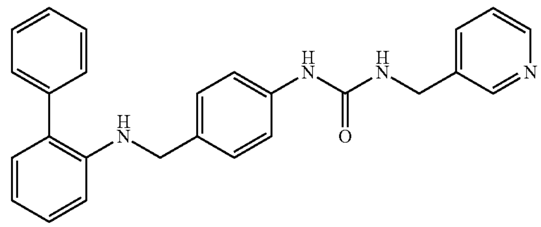 | 1-{4-[(Biphenyl-2-ylamino)methyl]phenyl}-3-(pyridin-3-ylmethyl)urea |
| R87 | 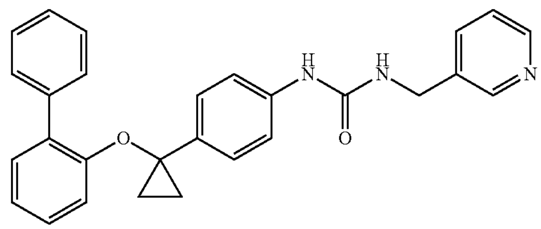 | 1-{4-[1-(Biphenyl-2-yloxy)cyclopropyl]phenyl}-3-(pyridin-3-ylmethyl)urea |
| R88 | 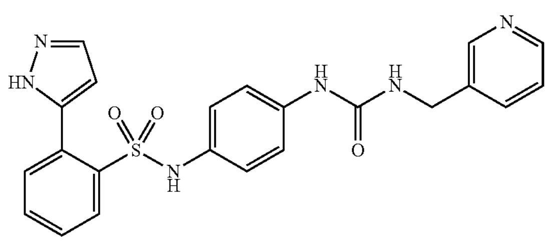 | 2-(1H-Pyrazol-5-yl)-N-(4-{[(pyridin-3-ylmethyl)carbamoyl]amino}phenyl)benzenesulfonamide |
| R89 | 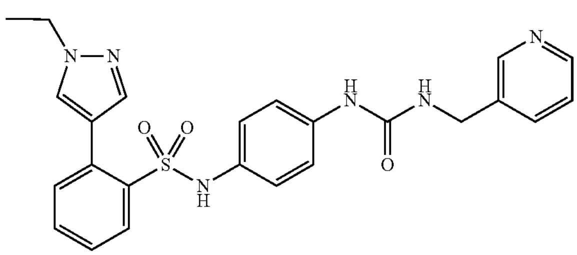 | 2-(1-Ethyl-1H-pyrazol-4-yl)-N-(4-{[(pyridin-3-ylmethyl)carbamoyl]amino}phenyl)benzenesulfonamide |
| R90 | 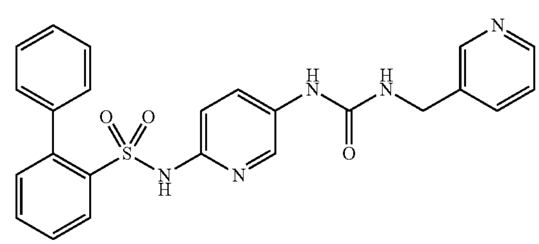 | N-(5-{[(Pyridin-3-ylmethyl)carbamoyl]amino}pyridin-2-yl)biphenyl-2-sulfonamide |

TABLE 6

Cytotoxicity of Selected Compound to HCT116 Cells in the Presence and Absence of 10 µM Nicotinic Acid

| Example Number | HCT116 72 h cytotoxicity (µM) | HCT116 72 h cytotoxicity with 10 µM Nicotinic Acid (µM) |
|---|---|---|
| R1 | 0.0007 | >10 |
| R2 | 0.0183 | >50 |
| R3 | 0.0014 | >10 |
| R4 | 0.2760 | >10 |
| R5 | 0.0016 | >10 |
| R6 | 1.6860 | >10 |
| R7 | 0.0088 | 22 |
| R8 | 3.1321 | >10 |
| R9 | 0.0415 | 12 |
| R10 | 1.1082 | >5 |
| R11 | 0.4239 | >50 |
| R12 | 9.6411 | 24.75 |
| R13 | 1.6121 | >50 |
| R14 | 7.3881 | 21.53 |
| R15 | 4.6864 | >50 |
| R16 | 3.2867 | >50 |
| R17 | 2.0502 | >50 |
| R18 | 6.8138 | >50 |
| R19 | 0.5857 | >50 |
| R20 | 0.1058 | >50 |
| R21 | 0.4349 | >50 |
| R22 | 0.3018 | >50 |
| R23 | 0.5388 | >50 |
| R24 | 11.9708 | 45 |
| R25 | 8.3251 | 37 |
| R26 | 0.0269 | 25 |
| R27 | 0.0871 | 37 |
| R28 | 0.3347 | 25 |
| R29 | 10.3366 | 25 |
| R30 | 1.3477 | 29 |
| R31 | 1.2696 | >50 |
| R32 | 0.1941 | >50 |
| R33 | 0.0046 | >50 |
| R34 | 1.1609 | >50 |
| R35 | 1.5263 | 2 |
| R36 | 6.0000 | >10 |
| R37 | 0.1685 | 5 |
| R38 | 0.0014 | >10 |
| R39 | 1.6202 | >10 |
| R40 | 1.0865 | >10 |
| R41 | 7.0825 | 6 |
| R42 | 0.3870 | >10 |
| R43 | 0.0986 | >10 |
| R44 | 0.0163 | >10 |
| R45 | 0.0048 | >10 |
| R46 | 0.0648 | >10 |
| R47 | 0.0335 | >10 |
| R48 | 0.0388 | >10 |
| R49 | 0.0049 | >10 |
| R50 | 0.0067 | >10 |
| R51 | 0.0095 | >10 |
| R52 | 0.0073 | >10 |
| R53 | 0.0068 | >10 |
| R54 | 0.0715 | >10 |
| R55 | 0.0488 | >1 |
| R56 | 0.0500 | >1 |
| R57 | 0.0005 | >10 |
| R58 | 0.0016 | >10 |
| R59 | 0.0006 | >5 |
| R60 | 0.0037 | >5 |
| R61 | 0.0018 | >1 |
| R62 | 0.0129 | >1 |
| R63 | 0.0016 | >10 |
| R64 | 0.0002 | >10 |
| R65 | 0.0005 | >1 |
| R66 | 0.0013 | 5 |
| R67 | 0.0003 | >1 |
| R68 | 0.0021 | >5 |
| R69 | 0.0013 | >1 |
| R70 | 0.0011 | >5 |
| R71 | 0.0132 | >5 |
| R72 | 0.0150 | >5 |
| R73 | 0.0010 | >5 |
| R74 | 0.0023 | >5 |
| R75 | 0.0303 | >5 |
| R76 | 0.0013 | >5 |
| R77 | 0.0017 | >5 |
| R78 | 0.0005 | >5 |
| R79 | 0.0889 | >5 |
| R80 | 0.0009 | >5 |
| R81 | 0.0054 | >5 |
| R82 | 0.0019 | >5 |
| R83 | 0.0015 | >5 |
| R84 | 0.0108 | >5 |
| R85 | 0.0013 | >5 |
| R86 | 0.0004 | 4 |
| R87 | 0.0011 | 3 |
| R88 | 0.0025 | >5 |
| R89 | 0.0342 | >5 |
| R90 | 0.0287 | >5 |

The results in Table 6 demonstrate that with the Naprt1-proficient cell line HCT116, the 90 compounds tested (Table 5) proved to be cytotoxic to varying degrees, but in all cases that cytotoxicity was reduced or relieved when 10 µM Nicotinic Acid was present concurrently. This "NA Rescue phenotype" observed in the presence of NA indicates that the 90 compounds tested exert their cytotoxicity through inhibition of Nampt and/or the Nam salvage pathway (FIG. 1), and that NA can be used to reduce or relieve undesirable cytotoxicity of these compounds to Naprt1-proficient cells (such as those in most normal human tissues), since such Naprt1-proficient cells are capable of generating NAD de novo from NA.

NMN and NAMN Rescue Cytotoxicity Assays

Other metabolites in the Nam salvage and de novo synthesis pathways, specifically NAMN (nicotinic acid mononucleotide) and NMN (nicotinamide mononucleotide), were tested in the same manner as NAD (above) to determine their ability to rescue the cytotoxicity of Nampt1 inhibitors. Rescue by NMN, the product of the Nampt-catalyzed step of the Nam salvage pathway, confirms that the cytotoxicity observed for the Nampt inhibitor is indeed due to Nampt inhibition. Rescue by NAMN, the product of the Naprt1-catalyzed step of the de novo synthesis pathway, in cell lines that failed to rescue with NA indicates that the failure of NA to rescue cytotoxicity is due to insufficiently low levels of Naprt1 enzyme expression or activity in that particular cell line. Cancer cells exhibiting this latter phenotype (i.e., failed rescue from Nampt inhibitor treatment by supplemented NAMN) would be particularly susceptible to treatment with Nampt inhibitors, since they are incapable of synthesizing NAD via the de novo synthesis pathway, the first and rate-limiting step of which is catalyzed by Naprt1. Such cancer cells would also be expected to exhibit very low to undetectable levels of Naprt1 expression, or may express a catalytically-inactive, mutant form of Naprt1.

Quantification of Naprt1 and Nampt by Western Blot

Frozen cell pellets were thawed and lysed in 0.5% Triton X-100, 50 mM HEPES [pH 7.4], 150 mM NaCl, 1 mM EDTA, 10% glycerol, and 1 mM DTT for 30 minutes at 4° C.

After centrifugation to remove cellular debris, proteins were resolved by electrophoresis and transferred to nitrocellulose membrane for antibody detection. Membranes were blocked in Starting Block T20 (TBS) (#37543; Thermo Scientific, Rockford, Ill.) and were probed sequentially with anti-Naprt1 (13549-1-AP rabbit; Proteintech Group, Inc., Chicago, Ill.), anti-Gapdh (#CB1001 mouse; Calbiochem, EMD4Biosciences, San Diego, Calif.) and anti-Nampt (sc-67020 rabbit; Santa Cruz Biotechnology, Inc., Santa Cruz, Calif.) antibodies. HRP-conjugated secondary antibodies (Santa Cruz Biotechnology, Inc., Santa Cruz, Calif.) and Super Signal West Dura Extended Duration Substrate (#34075; Thermo Scientific, Rockford, Ill.) were used for detection. Protein signals were quantified by imaging using an EC3 imaging system and VisionWorksSL software (UVP Bioimaging Systems; UVP, LLC, Upland, Calif.). The dynamic range of signal detection was enhanced by utilizing multiple exposure times. Naprt1 and Nampt protein levels were calculated as a percentage of GAPDH signal detected in each sample.

Quantification of Naprt1 by qRT-PCR

A panel of cancer cell lines and primary cells was screened for mRNA expression of Naprt1 mRNA by qRT-PCR. Untreated cell pellets were collected lysed in RLT buffer with 1% 3-Mercaptoethanol. RNA was isolated using an RNeasy spin column kit (74104; Qiagen, Inc., Valencia, Calif.), loaded in triplicate to a 96-well plate at 11 ng total RNA/well, and probed for Naprt1 with the TaqMan primer set Hs00292993_m1 (Life Technologies, Inc., Carlsbad, Calif.), using the QuantiTect probe RT-PCR kit (204443; Qiagen, Inc., Valencia, Calif.), with a final sample volume of 25 ul/well. Relative Naprt1 expression was assayed on the Applied Biosystems 7300 Real-Time PCR system thermal cycler (Life Technologies, Inc., Carlsbad, Calif.). The plate was heated to 50° C. for 30 minutes, followed by 95° C. for 15 minutes, followed by 40 cycles alternating between 95° C. for 15 seconds and 60° C. for 1 minute. Data was collected during the 60° C. step of each cycle, and cycle threshold values were interpolated onto a dilution curve of total RNA from the cell line SK– BR-3 to give relative values of the initial Naprt1 mRNA concentration for each sample. The average RNA concentration for each cell line was then expressed as a percentage of the RNA levels in SK– BR-3.

Naprt1 Expression Predicts Rescue with Nicotinic Acid Following Treatment with a Nampt Inhibitor Using the assays described above, the ability of NA to "rescue" cells from Nampt inhibitor-induced cytotoxicity was investigated.

Figure 6:
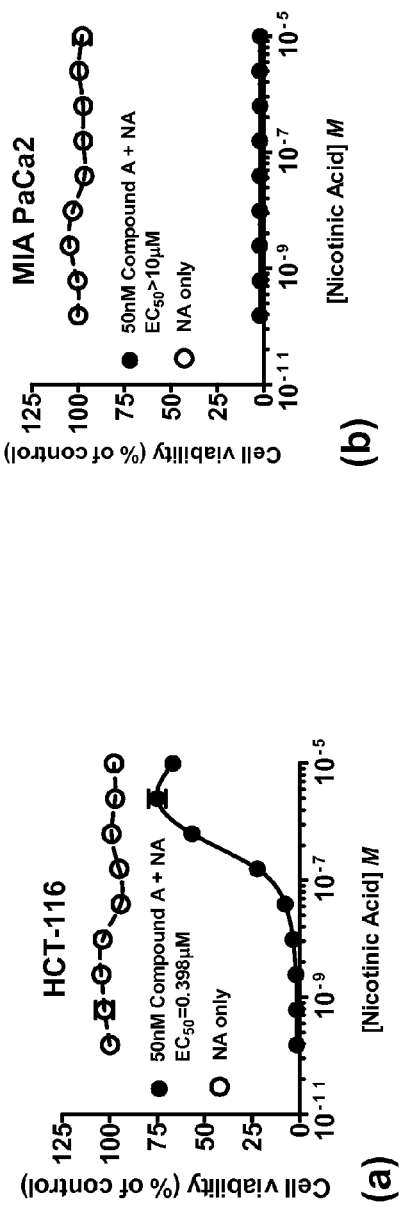
FIG. 6 shows that cytotoxicity resulting from treatment of cells with a particular Nampt inhibitor (Exemplary Compound A) can be rescued by the simultaneous administration of nicotinic acid (NA) for Naprt1-proficient HCT116 cells (a); but not for Naprt1-deficient Mia PaCa2 cells (b); NAPRT mRNA levels for Naprt1-proficient HCT116 cells were substantially higher than those of Naprt1-deficient Mia PaCa2 cells (as normalized to GAPDH mRNA levels) (c); Naprt expression, as assessed by lysate Western blot, is substantially greater in Naprt1-proficient HCT116 cells than in Naprt1-deficient Mia PaCa2 cells (d); and that immunohistochemistry of HCT116 and Mia PaCa2 xenograft tumors with an anti-Naprt antibody confirms higher levels of Naprt expression in the HCT116 xenograft tumor are displayed in (e).
Figure 6:
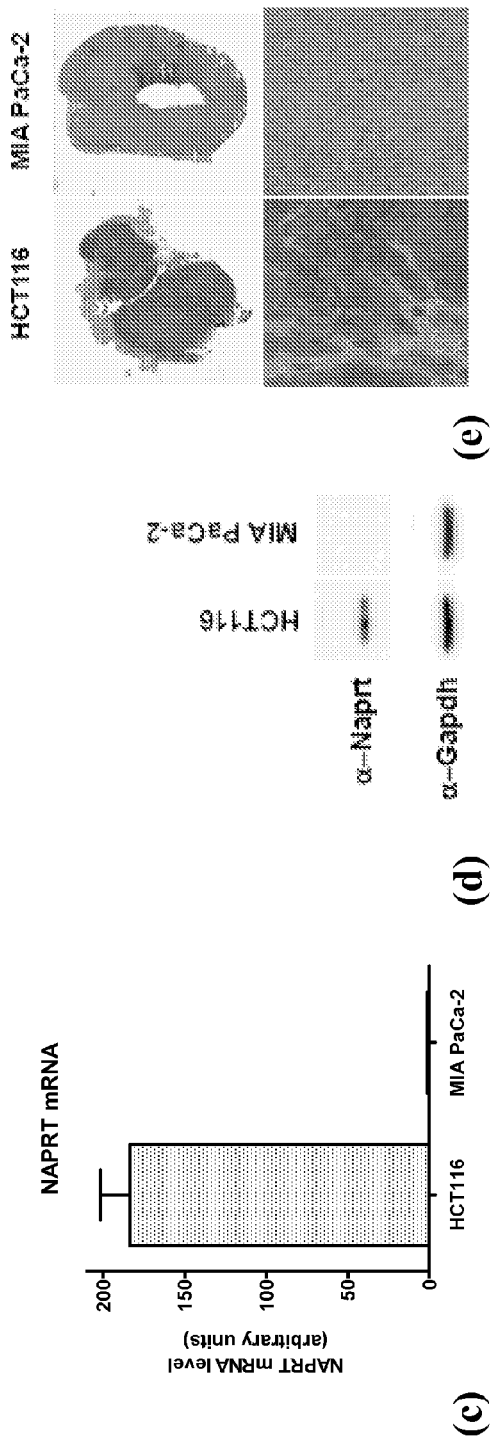

In the first set of experiments, two different cancer cell lines were employed. One of these cells lines, HCT116, was found to express substantial amounts of Naprt1, while the other, MIA PaCa2, showed no detectable expression of Naprt1. In view of these differences in levels of expression of Naprt, the HCT116 line was characterized as "Naprt1 proficient," while the MIA PaCa2 line was characterized as "Naprt1 deficient." For these experiments both cell lines were exposed to 50 nM Exemplary Compound A as described in the Nicotinic Acid Rescue Cytotoxicity Assays section, above. Rescue from Exemplary Compound A-induced cytotoxicity with NA was found to occur with an $EC_{50}$ of 400 nM in the Naprt1-proficient HCT-116 cell line (FIG. 6(a)), while a complete lack of rescue from Exemplary Compound A-induced cytotoxicity with NA (i.e., EC50>10 μM) was observed in the Naprt1-deficient MIA PaCa2 cell line (FIG. 6(b)). HCT116 and MIA PaCa-2 NAPRT mRNA levels were normalized to GAPDH mRNA and the results are illustrated in FIG. 6(c). In FIG. 6(d), Western blots for Naprt expression in HCT116 and MIA PaCa-2 cell lysates are displayed. In FIG. 6(e), the results of Naprt immunohistochemistry on HCT116 and MIA PaCa2 xenograft tumors are displayed.

To extend the results of these NA rescue studies further, the Naprt1 expression levels of a panel of 147 cancer cell lines was determined by Western blot, and expressed as a percentage of the expression level determined in Naprt1-proficient HCT116 cell line, and each of the cell lines was tested for a NA rescue phenotype using the procedure outlined above.

The results of these studies (depicted in FIG. 7(a)) indicate that, of the 147 cancer cell lines tested, 104 were found to exhibit "complete" rescue, 14 were found to exhibit "partial" rescue, and 41 were not rescued, according to the criteria set forth in the Nicotinic Acid Rescue Cytotoxicity Assays section, above. Median Naprt expression in cells completely rescued by NA was 55-fold greater than cell lines that are not rescued by NA. Further, the level of Naprt1 expression in a cancer cell line was found to generally predict the ability of the cell line to be rescued by NA from Nampt inhibitor-induced cytotoxicty.

These results not only show that Naprt1 expression level correlates with the ability of NA to rescue cancer cell lines from Nampt inhibitor-induced (i.e., Exemplary Compound A-induced) cytotoxicity, but demonstrate that, when exposed to Exemplary Compound A, a significant minority (i.e., 38%) of the cancer cell lines either failed to be rescued, or were only partially rescued, by supplementation with NA. These results suggest that the level of expression of the Naprt1 gene can be used to identify cancers that would remain sensitive to Nampt inhibitor-induced cytotoxicity, even when the patient having the cancer is concurrently being administered NA to limit unwanted toxicity in non-cancerous tissues, so long as the non-cancerous tissues themselves express sufficient quantities of Naprt1 to catalyze the de novo synthesis of NAD from NA. See FIG. 1.

To better understand what normal tissues could be protected from Nampt inhihbitor-induced cytotoxicity by the coadministration of NA, the level of Naprt1 expression levels in normal murine tissues lysates was determined by Western blot, and expressed as a percentage of the expression level determined in Naprt1-proficient HCT116 cell line. The results are shown in FIG. 7(b), with the mean shown by a solid line. The dotted line indicates expression level above which rescue by NA coadministration is likely, based on the results presented in FIG. 7(a). Most murine tissues express Naprt1 levels sufficient to support NA rescue. These data suggest that the cells of most vertebrate tissues have sufficient Naprt1 expression to direct NAD biosynthesis from supplemented NA, while, in accordance with the methods of the present invention, the Nampt-dependent Nam salvage pathway is blocked by administration of Nampt inhibitors.

The statistically significant (p<0.0001) difference in Naprt1 expression levels between rescued and non-rescued cell lines demonstrates that Naprt1 expression level is predictive of a NA rescue phenotype, such that higher-expressing lines tend to be rescued by NA coadministration, while lower-expressing lines tend to not be rescuable by NA coadministration.

Exemplary Compound a is Cytotoxic to a Wide Variety of Cancer Cell Types and Those Expressing Low Levels of Naprt1 are not Rescued by Nicotinic Acid Nampt is most active in adipose tissue, liver, kidney, immune cells, and intestine (Bogan, K. L and Brenner, C. Nicotinic acid, nicotinamide, and nicotinamide riboside: a molecular evaluation of $NAD^+$ precursor vitamins in human nutrition. *Annu Rev Nutr.* 28:115-305 (2008); and Revollo J R, et al. Nampt/PBEF/Visfatin regulates insulin secretion in beta cells as a systemic NAD biosynthetic enzyme. *Cell Metab*. November; 6(5):363-75 (2007)). Nevertheless, we sought to find out whether cancer cell lines of other origins are sensitive to Nampt inhibition.

Exponentially growing cells were plated in fresh growth media in a 96-well black, flat, clear-bottomed polystyrene microtiter plate (Packard View Plate 6005182). Twenty-four hours later, compounds were added from serial dilutions prepared in DMSO from 50 mM DMSO stock solutions. Each concentration of inhibitor was tested in duplicate at a final DMSO concentration of 0.4%. After 72 or 96 hours incubation, cell viability was quantified by measuring intracellular ATP levels using CellTiter-Glo (Promega Corporation, Madison, Wis.). Luminescence data was collected on a TopCount NXT plate reader (PerkinElmer, Waltham, Mass.). Experimental values were normalized to solvent controls and plotted versus compound concentration to determine the concentration required for a 50% reduction in cell viability.

Using the Cytotoxicity Assay outlined above, several exemplary compounds of the present invention ("Exemplary Compounds A, B, C, D, E, F, G, and H), and a known Nampt inhibitor ("Control Nampt Inhibitor") were tested and the results are shown in Tables 7A and 7B, below. Exemplary Compound A is Example Compound 296, or 1-{4-[(biphenyl-2-yloxy)methyl]phenyl}-3-(pyridin-3-ylmethyl)urea. Exemplary Compounds B and I are compounds represented by Formula IIIb5. Exemplary Compounds C, D, and H are compounds represented by Formula IIIb9. Exemplary Compound E, F, and G are compounds represented by Formula IIIb8. Killing was nearly complete (>80%) with all three compounds after 3 days, and was complete in all lines after 7 days. These data demonstrate that a wide variety of cancer cell types are susceptible to killing by the compounds of the present invention. Units are $TC_{50}$ ("Toxic Concentration required to cause 50% growth inhibition") in nanoMolar (nM).

TABLE 7A

| Cell Line | Cancer type | Exemplary Compound A 3 DAY | Exemplary Compound A 7 DAY | Exemplary Compound B 3 DAY | Exemplary Compound B 7 DAY | Exemplary Compound C 3 DAY | Control Nampt Inhibitor 3 DAY | Control Nampt Inhibitor 7 DAY |
|---|---|---|---|---|---|---|---|---|
| COLO205 | colon | 0.5 | 0.3 | 1.5 | 1.3 | 0.53 | 2.0 | 1.1 |
| DU145 | prostate | 3.9 | 2.7 | 16.5 | 8.9 | | 9.7 | 5.7 |
| DU4475 | breast | 0.1 | 0.1 | 0.4 | 0.1 | | 0.8 | 0.2 |
| HCC827 | NSCLC | 8.0 | 1.5 | 17.7 | 4.6 | 7.5 | 30.6 | 6.5 |
| HCT116 | colon | 0.6 | 0.4 | 2.4 | 2.3 | 0.51 | 3.5 | 1.6 |
| HCT-15 | colon | 0.7 | 1.0 | 13.7 | | | 3.8 | 3.2 |
| HOP92 | NSCLC | 17.0 | 4.3 | 44.6 | 10.1 | | 39.6 | 9.0 |
| HT1080 | sarcoma | 1.0 | 0.6 | 3.4 | 2.2 | 0.96 | 4.6 | 2.1 |
| HT29 | colon | 1.4 | 1.1 | 4.7 | 4.5 | 4.9 | 7.1 | 2.8 |
| KM12 | colon | 0.9 | 0.4 | 3.5 | 1.4 | | 4.4 | 1.8 |
| MDA-MB-231 | breast | 10.0 | 7.5 | 37.3 | 26.0 | | 31.0 | 17.4 |
| MIA PaCa-2 | pancreatic | 1.8 | 0.4 | 4.9 | 4.1 | 3.8 | 7.9 | 1.8 |
| NCI-H460 | NSCLC | 15.4 | | 53.2 | 63.5 | 15 | 36.9 | 19.8 |
| NCI-H522 | NSCLC | 1.0 | 0.4 | 2.8 | 1.3 | 0.97 | 4.0 | 1.2 |
| NCI-H69 | SCLC | 1.0 | | 3.0 | | | 3.3 | |
| NCI-N87 | gastric | 0.3 | 0.2 | 1.1 | 0.3 | 0.21 | 2.5 | 0.9 |
| OPM-2 | myeloma | 1.5 | | 3.8 | | 1.5 | 5.7 | |
| OVCAR3 | ovarian | 1.1 | 0.4 | 2.5 | 0.9 | | 3.7 | 1.3 |
| SU-DHL-4 | lymphoma | 1.5 | | | | 0.23 | | |
| SU-DHL-5 | lymphoma | 0.9 | | | | 0.19 | | |
| DB | lymphoma | 3.5 | | | | 1.1 | | |
| OCI-Ly19 | lymphoma | 1.2 | | | | 0.38 | | |
| NCI-H929 | myeloma | 2.5 | | | | 1.4 | | |
| U-87MG | glioma | 23 | | | | 17 | | |
| A172 | glioma | 1.1 | | | | 0.12 | | |
| SF-295 | glioma | 1.5 | | | | 0.37 | | |
| NCI-H1650 | NSCLC | 2.5 | | | | 0.28 | | |
| DMS-114 | SCLC | 0.16 | | | | 0.46 | | |
| NCI-H82 | SCLC | 1.1 | | | | 0.23 | | |

TABLE 7B

| Cell Line | Cancer type | Exemplary Compound D 3 DAY | Exemplary Compound E 3 DAY | Exemplary Compound F 3 DAY | Exemplary Compound G 3 DAY | Exemplary Compound H 3 DAY |
|---|---|---|---|---|---|---|
| COLO205 | colon | 1.5 | 0.22 | 1.1 | 0.14 | 8.6 |
| DU145 | prostate | | | | | |
| DU4475 | breast | | | | | |
| HCC827 | NSCLC | 62 | 14 | 19 | 11 | 325 |
| HCT116 | colon | 5.5 | 0.46 | 3.5 | 0.8 | 15 |
| HCT-15 | colon | | | | | |
| HOP92 | NSCLC | | | | | |
| HT1080 | sarcoma | 15 | 1.4 | 4.9 | 0.97 | 38 |
| HT29 | colon | 10 | 3.1 | 6.5 | 1.4 | 62 |
| KM12 | colon | | | | | |
| MDA-MB-231 | breast | | | | | |

TABLE 7B-continued

| Cell Line | Cancer type | Exemplary Compound D 3 DAY | Exemplary Compound E 3 DAY | Exemplary Compound F 3 DAY | Exemplary Compound G 3 DAY | Exemplary Compound H 3 DAY |
|---|---|---|---|---|---|---|
| MIA PaCa-2 | pancreatic | 17 | 4.3 | 16 | 2.3 | 68 |
| NCI-H460 | NSCLC | 211 | 65 | 69 | 39 | 795 |
| NCI-H522 | NSCLC | 2.8 | 0.39 | 1.1 | 0.14 | 14 |
| NCI-H69 | SCLC | | | | | |
| NCI-N87 | gastric | 1.8 | 0.24 | 0.8 | 0.18 | 7.3 |
| OPM-2 | myeloma | 4.2 | 1.8 | 2.3 | 0.6 | 35 |
| OVCAR3 | ovarian | | | | | |
| SU-DHL-4 | lymphoma | 2.5 | 0.28 | 1.8 | 0.11 | 7.4 |
| SU-DHL-5 | lymphoma | 3.1 | 0.08 | 0.35 | 0.08 | 1.1 |
| DB | lymphoma | 5 | 1.2 | 4.3 | 0.66 | 19 |
| OCI-Ly19 | lymphoma | 0.5 | 0.22 | 0.67 | 0.08 | 4.8 |
| NCI-H929 | myeloma | 5.2 | 1.5 | 3.9 | 0.23 | 17 |
| U-87MG | glioma | 62 | 74 | 43 | 17 | 1600 |
| A172 | glioma | 1.8 | 0.36 | 1.1 | 0.22 | 6.7 |
| SF-295 | glioma | 41 | 0.91 | 15 | 14 | 15 |
| NCI-H1650 | NSCLC | 4.3 | 0.59 | 1.7 | 0.25 | 9.6 |
| DMS-114 | SCLC | 15 | 0.82 | 3.5 | 3.3 | 4.5 |
| NCI-H82 | SCLC | 0.73 | 0.12 | 0.26 | 0.08 | 1.8 |

Nampt activity is greatest in adipose tissue, liver, kidney, immune cells, and intestine (Bogan, K. L and Brenner, C. Nicotinic acid, nicotinamide, and nicotinamide riboside: a molecular evaluation of NAD precursor vitamins in human nutrition. *Annu Rev Nutr.* 28:115-305 (2008); and Revollo J R, et al. Nampt/PBEF/Visfatin regulates insulin secretion in beta cells as a systemic NAD biosynthetic enzyme. *Cell Metab.* November; 6(5):363-75 (2007)). Nevertheless, experiments were conducted to discover whether cancer cell lines of other origins are sensitive to Nampt inhibition. Naprt 1 expression is highest in small intestine, liver and kidney (Hara N. et al. Elevation of cellular NAD levels by nicotinic acid and involvement of nicotinic acid phosphoribosyltransferase in human cells. *J. Biol. Chem.* 282:24574-24582 (2007)). Nevertheless, experiments were conducted to assess the level of Naprt1 expression across a wide range of cancer types represented by 183 cancer cell lines, and to assess whether these cancer cells can be rescued from Nampt inhibitor-induced cytotoxicity by NA. Using the assays outlined above and Exemplary Compound A (identified above), 183 cancer cell lines of different origins were tested for their susceptibility to cytotoxicity caused by Exemplary Compound A, and for the ability of NA to rescue these cells from this cytotoxicity. The results of the studies (Table 8, below) indicate that Exemplary Compound A is cytotoxic to a wide range of cancer cell types, and that a substantial percentage of these cancer cell types express insufficient levels of Naprt1 to be rescued by NA.

TABLE 8

Exemplary Compound A Cytotoxicity, NA Rescue, and Naprt1 Expression Across a Wide Range of Cancer Cell Types

| Cell line | Tissue | Cmpd A 3 day TC50 (nM) | Cmpd A 7 day TC50 (nM) | Rescued by NA? (partial indicates <70% rescue) | Naprt1 expression (% C.), Western (1, 4, 30 ug blots) | Naprt1 expression, qRT-PCR (% C.) |
|---|---|---|---|---|---|---|
| T24 | bladder | 1 | | Y | 11 | |
| no.11 | brain; glioma, anaplastic | | | Y (partial) | 1 | 3 |
| PFSK-1 | brain; malignant neuroectodermal tumor | <0.8 | | Y (partial) | 14 | 5.2 |
| H4 | brain; neuroglioma | | | Y (partial) | 4 | 2.0 |
| CCF-STTG1 | brain; astrocytoma | | | Y | 42 | 24 |
| SNB-75 | brain; astrocytoma | | | Y | 39 | 7.7 |
| SW 1088 | brain; astrocytoma | | | Y | 3 | 3.1 |
| SW 1783 | brain; astrocytoma | | | Y | 2 | 6.13 |
| DBTRG-05MG | brain; glioblastoma | 19 | | Y | 51 | 3.0 |
| U-87 MG | brain; glioblastoma/astrocytoma | 15 | | Y | 1 | 1.3 |
| Hs 683 | brain; glioma | | | Y | 18 | 6.2 |
| SF-539 | brain; gliosarcoma | | | Y | 28 | 7.2 |
| Daoy | brain; medulloblastoma | | | Y | 83 | 9.1 |
| LA-N-6 | brain; neuroblastoma | | | Y | | |
| SMS-KCNR | brain; neuroblastoma, ALK (R1275Q). | | | Y | | 1.9 |

TABLE 8-continued

Exemplary Compound A Cytotoxicity, NA Rescue,
and Naprt1 Expression Across a Wide Range of Cancer Cell Types

| Cell line | Tissue | Cmpd A 3 day TC50 (nM) | Cmpd A 7 day TC50 (nM) | Rescued by NA? (partial indicates <70% rescue) | Naprt1 expression (% C.), Western (1, 4, 30 ug blots) | Naprt1 expression, qRT-PCR (% C.) |
|---|---|---|---|---|---|---|
| KINGS-1 | brain; anaplastic astrocytoma (glioma) | 2 | | N | 6 | 0.29 |
| SF-268 | brain; astrocytoma, anaplastic | | | N | 1 | 0.9 |
| A172 | brain; glioblastoma | | | N | 1 | 0.5 |
| SNB-19 | brain; glioblastoma | | | N | 1 | 0.88 |
| U251 | brain; glioblastoma | | | N | 0 | 2.1 |
| SF-295 | brain; glioblstoma multiform | | | N | 1 | 1.1 |
| KNS-42 | brain; glioma | | | N | 1 | 0.8 |
| no.10 | brain; glioma, anaplastic | | | N | 5 | 0.59 |
| M059J | brain; malignant glioblastoma; glioma | | | N | 1 | 4 |
| CHLA-90 | brain; neuroblastoma | | | N | 0 | 8.4 |
| IMR-32 | brain; neuroblastoma | | | N | 2 | 1.4 |
| SK-N-SH | brain; neuroblastoma, metastatic | | | N | 0 | 0.47 |
| SH-SY5Y | brain; neuroblastoma; bone marrow met. | | | N | 3 | 1.28 |
| SK-N-FI | brain; neuroblastoma; bone marrow met. | | | N | 1 | 1.8 |
| SK-N-MC | brain; neuroepithelioma; supra-orbital met. | | | N | 2 | 1.4 |
| KELLY | brain; oligodendroglioma | | | N | 2 | 0.85 |
| BT-474 | breast | 4.3, 5.9, 12 | 1.1 | Y | 111 | |
| DU4475 | breast | 0.1 | 0.1 | Y | 28 | |
| HCC1937 | breast | 61 | 1.5 | Y | 27 | |
| MCF7 | breast | 2.2, 1.1 | | Y | 22 | |
| MDA-MB-231 | breast | 10, 9.1, 24 | 8 | Y | 29 | |
| MDA-MB-436 | breast | 17 | | Y | 234 | |
| SK-BR-3 | breast | 6.8 | | Y | 975 | 100 |
| BT-20 | breast | 13 | | | | |
| CAMA-1 | breast | 4.6 | | | | |
| T47D | breast | 0.8, <1.5 | | | | |
| COLO205 | colon | 0.5, <1.5 | 0.3 | Y | 563 | |
| HCT-116 | colon | 0.2-4.4 | 0.4 | Y | 100 | 32 |
| HCT-15 | colon | 0.7, 0.8, 2.3 | 1 | Y | 180 | |
| HT29 | colon | 1.4 | 1.1 | Y | 311 | |
| KM12 | colon | 0.9 | 0.4 | Y | 42 | |
| SW 480 | colon | 4 | | Y | 226 | |
| DLD-1 | colon | 1.7, 2.2 | | | | |
| SW-48 | colon | 2.3, 1.5 | | | | |
| Hs 414.T | fibrosarcoma | | | Y | 25 | 5.8 |
| Hs 93.T | fibrosarcoma | | | Y | 6 | 3.2 |
| SW 684 | fibrosarcoma | | | Y | 23 | 13 |
| SW 872 | fibrosarcoma | | | Y | 66 | 14 |
| HT1080 | fibrosarcoma | 1 | 0.6 | N | 0.9 | 2.5 |
| NCI-N87 | gastric | 0.3 | 0.2 | Y | 771 | |
| Huh7 | hepatocellular carcinoma | | | Y | 195 | 26.0 |
| SNU182 | hepatocellular carcinoma | | | Y | | |
| SNU449 | hepatocellular carcinoma | | | Y | 43 | 20.9 |
| HepG2 | hepatocellular carcinoma | | | N | 1 | 1.55 |
| ACHN | kidney | 3.7 | | Y | 14 | |
| A498 | kidney | 43 | | | | |
| BEAS-2B | lung (normal) | | | Y | 59 | 14 |
| IMR-90 | lung (normal) | | | Y | 18 | 5.4 |
| MRC-5 | lung (normal) | | | Y | 7 | 1.3 |
| Wi-38 | lung (normal) | | | Y | 9 | 6.3 |
| NCI-H596 | lung (NSCLC) | | | Y (partial) | 8 | 3.2 |
| A549 | lung (NSCLC) | 3.8, 9.3, 6.2 | | Y | 18 | |

TABLE 8-continued

Exemplary Compound A Cytotoxicity, NA Rescue,
and Naprt1 Expression Across a Wide Range of Cancer Cell Types

| Cell line | Tissue | Cmpd A 3 day TC50 (nM) | Cmpd A 7 day TC50 (nM) | Rescued by NA? (partial indicates <70% rescue) | Naprt1 expression (% C.), Western (1, 4, 30 ug blots) | Naprt1 expression, qRT-PCR (% C.) |
|---|---|---|---|---|---|---|
| Calu-1 | lung (NSCLC) | | | Y | 10 | 4.1 |
| Calu-6 | lung (NSCLC) | 11, 12 | | Y | 60 | 14 |
| EKVX | lung (NSCLC) | 4 | 1 | Y | 107 | |
| HOP18 | lung (NSCLC) | | | Y | 865 | 37 |
| HOP62 | lung (NSCLC) | 4 | | Y | 15 | |
| HOP92 | lung (NSCLC) | 17 | 4.3 | Y | 23 | |
| NCI-H1437 | lung (NSCLC) | | | Y | 285 | 13 |
| NCI-H1568 | lung (NSCLC) | | | Y | 470 | 31 |
| NCI-H1792 | lung (NSCLC) | | | Y | 45 | 12 |
| NCI-H1944 | lung (NSCLC) | | | Y | 258 | 52 |
| NCI-H1993 | lung (NSCLC) | | | Y | 176 | 41 |
| NCI-H2030 | lung (NSCLC) | | | Y | 65 | 44 |
| NCI-H2110 | lung (NSCLC) | | | Y | 17 | 14 |
| NCI-H226 | lung (NSCLC) | 62 | | Y | 41 | |
| NCI-H228 | lung (NSCLC) | | | Y | 51 | 31 |
| NCI-H23 | lung (NSCLC) | | | Y | 7 | 16 |
| NCI-H441 | lung (NSCLC) | | | Y | 80 | 32 |
| HCC78 | lung (NSCLC) | 1.7, 4.2 | | N | 3 | 0.8 |
| HCC827 | lung (NSCLC) | 8 | 1.5 | N | 0.8 | |
| NCI-H1650 | lung (NSCLC) | 1.5 | | N | 1 | 9.5 |
| NCI-H28 | lung (NSCLC) | | | N | 0 | 0.83 |
| NCI-H322 | lung (NSCLC) | | | N | 0 | 2.6 |
| NCI-H460 | lung (NSCLC) | 26 (n = 9) | 17 (n = 8) | N | 1.5 | 4.2 |
| NCI-H522 | lung (NSCLC) | 1.0, 2.9 | 0.4 | N | 2 | |
| NCI-H1299 | lung (NSCLC) | 4 | | | | |
| DMS-114 | lung (small cell) | | | Y | 41 | 5.4 |
| HCI-H209 | lung (small cell) | | | Y | | 5.2 |
| NCI-H146 | lung (small cell) | | | Y | 9 | 2.1 |
| NCI-H345 | lung (small cell) | | | Y | 12 | 4.5 |
| NCI-H82 | lung (small cell) | | | Y | 162 | 11 |
| SHP-77 | lung (small cell) | | | Y | 78 | 9.2 |
| NCI-H69 | lung (small cell) | 1 | | N | 4.7 | |
| NCI-H209 | lung (small cell) | | | | 44 | |
| MONO-MAC-6 | lymphocytic leukemia | | | Y (partial) | 86 | 26 |
| CCRF-CEM | lymphocytic leukemia | 2 | | Y | 26 | 4.9 |
| Jurkat | lymphocytic leukemia | | | Y | 3 | 13 |
| MOLT4 | lymphocytic leukemia | 6, <0.8 | | Y | 13 | 2.8 |
| THP-1 | lymphocytic leukemia | <0.8 | | Y | | 66.4 |
| KARPAS-299 | lymphocytic leukemia | 20 | | N | 2.5 | 2.3 |
| DEL | lymphoma | 41 | | Y (partial) | 5 | 2.4 |
| SR | lymphoma | 21 | | Y (partial) | 2.8 | |
| SU-DHL-4 | lymphoma | 0.84, 0.85 | | Y (partial) | 1 | 3.2 |
| SU-DHL-8 | lymphoma | 0.59, 0.59 | | Y (partial) | 2 | 4.3 |
| SUP-M2 | lymphoma | 2.2 | | Y (partial) | 4 | 3.9 |
| L-82 | lymphoma | 32 | | Y | 113 | 22 |
| OCI-LY-19 | lymphoma | 1.1, 1.4 | | Y | 126 | 1.6 |
| Ramos | lymphoma | 1.8 | | Y | 68 | 5.3 |
| SU-DHL-10 | lymphoma | 0.75, 0.83 | | Y | 62 | 4.5 |
| U-937 | lymphoma | 1.0, 0.89 | | Y | 584 | 43 |
| Daudi | lymphoma | 1.4, <0.8 | | N | 4 | 1.7 |
| H9 | lymphoma | 3.2 | | N | 2.5 | 3.2 |
| NAMALWA | lymphoma | 0.85, 0.85 | | N | 4 | |
| SR-786 | lymphoma | 1.1 | | N | 0 | 5.1 |
| SU-DHL-1 | lymphoma | 37 | | N | 0 | 0.91 |
| SU-DHL-5 | lymphoma | 0.57, 0.57 | | N | 1 | 1.4 |
| UACC-257 | melanoma | 27 | | Y | 360 | |
| LOX-IMVI | melanoma | 15 | | | | |
| MALME-3M | melanoma (lung metastasis) | 2.5 | | Y | 43 | 10 |
| A2058 | melanoma (lymph node metastasis) | 3.4 | | Y | 12 | |
| NIH-3T3 | mouse; fibroblast | 0.45 | | N | | |
| Hepa1-6 | mouse; hepatoma | 2.5 | | Y (partial) | | |
| RAW264.7 | mouse; leukemia | 14 | | N | | |

TABLE 8-continued

Exemplary Compound A Cytotoxicity, NA Rescue,
and Naprt1 Expression Across a Wide Range of Cancer Cell Types

| Cell line | Tissue | Cmpd A 3 day TC50 (nM) | Cmpd A 7 day TC50 (nM) | Rescued by NA? (partial indicates <70% rescue) | Naprt1 expression (% C.), Western (1, 4, 30 ug blots) | Naprt1 expression, qRT-PCR (% C.) |
|---|---|---|---|---|---|---|
| MLE-12 | mouse; lung | 4 | | N | | |
| B16-F10 | mouse; melanoma | 80 | | | | |
| NOMO-1 | myelogenous leukemia | <0.8 | | Y (partial) | 100 | 4.8 |
| SKM-1 | myelogenous leukemia | <0.8 | | Y (partial) | 162 | 30 |
| HL-60 | myelogenous leukemia | 5.3 | | Y | 70 | |
| K562 | myelogenous leukemia | 5.7 | | Y | 102 | 15 |
| MOLM-13 | myelogenous leukemia | | | Y | 36 | 15 |
| MV-4-11 | myelogenous leukemia | | | Y | 138 | 30 |
| NB-4 | myelogenous leukemia | <0.8 | | Y | 11 | 3.3 |
| KU 812 | myelogenous leukemia | | | N | 2 | 0.03 |
| K562 | myelogenous leukemia (CML) | | | Y | 65 | 22.5 |
| MEG-01 | myelogenous leukemia (CML) | 6, 1.2 | | Y | 438 | 76.3 |
| MOLP-8 | myeloma | | | Y (partial) | 55 | 5.3 |
| RPMI-8226 | myeloma | 6 | | Y (partial) | 373 | 47 |
| KMS-11 | myeloma | <0.8, 1.9 | | Y | 5 | 4.7 |
| MC/CAR | myeloma | 8.2 | | Y | 130 | 5 |
| AMO-1 | myeloma | | | N | 2 | 2.4 |
| NCI-H929 | myeloma | 6.4, 1.1 | | N | 5.5 | 0.29 |
| OPM-2 | myeloma | 1.5, 1.2, 4.1 | | N | 3.2 | |
| U266 | myeloma | 18, 10.3 | 1.5 | N | 0 | 1.7 |
| MM.1R | myeloma | 1.5 | | | | |
| MM.1S | myeloma | 1.2 | | | | |
| JJN3 | myeloma (plasma cell leukemia) | 0.9 | | Y | 127 | 47.0 |
| Saos-2 | osteosarcoma | | | Y | 0 | 3.08 |
| SJSA1 | osteosarcoma | | | Y | 0 | 12.0 |
| SK-ES-1 | osteosarcoma | | | Y | 9 | 11.1 |
| HOS | osteosarcoma | <0.8 | | N | 1 | 0.59 |
| MG-63 | osteosarcoma | | | N | 0 | 4.06 |
| U-2 OS | osteosarcoma | 2.2 | | N | 1 | 8.2 |
| OVCAR-3 | ovary | 1.1, <0.8 | 0.4 | Y | 46 | |
| OVCAR-8 | ovary | 0.5, <0.8 | | Y | 463 | |
| UWB1.289 | ovary | 2.4, 2.5 | | Y | 467 | |
| IGR-OV1 | ovary | 2 | | | | |
| OVCAR-4 | ovary | 2.8 | | | | |
| OVCAR-5 | ovary | 1.5 | | | | |
| SK-OV-3 | ovary | 1.2 | | | | |
| AsPC-1 | pancreas | 1.3, 1.6, 3.9 | | Y | 552 | 106 |
| BxPC-3 | pancreas | 11 | | Y | 605 | |
| Capan-1 | pancreas | 8.4, 17 | | Y | 744 | 254 |
| CFPAC-1 | pancreas | 1.5, 4 | | Y | 1261 | |
| Hs 766T | pancreas | 4.7 | | Y | 328 | 106 |
| Panc-1 | pancreas | 1.4, 3.5 | | Y | 15 | 73 |
| MiaPaCa2 | pancreas | 1.8 | 0.4 | N | 2 | 2.4 |
| SU.86.86 | pancreas | 4.3 | | | | |
| PBMC | primary blood | | | Y | | 4.4 |
| SAEC | primary lung | 15,000 (?) | | Y | | 7.9 |
| keratinocytes | primary skin | 2.9 | <0.4 | Y | | 14 |
| hFLS-RA | primary synoviocytes | >25,000 | >25,000 | | | 2 |
| DU145 | prostate | 3.9, 3.8 | 3 | Y | 92 | 7.4 |
| LNCAP | prostate | 5.7, 1.5 | | Y | 654 | |
| 22RV1 | prostate | 8.4 | | | | |
| PC-3 | prostate | <1.5 | | | | |
| VCaP | prostate | >10,000 (n = 2) | 14 | | | |
| MALME-3 | skin (normal) | >5,000 | 0.9 | Y | 27 | 2.6 |

Table 9, below, summarizes the results obtained for 154 of the 183 cell lines tested and reported in Table 8, above. Notably, at least one-quarter of cell lines representing brain cancers, liver cancers, non-small cell lung cancers, lymphomas, myelomas and osteosarcomas failed to be rescued from Exemplary Compound A-induced cytotoxicity by co-administration of NA. These results suggest that co-administration of NA with Exemplary Compound A and other Nampt inhibitors, may be indicated for a broad spectrum of tumors to facilitate administration of Nampt inhibitor dosages having maximal tumoricidal activity, while limiting undesirable NAD depletion and toxicity in normal host tissues. These results also suggest that quantification of Naprt1 expression can be useful as a companion diagnostic to identify patients whose cancers are most likely to respond to co-administration of NA with Nampt inhibitors such as Exemplary Compound A.

TABLE 9

Exemplary Compound A-Induced Cytotoxicity in a Wide Range of Cancer Types is Not Rescued by NA Co-Administration

| Cancer type | Number of cell lines tested | Fraction not rescued by NA |
| --- | --- | --- |
| bladder | 1 | 0% |
| brain | 30 | 53% |
| breast | 7 | 0% |
| colon | 6 | 0% |
| fibrosarcoma | 5 | 20% |
| kidney | 5 | 20% |
| liver | 4 | 25% |
| lung, NSCLC | 26 | 27% |
| lung, small cell | 7 | 14% |
| lymphocytic leukemia | 6 | 17% |
| lymphoma | 16 | 38% |
| melanoma | 3 | 0% |
| myelogenous leukemia | 10 | 10% |
| myeloma | 9 | 44% |
| osteosarcoma | 6 | 50% |
| ovary | 3 | 0% |
| pancreas | 7 | 14% |
| prostate | 2 | 0% |
| gastric | 1 | 0% |
| TOTAL | 154 | |

Exemplary Compound A-Induced NAD Depletion, Tumor Regression and NA Rescue in HCT116 Xenografts Exemplary Compound A was tested for its ability to deplete NAD levels and promote tumor regression in an HCT116 (i.e., a Naprt-proficient cancer) murine xenograft model. Three million HCT116 human colon carcinoma cells were injected subcutaneously into nu/nu mice to form tumors. Dosing was started ten days later when median tumor volume was >100 mm$^3$.

Exemplary Compound A was administered orally once on day 0 (arrow) to HCT116 tumor-bearing xenograft mice and NAD levels were determined for tumor lysates every other day for 8 days. Administration of Exemplary Compound A resulted in a 94% depletion of NAD after two days, but this decrease was followed by a gradual, but incomplete, increase in NAD over the following six days (FIG. 8(a)).

Figure 8:
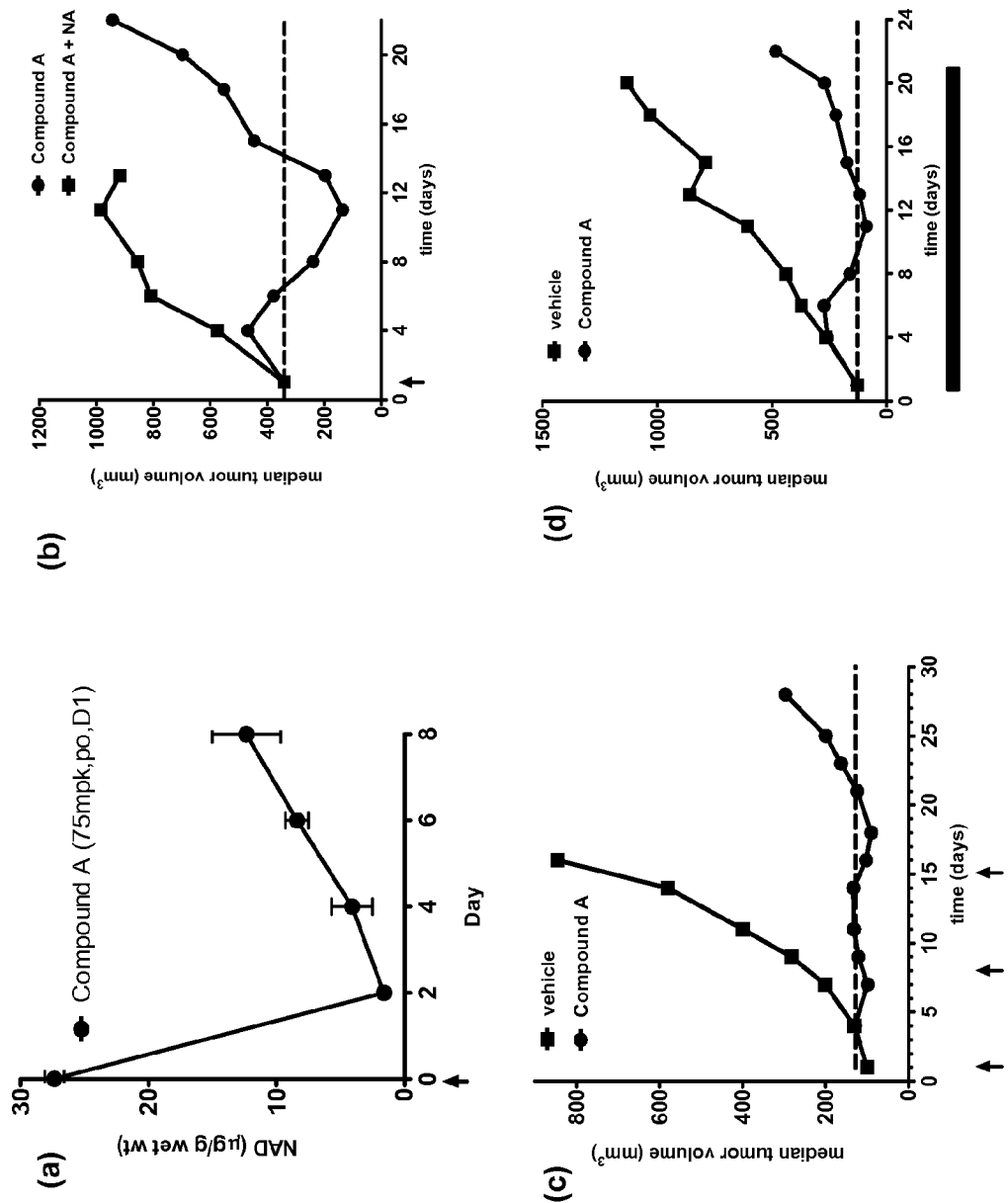
FIG. 8 documents Exemplary Compound A-induced NAD depletion in lysates of HCT116 xenograft tumors (a); inhibition of Exemplary Compound A-mediated HCT116 xenograft tumor growth inhibition by coadministration of NA, demonstrating that Exemplary Compound A acts by inhibiting the Nampt-catalyzed NAD salvage pathway (b), and efficacy of Exemplary Compound A at inhibiting growth of Naprt1-proficient HCT116 xenografts under intermittent (c) and continuous (d) dosing regimens.

Exemplary Compound A was administered orally to HCT116 tumor-bearing xenograft mice once (arrow) at the maximum tolerated dose of 75 mg/kg with or without simultaneous delivery of NA by Alzet pump (470 mg/kg/day for three days) (FIG. 8(b)). Tumor regression induced by the single dose of Exemplary Compound A (lower line) alone was completely prevented in the presence of NA (upper line).

The effect of weekly administration of Exemplary Compound A on tumor growth was examined in murine HCT116 xenograft models (FIG. 8(c)). HCT116 tumor-bearing xenograft mice were orally dosed with 75 mg/kg Exemplary Compound A weekly for three cycles (arrows), resulting in a maximal tumor response of 10% regression on day 18.

The effect of daily administration of Exemplary Compound A on tumor growth was examined in murine HCT116 xenograft models (FIG. 8(d)). HCT116 tumor-bearing xenograft mice were orally dosed with 10 mg/kg Exemplary Compound A daily for 21 days (black bar), resulting in a maximal tumor response of 32% regression on day 11.

Figure 9:
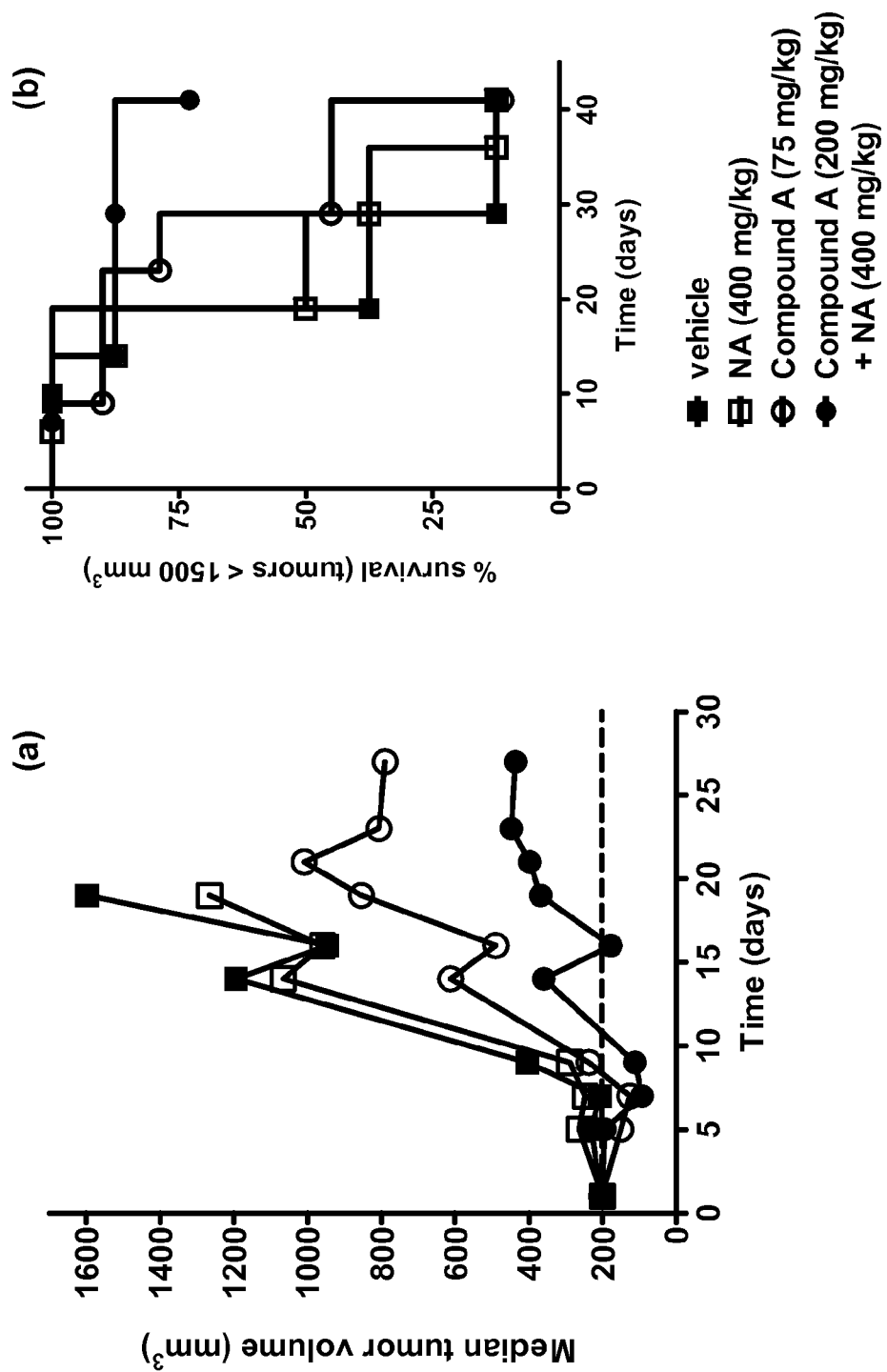
FIG. 9 documents that co-administration of NA allows for enhanced tumoricidal effect of an increased dosage of Exemplary Compound A when combined with NA (darkened circles) in an Naprt1-deficient MIA PaCa2 xenograft model of cancer in mice, as measured by changes in tumor volume (a) and % survival (b).

Co-Administration of NA Enhances Effect of Exemplary Compound A in Naprt1-Deficient MIAPaCa-2 Xenografts Exemplary Compound A was tested for its ability to suppress tumor growth, and promote survival in MIAPaCa-2 human pancreatic carcinoma (i.e., a Naprt-deficient cancer) murine xenograft models (FIG. 9). Tumor growth expressed as increased median tumor volume is shown in FIG. 9(a). In these experiments, MIAPaCa-2 tumor-bearing mice with a median tumor volume of 202 mm$^3$ were orally dosed on days 1, 10 and 19 with either vehicle, 75 mg/kg Exemplary Compound A or 200 mg/kg Exemplary Compound A in combination with 400 mg/kg NA, or were orally dosed daily with 400 mg/kg NA for 21 days. See key below FIG. 9(b). NA was always administered one hour prior to dosing with Exemplary Compound A or vehicle.

Exemplary Compound A at 75 mg/kg (the maximum tolerated dose (MTD)) induced 53% tumor growth inhibition (TGI) on day 19 relative to vehicle. Combination with NA allowed dosing of Exemplary Compound A above the MTD at 200 mg/kg, and this increased dose resulted in an increase in TGI to 88% on day 19 (FIG. 9(a)).

The survival of mice from the same experiment is shown in FIG. 9(b). Exemplary Compound A administered at 200 mg/kg in combination with 400 mg/kg NA significantly increased survival, with only two animals having tumor volumes >1500 mm3 at the end of the study on Day 40, compared to eight in the other cohorts.

These data (FIGS. 9(a) and 9(b)) demonstrate that Nampt inhibitors, such as Exemplary Compound A, can be given at dosages higher than their normal MTD if NA is co-administered with the Nampt inhibitor. They also demonstrate that coadministration of NA with an elevated dose of a Nampt inhibitor (i.e., 200 mg/kg Exemplary Compound A) suppresses tumor growth to a greater extent than the normal MTD of the same Nampt inhibitor (i.e., 75 mg/kg Exemplary Compound A) for Narpt1-deficient cancers, as exemplified by the MIAPaCa-2 human pancreatic carcinoma tumors in the murine xenograft model used in these experiments.

Effects of NA on Survival and Body Weight in Mice Administered a Lethal Dose of Exemplary Compound A.

Figure 10:
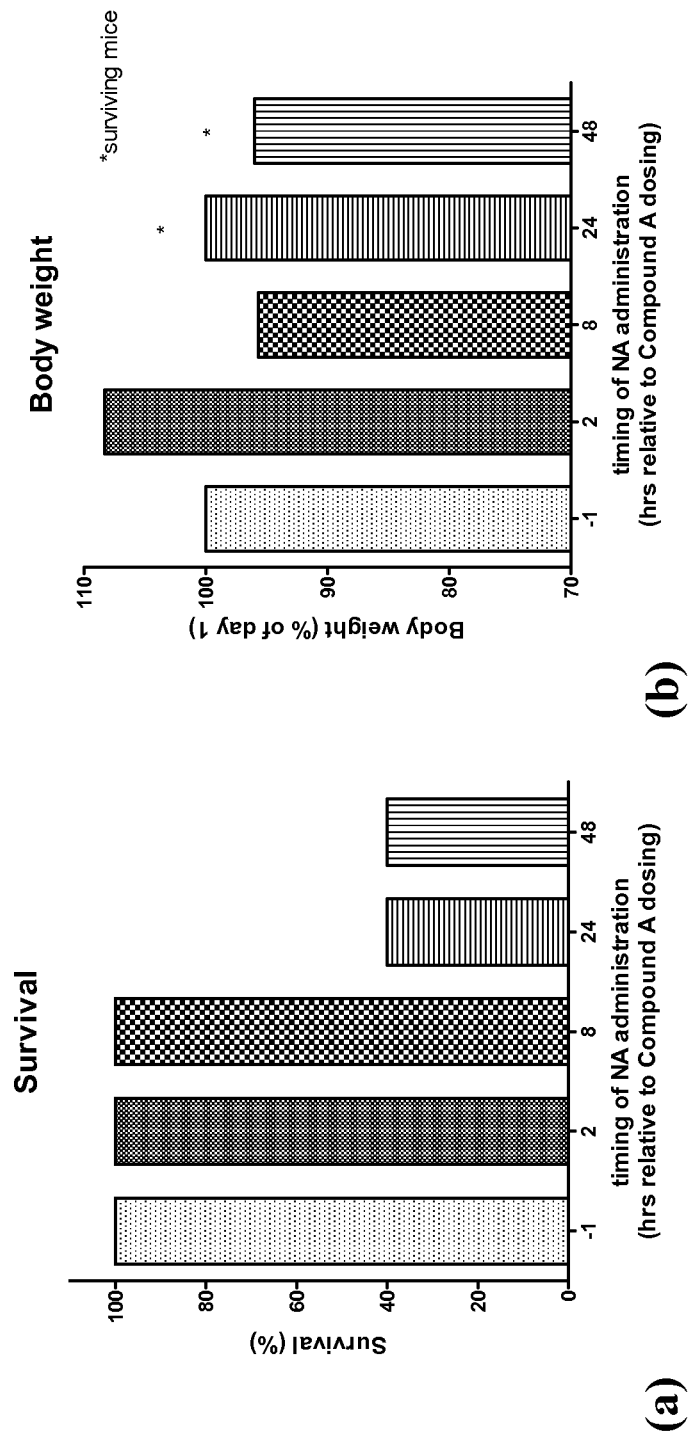
FIG. 10(a) illustrates effects of NA on survival as a function of timing of NA administration relative to Exemplary Compound A, 15 days after Exemplary Compound A administration.
FIG. 10(b) illustrates effects of NA on body weight as a function of timing of NA administration relative to Exemplary Compound A, 15 days after Exemplary Compound A administration.

FIG. 10(a) illustrates effects of NA on survival as a function of timing of NA administration relative to Exemplary Compound A, 15 days after Exemplary Compound A administration. A single oral dose of 300 mg/kg of Exemplary Compound A was completely lethal to mice by 5 days (cohorts of 5). Oral NA (3 g/kg) completely blocked Exemplary Compound A lethality when given 1 h prior or up to 8 h following Exemplary Compound A administration. FIG. 10(b) illustrates effects of NA on body weight as a function of timing of NA administration relative to Exemplary Compound A, 15 days after Exemplary Compound A administration. Body weights remained stable for mice with NA co-administration 1 h prior or up to 8 h following Exemplary Compound A administration. Thus, NA co-administration can be used to prevent or rescue from toxicity associated with Nampt inhibition.

Correlation Between In Vitro and In Vivo Exemplary Compound a Potency

Figure 11:
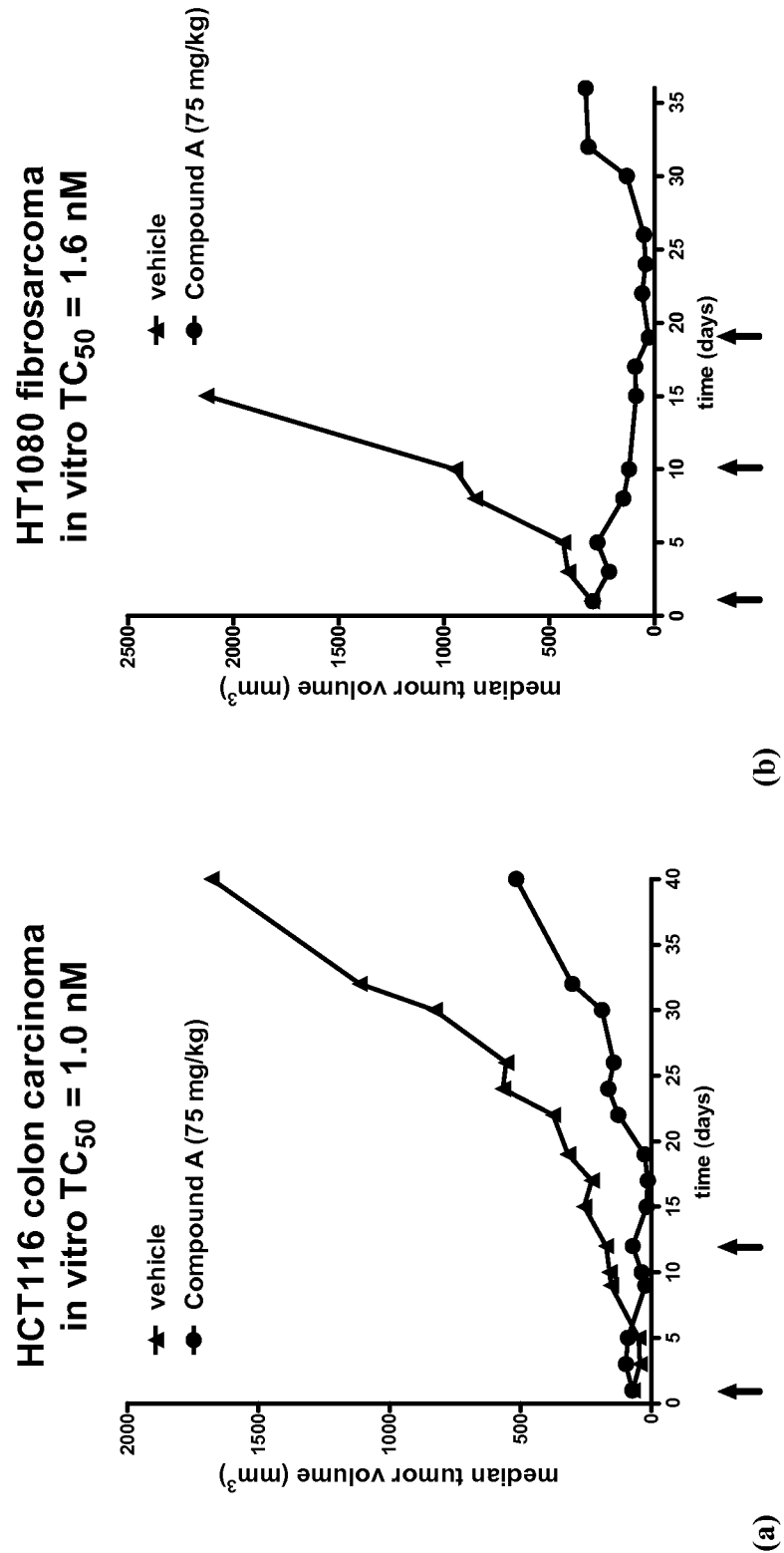
FIG. 11(a) depicts the change in tumor volume over time for mice with HCT116 colon carcinoma xenografts that were administered Exemplary Compound A.
FIG. 11(b) depicts results for mice with HT1080 fibrosarcoma xenografts that were administered Exemplary Compound A.
Figure 12:
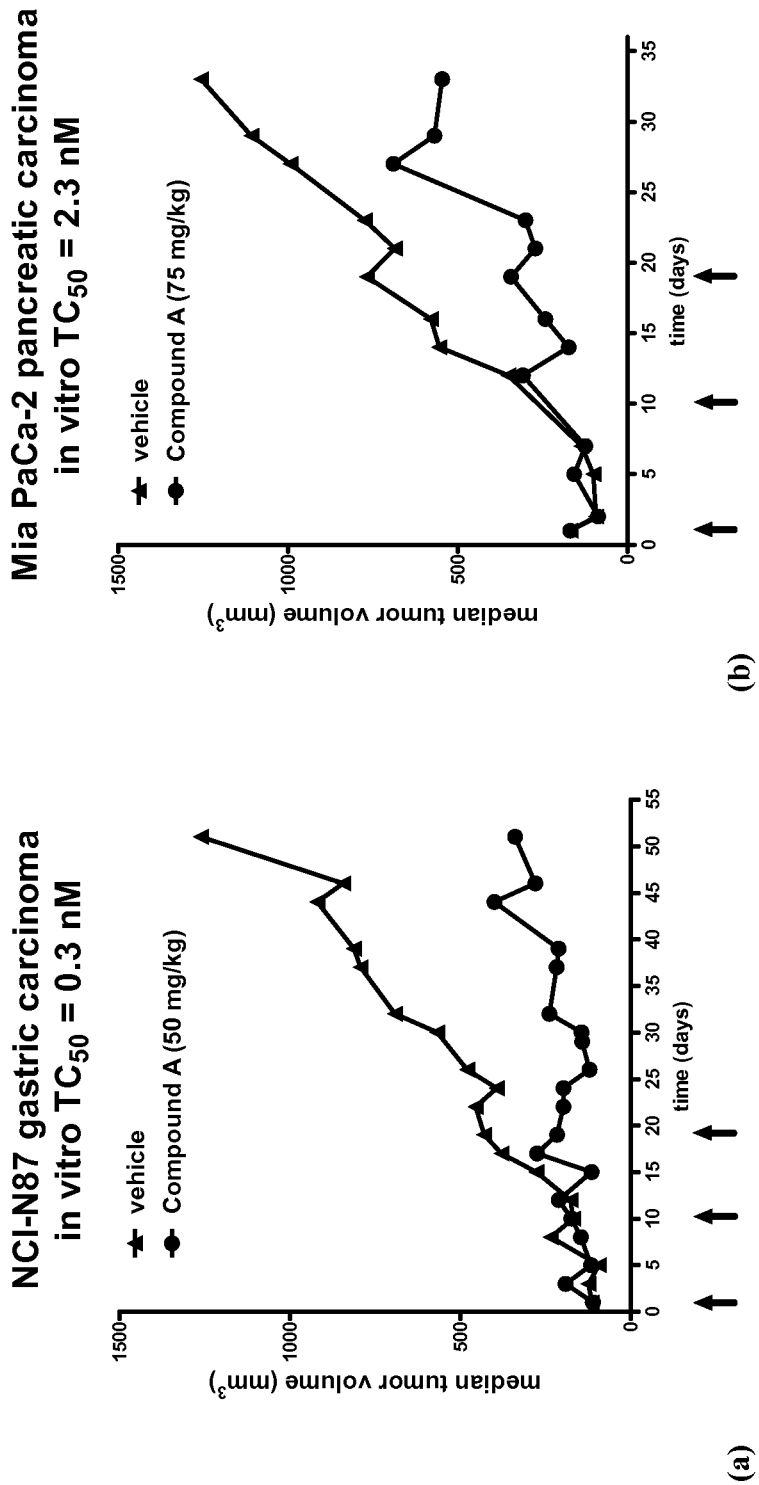
FIG. 12(a) depicts the change in tumor volume over time for mice with NCI-N87 gastric carcinoma xenografts that were administered Exemplary Compound A.
FIG. 12(b) depicts tumor volume over time for mice with Mia PaCa-2 pancreatic carcinoma xenografts that were administered Exemplary Compound A.
Figure 13:
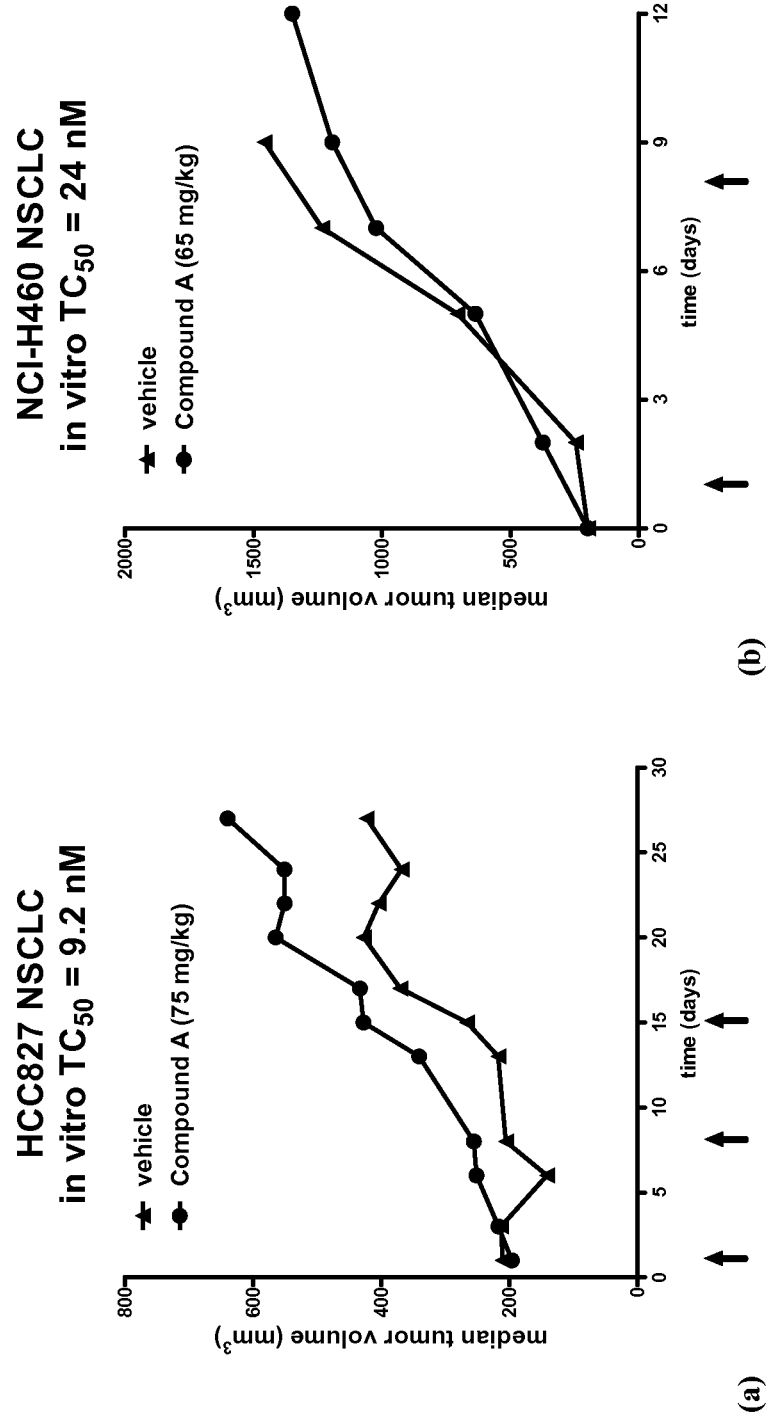
FIG. 13(a) depicts the change in tumor volume over time for mice with HCC827 non-small cell lung cancer (NSCLC) xenografts that were administered Exemplary Compound A.
FIG. 13(b) depicts tumor volume over time for mice with NCI-H460 NSCLC xenografts that were administered Exemplary Compound A.

Responses to Exemplary Compound A in six xenograft models compared with in vitro potencies. FIG. 11(a) illustrates tumor volume over time for mice with HCT116 colon carcinoma xenografts that were administered Exemplary Compound A. FIG. 11(b) illustrates results for mice with HT1080 fibrosarcoma xenografts that were administered Exemplary Compound A. FIG. 12(a) illustrates tumor volume over time for mice with NCI-N87 gastric carcinoma xenografts that were administered Exemplary Compound A. FIG. 12(b) illustrates tumor volume over time for mice with Mia PaCa-2 pancreatic carcinoma xenografts that were administered Exemplary Compound A. FIG. 13(a) illustrates tumor volume over time for mice with HCC827 non-small cell lung cancer (NSCLC) xenografts that were administered Exemplary Compound A. FIG. 13(b) illustrates tumor volume over time for mice with NCI-H460 NSCLC xenografts that were administered Exemplary Compound A. Nude mice bearing tumors from the indicated human cell lines were dosed at 7-12 day intervals for 2 or 3 cycles with vehicle, 50, 65 or 75 mg/kg Exemplary Compound A (cohorts of 10) in the six human xenograft models as indicated. Mice were sacrificed when tumor volumes exceeded 1500 mm$^3$. In vitro $TC_{50}$ values were determined by incubating cells with Exemplary Compound A at various concentrations for 72 h. Cell viability was determined by measuring ATP using CellTiter Glo® (Promega Corporation, Madison, Wis.). GraphPad Prism software (GraphPad Software, Inc., La Jolla, Calif.) was used to calculate $TC_{50}$ values. Xenograft response to Exemplary Compound A parallels in vitro potency.

Inverse Correlation Between In Vitro Exemplary Compound a Potency and Expression of Nampt NAD metabolism enzymes were quanitified in tumor cell lines used for the xenograft studies above. Expression levels of the NAD metabolism enzymes Naprt, Qprt, Nampt and Parp-1 were determined using Western blot. Nampt was the only enzyme in the panel that showed significant correlation with Exemplary Compound A $TC_{50}$ values, cell line basal NAD levels, or Exemplary Compound A NAD depletion $IC_{50}$ values. Nampt expression, but not Naprt, Qprt or Parp-1 expression, inversely correlates with tumoricidal and NAD depletion potency and directly correlates with basal NAD levels in the xenograft cell lines.

Correlation Between NAD Metabolism and Tumoricidal Activity

Potency of Exemplary Compound A-induced NAD depletion in tumor cell lines used for the xenograft studies above was determined. Cellular NAD levels were determined using a coupled biochemical reaction following treatment for 18 h with various doses of Exemplary Compound A. NAD depletion potency correlates with basal NAD levels and tumoricidal potency. Thus, Exemplary Compound A tumoricidal activity is due to Nampt inhibition. Nampt expression inversely correlates with NAD depletion and tumoricidal potency of Exemplary Compound A in tumor cell lines. Therefore, Nampt expression may have utility as a companion diagnostic for determining whether a patient's tumor, or a class of tumors, is sensitive to Nampt inhibition.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be understood that certain changes and modifications can be practiced within the scope of the appended claims.

What is claimed is:

1. A method of treating cancers associated with low level expression of nicotinic acid phosphoribosyltransferase 1 (Naprt1), comprising:
    identifying a cancer associated with a low level of Naprt1 expression; and
    administering to a subject in need thereof, a composition comprising a therapeutically effective amount of a compound of Formulae I-IVc or a compound of Tables 1 or 2, or a pharmaceutically acceptable salt thereof.

2. The method of claim 1, wherein identifying a cancer associated with a low level of Naprt1 expression comprises determining the level of expression of Naprt1 protein in cells of the cancer.

3. The method of claim 2, wherein determining the level of expression of Naprt1 protein is by way of a Western Blot.

4. The method of claim 2, wherein determining the level of expression of Naprt1 protein is by way of an Enzyme-Linked Immunosorbant Assay (ELISA).

5. The method of claim 1, wherein identifying a cancer associated with a low level of Naprt1 expression comprises determining the level of expression of the mRNA transcript encoding the Naprt1 protein in cells of the cancer.

6. The method of claim 5, wherein determining the level of expression of the mRNA transcript encoding the Naprt1 protein is by way of a Northern Blot.

7. The method of claim 5, wherein determining the level of expression of the mRNA transcript encoding the Naprt1 protein is by way of quantitative RT-PCR.

8. The method of claim 1, wherein said cancer is associated with low expression levels of nicotinamide phosphoribosyltransferase (Nampt).

9. The method of claim 8, further comprising determining whether said cancer expresses low levels of the Nampt.

10. The method of claim 1, further comprising determining whether said cancer is associated with nicotinic acid (NA) Rescue Phenotype.

11. The method of claim 10, wherein said cancer is associated with NA Rescue Phenotype.

12. The method of claim 1, further comprising administering nicotinic acid to said subject.

13. A method of treating cancers associated with low level expression of nicotinic acid phosphoribosyltransferase 1 (Naprt1), comprising:
    identifying a cancer associated with a low level of Naprt1 expression,
    administering to a subject in need thereof, a composition comprising a therapeutically effective amount of: (i) nicotinic acid; (ii) a compound of Formulae I-IVc or a compound of Tables 1 or 2, or a pharmaceutically acceptable salt thereof.

14. The method of claim 13, wherein said nicotinic acid is administered prior to the therapeutically effective amount of a compound of Formulae I-Formulae I-IVc or a compound of Tables 1 or 2, or a pharmaceutically-acceptable salt thereof.

15. The method of claim 13, wherein said nicotinic acid is administered at the same time as the therapeutically effective amount of a compound of Formulae I-IVc or a compound of Tables 1 or 2, or a pharmaceutically-acceptable salt thereof.

16. The method of claim 13, wherein said nicotinic acid is administered after the therapeutically effective amount of a compound of Formulae I-IVc or a compound of Tables 1 or 2, or a pharmaceutically-acceptable salt thereof.

17. The method of claim 16, wherein said nicotinic acid is administered as part of the same dosage form comprising the therapeutically effective amount of a compound of Formulae I-IVc or a compound of Tables 1 or 2, or a pharmaceutically-acceptable salt thereof.

\* \* \* \* \*